(12) United States Patent
Justice et al.

(10) Patent No.: US 11,015,154 B2
(45) Date of Patent: May 25, 2021

(54) METHODS FOR IDENTIFYING INTERACTIONS AMONGST MICROORGANISMS

(71) Applicant: The Regents of the University of California, Oakland, CA (US)

(72) Inventors: Nicholas B. Justice, Oakland, CA (US); Adam P. Arkin, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 576 days.

(21) Appl. No.: 15/807,498

(22) Filed: Nov. 8, 2017

(65) Prior Publication Data

US 2018/0127796 A1    May 10, 2018

Related U.S. Application Data

(60) Provisional application No. 62/466,613, filed on Mar. 3, 2017, provisional application No. 62/419,898, filed on Nov. 9, 2016.

(51) Int. Cl.
| | | |
|---|---|---|
| *C12Q 1/02* | (2006.01) | |
| *C12Q 1/689* | (2018.01) | |
| *G16B 40/00* | (2019.01) | |
| *C12C 1/02* | (2006.01) | |

(52) U.S. Cl.
CPC ............... *C12C 1/02* (2013.01); *C12Q 1/025* (2013.01); *C12Q 1/689* (2013.01); *C12Q 2600/158* (2013.01); *G16B 40/00* (2019.02)

(58) Field of Classification Search
None
See application file for complete search history.

(56) References Cited

U.S. PATENT DOCUMENTS

| | | | |
|---|---|---|---|
| 8,071,295 B2 | 12/2011 | Ashby | |
| 8,771,940 B2 | 7/2014 | Andersen et al. | |
| 9,150,851 B2 | 10/2015 | Wigley et al. | |
| 9,206,680 B2 | 12/2015 | Ashby et al. | |
| 9,260,713 B2 | 2/2016 | Wigley et al. | |
| 9,365,847 B2 | 6/2016 | Wigley et al. | |
| 9,593,382 B2 | 3/2017 | Kunin et al. | |
| 2005/0026188 A1 | 2/2005 | Van Kessel et al. | |
| 2010/0029498 A1 | 2/2010 | Gnirke et al. | |
| 2012/0165215 A1 | 6/2012 | Andersen et al. | |
| 2014/0082770 A1 | 3/2014 | Wigley et al. | |
| 2014/0109249 A1 | 4/2014 | Turner et al. | |
| 2014/0115731 A1 | 4/2014 | Turner et al. | |
| 2015/0191720 A1 | 7/2015 | Beilinson et al. | |
| 2015/0250116 A1 | 9/2015 | Wigley et al. | |
| 2015/0259728 A1 | 9/2015 | Cutliffe et al. | |
| 2015/0337363 A1 | 9/2015 | Andersen et al. | |
| 2015/0337349 A1* | 11/2015 | Kuczynski | A61K 31/4458 435/6.15 |
| 2016/0108435 A1 | 4/2016 | Ashby et al. | |
| 2016/0145670 A1 | 5/2016 | Steger et al. | |
| 2016/0289667 A1 | 10/2016 | Wigley et al. | |
| 2016/0330976 A1 | 11/2016 | Mitter et al. | |
| 2017/0020138 A1 | 1/2017 | Von Maltzahn et al. | |
| 2017/0086402 A1 | 3/2017 | Meadows-Smith et al. | |
| 2017/0196921 A1* | 7/2017 | Embree | A23L 33/135 |

FOREIGN PATENT DOCUMENTS

| | | |
|---|---|---|
| EP | 2206791 | 7/2016 |
| WO | WO 2008/076697 | 6/2008 |
| WO | WO 2015/170979 | 11/2015 |
| WO | WO 2016/106089 | 6/2016 |
| WO | WO 2016/106184 | 6/2016 |
| WO | WO 2016/109758 | 7/2016 |
| WO | WO 2016/130586 | 8/2016 |
| WO | WO 2016/154602 | 9/2016 |
| WO | WO 2016/172380 | 10/2016 |
| WO | WO 2017/011602 | 1/2017 |
| WO | WO 2017/087908 | 5/2017 |
| WO | WO 2017/096385 | 6/2017 |

OTHER PUBLICATIONS

Beeman et al. The ISME Journal, 2011, 5, 1077-1085.*
Banerjee et al. Soil Biology & Biochemistry 97, 2016 188-198.*
Dam et al. NPJ systems biology and applications, (2016) vol. 2, pp. 16007.*
Alkema et al., Microbial bioinformatics for food safety and production, Briefings in Bioinformatics, Jun. 2015, 17(2): 283-292.
Bar-Massada, Complex relationships between species niches and environmental heterogeneity affect species co-occurrence patterns in modelled and real communities, Proceedings of the Royal Society B: Biological Sciences, Aug. 2015, 282:20150927.
Beresford et al., Recent advances in cheese microbiology, International Dairy Journal, Jul. 2001, 11(4-7):259-274.
Bergey's Manual of Systematic Bacteriology, vol. 2: The Proteobacteria, Parts A-C, 2nd Edition, Garrity, et al. (Eds.), Jul. 2005, Springer-Verlag, New York, NY.
Bergey's Manual of Systematic Bacteriology, vol. 3: The Firmicutes, 2nd Edition, Vos, et al. (Eds.), Oct. 2009, Springer-Verlag, New York, NY.
Blodgett et al., Several MPN models for serial dilutions with suppressed growth at low dilutions, Food Microbiology, Feb. 1998, 15(1):91-99.
Blodgett, Measuring improbability of outcomes from a serial dilution test, Communications in Statistics—Theory and Methods, Dec. 2002, 31(12):2209-2223.

(Continued)

*Primary Examiner* — Michael L Borin
(74) *Attorney, Agent, or Firm* — Sheppard, Mullin, Richter & Hampton LLP

(57) ABSTRACT

Disclosed herein are methods, compositions, and systems for determining specific microbial taxa, within a complex consortia of mixed taxa, which are interacting with each other in an environment of interest. In some embodiments, after diluting a sample comprising multiple different taxa of microorganisms, dilutions of the sample are cultivated for determining taxonomic information and interactions of multiple taxa of microorganisms in the sample.

60 Claims, 25 Drawing Sheets

Specification includes a Sequence Listing.

(56) References Cited

OTHER PUBLICATIONS

Cadotte et al., Constructing nature: laboratory models as necessary tools for investigating complex ecological communities, Advances in Ecological Research, Dec. 2005, 37:333-353.

Caporaso et al., QIIME allows analysis of high-throughput community sequencing data, Nature Methods, May 2010, 7(5):335-336.

Chase, Drought mediates the importance of stochastic com-munity assembly, Proceedings of the National Academy of Sciences of the United States of America, Oct. 2007, 104(44):17430-17434.

Cho et al., The human microbiome: at the interface of health and disease, Nature Reviews Genetics, Apr. 2012, 13(4):260-270.

Daims, et al., Wastewater treatment: a model system for microbial ecology, Trends in Biotechnology, Nov. 2006, 24(11):483-489.

Desantis et al., Greengenes, a chimera-checked 16S rRNA gene database and workbench compatible with ARB, Applied and Environmental Microbiology, Jul. 2006, 72(7):5069-5072.

Drake et al., Microcosms as models for generating and testing community theory, Ecology, Apr. 1996, 77(3):670-677.

Drancourt et al., 16S ribosomal DNA sequence analysis of a large collection of environmental and clinical unidentifiable bacterial isolates, Journal of Clinical Microbiology, Oct. 2000, 38(10):3623-3630.

Edgar et al., UCHIME improves sensitivity and speed of chimera detection, Bioinformatics, Aug. 2011, 27(16):2194-2200, https://doi.org/10.1093/bioinformatics/btr381.

Fadrosh et al., An improved dual-indexing approach for multiplexed 16S rRNA gene sequencing on the Illumina MiSeq platform, Microbiome, Feb. 2014. 2:6, https://doi.org/10.1186/2049-2618-2-6.

Falk et al., Microbial community dynamics in replicate membrane bioreactors—natural reproducible fluctuations, Water Research, Feb. 2009, 43(3):842-852.

Falkowski et al., The microbial engines that drive Earth's biogeochemical cycles, Science, May 2008, 320(5879):1034-1039.

Francisco et al., Acridine orange-epifluorescence technique for counting bacteria in natural waters, Transactions of the American Microscopical Society, Jul. 1973, 92(3):416-421.

Frank et al., Quantitative metagenomic analyses based on average genome size normalization, Applied and Environmental Microbiology, Apr. 2011, 77(7):2513-2521.

Gage et al., Use of green fluorescent protein to visualize the early events of symbiosis between rhizobium meliloti and alfalfa (*Medicago sativa*), Journal of Bacteriology, Dec. 1996, 178(24):7159-7166.

Garthright et al., FDA's preferred MPN methods for standard, large or unusual tests, with a spreadsheet, Food Microbiology, Aug. 2003, 20(4):439-445.

Guidelines for the conservation and characterization of plant, animal, and microbial genetic resources for food and agriculture, INEA, Gruppo di Lavoro Biodiversita in Agricultura, Oct. 2012, 74 pages.

Haas et al., Regulation of antibiotic production in root-colonizing *Pseudomonas* spp. and relevance for biological control of plant disease, Annual Review of Phytopathology, Sep. 2003, 41:117-153.

Hemme et al., Comparative metagenomics reveals impact of contaminants on groundwater microbiomes, Frontiers in Microbiology, Oct. 2015, 6(1205), https://doi.org/10.3389/fmicb.2015.01205.

Heylen et al., Cultivation of denitrifying bacteria: optimization of isolation conditions and diversity study, Applied and Environmental Microbiology, Apr. 2006, 72(4):2637-2643, https://doi.org/10.1128/AEM.72.4.2637-2643.2006.

Hibbing et al., Bacterial competition: surviving and thriving in the microbial jungle, Nature Reviews Microbiology, Jan. 2010, 8(1):15-25.

Hillerislambers et al., Rethinking community assembly through the lens of coexistence theory, Annual Review of Ecology, Evolution, and Systematics, Dec. 2012, 43:227-248.

Janssen et al., Improved culturability of soil bacteria and isolation in pure culture of novel members of the divisions acidobacteria, actinobacteria, proteobacteria, and verrucomicrobia, Applied and Environmental Microbiology, May 2002, 68(5):2391-2396.

Jarvis et al., Reconsideration of the derivation of most probable numbers, their standard deviations, confidence bounds and rarity values, Journal of Applied Microbiology, Jun. 2010, 109:1660-1667.

Jessup et al., Big questions, small worlds: microbial model systems in ecology, Trends in Ecology and Evolution, Apr. 2004, 19(4):189-197.

Jones et al., Phylogenetic analysis of nitrite, nitric oxide, and nitrous oxide respiratory enzymes reveal a complex evolutionary history for denitrification, Molecular Biology and Evolution, Sep. 2008, 25(9):1955-1966, https://doi.org/10.1093/molbev/msn146.

Justice et al., Environmental selection, dispersal, and organism interactions shape community assembly in high-throughput enrichment culturing, Applied and Environmental Microbiology, Oct. 2017, 83(20):e01253-17, https://doi.org/10.1128/AEM.01253-17.

Kozich et al., Development of a dual-index sequencing strategy and curation pipeline for analyzing amplicon sequence data on the MiSeq Illumina sequencing platform, Applied and Environmental Microbiology, Sep. 2013, 79(17):5112-5120, https://doi.org/10.1128/AEM.01043-13.

Langenheder et al., Structure and function of bacterial communities emerging from different sources under identical conditions, Applied and Environmental Microbiology, Jan. 2006, 72(1):212-220, https://doi.org/10.1128/AEM.72.1.212-220.2006.

Nemergut et al., Patterns and processes of microbial community assembly, Microbiology and Molecular Biology Reviews, 77(3):342-356, https://doi.org/10.1128/MMBR.00051-12.

Ofiţeru et al., Combined niche and neutral effects in a microbial wastewater treatment community, Proceedings of the National Academy of Sciences of the United States of America, Aug. 2010, 107(35):15345-15350, https://doi.org/10.1073/pnas.1000604107.

Oksanen et al., Vegan: community ecology package, R package version 2.4-6, Jan. 2018, R Core Development Team, Vienna, Austria, https://CRAN.R-project.org/package=vegan.

Pagaling et al., Community history affects the predictability of microbial ecosystem development, The ISME Journal, Jan. 2014, 8(1):19-30, https://doi.org/10.1038/ismej.2013.150.

Peter et al., Function-specific response to depletion of microbial diversity, The ISME Journal, Feb. 2011, 5(2):351-361, https://doi.org/10.1038/ismej.2010.119.

Philippot et al., Loss in microbial diversity affects nitrogen cycling in soil, The ISME Journal, Aug. 2013, 7(8):1609-1619, https://doi.org/10.1038/ismej.2013.34.

Price et al., The effects of circumcision on the penis microbiome, PLoS One, Jan. 2010, 5(1):e8422, https://doi.org/10.1371/journal.pone.0008422.

Rodriguez et al., Stress tolerance in plants via habitat-adapted symbiosis, The ISME Journal, Feb. 2008, 2:404-416.

Shannon et al., Cytoscape: a software environment for integrated models of biomolecular interaction networks, Genome Research, Nov. 2003, 13(11):2498-2504, https://doi.org/10.1101/gr.1239303.

Sharon et al., Accurate, multi-kb reads resolve complex populations and detect rare microorganisms, Genome Research, Feb. 2015, 25:534-543.

Spain et al., Nitrate-reducing bacteria at the nitrate and radionuclide contaminated Oak Ridge Integrated Field Research Challenge site: a review, Geomicrobiology Journal, Jun. 2011, 28(5-6):418-429, https://doi.org/10.1080/01490451.2010.507642.

Sunagawa et al., Metagenomic species profiling using universal phylogenetic marker genes, Nature Methods, Oct. 2013, 10:1196-1199.

Szabó et al., Importance of rare and abundant populations for the structure and functional potential of freshwater bacterial communities, Aquatic Microbial Ecology, Apr. 2007, 47(1):1-10, https://doi.org/10.3354/ame047001.

The Prokaryotes: A Handbook on the Biology of Bacteria, 3rd Edition, Dworkin et al. (Eds.), Springer-Verlag, New York, NY, Dec. 2006.

Valdes et al., Draft genome sequence of Janthinobacterium lividum strain MTR reveals its mechanism of capnophilic behavior, Standards in Genomic Sciences, Nov. 2015, 10(1):110, https://doi.org/10.1186/s40793-015-0104-z.

(56) References Cited

OTHER PUBLICATIONS

Vanwonterghem et al., Deterministic processes guide long-term synchronised population dynamics in replicate anaerobic digesters, The ISME Journal, Oct. 2014, 8(10):2015-2028, https://doi.org/10.1038/ismej.2014.50.

Veech, A probabilistic model for analysing species co-occurrence, Global Ecology Biogeography, Feb. 2013, 22(2):252-260.

Vellend, Conceptual synthesis in community ecology, The Quarterly Review of Biology, Jun. 2010, 85(2):183-206, https://doi.org/10.1086/652373.

Větrovský et al., The variability of the 16S rRNA gene in bacterial genomes and its consequences for bacterial community analyses, PLoS One, Feb. 2013, 8(2):e57923, https://doi.org/10.1371/journal.pone.0057923.

Widder et al., Challenges in microbial ecology: building predictive understanding of community function and dynamics, The ISME Journal, Nov. 2016, 10(11):2557-2568, https://doi.org/10.1038/ismej.2016.45.

Zhang et al., PEAR: a fast and accurate Illumina Paired-End reAd merger, Bioinformatics, Mar. 2014, 30(5):614-620, https://doi.org/10.1093/bioinformatics/btt593.

Zhao et al., Identification and characterization of the endophytic plant growth prompter Bacillus Cereus strain mq23 isolated from Sophora Alopecuroides root nodules, Brazilian Journal of Microbiology, Jun. 2011, 42(2):567-575.

Zhou et al., Stochastic assembly leads to alternative communities with distinct functions in a bioreactor microbial community, mBio, Mar. 2013, 4(2):e00584-12, https://doi.org/10.1128/mBio.00584-12.

\* cited by examiner

METHODS FOR IDENTIFYING INTERACTIONS AMONGST MICROORGANISMS

RELATED APPLICATIONS

The present application claims priority under 35 U.S.C. § 119(e) to U.S. Provisional Application No. 62/419,898, filed on Nov. 9, 2016; and U.S. Provisional Application No. 62/466,613, filed on Mar. 3, 2017. The content of each of these related applications is incorporated herein by reference in its entirety.

STATEMENT REGARDING FEDERALLY SPONSORED R&D

This invention was made during work supported by U.S. Department of Energy under Contract No. DE-AC02-05CH11231, and by the National Institutes of Health and the National Institute of General Medical Sciences under Award No. 1F32GM113547-01. The government has certain rights in this invention.

REFERENCE TO SEQUENCE LISTING

The present application is being filed along with a Sequence Listing in electronic format. The Sequence Listing is provided as a file entitled Sequence_Listing_LBNL_089A.txt, created on Oct. 17, 2017, which is 864 bytes in size. The information in the electronic format of the Sequence Listing is incorporated herein by reference in its entirety.

BACKGROUND

Field

The present disclosure relates to generally to microbial population analysis and more particularly to identification and analysis of interactions amongst microorganisms.

Description of the Related Art

Very few tools exist for evaluating and understanding multi-species processes. Current methods to predict organism interactions can be limited by the accuracy of gene annotations and metabolic models on which they are based. Other methods, such as computational modeling, may fail to capture cultivability information. Classical methods of co-incubation of organisms are low throughput and do not simultaneously evaluate all possible interactions from a mixed consortia in a given cultivation condition. There is a need for methods that overcome these limitations.

SUMMARY

Disclosed herein is a method for determining microbial interactions. The microbes can comprise prokaryotes, eukaryotes, or any combination thereof. In some embodiments, the method comprises: diluting a sample to form a plurality of dilutions of the sample, wherein the sample comprises a plurality of taxa of microorganisms; cultivating (or enriching) the plurality of dilutions of the sample in a first cultivation condition; determining taxonomic information of taxa in the plurality of dilutions of the sample cultivated in the first cultivation condition, wherein the taxonomic information comprises the abundance of each taxon of the taxa in the plurality of dilutions of the sample cultivated in the first cultivation condition; and determining, based on the taxonomic information of the taxa in the plurality of dilutions of the sample cultivated in the first cultivation condition, interactions of the plurality of taxa of microorganisms in the sample in the first cultivation condition. In some embodiments, the method comprises designing a microbial community with the property of interest. In some embodiments, the method is multiplexed.

In some embodiments, diluting the sample to form plurality of dilutions of the sample comprises: diluting the sample serially to form a plurality of serial dilutions of the sample. The plurality of serial dilutions of the sample can comprise about 1:10, 1:100, 1:1000, or 1:10000 dilutions of the sample. The plurality of serial dilutions of the sample can comprise dilutions of a number of (for example, 1 to 9) orders of magnitudes of the sample. The plurality of serial dilutions of the sample comprises about 2, 3, 4, 5, 6, 7, 8, 9, or 10 folds dilutions of the sample.

In some embodiments, determining the taxonomic information of the plurality of dilutions of the sample cultivated in the first cultivation condition comprises: determining the taxonomic information of the plurality of dilutions of the sample cultivated in the first cultivation condition based on sequencing (e.g., gene amplicon sequencing) of one or more of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof). Determining the taxonomic information of the taxa in the plurality of dilutions of the sample cultivated in the first cultivation condition can comprise: determining one or more errors in the taxonomic information of the taxa in the dilutions; and removing at least one of the one or more errors in the taxonomic information of the taxa dilutions. The one or more errors in the taxonomic information of the taxa can be a result of a barcode sequencing error or a contamination of a reagent used in determining the taxonomic information of the taxa in the dilutions.

In some embodiments, the method comprises: cultivating a control sample in the first cultivation condition, wherein determining the taxonomic information of the taxa in the dilutions comprises: comparing the taxonomic information of the taxa in the dilutions to the control sample cultivated in the first cultivation condition. The control sample can be cultivated in the absence of the sample or the plurality of dilutions of the sample.

In some embodiments, each taxon of the taxa corresponds to an operational taxonomic unit (OTU), a species, a genus, or a family. In some embodiments, the sample is an environmental sample, a clinical sample, an agricultural sample, an industrial sample, or a combination thereof. In some embodiments, the abundance of the each taxon of the taxa in the dilutions is determined based on a threshold. The abundance of the each taxon of the taxa in the dilutions can comprise a relative abundance of the each taxon of the taxa in the dilutions.

In some embodiments, determining the interactions of the plurality of taxa of microorganisms comprises determining a pair of taxa that positively or negatively interact with each other. The pair of taxa can negatively interact with each other if one taxon of the pair of the taxa inhibits growth or maintenance of the other taxon of the pair of taxa. In some embodiments, determining the interactions of the plurality of taxa of microorganisms comprises: determining, based on a null model of community assembly and the taxonomic information of the taxa in the plurality of dilutions of the sample cultivated in the first cultivation condition, taxa that occur together significantly non-randomly in the plurality of dilutions of the sample cultivated in the first cultivation condition. Determining the taxa that occur together significantly non-randomly in the plurality of dilutions of the sample cultivated in the first cultivation condition can comprises: determining co-occurrence probabilities of taxa in the plurality of dilutions of the sample cultivated in the first cultivation condition.

In some embodiments, cultivating the plurality of dilutions of the sample in the first cultivation condition comprises cultivating the plurality of dilutions of the sample in the first cultivation condition for a plurality of time durations. The plurality of time durations can be, for example, about 1 minute, 30 minutes, 1 hour, 6 hours, 12 hours, 18 hours, 1 day, 2 days, 3 days, 4 days, 5 days, 6 days, 1 week, 2 weeks, 3 weeks, 4 weeks, 1 month, 2 months, 6 months, 9 months, 1 year, a range between any two of these values, or a combination thereof.

In some embodiments, the method comprises: cultivating the plurality of dilutions of the sample in a second cultivation condition; determining taxonomic information of the taxa in the plurality of dilutions of the sample cultivated in the second cultivation condition, wherein the taxonomic information comprises the abundance of each taxon of the taxa in the plurality of dilutions of the sample cultivated in the second cultivation condition; and determining, based on the taxonomic information of the taxa in the plurality of dilutions of the sample cultivated in the second cultivation condition, interactions of the plurality of taxa of microorganisms in the sample in the second cultivation condition.

In some embodiments, the interactions of the plurality of taxa of microorganisms in the sample in the first cultivation condition comprises biotic interactions of the plurality of taxa of microorganisms in the sample in the first cultivation condition. The first cultivation condition can comprise an aerobic cultivation condition, and wherein the second cultivation condition comprises an anaerobic cultivation condition. The anaerobic cultivation condition can comprise a nitrate-reducing cultivation condition. The nitrate-reducing cultivation condition can comprise presence of $NO_3$.

In some embodiments, the method comprises: determining differences between the interactions of the plurality of taxa of microorganisms in the sample in the first cultivation condition and the interactions of the plurality of taxa of microorganisms in the sample in the second cultivation condition. The method can comprise determining, based on the interactions of the plurality of taxa of microorganisms in the sample in the first cultivation condition and the interactions of the plurality of taxa of microorganisms in the sample in the second cultivation condition, a preferred cultivation condition. In some embodiments, the first cultivation condition comprises the presence of a microorganism. The first cultivation condition can be an environment of interest.

In some embodiments, the method comprises: determining, based on the interactions of the plurality of taxa of microorganisms in the sample in the first cultivation condition, the fitness of a taxon of the taxa in the first cultivation condition. In some embodiments, the method comprises: determining, based on the interactions of the plurality of taxa of microorganisms in the sample in the first cultivation condition, two or more taxa that contribute to a property of interest. The property of interest can comprise performing a specific metabolic function, a molecular of interest, a molecular of interest, a perturbation, or any combination thereof. The property of interest can relate to a health, medical, industrial, or agricultural related process.

Disclosed herein are systems, methods, devices, and kits for determining microbial interactions. In some embodiments, the method comprises: diluting a sample comprising a plurality of taxa of microorganisms to form a plurality of dilutions of the sample; cultivating a first subset the plurality of dilutions of the sample in a first cultivation condition; subjecting the first subset of the plurality of dilutions of the sample to sequencing to generate taxonomic information for taxa in the plurality of dilutions of the sample cultivated in the first cultivation condition, wherein the taxonomic information comprises an abundance of at least one taxon of the taxa in the plurality of dilutions of the sample cultivated in the first cultivation condition; and analyzing, based on the taxonomic information of the taxa in the first subset of the plurality of dilutions of the sample cultivated in the first cultivation condition, interactions of the plurality of taxa of microorganisms in the sample in the first cultivation condition.

In some embodiments, diluting the sample to form plurality of dilutions of the sample comprises diluting the sample serially to form a plurality of serial dilutions of the sample. The plurality of serial dilutions of the sample can comprise dilutions of the sample of about 1:10, 1:100, 1:1000, or 1:10000 dilution. The plurality of serial dilutions of the sample can comprise dilutions of 1-9 orders of magnitude of the sample. The plurality of serial dilutions of the sample can comprise about 2, 3, 4, 5, 6, 7, 8, 9, or 10 fold dilutions of the sample.

In some embodiments, the at least one taxon of the taxa in the first subset of the plurality of dilutions of the sample cultivated in the first cultivation condition corresponds to an operational taxonomic unit (OTU). The at least one taxon of the taxa in the first subset of can the plurality of dilutions of the sample cultivated in the first cultivation condition correspond to a species, a genus, or a family.

In some embodiments, subjecting the first subset of the plurality of dilutions of the sample to sequencing to generate taxonomic information for taxa in the plurality of dilutions of the sample cultivated in the first cultivation condition comprises: determining the taxonomic information for the first subset of the plurality of dilutions of the sample cultivated in the first cultivation condition based on sequencing of one or more of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof. Subjecting the first subset of the plurality of dilutions of the sample to sequencing to generate taxonomic information for taxa in the plurality of dilutions of the sample cultivated in the first cultivation condition can comprise: performing error correction to remove one or more errors in the taxonomic information for the first subset of the taxa in the plurality of dilutions of the sample cultivated in the first cultivation condition. The one or more errors in the taxonomic information of the taxa is a result of a barcode sequencing error or contamination of a reagent used in determining the taxonomic information of the taxa in the dilutions of the sample cultivated in the first cultivation condition.

In some embodiments, the method comprises: cultivating a control sample in the first cultivation condition, wherein subjecting the first subset of the plurality of dilutions of the sample to sequencing comprises: comparing the taxonomic information for the first subset of the taxa in the plurality of dilutions of the sample cultivated in the first cultivation condition to the control sample cultivated in the first cultivation condition. The control sample can be cultivated in the absence of the sample cultivated in the first cultivation condition or the plurality of dilutions of the sample cultivated in the first cultivation condition. The abundance of the at least one taxon of the taxa in the plurality of dilutions can be determined based on a threshold. The abundance of the at least one taxon of the taxa in the plurality of dilutions can comprise a relative abundance of the at least one taxon of the taxa in the plurality of dilutions.

In some embodiments, analyzing the interactions of the plurality of taxa of microorganisms comprises determining a pair of taxa that positively or negatively interact with each other. The pair of taxa negatively can interact with each other if one taxon of the pair of the taxa inhibits growth or maintenance of the other taxon of the pair of taxa. Analyzing the interactions of the plurality of taxa of microorganisms can comprise: based on a null model of community assembly and the taxonomic information of the taxa in the first subset of the plurality of dilutions of the sample cultivated in the first cultivation condition, using a computer processor to analyze taxa that occur together non-randomly in the plurality of dilutions of the sample cultivated in the first cultivation condition. Analyzing the taxa that occur together non-randomly in the plurality of dilutions of the sample cultivated in the first cultivation condition can comprise: determining co-occurrence probabilities of taxa in the plurality of dilutions of the sample cultivated in the first cultivation condition.

In some embodiments, the interactions of the plurality of taxa of microorganisms in the sample in the first cultivation condition comprises biotic interactions of the plurality of taxa of microorganisms in the sample in the first cultivation condition. In some embodiments, cultivating the first subset of the plurality of dilutions of the sample in the first cultivation condition comprises cultivating the first subset of the plurality of dilutions of the sample in the first cultivation condition, in parallel, for a plurality of time durations. The plurality of time durations can comprise about 1 minute, 1 hour, 1 day, 1 week, 1 month, 1 year, or a combination thereof.

In some embodiments, the method comprises: cultivating a second subset of the plurality of dilutions of the sample in a second cultivation condition; subjecting the second subset of the plurality of dilutions of the sample to sequencing to generate taxonomic information of the taxa in the second subset of the plurality of dilutions of the sample cultivated in the second cultivation condition; and analyzing, based on the taxonomic information of the taxa in the second subset of the plurality of dilutions of the sample cultivated in the second cultivation condition, interactions of the plurality of taxa of microorganisms in the sample in the second cultivation condition. The first subset and second subset can be separately cultivated in the first cultivation condition and the second cultivation condition, respectively. The first subset and the second subset can be different. The first subset of the plurality of dilutions of the sample in the first cultivation condition can comprise less than the plurality of dilutions of the sample. The first cultivation condition can comprise an aerobic cultivation condition, and the second cultivation condition can comprise an anaerobic cultivation condition. The anaerobic cultivation condition can comprise a nitrate-reducing cultivation condition. The nitrate-reducing cultivation condition can comprise presence of $NO_3$. The method can comprise: generating differences between the interactions of the plurality of taxa of microorganisms in the sample in the first cultivation condition and the interactions of the plurality of taxa of microorganisms in the sample in the second cultivation condition. The method can comprise: determining, based on the interactions of the plurality of taxa of microorganisms in the sample in the first cultivation condition and the interactions of the plurality of taxa of microorganisms in the sample in the second cultivation condition, a preferred cultivation condition.

In some embodiments, the first cultivation condition comprises the presence of a microorganism. The first cultivation condition can be an environment of interest. The method can comprise: determining, based on the interactions of the multiple different taxa of microorganisms in the sample in the first cultivation condition, the fitness of a taxon of the taxa in the first cultivation condition. The method can comprise: determining, based on the interactions of the multiple different taxa of microorganisms in the sample in the first cultivation condition, two or more taxa that contribute to a property of interest. The property of interest can be, or comprise, performing a specific metabolic function, producing a molecule of interest, modifying a molecule of interest, stability in response to a perturbation, or any combination thereof. The method can comprise designing a microbial community with the property of interest.

In some embodiments, the property of interest comprises imparting a beneficial phenotypic trait to an organism, such as an animal or a plant. Cultivating the first subset of the plurality of dilutions of the sample can comprise cultivating the first subset of the plurality of dilutions of the sample in the presence of the organism. The organism can be from an environment sample, a clinical sample, an agricultural sample, an industrial sample, or any combination thereof. The environmental sample can comprise air, soil, water, or any combination thereof. The clinical sample can comprise an oral sample, a skin sample, a gut sample, or any combination thereof. The agricultural sample can comprise a sample of any crop, such as corn, wheat, rice, or any combination thereof. The agricultural sample can comprise a sample obtained from an animal, such as a cow, a pig, a chicken, fish, a population thereof, or any combination thereof. The industrial sample can comprise a tissue culture sample, a bacterial sample, a fungal sample, or any combination thereof. The building environment sample can comprise a sample obtained from a house, a hospital, or a car. The pet sample can be a sample obtained from a pet, such as a cat, a dog, fish, or any combination thereof. In some embodiments, the method comprises determining In some embodiments, the interactions are indicative of how at least the first cultivation condition alters one or more of cultivability, competitive fitness, or interspecific interactions of the plurality of taxa of microorganisms in at least the first cultivation condition. The interactions can be indicative of how at least the second cultivation condition alters one or more of cultivability, competitive fitness, or interspecific interactions of the plurality of taxa of microorganisms in at least the second cultivation condition. The interactions can be analyzed using (i) presence or absence data for each of the at least one taxon of the taxa and (ii) taxa that occur together non-randomly in the plurality of dilutions of the sample cultivated in the first cultivation condition or the second cultivation condition.

In some embodiments, the taxonomic information for taxa in the first subset of the plurality of dilutions or taxa in the second subset of the plurality of dilutions comprises cultivable abundance information. The interactions can be analyzed using taxonomic information comprising sequences of one or more of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof. For one or more taxa in the sample, the interactions of the plurality of taxa of microorganisms in the sample in the first cultivation condition can be different from the interactions of the plurality of taxa of microorganisms in the sample in the second cultivation condition, and are thereby indicative of one or more condition-specific interactions.

Disclosed herein are systems and methods for conducting a multi-variate assay of a plurality of taxa of microorganisms in a sample to generate an output indicative of the fitness of one or more taxa in the sample. In some embodiments, the method comprises: obtaining the sample comprising a plurality of taxa of microorganisms; generating a plurality of subcultures from the sample; adjusting variables for one or more subcultures in the plurality of subcultures, the variables comprising: one or more biotic conditions, and one or more abiotic conditions, assaying the plurality of taxa in the plurality of subcultures; and generating an output indicative of the fitness of the one or more taxa in the microbial population with respect to at least one of the one or more variables.

In some embodiments, the subcultures comprise a plurality of dilutions of the sample. Each of the subcultures in the plurality can be subject to a unique combination of (i) and (ii). The one or more taxa can comprise one or more positively associated microbes. The method can comprise selecting the one of more taxa based on competitive fitness when subject to one or more abiotic conditions. The one or more biotic conditions can differ based on an abundance of one or more taxa. Assaying in (d) can comprise sequencing.

Disclosed herein are computer systems and methods for identifying a plurality of co-occurring outputs in a plurality of strings. In some embodiments, the method comprises: a computer processor programmed to: receive a file comprising a plurality of strings, each string (1) indexed by a first parameter and a second parameter and (2) corresponding to an output; quantify an abundance of each of the plurality of strings indexed by the first parameter and the second parameter to generate a plurality of string counts, each string count of the plurality corresponding to the output to generate a plurality of string counts; and process the plurality of string counts to generate the plurality of co-occurring outputs in the plurality of strings, wherein the plurality of co-occurring outputs is significantly non-random when processed with respect to the first parameter and the second parameter; save the plurality of co-occurring outputs to a memory; a memory coupled to the computer processor; and a display coupled to the computer processor.

In some embodiments, the plurality of strings comprises sequence information. The sequence information can correspond to a plurality of taxa of microorganisms in a sample. The sequence information can comprise sequences of one or more of 16 S rRNA, 12S rRNA, 18 S rRNA, 28S rRNA, 13S rRNA and 23S rRNA, internal transcribed spacer (ITS), ITS1, ITS2, cytochrome oxidase I (COI), cytochrome b, or any combination thereof. The first parameter can comprise a degree of dilution for a sample comprising a plurality of taxa of microorganisms. The second parameter can correspond to one or more cultivation conditions. The preselected output can comprise a taxon.

BRIEF DESCRIPTION OF THE DRAWINGS

FIG. 6 panel (B) is a bar chart showing that for each experiment and dilution, the mean number of OTUs assigned. Error bars represent standard deviations. Statistical significance between means was tested using Student's t test for the first three dilutions ($10^{-1}$ to $10^{-3}$). Significance (P<0.05) is marked with an asterisk. ND, no data acquired for that set of samples.

DETAILED DESCRIPTION

Figure 1:
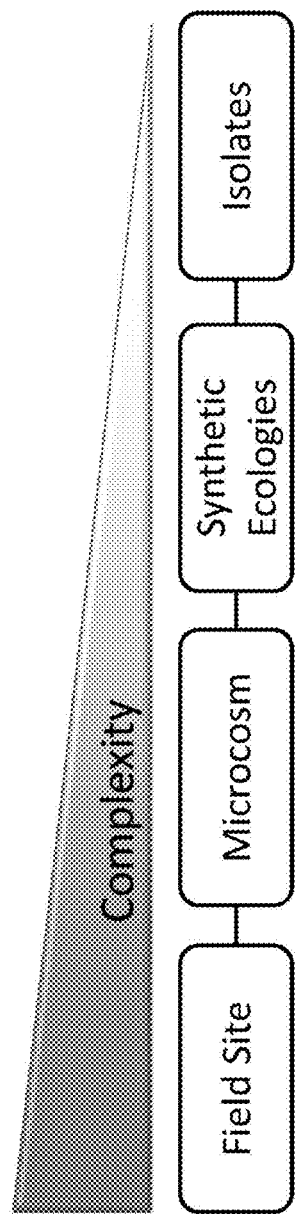
FIG. 1 shows that complexities of community compositions decrease from a sample obtained at a field site, to a microcosm, to synthetic ecologies, and to isolates.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

Disclosed herein is a method for determining microbial interactions. In some embodiments, the method comprises: diluting a sample to form a plurality of dilutions of the sample, wherein the sample comprises a plurality of taxa of microorganisms; cultivating the plurality of dilutions of the sample in a first cultivation condition; determining taxonomic information of taxa in the plurality of dilutions of the sample cultivated in the first cultivation condition, wherein the taxonomic information comprises the abundance of each taxon of the taxa in the plurality of dilutions of the sample cultivated in the first cultivation condition; and determining, based on the taxonomic information of the taxa in the plurality of dilutions of the sample cultivated in the first cultivation condition, interactions of the plurality of taxa of microorganisms in the sample in the first cultivation condition.

Bacterial population structures can be central to explaining microbial ecosystem function and properties. One goal of microbial ecology is to identify and quantify the forces that lead to observed population distributions and dynamics. However, the ecological forces that shape community structures—including species interactions—may be myriad and complex, leaving gaps in understanding and predicting microbial community structure and functioning. These forces, which include environmental selection, dispersal, and organism interactions, may be often difficult to assess in natural environments. The methods disclosed herein can be used to examine microbial community assembly, uncover species interactions, and examine the influence of abiotic factors in microbial community structure. In some embodiments, the method can comprise varying the number of organisms (e.g., systematically) found in each of a number of enrichment cultures (e.g., ~1,000) started from a single groundwater inoculum. In some embodiments, the method can comprise inoculating the groundwater (containing ~37,000 cells per ml) into different culture conditions (e.g., both aerobic and anaerobic nitrate-reducing cultures) that span a number of dilutions (e.g., 5 dilutions spanning from $10^{-1}$-$10^{-5}$). Following incubation, the method can comprise evaluating community structures. For example, evaluating community structures can include gene sequencing, such as gene amplicon sequencing, of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof.

In some instances, species richness may decrease with increasing inoculum dilution as low abundance organisms are removed. Different culture conditions (e.g., aerobic and anaerobic communities) can result in different community compositions and taxonomic memberships, for example, at high inoculum concentrations. In some embodiments, the method can comprise estimating abundance (as cultivable units/ml of each taxon) of each taxon in the initial sample in different culture conditions (e.g., aerobic and anaerobic conditions) using a most probable number method. For example, only ~5-7% of cells from the initial inoculum may be cultured. In some embodiments, the method can comprise using the initial estimated abundances of each OTU to develop a null model of community assembly. The method can compare the null model of community assembly with the measured data to bin organisms as putative strong or weak competitors. Although strong competitors may be rare (e.g., <5% of cultivated taxa), they may drastically shape community structures when present. In some embodiments, the method can comprise calculating co-occurrence probabilities for abundant taxa to infer putative positive or negative interspecific interactions amongst organisms. For example, nearly twice as many interactions may detected in anaerobic samples as aerobic samples, with many of the negative interactions pointing to antagonistic relationships between species of the Bacillaceae with species of Oxalobacteraceae, Paneibacillaceae, and Pseudomonadaceae.

Thus, the method disclosed herein can show how abiotic and biotic factors interact to structure microbial communities.

The methods disclosed herein can link microbial community structures with selective and stochastic forces through highly replicated subsampling and enrichment of a single environmental inoculum. In some embodiments, groundwater from a well-studied natural aquifer can be serially diluted and inoculated into nearly 1,000 aerobic and anaerobic nitrate-reducing cultures, and the final community structures can be evaluated with gene sequencing, such as gene amplicon sequencing, of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b. The frequency and abundance of individual operational taxonomic units (OTUs) can be analyzed to understand how probabilistic immigration, relative fitness differences, environmental factors, and organismal interactions contributed to divergent distributions of community structures. A most probable number (MPN) method can be used to estimate the natural condition-dependent cultivable abundance of each of the OTU (e.g., ~400) cultivated in our study and infer the relative fitness of each. Additionally, condition-specific organism interactions can be inferred. The high-replicate culturing approach of the present disclosure can be used in dissecting the interplay between overlapping ecological forces and taxon-specific attributes that underpin microbial community assembly.

In some embodiments, through highly replicated culturing, in which inocula are subsampled from a single environmental sample, how selective forces, interspecific interactions, relative fitness, and probabilistic dispersal shape bacterial communities can be empirically determined. The methods disclosed herein offer a novel approach to untangle not only interspecific interactions but also taxon-specific fitness differences that manifest across different cultivation conditions and lead to the selection and enrichment of specific organisms. Additionally, the methods can be used for estimating the number of cultivable units of each OTU in the original sample through the MPN approach FIG. 1 shows that complexities of community compositions decrease from a sample obtained at a field site, to a microcosm, to synthetic ecologies, and to isolates. Microbial communities are central players in Earth's biogeochemical cycles, human health, biotechnological processes such as wastewater treatment and the production of foods. Underpinning all of these communities' structure, function, and evolution are the ecological forces of dispersal, drift, selection, and speciation. Even on short timescales—in which one can ignore evolutionary mechanisms of diversification—drift, selection, and dispersal interact to turnover populations of organisms in both predictable and unpredictable ways. Unpredictable changes in community structure are rooted in random dispersal and drift while predictable changes are caused by deterministic fitness differences and environmental selection. Capturing the influence of these processes is central to predicting and controlling microbial community structure and function.

Although selective processes can lead to more predictable community compositions, the processes themselves are complex and numerous, and can stem from biotic sources, abiotic sources, or feedback loops between biotic and abiotic factors. There are numerous examples of biotic relationships (e.g., competitive interactions) amongst microorganisms. Thus, there is a need for exploring how biotic relationships change as function of the environment in which they are found. Moreover, assessment of the impact of selective forces in microbial community structure is hampered by the complexity of natural systems, including the extraordinary diversity of organisms, the numerous uncontrolled (or unmeasured) environmental and historical factors, and large and variegated scales of distance and time. The reduction of these complexities through the use of well-defined experimental platforms (e.g., microcosms) offers a tremendous advantage. In comparison to studies done in situ, laboratory microcosms allow direct evaluations of community responses to known and controlled variables, while minimizing the influence of unmeasured factors like resource heterogeneity and historical differences across sites. Furthermore, microcosms allow the preservation of compositional and functional diversity of the seed community, and as such, assembly rules garnered from controlled laboratory experiments can be used to better understand and inform the factors that structure microbial communities in the field.

In microcosm experiments inoculated with complex and undefined multispecies consortia, there are a number of experiments offering conflicting views regarding the importance of selective forces, and the attendant increase in reproducibility, in the assembly of microbial communities. In some systems, highly reproducible communities formed even from different inocula incubated under similar conditions, which is evidence of niche-based processes and strong selective forces. On the other hand, some systems exhibit divergent community structures, accounted for by distribution of rare taxa in the inoculum, different source communities, and stochastic colonization processes. Although results from each of these experiments depend on their own unique source inocula and selective conditions, they highlight the need for a more unified understanding of how both predictable processes (e.g., selection) and unpredictable processes (e.g., random colonization and stochastic drift) interact to shape microbial community assembly.

Figure 2:
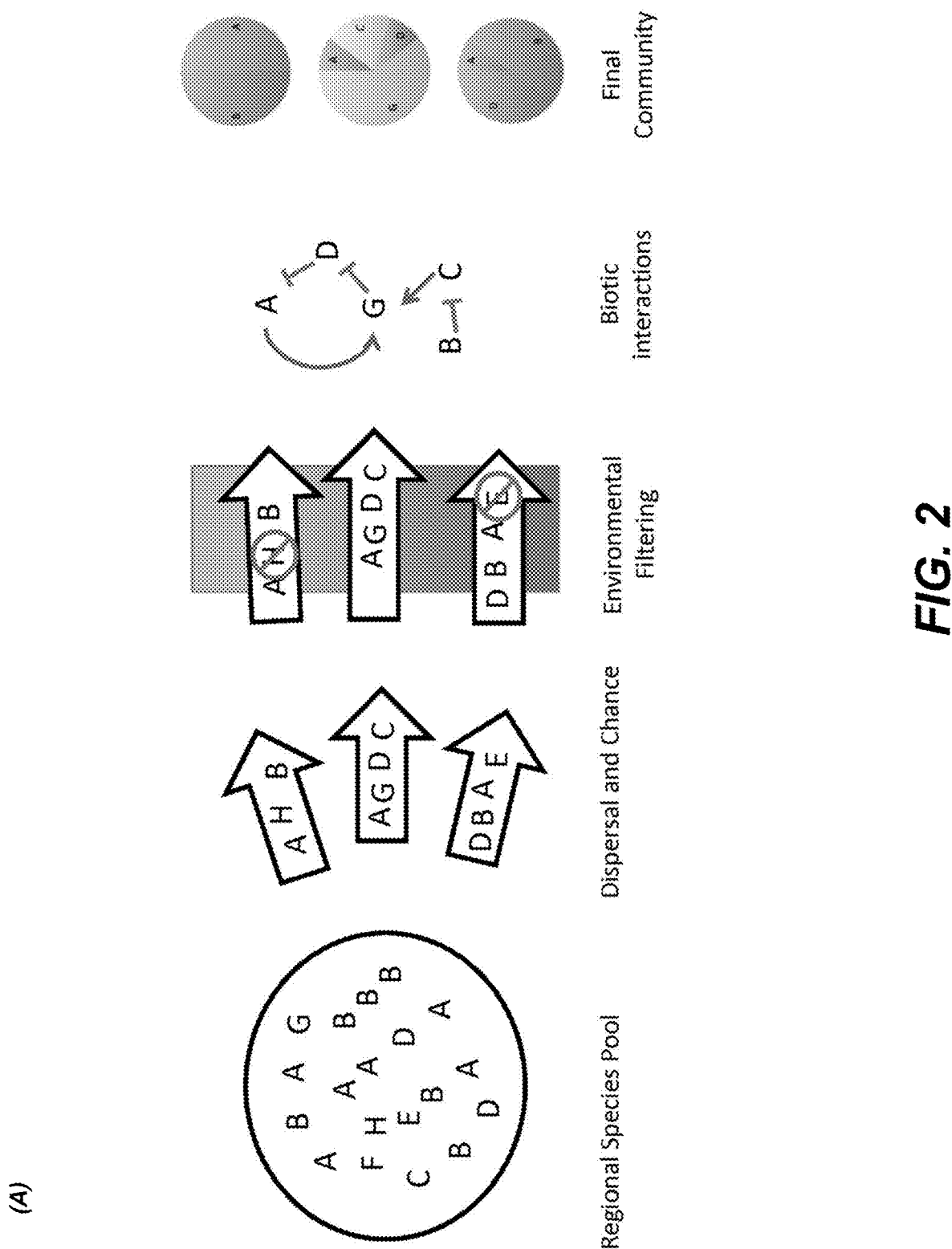
FIG. 2, panels (A)-(C) show a non-limiting exemplary schematic illustration of community assembly.
Figure 2:
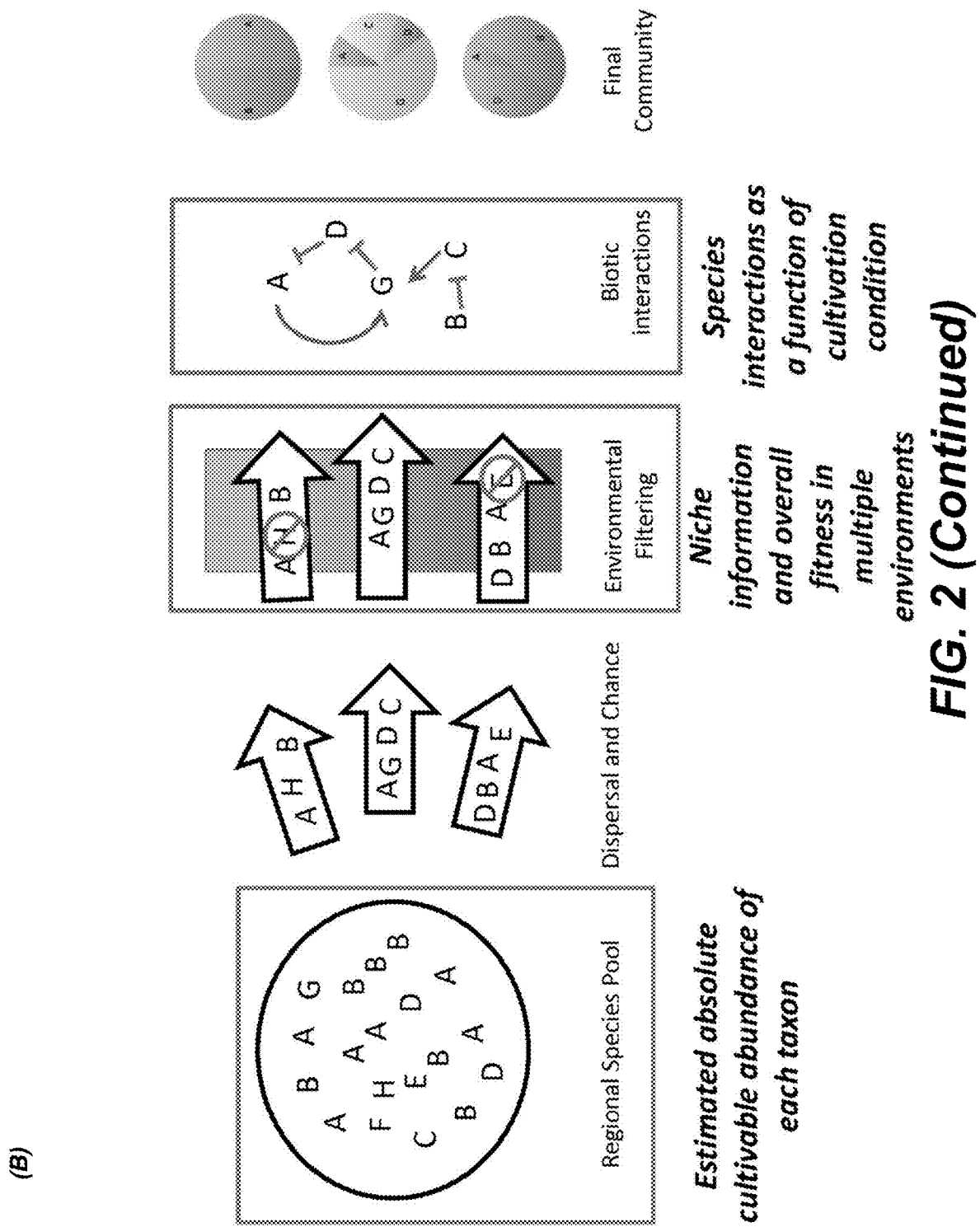
Figure 2:
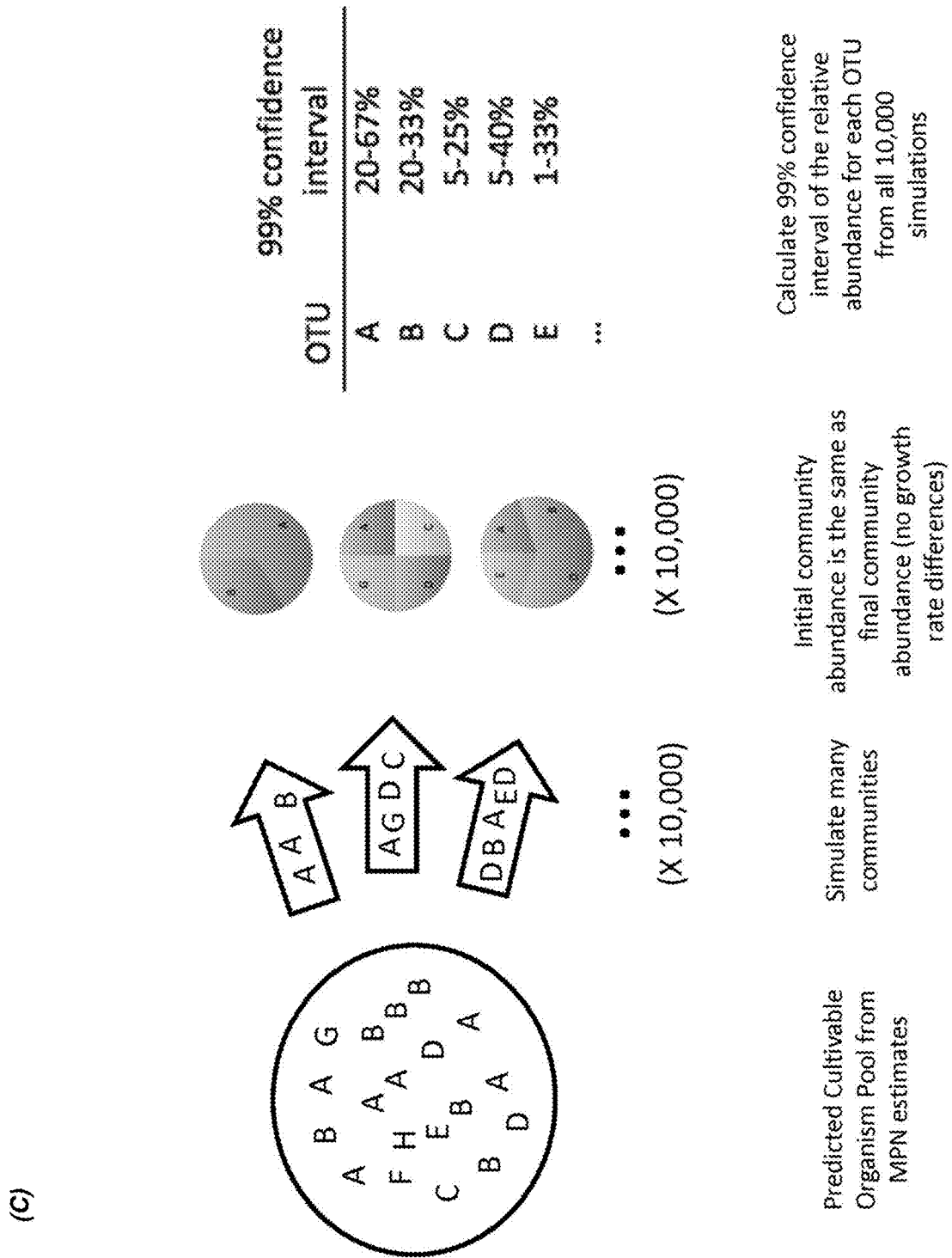

FIG. 2, panels (A)-(C) show a non-limiting exemplary schematic illustration of community assembly. A sample (e.g., a regional species pool) of OTUs or microorganisms of different species can include microorganisms of different abundances. The sample can be diluted into a plurality of dilutions of the sample. Through dispersal and chance, a subpopulation of OTUs of the sample is present in each dilution. The dilutions of the sample can be cultivated or enriched under different abiotic selective factors (e.g., aerobic or anaerobic cultivation conditions).

Abiotic selective factors (also referred to as environmental filtering) and biotic interactions among microorganisms affect the final community of OTUs present in a cultivated dilution of the sample. Biotic interactions can include species interactions which may be affected by cultivation conditions. The final community of microorganisms in a microwell can provide niche information and overall fitness of microorganisms in the cultivation condition. Accordingly, a large number of possible interactions amongst OTUs can be determined.

To determine the relative abundance of each OTU in the sample, cultivable organism pool can be predicted from MPN estimates. Using the initial estimated abundances, a number of communities (e.g., 10000) can be simulated using a null model of community assembly. The taxonomic information of the communities simulated can be compared with the taxonomic information of the plurality of dilutions of the sample cultivated. The number of communities simulated can be different in different implementations. In some embodiments, the number of communities simulated can be, or about, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, 100000000, or a number or a range between any two of these values. In some embodiments, the number of communities simulated can be at least, or at most, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, or 100000000. Final relative abundances can be simulated from initial estimated abundances simulated by assuming no net positive or negative interactions, all growth rates are identical, and detection is unbiased. The number of communities simulated can be related to the number of combinations of cultivation conditions, dilutions, and replicates of each dilution cultivated. In some embodiments, the number of communities simulated can be, or about, 0.0000000001, 0.000000001, 0.00000001, 0.0000001, 0.000001, 0.00001, 0.0001, 0.001, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 1000, 10000, 100000, 1000000, 10000000, 100000000, 1000000000 times, or a number or a range between any two of these values, the number of combinations of cultivation conditions, dilutions, and replicates of each dilution cultivated. In some embodiments, the number of communities simulated can be at least, or at most, 0.0000000001, 0.000000001, 0.00000001, 0.0000001, 0.000001, 0.00001, 0.0001, 0.001, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 1000, 10000, 100000, 1000000, 10000000, 100000000, or 1000000000 times the number of combinations of cultivation conditions, dilutions, and replicates of each dilution cultivated.

The confidence level of the relative abundances can be different in different implementations. In some implementations, the confidence level of the relative abundances can be, or about, 80%, 85%, 90%, 91%, 92%, 93%, 94%, 95%, 96%, 97%, 98%, 99%, 99.9%, or a number or a range between any two of these values. In some implementations, the confidence level of the relative abundances can be at least, or at most, 80%, 85%, 90%, 91%, 92%, 93%, 94%, 95%, 96%, 97%, 98%, 99%, or 99.9%.

Figure 3:
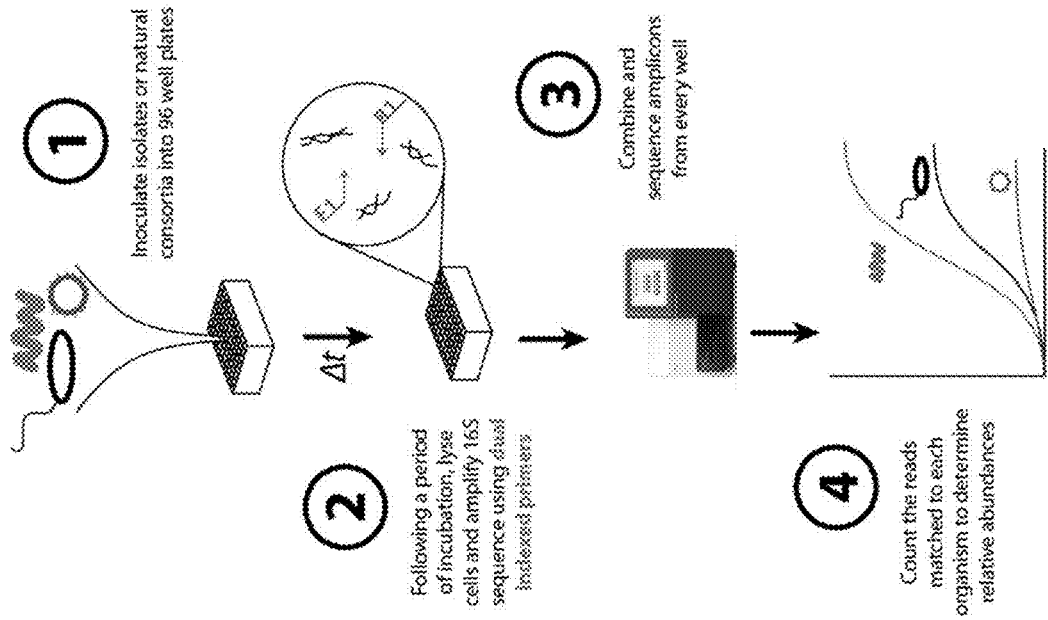
FIG. 3 shows a schematic illustration of a non-limiting exemplary method of determining relative abundances of organisms in a sample.

FIG. 3 shows a schematic illustration of a non-limiting exemplary method of determining relative abundances of organisms in a sample. The method can be used to determine one or more of the following: (i) How much do community structures vary as a function of probabilistic recruitment from a single regional species pool? (ii) How do abiotic selective factors such as homogenizing environment (e.g., shaking) and terminal electron accepting conditions influence and structure these communities? (iii) How do various taxonomic groups respond to these differentiated selective processes? (iv) How do species interactions change as a function of environmental factors?

The method can include inoculating a sample of microorganisms (e.g., isolates, natural consortia, or dilutions of isolates or natural consortia) into microwells of one or more microwell plates. The number of microwells per microwell plate can be different in different implementations. In some embodiments, a microwell plate can include, or about, 96, 384, 1536, 2000, 3000, 4000, 5000, 6000, 7000, 8000, 9000, 10000, 20000, 30000, 40000, 50000, 60000, 70000, 80000, 90000, 100000, or a number or a range between any two of these values, microwells. In some embodiments, a microwell plate can include at least, or at most, 96, 384, 1536, 2000, 3000, 4000, 5000, 6000, 7000, 8000, 9000, 10000, 20000, 30000, 40000, 50000, 60000, 70000, 80000, 90000, or 100000 microwells. The method can comprise systematically manipulating bacterial diversity by subsampling a single "regional" species pool at several dilutions in order to create many "local" communities that varied in their membership.

Following a period of incubation (also referred to as cultivation or enrichment), the method can comprise determining taxonomic information of microorganisms in the one or more microwell plates. Taxonomic information can be determined using amplicon sequencing (e.g., amplicon sequencing of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof) after lysing the microorganisms or cells and combining amplicons from every microwell or a majority of the microwells. Thus, in exemplary embodiments, the method can leverage the large multiplexing capabilities of Illumina 16S rRNA amplicon sequencing with a highly replicated enrichment experiment in order to examine how selective forces shape community assembly in the presence of random dispersal. The method can comprise counting the reads matched to each organism to determine relative abundances of microorganisms in each microwell (or the majority of the microwells).

From the relative abundances of the microorganism, interactions amongst the microorganisms in the sample can be determined. Thus, the method can be used to determine how cultivation conditions or environmental factors (such as an unstructured aerobic environment and a structured nitrate-reducing environment) shape community assembly by altering the cultivability, competitive fitness, and interspecific interactions of community members.

Figure 4:
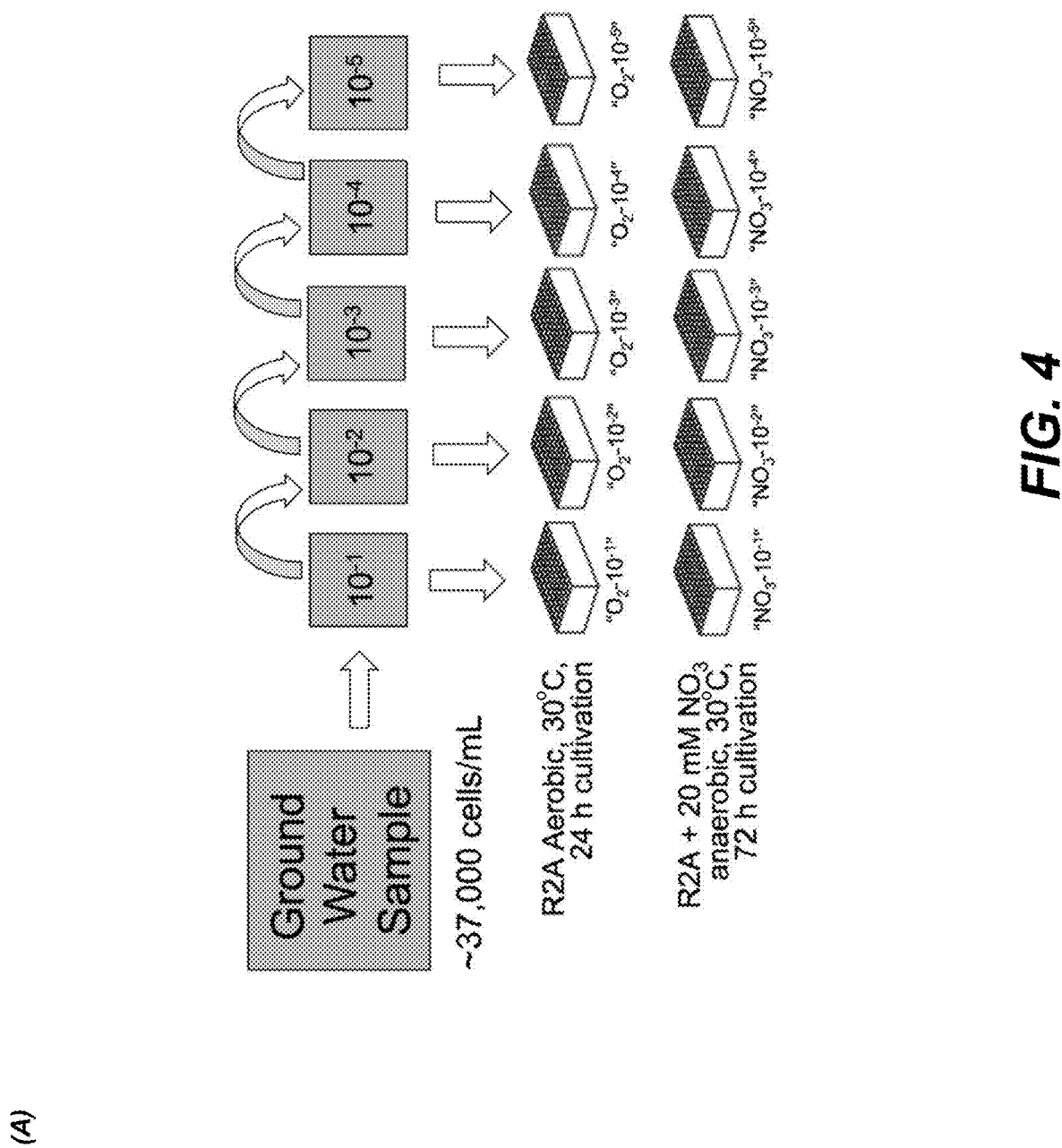
FIG. 4, panels (A)-(E) show a schematic illustration of a non-limiting exemplary method of identifying interactions amongst microorganisms.
Figure 4:
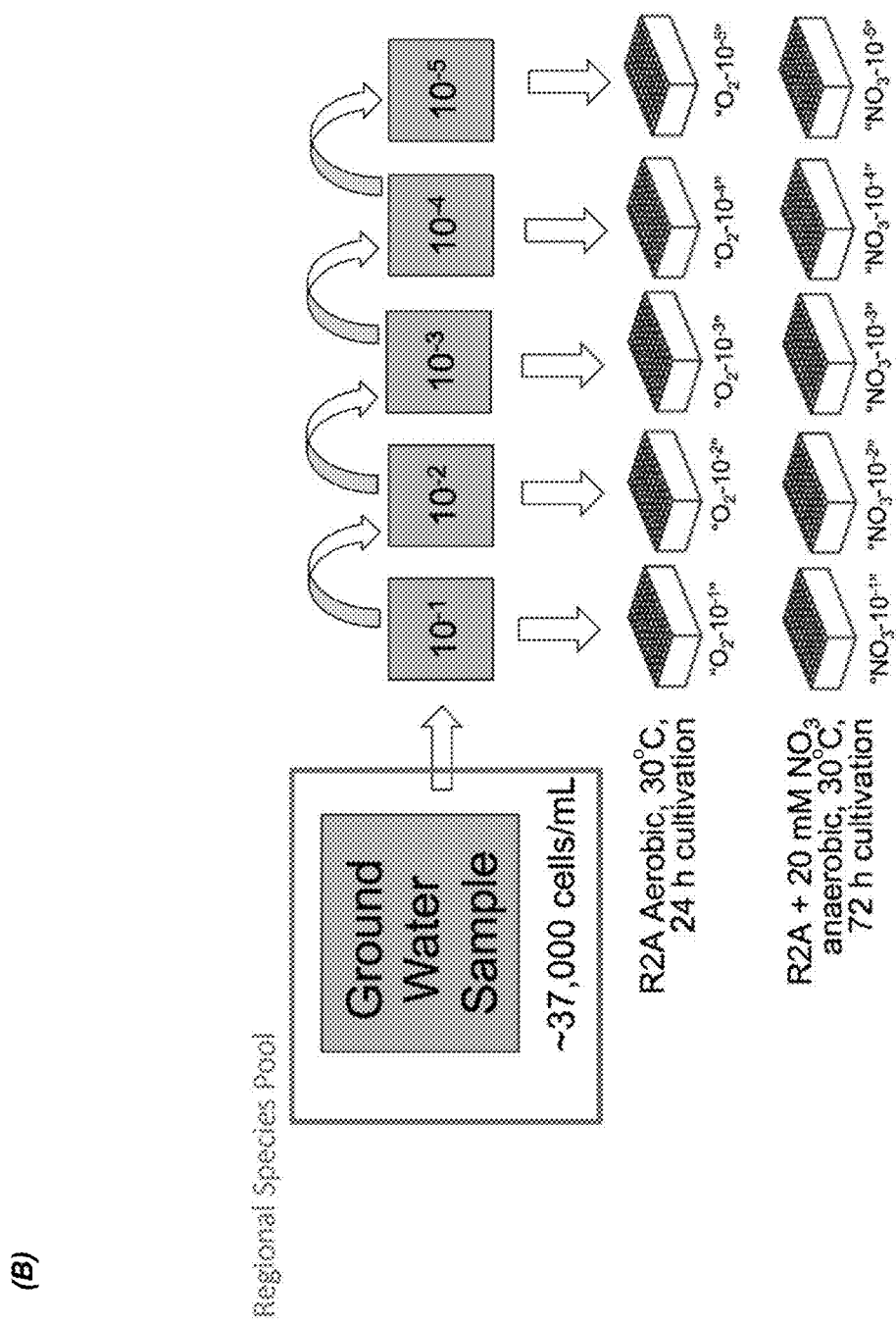
Figure 4:
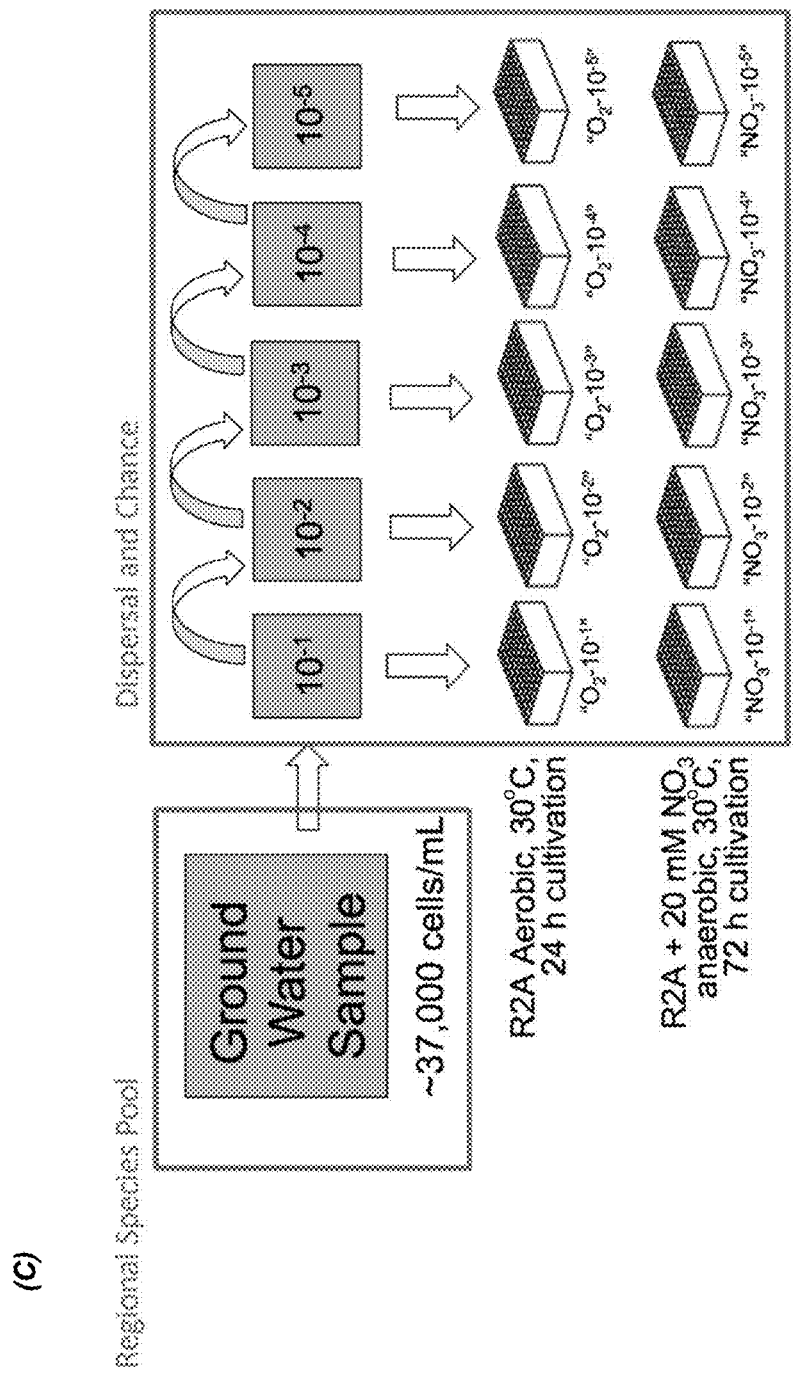
Figure 4:
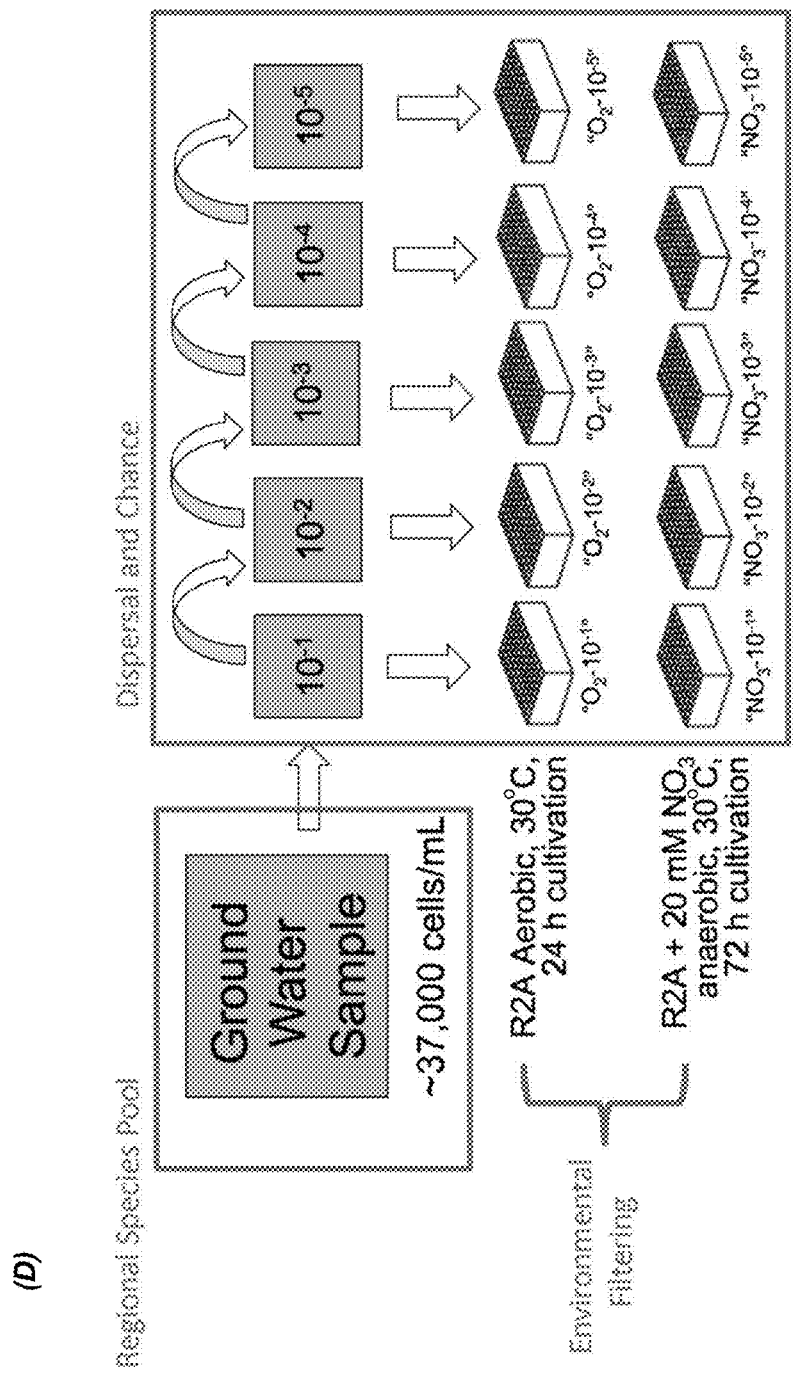
Figure 4:
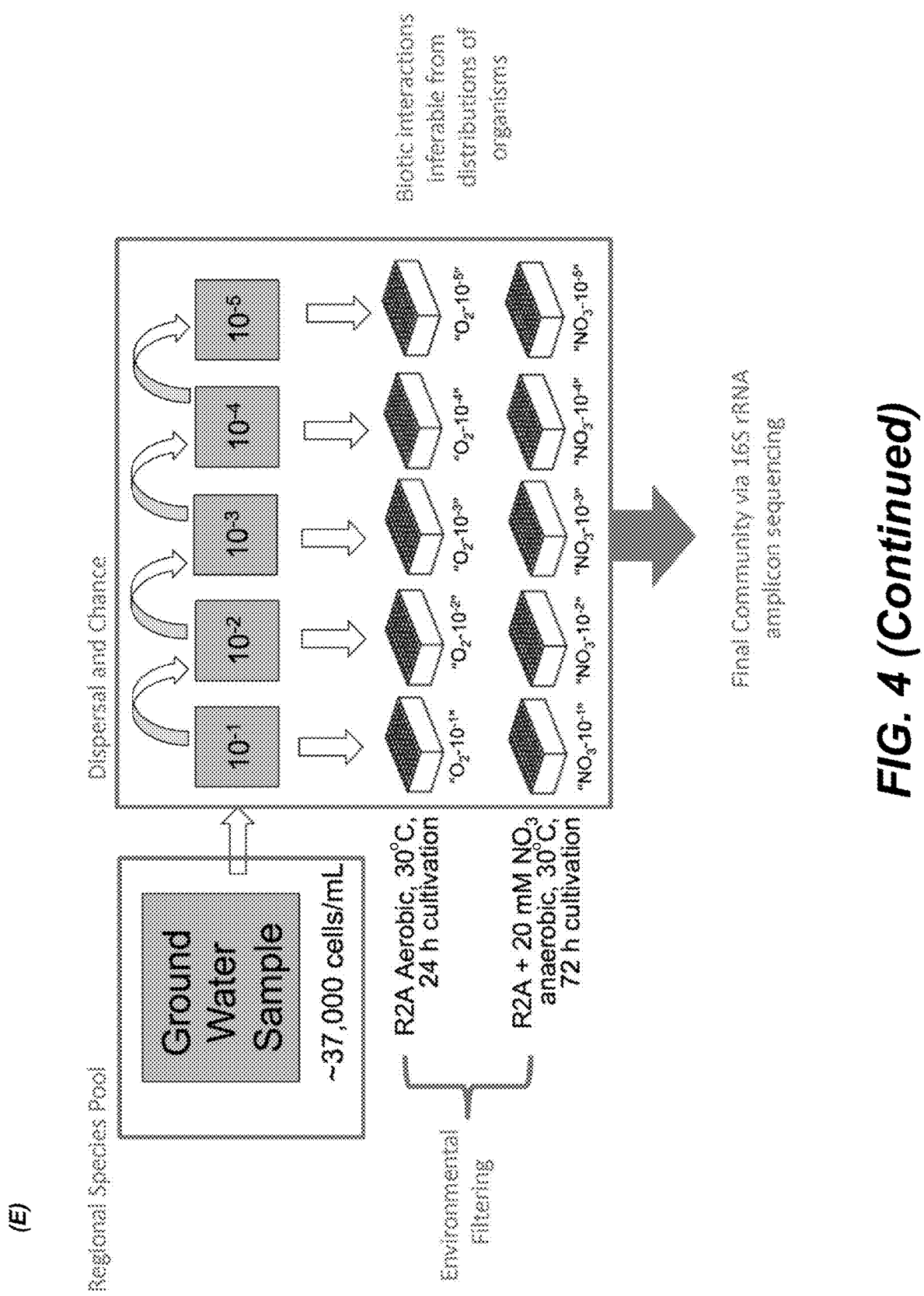

FIG. 4, panels (A)-(E) show a schematic illustration of a non-limiting exemplary method of identifying interactions amongst microorganisms. The ecological forces that shape microbial community structures are myriad and complex, limiting predictions of microbial turnover and ecosystem functioning. To examine how environmental selection, probabilistic immigration, and species interactions influence microbial community assembly the number of organisms can be systematically varied, from a single inoculum, founding each of ~1,000 enrichment cultures. Groundwater (e.g., containing ~37,000 cells ml$^{-1}$) can be serially diluted and inoculated into both aerobic and anaerobic nitrate-reducing cultures and final community structures were evaluated with 16S rRNA gene amplicon sequencing. Aerobic and anaerobic environments selected for different communities and species richness can decrease with increasing inoculum dilution as low abundance organisms were removed. The absolute cultivable abundance of every OTU in the inoculum can be estimated by leveraging a most probable number (MPN) technique with the 16S rRNA amplicon sequencing data. The estimates of cultivable OTU abundances in the inoculum can be used to construct a null model of community assembly that, when compared to measured taxa abundances, can show that rare taxa can often the most competitive. Furthermore, positive and negative interspecific interactions can be inferred amongst organisms using co-occurrence probabilities. Together, the methods disclosed herein can elucidate how organism fitness, species interactions, and abiotic selective factors contribute to microbial community assembly.

The cultivable abundance can be a function of both the number of cells of that organism in the inoculum as well as their ability to replicate under the prescribed cultivation condition. For example, an overall number of cultivable cells can be estimated using absorbance data (e.g., $OD_{600}$ data). Sequencing data of the cultivations can be used to obtain the OTU-specific (e.g., a taxon-specific) cultivable units per ml. For example, the sequencing data (such as 16S rRNA sequencing data, or sequencing data of another gene amplicon sequencing method) can be used to distinguish different OTUs (e.g., different taxa) and to determine actual cultivable abundances (e.g., number of cultivable units per ml) in the inoculum.

In some embodiments, the most probable number (MPN) technique can be used to calculate the cultivable abundance of one or more (e.g., every) taxon in an inoculum. This technique can provide the most probable number of cultivable units of an organism in an inoculum sample given a distribution of positive and negative outgrowths at several dilutions. Rarity values for each OTU's MPN-estimated cultivable abundance can be calculated by, for example, dividing the likelihood of the observed outcome by the largest likelihood of any outcome at that same estimated inoculum concentration.

To determine which OTUs may be the stronger competitors (e.g., strongest competitors) and which may be the weaker competitors (e.g., weakest competitors), the average relative abundance of each OTU, across replicates, can be compared with its average expected abundance. Expected abundances can be derived by simulating the assembly of many communities using the cultivable units per ml for each OTU estimated from MPN analyses. The communities can be assembled in a null model in which no organism interactions or fitness differences are allowed. This model can serve as a metric against which to measure and compare the strength of nonrandom forces (e.g., relative fitness in light of environmental selection). For each dilution and experimental condition, a number of communities can be simulated. The number of communities simulated can be different in different implementations. For example, the number of communities simulated can be, or about, 100, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. As another example, the number of communities simulated can be at least, or at most, 100, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In each simulation, the number of seeded cells for a given OTU can be randomly sampled from a statistical distribution (e.g., a Poisson distribution) with a mean value equal to the expected number of cells for that OTU under the condition/dilution. In some embodiments, To account for potential error in the MPN-estimated cell abundances, both the mean number of cells for each OTU and the total number of cells (sum of all OTU's abundance) can be allowed to vary by, for example, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4, 5 or more fold. A confidence interval can be calculated for the percent relative abundance of each OTU in all simulated communities for the condition/dilution. In some embodiments, the confidence interval can be, or about, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, or a number or a range between any two of these values. In some embodiments, the confidence interval can be, or about, 80%, 81%, 82%, 83%, 84%, 85%, 86%, 87%, 88%, 89%, 90%, 91%, 92%, 93%, 94%, 95%, 96%, 97%, 98%, 99%, 99.9%, or 99.99%.

OTUs can be classified as strong or weak competitors under each condition by comparing measured organism abundance with predicted organism abundance in a null model of community assembly in which all organisms have identical growth properties (no net positive or negative growth differences, and no interaction between OTUs). Using the estimated initial cultivable abundances of each OTU, the seeding and cultivation of a number of replicate communities from the lowest dilution inoculum in different environments can be simulated. In some implementations, the lowest dilution cultures can be the focus since these cultures represent the greatest inclusion of taxa and thus overall highest expected frequency of competition. These estimated average abundances can be compared to the measured average abundance of each OTU and identified OTUs whose measured relative abundances are higher or lower than the predicted abundances at the confidence level. For example, the frequency at which each OTU is identified can be used to create expectations of how abundant taxa are during inoculation. These expected values can be compared to observed postcultivation average abundances.

Disclosed herein is a method for determining microbial interactions. In some embodiments, the method comprises: diluting a sample (e.g., a ground water sample or a regional species pool) to form a plurality of dilutions of the sample (e.g., via dispersal or chance), wherein the sample comprises a plurality of taxa of microorganisms; cultivating (or enriching) the plurality of dilutions of the sample in a first cultivation condition (also referred to as environmental filtering); determining taxonomic information of taxa in the plurality of dilutions of the sample cultivated in the first cultivation condition (e.g., using gene amplicon sequencing, such as gene amplicon sequencing of 16S rRNA, 12S rRNA, 18S rRNA, 28S rRNA, 13S rRNA and 23S rRNA, internal transcribed spacer (ITS), ITS1, ITS2, cytochrome oxidase I (COI), or cytochrome b), wherein the taxonomic information comprises the abundance of each taxon of the taxa in the plurality of dilutions of the sample cultivated in the first cultivation condition; and determining, based on the taxonomic information of the taxa in the plurality of dilutions of the sample cultivated in the first cultivation condition, interactions (e.g., biotic interactions) of the plurality of taxa of microorganisms in the sample in the first cultivation condition. In some embodiments, the method comprises designing a microbial community with the property of interest.

In some embodiments, diluting the sample to form plurality of dilutions of the sample comprises: diluting the sample serially to form a plurality of serial dilutions of the sample. Organisms in the plurality of serial dilutions of the sample can be due to dispersal or chance. The plurality of serial dilutions can be different in different implementations. In some embodiments, the plurality of serial dilutions of the sample can comprise, or about, 1:10, 1:100, 1:1000, 1:10000, 1:100000, 1:1000000, 1:10000000, 1:100000000, 1:1000000000, or a number or a range between any two of these values, dilutions of the sample. In some embodiments, the plurality of serial dilutions of the sample can comprise at least, or at most, 1:10, 1:100, 1:1000, 1:10000, 1:100000, 1:1000000, 1:10000000, 1:100000000, or 1:1000000000 dilutions of the sample. For example, a sample can be diluted 10 times into a 1:10 dilution of the sample using, for example, a buffer. The 1:10 dilution of the sample can be diluted 10 times into a 1:100 dilution of the sample. The plurality of serial dilutions can comprise the 1:10 dilution of the sample, 1:100 dilution of the sample, and other dilutions of the sample similarly prepared. As another example, a sample can be diluted 10 times into a 1:10 dilution of the sample using, for example, a buffer. The sample can be diluted 100 times into a 1:100 dilution of the sample. The plurality of serial dilutions can comprise the 1:10 dilution of the sample, 1:100 dilution of the sample, and other dilutions of the sample similarly prepared.

The plurality of serial dilutions of the sample can comprise dilutions of a number of orders of magnitudes of the sample. In some embodiments, the plurality of serial dilutions of the sample comprises, or about, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, or a number or range between any two of these values, folds dilutions of the sample. In some embodiments, the plurality of serial dilutions of the sample comprises at least, or at most, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 folds dilutions of the sample.

In some embodiments, each dilution is cultivated in replicates and tested. In some embodiments, the method is multiplexed. For example, the number of combinations of cultivation conditions, dilutions, and replicates can be, or be about, 10, 20, 30, 40, 50, 60, 70, 80, 90, 100, 200, 300, 400, 500, 600, 700, 800, 900, 1000, 10000, 100000, 1000000, 10000000, 100000000, 1000000000, or a number or a range between any two of these values. As another example, the number of combinations of cultivation conditions, dilutions, and replicates for each dilution tested can be at least, or at most, 10, 20, 30, 40, 50, 60, 70, 80, 90, 100, 200, 300, 400, 500, 600, 700, 800, 900, 1000, 10000, 100000, 1000000, 10000000, 100000000, or 1000000000. For example, if the number of cultivation condition is 2, the number of dilutions is 5 (e.g., 1:10, 1:100, 1:1000, 1:10000, and 1:100000), and the number of replicates for each dilution cultivated and tested is 100000, then the number of combinations of cultivation conditions, dilutions, and replicates is 1000000 (2×5×10000). As another example, if the number of cultivation condition is 10, the number of dilutions is 5 (e.g., 1:10, 1:100, 1:1000, 1:10000, and 1:100000), and the number of replicates for each dilution cultivated and tested is 100000, then the number of combinations of cultivation conditions, dilutions, and replicates is 2500000 (5×5×10000).

In some embodiments, determining the taxonomic information of the plurality of dilutions of the sample cultivated in the first cultivation condition comprises: determining the taxonomic information of the plurality of dilutions of the sample cultivated in the first cultivation condition using 16S rRNA gene amplicon sequencing. Determining the taxonomic information of the taxa in the plurality of dilutions of the sample cultivated in the first cultivation condition can comprise: determining one or more errors in the taxonomic information of the taxa in the dilutions; and removing at least one of the one or more errors in the taxonomic information of the taxa dilutions. The one or more errors in the taxonomic information of the taxa can be a result of a barcode sequencing error or a contamination of a reagent used in determining the taxonomic information of the taxa in the dilutions.

In some embodiments, the method comprises: cultivating a control sample in the first cultivation condition, wherein determining the taxonomic information of the taxa in the dilutions comprises: comparing the taxonomic information of the taxa in the dilutions to the control sample cultivated in the first cultivation condition. The control sample can be cultivated in the absence of the sample or the plurality of dilutions of the sample.

In some embodiments, each taxon of the taxa corresponds to an operational taxonomic unit (OTU), a species, a genus, or a family. In some embodiments, the sample is an environmental sample, a clinical sample, an agricultural sample, an industrial sample, a ground water sample, a regional species pool, or any combination thereof. In some embodiments, the abundance of the each taxon of the taxa in the dilutions is determined based on a threshold. The abundance of the each taxon of the taxa in the dilutions can comprise a relative abundance of the each taxon of the taxa in the dilutions.

In some embodiments, an environmental sample can be, or comprise, air, soil, water, or any combination thereof. A clinical sample can be, or comprise, an oral sample, a skin sample, a gut sample, or any combination thereof. An agricultural sample can be, or comprise, a sample of any crop, such as corn, wheat, rice, or any combination thereof. Alternatively, or additionally, an agricultural sample can be, or comprise, a sample obtained from an animal, such as a cow, a pig, a chicken, fish, a population thereof, or any combination thereof. An industrial sample can be, or comprise, a tissue culture sample, a bacterial sample, a fungal sample, or any combination thereof. A building environment sample can be, or comprise, a sample obtained from a house, a hospital, or a car. A pet sample can be a sample obtained from a pet, such as a cat, a dog, fish, or any combination thereof.

In some embodiments, determining the interactions of the plurality of taxa of microorganisms comprises determining a pair of taxa that positively or negatively interact with each other. The pair of taxa negatively interacts with each other if one taxon of the pair of the taxa inhibits growth or maintenance of the other taxon of the pair of taxa. In some embodiments, determining the interactions of the plurality of taxa of microorganisms comprises: determining, based on a null model of community assembly and the taxonomic information of the taxa in the plurality of dilutions of the sample cultivated in the first cultivation condition, taxa that occur together significantly non-randomly in the plurality of dilutions of the sample cultivated in the first cultivation condition. Determining the taxa that occur together significantly non-randomly in the plurality of dilutions of the sample cultivated in the first cultivation condition can comprise: determining co-occurrence probabilities of taxa in the plurality of dilutions of the sample cultivated in the first cultivation condition.

In some embodiments, cultivating the plurality of dilutions of the sample in the first cultivation condition comprises cultivating the plurality of dilutions of the sample in the first cultivation condition for a plurality of time durations. The plurality of time durations can be different in different implementations. In some embodiments, the plurality of time durations can comprise, or about, 1 minute, 1 hour, 1 day, 1 week, 1 month, 1 year, or a number or a range between any two of these values. In some embodiments, the plurality of time durations can comprise at least, or at most, 1 minute, 1 hour, 1 day, 1 week, 1 month, or 1 year.

In some embodiments, the method comprises: cultivating the plurality of dilutions of the sample in a second cultivation condition; determining taxonomic information of the taxa in the plurality of dilutions of the sample cultivated in the second cultivation condition, wherein the taxonomic information comprises the abundance of each taxon of the taxa in the plurality of dilutions of the sample cultivated in the second cultivation condition; and determining, based on the taxonomic information of the taxa in the plurality of dilutions of the sample cultivated in the second cultivation condition, interactions of the plurality of taxa of microorganisms in the sample in the second cultivation condition.

In some embodiments, the interactions of the plurality of taxa of microorganisms in the sample in the first cultivation condition comprises biotic interactions of the plurality of taxa of microorganisms in the sample in the first cultivation condition. The first cultivation condition can comprise an aerobic cultivation condition, and wherein the second cultivation condition comprises an anaerobic cultivation condition. The anaerobic cultivation condition can comprise a nitrate-reducing cultivation condition. The nitrate-reducing cultivation condition can comprise presence of $NO_3$.

In some embodiments, the method comprises: determining differences between the interactions of the plurality of taxa of microorganisms in the sample in the first cultivation condition and the interactions of the plurality of taxa of microorganisms in the sample in the second cultivation condition. The method can comprise determining, based on the interactions of the plurality of taxa of microorganisms in the sample in the first cultivation condition and the interactions of the plurality of taxa of microorganisms in the sample in the second cultivation condition, a preferred cultivation condition. In some embodiments, the first cultivation condition comprises the presence of a microorganism. The first cultivation condition can be an environment of interest.

In some embodiments, the method comprises: determining, based on the interactions of the plurality of taxa of microorganisms in the sample in the first cultivation condition, the fitness of a taxon of the taxa in the first cultivation condition. In some embodiments, the method comprises: determining, based on the interactions of the plurality of taxa of microorganisms in the sample in the first cultivation condition, two or more taxa that contribute to a property of interest. The property of interest can comprise performing a specific metabolic function, a molecular of interest, a molecular of interest, a perturbation, or any combination thereof. The property of interest can relate to a health, medical, industrial, or agricultural related process.

In some embodiments, the property of interest comprises imparting a beneficial phenotypic trait to an organism, such as an animal or a plant. Cultivating the first subset of the plurality of dilutions of the sample can comprise cultivating the first subset of the plurality of dilutions of the sample in the presence of the organism. The organism can be from an environment sample, a clinical sample, an agricultural sample, an individual sample, or any combination thereof. The environmental sample can comprise air, soil, water, or any combination thereof. The clinical sample can comprise an oral sample, a skin sample, a gut sample, or any combination thereof, of a subject (e.g., a human subject). The agricultural sample can comprise a sample of any crop, such as corn, wheat, rice, or any combination thereof. The agricultural sample can comprise a sample obtained from an animal, such as a cow, a pig, a chicken, fish, a population thereof, or any combination thereof. The industrial sample can comprise a tissue culture sample, a bacterial sample, a fungal sample, or any combination thereof. The building environment sample can comprise a sample obtained from a house, a hospital, or a car. The pet sample can be a sample obtained from a pet, such as a cat, a dog, fish, or any combination thereof.

In some embodiments, the method can be used to determine the specific microbial taxa, within a complex consortium of mixed taxa, that are interacting with each other within an environment of interest. By determining pairs of taxa positively or negatively interacting within a microbial community in a given cultivation condition, the methods, systems and compositions disclosed herein enable the design and management of microbial communities used in health, industrial or agricultural processes.

In some embodiments, the methods described herein may be applied to microbial community engineering applications to improve agricultural yields, design probiotic applications in humans or livestock or to engineer increased industrial fermenter yields. In other embodiments, the present methods provide for simultaneous evaluation of a large number of possible interactions from a mixed consortium, in a high throughput and accurate manner.

In some embodiments, a sample (such as an environmental sample, a clinical sample, an agricultural sample, an industrial sample, or a combination thereof) is inoculated into a large number of separate enrichment cultures and cultivated under conditions appropriate to detect interactions of interests so that each enrichment culture represents a small fraction of the original community complexity. Then DNA is extracted and taxonomic information is acquired from each culture. Presence/absence data on each taxon is used to determine taxa that occur together in significantly non-random patterns across all enrichment cultures. Compared to a bottom-up, one-by-one comparison of several species of interest, this top-down approach quickly queries potential interactions among assemblages of co-occurring microorganisms.

Strings and Outputs

Nucleic acid sequences can be represented as strings of data. A string can be a sequence of elements, typically characters, using character encoding. A string can be implemented as an array data structure of bytes (or words). A string can be representative of or correspond to one or more outputs. An output can comprise, for example, a taxon or taxa determined using a string. As a non-limiting example, a string can comprise a 16S rRNA sequence (or a sequence of 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof) corresponding to an output comprising a taxon, e.g., an Operational Taxonomic Unit ("OTU"), of a microorganism in a sample.

Strings can be counted or quantified to determine an abundance of at least one taxon of the taxa in a sample. Strings can be quantified with respect to one or more parameters. The one or more parameters may include dilution, cultivation condition, and/or cultivation time. As a non-limiting example, strings counts can be determined for a given dilution of a sample ("a first parameter") cultivated under a particular condition (i.e., aerobic/anaerobic, "a second parameter"). Strings can be indexed with respect to the one or more parameters. As a further non-limiting example, string counts with respect to the first parameter and the second parameter can be indicative of an abundance of a taxon present when cultivated at a given dilution and cultivation condition.

An output, such as an OTU, can co-occur with one or more different outputs corresponding to one or more strings in a plurality of strings. Co-occurring outputs, e.g., OTUs or taxa, in a plurality of microorganism can be indicative of interactions of a plurality of taxa of microorganisms in a population of microorganisms.

Computer Control Systems

Figure 5:
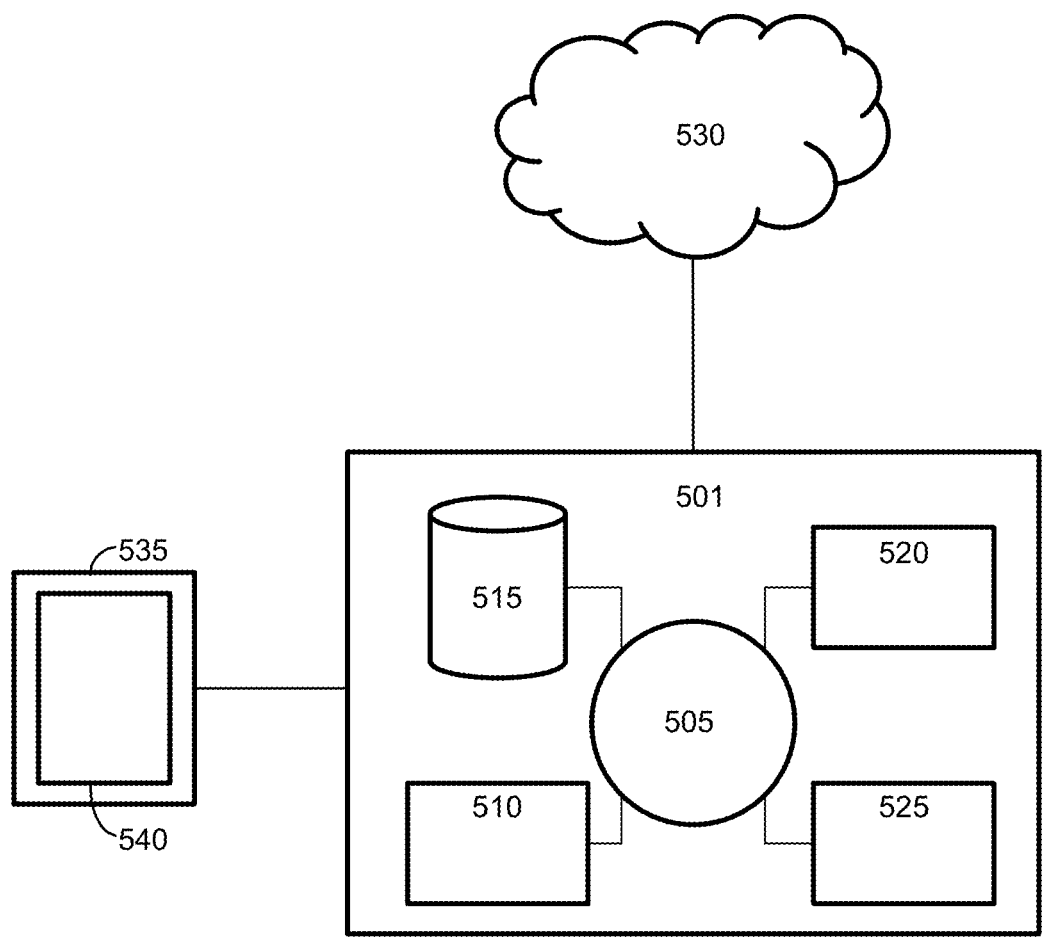
FIG. 5 a block diagram of an illustrative computing system configured to implement methods of the disclosure.

The present disclosure provides computer control systems that are programmed to implement methods of the disclosure. FIG. 5 shows a computer system 501 that is programmed or otherwise configured to implement any of the methods disclosed herein. For example, the computer system 501 can be programmed or otherwise configured to process information regarding a plurality of strings and identify subsets within the plurality comprising strings that co-occur in view of one or more parameters, and, optionally, process data regarding microorganism quantification to determine an abundance of one or more outputs (e.g., most probable number analysis, cultivable abundance determinations). The computer system 501 can regulate various aspects of processing the strings of the present disclosure. Non-limiting examples include analyzing which strings of a plurality co-occur in view of one or more parameters (e.g., dilution or cultivation condition) to, for example, determine the relative fitness of a taxon in response to biotic (e.g., interactions between microorganisms in a sample) and/or abiotic (e.g., environmental conditions such as aerobic/anaerobic) stimuli. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a microbiologist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, an output indicative of string co-occurrence or interactions of a plurality of taxa of microorganisms, as represented by strings. Examples of UI's include, without limitation, a graphical user interface (GUI) and web-based user interface.

Methods and systems of the present disclosure can be implemented by way of one or more algorithms or methods. A method can be implemented by way of software upon execution by the central processing unit 505. The method can, for example, simulate a null model of community assembly and analyze a plurality of strings for a non-random co-occurrence of two or more strings in the plurality. Other exemplary applications of algorithms or methods implemented by way of software include bioinformatics methods for sequence read processing (e.g., merging, filtering, trimming, clustering), alignment and calling, and processing of string data and optical density data (e.g., most probable number and cultivable abundance determinations).

In an exemplary embodiment, a computer system may comprise a computer processor programmed to receive a file comprising a plurality of strings indexed by a first parameter (e.g., a dilution) and a second parameter (e.g., a cultivation condition) each of the strings corresponding to an output (e.g., OTU) and, optionally, cultivable abundance data for each of the outputs. Optionally, the computer processor may be programmed to generate cultivable abundance data by calculating rarity values for each output's (e.g. OTU's) estimated cultivable abundance. The processor can be programmed to quantify an abundance of strings or sequence reads for each output and filter outputs included as a result of possible error. The processor can process string counts for each of the outputs by executing a software program that detect co-occurrence patterns with respect to a first parameter (e.g., dilution) and a second parameter (i.e., environmental or cultivation condition). Co-occurring or co-occurrence outputs with significant positive and negative associations may be saved to a memory, and optionally, displayed on a graphical user interface.

EXAMPLES

Some aspects of the embodiments discussed above are disclosed in further detail in the following examples, which are not in any way intended to limit the scope of the present disclosure.

Example 1

Initial Sample Characterization and Estimates of Cultivable Populations

This example demonstrates initial sample characterization and estimates of cultivable populations based on $OD_{600}$ measures and sequencing.

Sampling and Cell Counting

Groundwater was collected from an uncontaminated well (FW301: N35.94106884 and W84.33618124) at the Oak Ridge Field Research Site on May 5, 2015. The well was considered uncontaminated because, unlike many other wells at the Oak Ridge Field Research Site, it did not sample groundwater from the radioactive and hazardous contaminant plume emanating from the former waste disposal ponds. Prior to the collection of samples, approximately 10 liters (L) of groundwater was pumped until pH, conductivity, and oxidation-reduction (redox) values were stabilized. Following this purge, approximately 50 ml was pumped from the midscreen level into a sterilized serum vial minimizing residual headspace. The vial was sealed and shipped overnight at 4° C. to the laboratory for cultivation. An additional ~40 milliliters (ml) of water sample was taken immediately following the first and preserved with 4% formaldehyde and stored at 4° C. for cell counting. Initial inoculum cell counts were determined using the acridine orange direct count (AODC) method. A 20 ml volume was filtered through a 0.2 µm pore size black polycarbonate membrane (Whatman International Ltd., Piscataway, N.J.) supported by a vacuum filtration sampling manifold (Millipore Corp., Billerica, Mass.). Filtered cells were stained with 25 mg/ml acridine orange for 2 minutes in the dark. Unbound stain was rinsed through the membrane with 10 ml filter sterilized 1× phosphate-buffer saline (PBS; Sigma Aldrich Corp., St. Louis, Mo.). The rinsed membrane was mounted onto a slide and cells were imaged with a fluorescein isothiocyanate (FITC) filter on a Zeiss Axioskop (Carl Zeiss, Inc., Germany).

The initial inoculum was estimated to contain 37,000 cells/ml based on acridine orange direct count (AODC). Based on this initial cell count, the enrichments that received the most concentrated inoculum thus received 3,700 cells $ml^{-1}$, and those enrichments receiving the most dilute inoculum started with an average of only ~0.37 cells $ml^{-1}$. Following cultivation, all wells that received the two most concentrated inocula ($10^{-1}$ and $10^{-2}$ final inoculum density) showed population growth (as measured by optical density at 600 nm ($OD_{600}$) (See Table 1).

TABLE 1

Population growth determined by $OD_{600}$ measures and sequencing for inocula of different concentrations under anaerobic and aerobic growth conditions. The table shows the number of wells with positively identified growth from each of ten 96-well plates comprised of five dilutions ($10^{-1}$-$10^{-5}$) cultivated both aerobically and anaerobically. Two methods, $OD_{600}$ measurement and sequencing, were used to determine if growth in a well was positive. For example, for the $10^{-1}$ dilution, 96 wells were identified to have positive growth with $OD_{600}$ measurement, and 94 wells were identified to have positive growth with sequencing. In some cases $OD_{600}$ detected growth above background while sequencing provided no reads, and in other cases sequencing succeeded despite there being no detectable growth.

|  |  | $OD_{600}$ | sequencing |
|---|---|---|---|
| Anaerobic | $10^{-1}$ | 96 | 94 |
|  | $10^{-2}$ | 96 | 96 |
|  | $10^{-3}$ | 69 | 54 |
|  | $10^{-4}$ | 12 | 0 |
|  | $10^{-5}$ | 1 | 1 |
| Aerobic | $10^{-1}$ | 96 | 96 |
|  | $10^{-2}$ | 96 | 96 |
|  | $10^{-3}$ | 79 | 79 |
|  | $10^{-4}$ | 13 | 22 |
|  | $10^{-5}$ | 4 | 3 |

Inoculation and Culturing

Five milliliters of the groundwater sample was diluted serially four times into a 4 mM phosphate-buffered saline solution (pH 7.4) at a 1:10 ratio. For aerobic experiments, 100 µl of the original undiluted sample and the four serially diluted samples (1:10, 1:100, 1:1,000, 1:10,000) were each inoculated into deep-well 96-well plates with each well containing 900 µl of autoclaved R2A media (HiMedia, Mumbai, India). Thus, each dilution was inoculated into 96 replicates. Plates were sealed with breathable plate seals and placed on a 30° C. shaking incubator (Infors HT, Switzerland) at 750 rpm. All experiments were designated by the incubation condition (e.g., 02) and the dilution with respect to original sample (e.g., $10^{-1}$, $10^{-2}$, etc.), giving five sets of incubations: $O_2$-$10^4$, $02$-$10'$, $O_2$-$10^{-3}$, $O_2$-$10^{-1}$, and $O_2$-$10^{-5}$. Anaerobic experiments were inoculated from the same dilutions, but into R2A that had been supplemented with 20 mM sodium nitrate (Sigma-Aldrich, St. Louis, Mo., USA). The anaerobic experiments were immediately transferred into an anaerobic glove bag (Coy, Grass Lake, Mich., USA) containing a $N_2$:$H_2$:$CO_2$ atmosphere (85:10:5) and cultivated, unshaken, at 30° C. for ~96 hours. The aerobic and anaerobic experiments were both cultivated until visible growth had occurred in some wells, and the anaerobic experiments thus necessitated a longer incubation. These experiments were referred to as $NO_3$-$10^{-1}$, $NO_3$-$10^{-2}$, $NO_3$-$10^{-3}$, $NO_3$-$10^{-4}$, and $NO_3$-$10^{-5}$. In addition to plates inoculated with the groundwater, two additional plates were inoculated with 100 µl of PBS solution and served as a negative control sample for growth under both aerobic and anaerobic conditions.

Anaerobic experiments with initial inoculum densities of $10^{-3}$, $10^{-4}$, and $10^{-5}$, had 69, 12, and 1 positive-growth wells, respectively. Similarly, the aerobic experiments had 79, 13, and 4 positive-growth wells from those same inocula. Using, these data, the original sample was calculated to be between 1,400 and 2,200 cultivable cells per milliliter at the 95% confidence level with 1,700 cells per ml being most probable for aerobic cultivation conditions and between 1,000 and 1,600 cultivable cells per milliliter with 1,400 cells per ml being most probable for the anaerobic conditions. Thus, approximately 4% of the total cells counted by the AODC method appear to be cultivable under these conditions (3.8% under nitrate-reducing conditions and 4.6% under aerobic conditions).

DNA Extraction and PCR

Two-hundred microliter aliquots of culture were extracted using the Wizard SV 96 Genomic DNA purification system (Promega, Madison, Wis., USA) as per manufacturer's specifications. In addition to the samples, we extracted 36 no-inoculum control samples and 24 extraction blanks. The extraction blanks were DNA extractions carried out solely on the extraction reagents themselves and thus serve as a control sample for contaminating DNA both in the extraction and the downstream PCR. DNA was quantified with the Quant-iT double-stranded DNA assay kit (Life Technologies, Eugene, Oreg., USA). Samples were normalized so that ~5 ng of each sample was input into each 20 µl PCR. Some samples, such as extraction blanks, received less than 5 ng, as they were limited by the concentrations of the extracted DNA. Primers used in the PCRs amplified the V34 hypervariable regions of the 16S gene (341F: 5'-CCTACGGGAGGCAGCAG (SEQ ID NO. 1), and 806R: 5'-GGACTACHVGGGTWTCTAAT (SEQ ID NO. 2)). Both forward and reverse primers contained TruSeq Illumina adapters, barcodes, phasing, and linker sequences and were similar to previously described designs, with the exception that the barcodes here were included so as to be part of sequencing read instead of a separate indexing read. Each PCR mixture contained 4 µl of 5× Phusion high-fidelity (HF) Buffer, 0.2 µl of Phusion High-Fidelity DNA polymerase, 200 µM dinucleoside triphosphates (dNTPs), 3% dimethyl sulfoxide (DMSO), and each primer at a concentration of 0.05 µM. All PCR reagents were obtained from NEB (Ipswitch, Mass., USA) except for primers, which were synthesized and PAGE purified by IDT (Coralville, Iowa, USA). The thermal cycling conditions were as follows: an initial denaturation at 98° C. for 30 s, followed by 30 cycles at 98° C. for 10 s, 50° C. for 30 s and 72° C. for 30 s, with a final extension at 72° C. for 7 min. Following PCR, samples from the same experiment and dilution (i.e., plate) were pooled and purified with Zymo Clean and Concentrator kits (Irvine, Calif., USA), and quantified with quantitative PCR (qPCR; Kapa Biosystems, Wilmington Mass., USA). Each of the 11 pooled PCR products (each representing 96 samples) was then normalized and combined.

Sequencing and OTU Calling

The single aliquot of all combined PCRs was diluted and denatured according to the MiSeq reagent kit preparation guide (Illumina, San Diego, Calif., USA). A sample concentration of 6 pM was loaded and sequenced on a 600-cycle (2×300 paired ends) MiSeq kit without PhiX. Paired-end reads overlapped and were merged with PEAR under default parameters (minimum overlap of 10 bases and P=0.01). Merged reads were quality filtered with custom scripts in which each read was matched to both forward and reverse barcodes allowing for zero mismatches, and kept only if the maximum expected errors in the whole read was less than or equal to 2 (https://github.com/polyatail/arkin, the content of which is incorporated herein in its entirety). Additional trimming removed reads that did not contain both forward and reverse primer sequences or were less than 420 base pairs (bps). Finally, the remaining reads were trimmed of chimeric sequences using UCHIME against the GreenGenes database, resulting in 9,026,027 high-quality reads across all samples. Reads were clustered with QIIME 1.9.0 using the pick_open_references.py script and a 97% clustering threshold. Taxonomic calls were made against the GreenGenes database v 13_5 with a minimum cluster size of 2.

In addition to optical density measurements, DNA was extracted from each well and the 16S rRNA gene amplified and sequenced. Across all 960 cultivated communities, $OD_{600}$ and sequencing data were in agreement in regard to detectable growth in 893 cases (93.0%). There were 23 samples with positive growth by sequencing that did not exceed the $OD_{600}$ thresholds, and 44 samples with growth by optical density that did not exceed read count thresholds. The numbers of positive-growth wells by both methods for each experiment and dilution are shown in Table 1.

Altogether, these data indicate that growth determined by $OD_{600}$ measures and sequencing data were consistent for the majority of cultivated communities.

Example 2

Probabilistic Immigration and Environmental Conditions Shape Microbial Community Structure This example demonstrates probabilistic immigration and environmental conditions can shape microbial community structure as determined using 16S rRNA gene amplicon sequencing.

Figure 6:
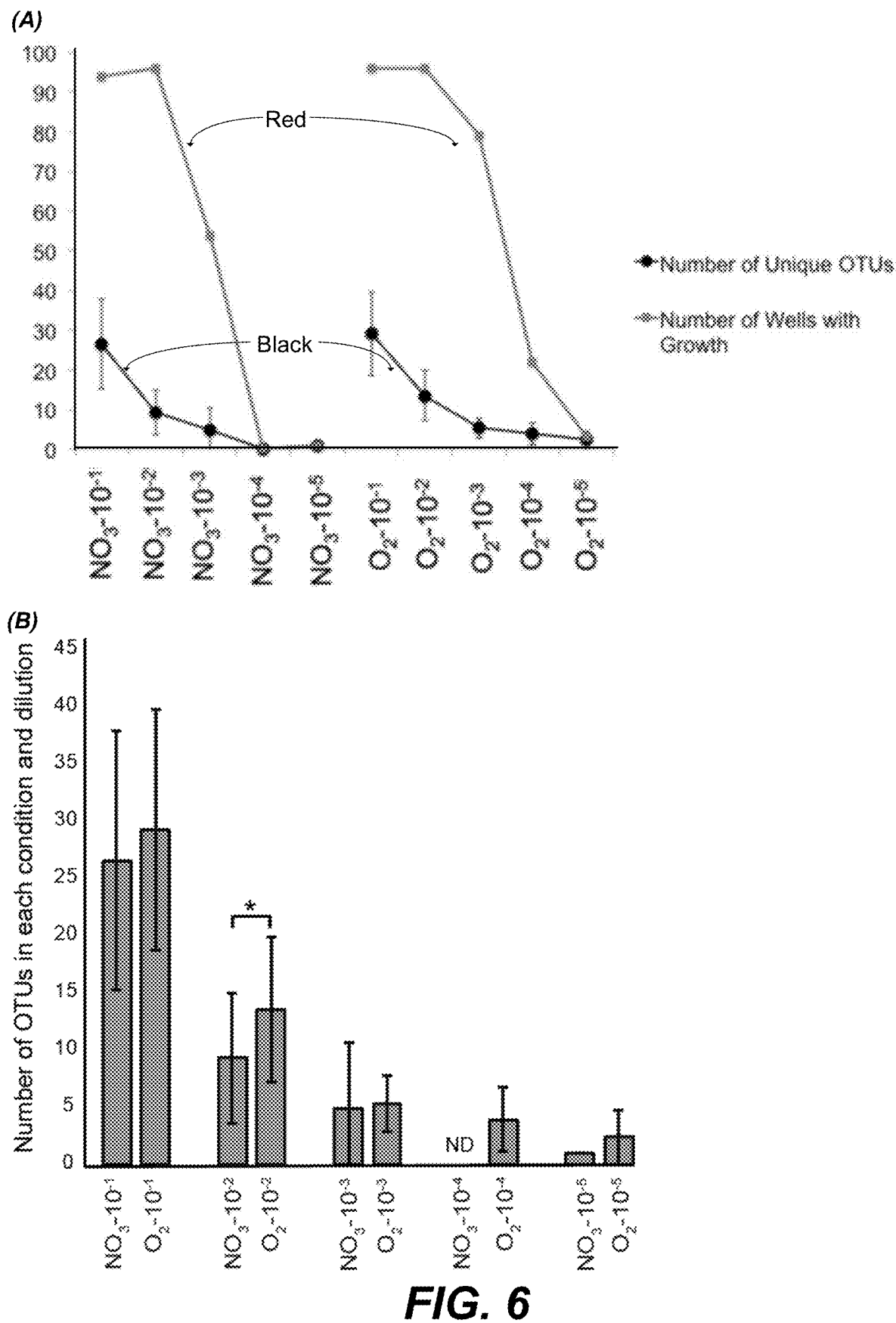
FIG. 6 panel (A) shows for each experiment and dilution, the number of unique wells with detectable growth by sequencing-based methods (red lines) and the number of OTUs assigned (black lines). Error bars represent standard deviations. Statistical significance between means was tested using Student's t test for the first three dilutions ($10^{-1}$-$10^{-3}$). Significance (p value<0.05), is marked with an asterisk. ND indicates no data acquired for that set of 734 samples.

Based on 16S rRNA gene amplicon sequencing data, enrichment cultures started with the highest inoculum concentrations had the highest operational taxonomic unit (OTU) richness. The communities receiving the most concentrated inoculum had statistically similar numbers of OTUs under nitrate-reducing and aerobic conditions (t test, P=0.10), with the nitrate-reducing communities averaging 26.5 OTUs (n=94; standard deviation (SD), 11.27 OTUs) and the aerobic communities averaging 29.2 (n=96; SD, 10.53 OTUs). OTU richness declined in experiments that received less concentrated inocula (FIG. 6). In the $10^{-2}$ dilutions, the aerobic communities tended to have higher species richness than the nitrate-reducing communities (t test, P=2.09e-06), with nitrate-reducing cultures having on average 9.3 OTUs (n=96; SD, 5.7 OTUs) and the aerobically cultivated communities with 13.5 OTUs (n=96; SD, 6.4 OTUs). Aerobic communities that received the most diluted inoculum had on average only 2.3 OTUs (n=3; SD, 2.31 OTUs), and only a single OTU in a single sample was detected in the nitrate-reducing communities begun with the most dilute inoculum. In addition to species richness, how evenly communities were structured with Pielou's index were quantified. At all dilutions, the anaerobic communities showed significantly reduced evenness (FIG. 7), despite being seeded from the same populations that seeded the aerobic communities. These results indicated that the anaerobic cultivation conditions favor the outgrowth of a smaller number of taxa, results consistent with stronger selective forces under the anaerobic conditions.

Figure 8:
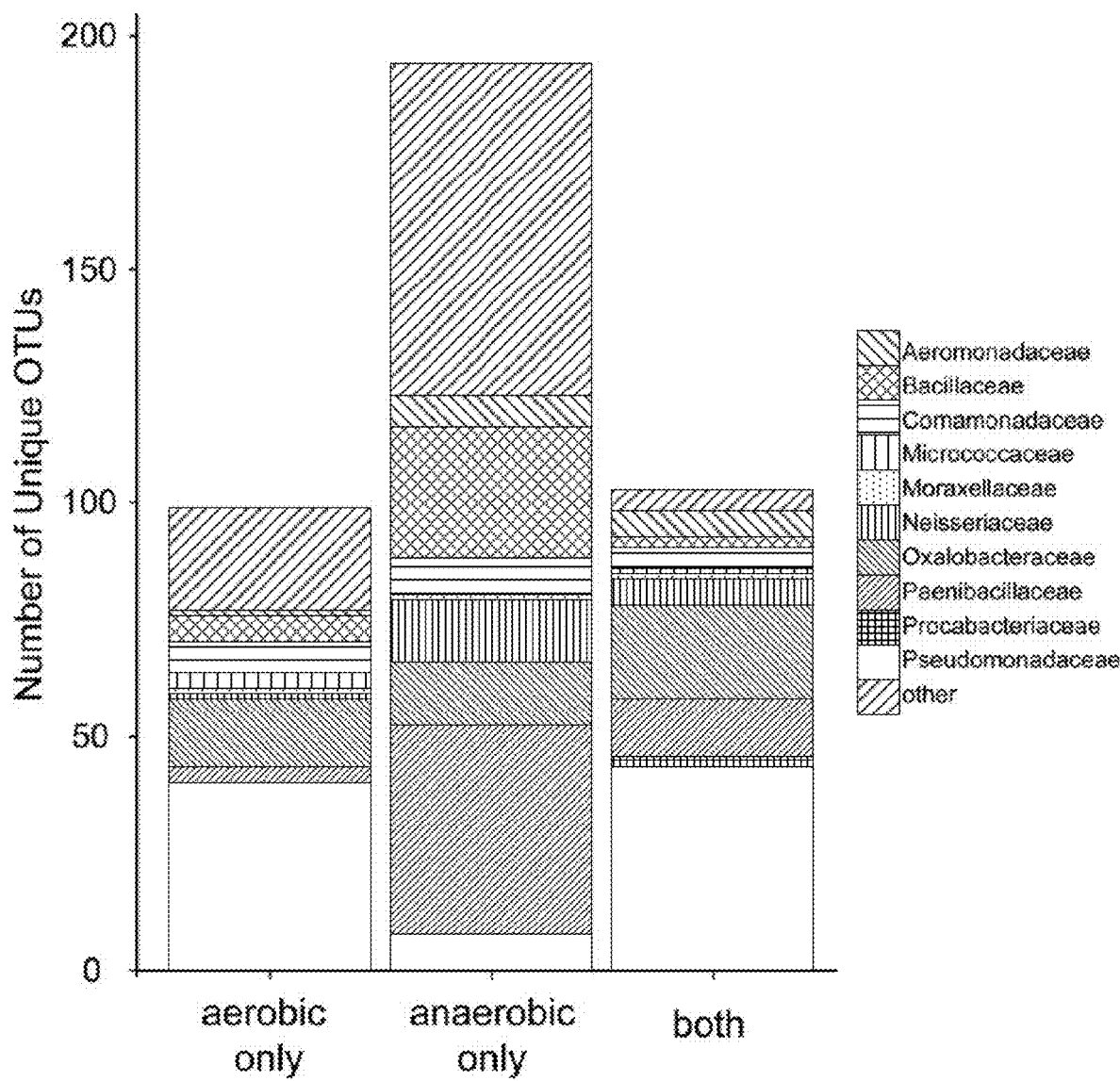
FIG. 8 shows Number of OTUs found uniquely in anaerobic enrichments or aerobic enrichments, as well as OTUs identified in both.

Overall, there were 399 unique OTUs identified across all cultures. Of these, 197 OTUs were found only in nitrate-reducing cultures, 99 OTUs only in aerobic cultures, and 103 OTUs in both aerobic and nitrate-reducing samples (FIG. 8). Some families, like the Pseudomonadaceae, had fewer OTUs unique to anaerobic samples (n=8) than OTUs unique to aerobic samples (n=40). Other families, like the Paenibacillaceae, had a larger number of OTUs uniquely identified in anaerobic samples (n=44) than identified in aerobic samples (n=4).

Figure 9:
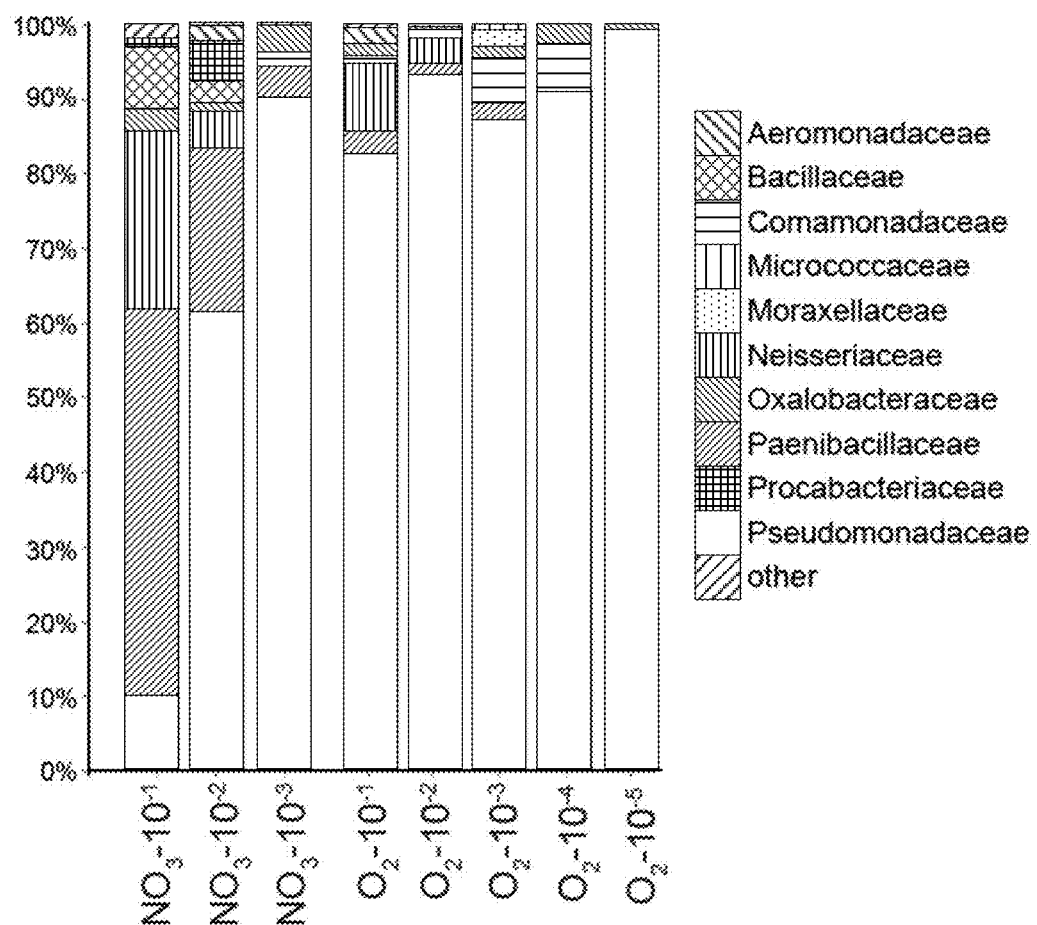
FIG. 9 shows relative abundance of summed read counts belonging to most abundant families in each dilution and cultivation condition.
Figure 10:
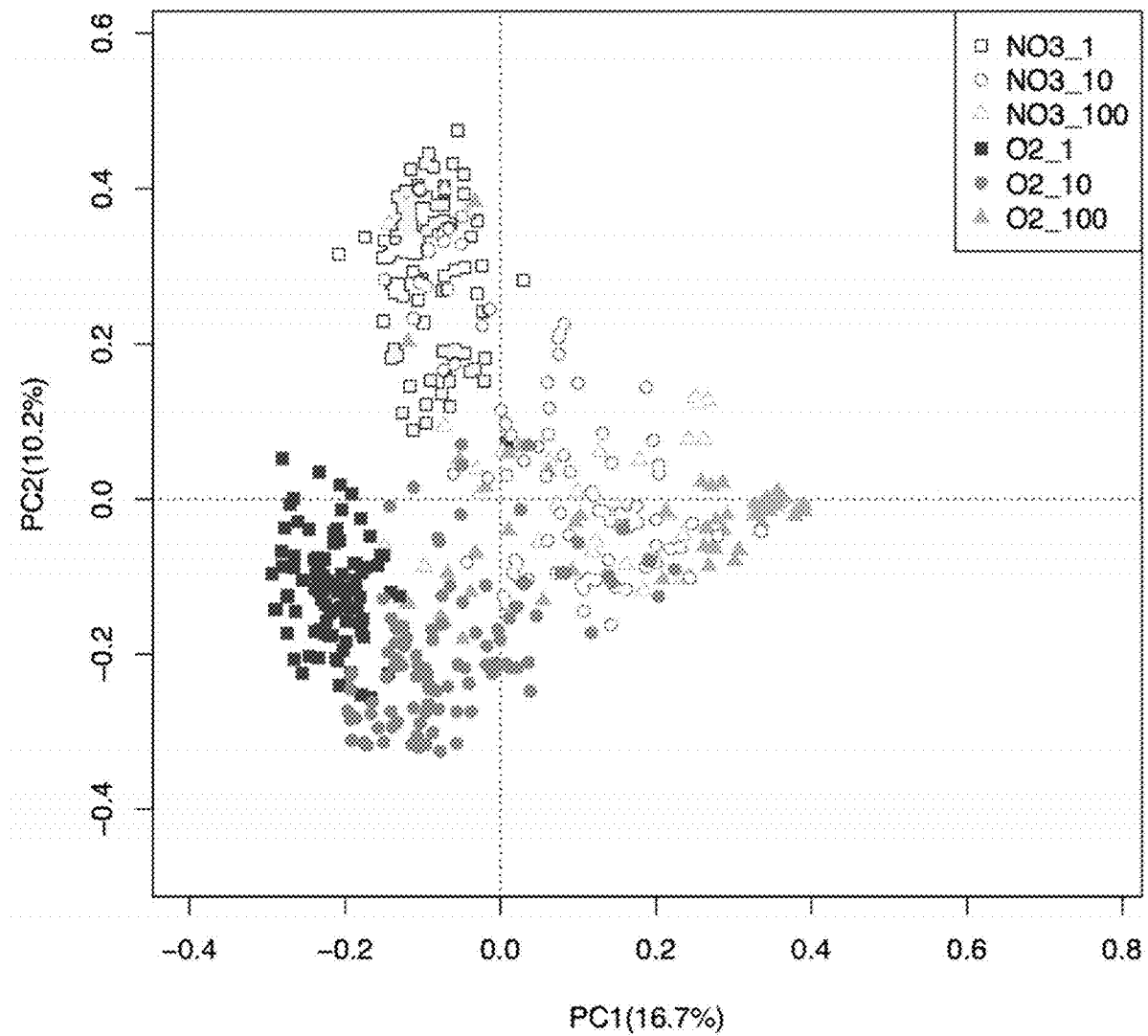
FIG. 10 shows principal component analysis of the Hellinger-transformed OTU presence/absence data for the first three dilutions in both aerobic and nitrate-reducing environments. Note that NO3_1 corresponds to $NO_3$-$10^{-1}$, NO3_10 corresponds to $NO_3$-$10^{-2}$, etc.

In addition to varied membership, communities enriched on aerobic and anaerobic samples differed in community composition, especially between samples started with the most concentrated inoculum (FIG. 9). For example, members of the family Pseudomonadaceae constitute 82.5% of reads in the $O_2$-$10^{-1}$ enrichments, but only 10.3% in the $NO_3$-$10^{-1}$ communities. The $NO_3$-$10^{-1}$ community also has a higher percentage of reads assigned to the Paenibacillaceae (51.1%) and Neisseriaceae (24.1%) families then the $O_2$-$10^{-1}$ communities (3.3% and 9.4% respectively). In cultures started with more dilute inocula, however, the community structures of aerobic and anaerobic samples were more similar to one another (FIG. 10). In large part this can be attributed to the dominance of a single OTU in cultures started with more dilute inocula ("New.ReferenceOTU30", Pseudomonas sp., FIG. 11). The abundance of this OTU in cultures started from more dilute inocula was indicative of its higher cultivable abundance in the initial sample, precluding it from being removed by successive dilutions. Most OTUs (69.3% in anaerobic samples and 64.4% in aerobic samples) were identified in communities started from only in the two most concentrated inocula, reflecting their low cultivable abundance in the groundwater inoculum and resultant extinction upon dilution. Conversely, only 13.3% of the OTUs in anaerobic samples were limited to communities cultivated from more dilute inocula ($NO_3$-$10^{-3}$ through $NO_3$-$10^{-5}$), and only 3.9% of aerobically-identified OTUs were limited to those communities from the more dilute inocula ($O_2$-$10^{-3}$ through $O_2$-$10^{-5}$).

Figure 11:
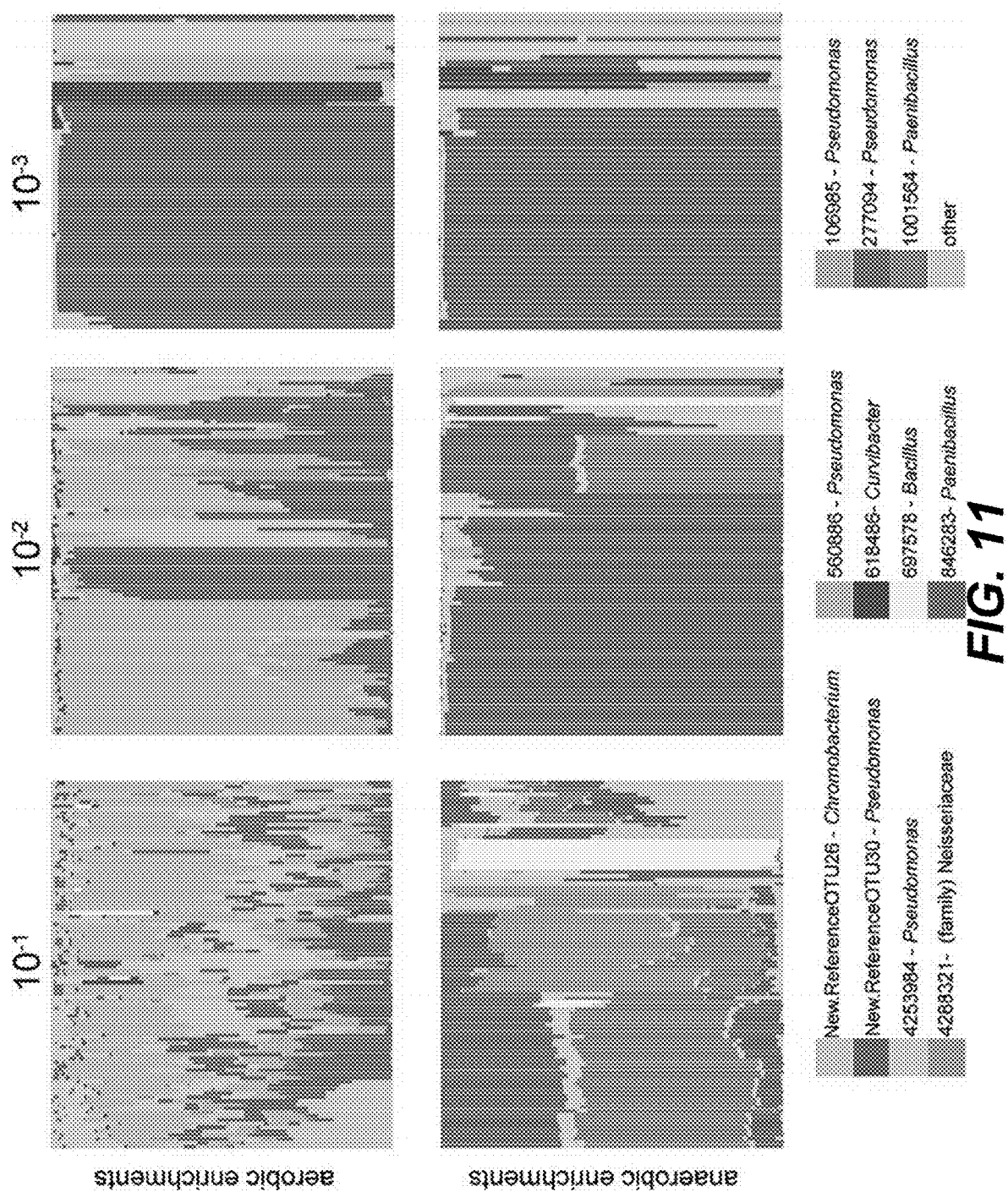
FIG. 11 shows relative abundance of OTUs (y-axes) across all communities (x-axes) in the first four dilutions of aerobic enrichments and first three dilutions of anaerobic, nitrate-reducing enrichments. Only the most abundant 11 OTUs are shown for clarity.
Figure 12:
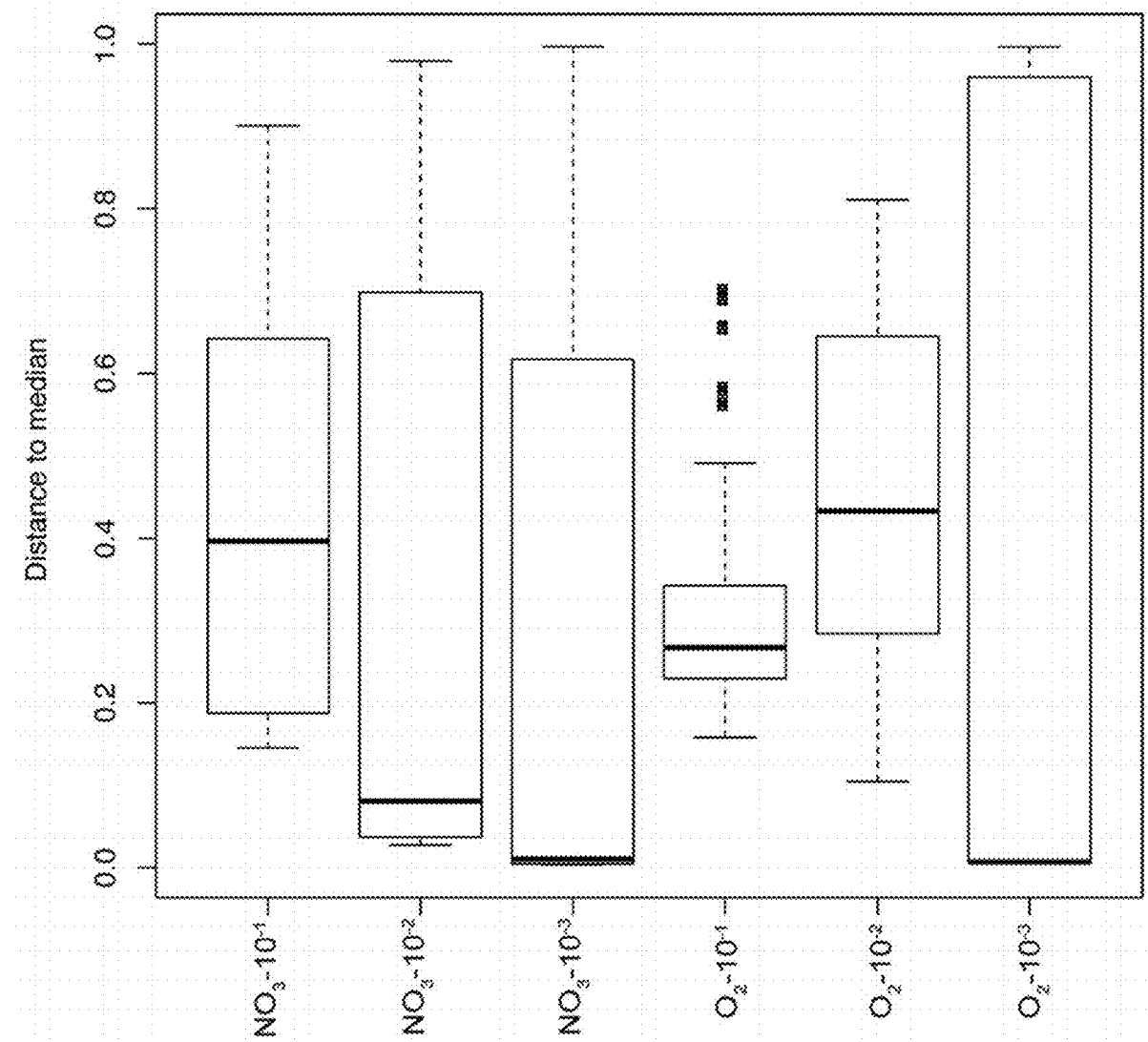
FIG. 12 is a bar chart showing an analysis of group dispersions calculated by measuring each community's distance from a median point in multivariate space using Bray-Curtis dissimilarity. Higher median values indicate more within-group variation, and lower values indicate more homogeneous communities.

The dispersion of community structures in each dilution and under each condition was quantified in order to examine how probabilistic processes and environmental selection interact and contribute to stabilizing or destabilizing the range of community structure outcomes. Stochastic recruitment drove variation among replicate communities of a condition and dilution. Communities may be formed from fewer taxa, either because of selective filtering or removal by dilution, which would tend to be more similar to each other. Among communities formed from the most concentrated inocula, the aerobically cultivated communities were typically more similar to each other than the nitrate-reducing communities (FIG. 12). The dominance of one or several of a small subset of organisms in the anaerobic communities drove the divergence in community structure outcomes (FIG. 11). Conversely, in the communities formed from the next inoculum dilutions ($NO_3$-$10^{-2}$ and $O_2$-$10^{-2}$), the nitrate-reducing communities were actually more similar to each other than the aerobic communities are (FIG. 12). At this dilution, the selective pressures of the nitrate-reducing conditions prevented a number of OTU populations from growing as they did in the aerobic cultures. By the third dilution ($10^{-3}$), most communities under either condition were very similar to each other (e.g., the median of the distances are low); however, there was a larger range of community dispersions. These data reflected that fact that most communities at these dilutions were dominated by a single OTU, precluding significant dissimilarities between them.

Figure 13:
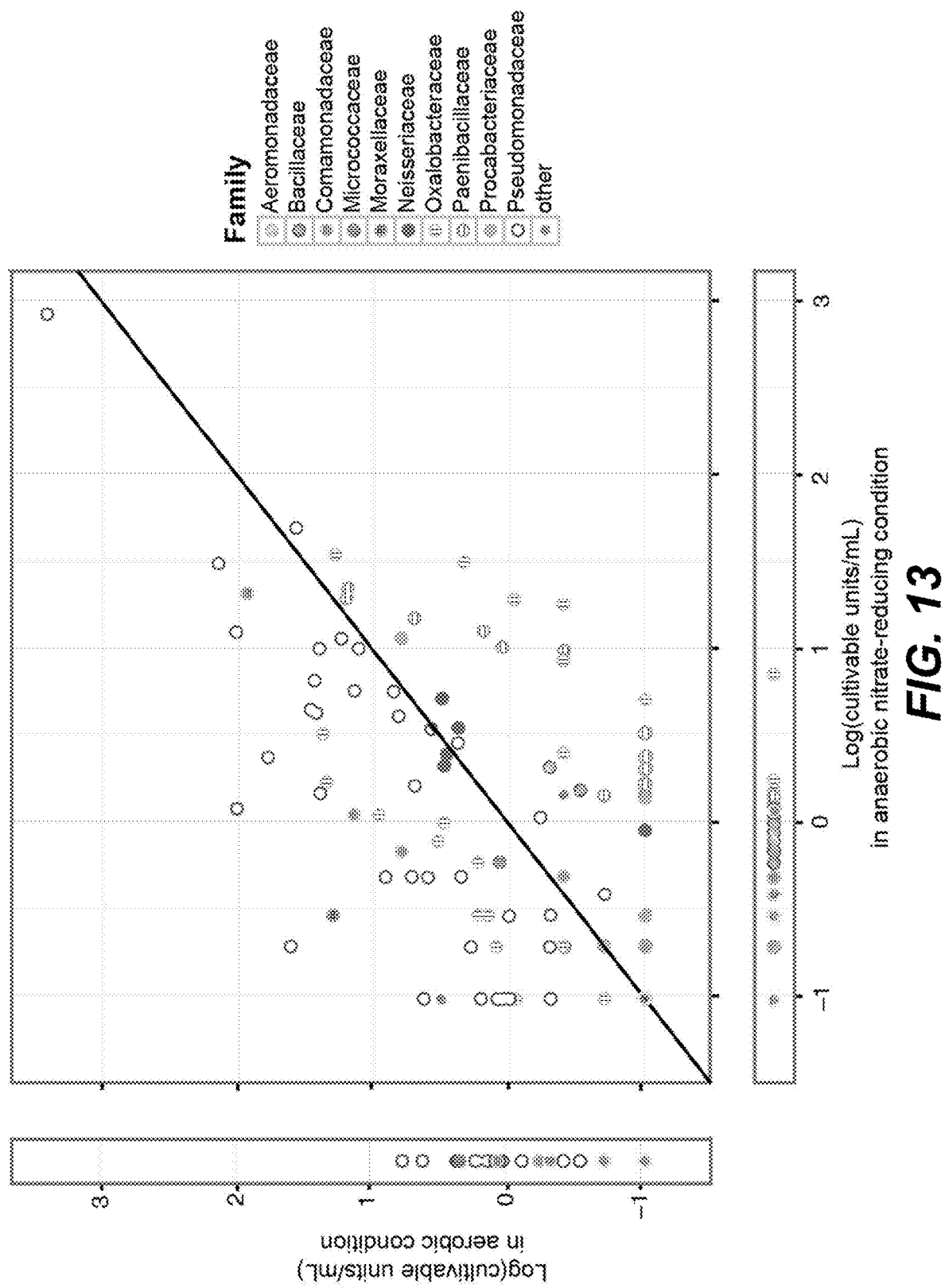
FIG. 13 shows most probable number estimates of cultivable units per ml for each OTU, colored by Family, in both anaerobic and aerobic conditions. Line of perfect concordance is shown to clarify OTUs more cultivable in aerobic versus anaerobic conditions.

Environmental selection shaped cultivable fraction of inoculum. For each OTU under each culture condition, the frequency the OTU was identified across multiple dilution levels was used to estimate the most probable number of cultivable units in the original inoculum sample. Since cultivability was condition-dependent, how these numbers varied between aerobic and anaerobic samples were compared (FIG. 13). Notably, members of the Pseudomonadaceae, Comamonadaceae, and Micrococcaceae tended to be more cultivable under aerobic cultures, while OTUs assigned to the Paenibacillaceae and Bacillaceae tended to be more frequently found in the anaerobic cultures. Members of the Oxalobacteraceae, on the other hand, could be more cultivable under either aerobic or anaerobic conditions.

Figure 14:
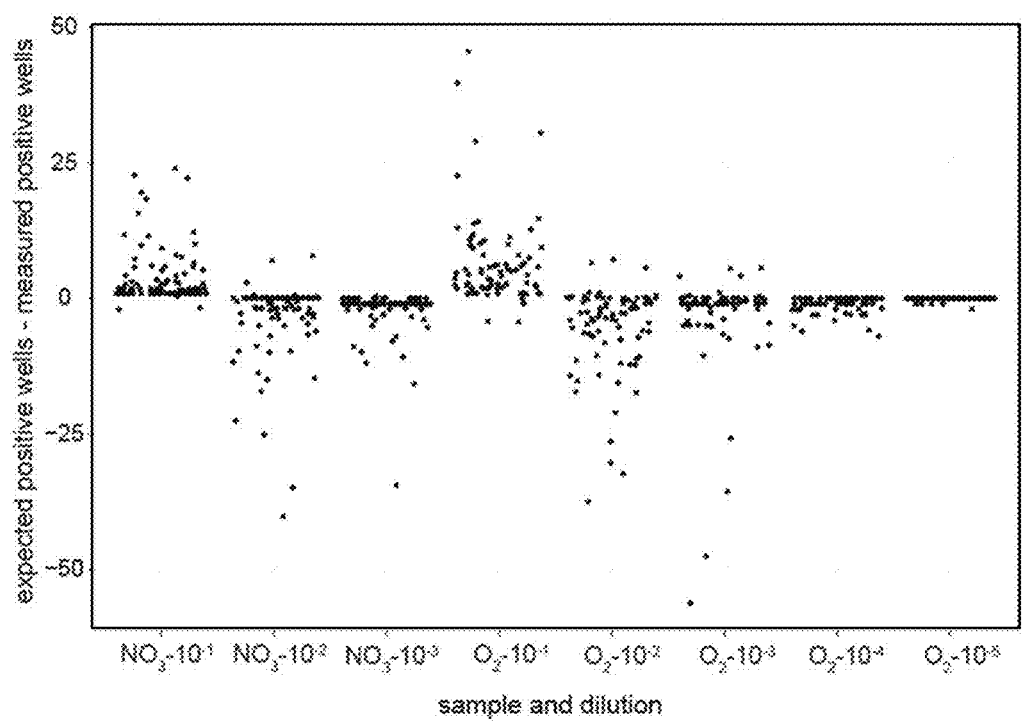
FIG. 14 shows for each OTU, the expected number of wells (calculated from the most probable number (MPN)-estimated cultivable units/ml in the inoculum) minus the actual measured number of wells that OTU was found in for each experiment/dilution. Positive values indicate instances where an OTU was detected in fewer enrichment communities than expected, and negative values indicate where an OTU was detected more than expected based on the cultivable units/ml MPN estimate.

Most probable number (MPN) calculations were built upon several assumptions, including that each OTU was randomly mixed and different OTUs do not repel each other, assumptions that may not hold for natural bacterial communities. Rarity values for each MPN were calculated as a means of assessing the extent to which these assumptions hold. Rarity values assess the probability that our observed detections of each OTU was likely to have occurred given the calculated MPN, and was calculated by dividing the likelihood of the observed outcome by the largest likelihood of any outcome at that same MPN. And 38.6% and 32.8% of OTUs from aerobic and anaerobic cultures, respectively, had distribution frequencies categorized as unlikely or extremely unlikely (rarity values <0.05). Of those MPN estimations with unlikely or extremely unlikely distributions, nearly all had lower than expected number of positive observations from high-inoculum cultures, and a concomitant higher than expected number of positive observations in low-inoculum cultures (FIG. 14). Explanations for this behavior include competitive mechanisms in low-dilution cultures preventing growth and detection of these OTUs, or clumps of co-localized OTUs in the initial inoculum being broken up upon dilution—leading to a higher than expected number of observations in low-dilution cultures.

The highly replicated design simulated passive dispersal of a community into many local environments. As such, an organism's initial abundance in any given local community, indeed the chance it arrived in that community at all, was a function of its abundance in the inoculum. In agreement with that expectation, species richness declined with increasing dilution of the inoculum, as did the number of wells with positive detectable growth (Table 2). Similar dilution-to-extinction approaches have been used previously to examine the link between biodiversity and ecosystem functioning. Here, however, the high replication at each dilution allows us to extrapolate the abundance of each OTU in the initial inoculum by examining the number of communities in which each OTU was found in at each. It was estimated, using an MPN technique, the absolute cultivable abundance of each taxon in the inoculum, data unobtainable from 16S rRNA amplicon sequencing of the inoculum alone. It was estimated that the most abundant *Pseudomonas* OTU (New.ReferenceOTU30), for instance, had approximately 840 cultivable units per ml in anaerobic conditions, and 2,590 cultivable units per ml in aerobic conditions (Table 2) Although MPN techniques have been used for estimation of bacterial abundance in some applications, the application of 16S rRNA amplicon sequencing to the approach offers the advantage of estimating cultivability of a large number of taxa simultaneously. Many taxa had extremely small cultivable populations in the inoculum. In fact, 66.8% of OTUs cultivable under aerobic conditions and 78.3% of those cultivable in anaerobic conditions were estimated to have less than one cultivable unit per milliliter. These results reflect the diversity and high number of low abundance species in the inoculum, consistent with previous results. Importantly, these results also highlight the need for careful consideration of experimental design, volume of inoculum used, and microbial density and diversity in the inoculum when evaluating reproducibility across any enrichment experiment.

Note that having the 16S rRNA amplicon sequencing of the inoculum would add an exciting dimension to this analysis, including the extent to which detected taxa in the inoculum were cultivable and how well cultivable abundances align with OTU abundances. However, insufficient biomass for adequate extraction and sequencing was obtained from the inoculum, and these data were not collected. Further, although the inoculum was submitted to two different selective regimes, they share a cultivation medium, R2A, which may select against large fractions of the inoculum community (e.g., approximately 4% of the cells counted by microscopy were cultivated). The use of other cultivation media would not only offer opportunities to recover different fractions of the inoculum but could also be used to dissect how specific selective factors impact the fitness of different populations.

TABLE 2

Growth of OTUs under different environmental conditions. Table 2 shows each OTU identified in this example, including the taxonomic identification, frequency of identification in each community, estimated MPN, rarity category, and percent of cultivable community in inoculum.

| | Column Number | | | | |
|---|---|---|---|---|---|
| Row Number | 1 kingdom | 2 phylum | 3 class | 4 order | 5 family |
| 1 | k_Bacteria; | p_Proteobacteria; | c_Betaproteobacteria | | |
| 2 | k_Bacteria; | p_Proteobacteria; | c_Betaproteobacteria; | o_Neisseriales; | f_Neisseriaceae |
| 3 | k_Bacteria; | p_Proteobacteria; | c_Gammaproteobacteria; | o_Pseudomonadales; | f_Pseudomonadaceae; |
| 4 | k_Bacteria; | p_Proteobacteria; | c_Betaproteobacteria; | o_Burkholderiales; | f_Oxalobacteraceae |
| 5 | k_Bacteria; | p_Proteobacteria; | c_Betaproteobacteria; | o_Burkholderiales; | f_Oxalobacteraceae; |
| 6 | k_Bacteria; | p_Proteobacteria; | c_Betaproteobacteria; | o_Neisseriales; | f_Neisseriaceae |
| 7 | k_Bacteria; | p_Firmicutes; | c_Bacilli; | o_Bacillales; | f_Paenibacillaceae; |
| 8 | k_Bacteria; | p_Firmicutes; | c_Bacilli; | o_Bacillales; | f_Paenibacillaceae; |
| 9 | k_Bacteria; | p_Firmicutes; | c_Bacilli; | o_Bacillales; | f_Paenibacillaceae; |
| 10 | k_Bacteria; | p_Firmicutes; | c_Bacilli; | o_Bacillales; | f_Paenibacillaceae; |
| 11 | k_Bacteria; | p_Proteobacteria; | c_Betaproteobacteria; | o_Burkholderiales; | f_Comamonadaceae; |
| 12 | k_Bacteria; | p_Firmicutes; | c_Bacilli; | o_Bacillales; | f_Paenibacillaceae; |
| 13 | k_Bacteria; | p_Proteobacteria; | c_Gammaproteobacteria; | o_Pseudomonadales; | f_Pseudomonadaceae; |
| 14 | k_Bacteria; | p_Proteobacteria; | c_Gammaproteobacteria; | o_Pseudomonadales; | f_Pseudomonadaceae; |
| 15 | k_Bacteria; | p_Proteobacteria; | c_Gammaproteobacteria; | o_Pseudomonadales; | f_Pseudomonadaceae; |
| 16 | k_Bacteria; | p_Proteobacteria; | c_Betaproteobacteria; | o_Neisseriales; | f_Neisseriaceae |
| 17 | k_Bacteria; | p_Firmicutes; | c_Bacilli; | o_Bacillales; | f_Paenibacillaceae; |
| 18 | k_Bacteria; | p_Proteobacteria; | c_Gammaproteobacteria; | o_Pseudomonadales; | f_Pseudomonadaceae; |
| 19 | k_Bacteria; | p_Proteobacteria; | c_Betaproteobacteria | | |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | |
|---|---|---|---|---|---|
| 20 | k_Bacteria; | p_Proteobacteria; | c_Betaproteobacteria; | o_Neisseriales; | f_Neisseriaceae; |
| 21 | k_Bacteria; | p_Verrucomicrobia; | c_[Spartobacteria]; | o_[Chthoniobacterales]; | f_[Chthoniobacteraceae]; |
| 22 | k_Bacteria; | p_Proteobacteria; | c_Betaproteobacteria; | o_Neisseriales; | f_Neisseriaceae; |
| 23 | k_Bacteria; | p_Proteobacteria; | c_Betaproteobacteria; | o_Burkholderiales; | f_Oxalobacteraceae; |
| 24 | k_Bacteria; | p_Proteobacteria; | c_Alphaproteobacteria; | o_Caulobacterales; | f_Caulobacteraceae; |
| 25 | k_Bacteria; | p_Firmicutes; | c_Bacilli; | o_Bacillales; | f_Paenibacillaceae; |
| 26 | k_Bacteria; | p_Firmicutes; | c_Bacilli; | o_Bacillales; | f_Paenibacillaceae; |
| 27 | k_Bacteria; | p_Firmicutes; | c_Bacilli; | o_Bacillales; | f_Paenibacillaceae; |
| 28 | k_Bacteria; | p_Proteobacteria; | c_Gammaproteobacteria; | o_Aeromonadales; | f_Aeromonadaceae; |
| 29 | k_Bacteria; | p_Firmicutes; | c_Clostridia; | o_Clostridiales; | f_Lachnospiraceae; |
| 30 | k_Bacteria; | p_Proteobacteria; | c_Betaproteobacteria; | o_Neisseriales; | f_Neisseriaceae |
| 31 | k_Bacteria; | p_Firmicutes; | c_Bacilli; | o_Bacillales; | f_Paenibacillaceae; |
| 32 | k_Bacteria; | p_Proteobacteria; | c_Gammaproteobacteria; | o_Pseudomonadales; | f_Pseudomonadaceae; |
| 33 | k_Bacteria; | p_Firmicutes; | c_Bacilli; | o_Bacillales; | f_Paenibacillaceae; |
| 34 | k_Bacteria; | p_Firmicutes; | c_Bacilli; | o_Bacillales; | f_Paenibacillaceae; |
| 35 | k_Bacteria; | p_Bacteroidetes; | c_[Saprospirae]; | o_[Saprospirales]; | f_Chitinophagaceae; |
| 36 | k_Bacteria; | p_Firmicutes; | c_Bacilli; | o_Bacillales; | f_Paenibacillaceae; |
| 37 | k_Bacteria; | p_Firmicutes; | c_Clostridia; | o_Clostridiales; | f_Lachnospiraceae; |
| 38 | k_Bacteria; | p_Firmicutes; | c_Bacilli; | o_Bacillales; | f_Paenibacillaceae; |
| 39 | k_Bacteria; | p_Cyanobacteria; | c_4C0d-2; | o_MLE1-12; | f_; |
| 40 | k_Bacteria; | p_Firmicutes; | c_Bacilli; | o_Bacillales; | f_Paenibacillaceae; |
| 41 | k_Bacteria; | p_Firmicutes; | c_Bacilli; | o_Bacillales; | f_Paenibacillaceae; |
| 42 | k_Bacteria; | p_Proteobacteria; | c_Gammaproteobacteria; | o_Pseudomonadales; | f_Pseudomonadaceae; |
| 43 | k_Bacteria; | p_Proteobacteria; | c_Betaproteobacteria; | o_Neisseriales; | f_Neisseriaceae; |
| 44 | k_Bacteria; | p_Proteobacteria; | c_Betaproteobacteria; | o_Burkholderiales; | f_Oxalobacteraceae; |
| 45 | k_Bacteria; | p_Proteobacteria; | c_Gammaproteobacteria; | o_Pseudomonadales; | f_Pseudomonadaceae; |
| 46 | k_Bacteria; | p_Firmicutes; | c_Bacilli; | o_Bacillales; | f_Bacillaceae; |
| 47 | k_Bacteria; | p_Firmicutes; | c_Bacilli; | o_Bacillales; | f_Paenibacillaceae; |
| 48 | k_Bacteria; | p_Proteobacteria; | c_Gammaproteobacteria; | o_Pseudomonadales; | f_Pseudomonadaceae; |
| 49 | k_Bacteria; | p_Proteobacteria; | c_Gammaproteobacteria; | o_Enterobacteriales; | f_Enterobacteriaceae; |
| 50 | k_Bacteria; | p_Firmicutes; | c_Bacilli; | o_Bacillales; | f_Paenibacillaceae; |
| 51 | k_Bacteria; | p_Firmicutes; | c_Bacilli; | o_Bacillales; | f_Paenibacillaceae; |
| 52 | k_Bacteria; | p_Proteobacteria; | c_Gammaproteobacteria; | o_Pseudomonadales; | f_Pseudomonadaceae; |
| 53 | k_Bacteria; | p_Proteobacteria; | c_Gammaproteobacteria; | o_Pseudomonadales; | f_Pseudomonadaceae; |
| 54 | k_Bacteria; | p_Firmicutes; | c_Bacilli; | o_Bacillales; | f_Paenibacillaceae; |
| 55 | k_Bacteria; | p_Bacteroidetes; | c_Flavobacteriia; | o_Flavobacteriales; | f_Flavobacteriaceae; |
| 56 | k_Bacteria; | p_Proteobacteria; | c_Betaproteobacteria; | o_Burkholderiales; | f_Oxalobacteraceae; |
| 57 | k_Bacteria; | p_Firmicutes; | c_Bacilli; | o_Bacillales; | f_Paenibacillaceae; |
| 58 | k_Bacteria; | p_Proteobacteria; | c_Betaproteobacteria; | o_Burkholderiales; | f_Oxalobacteraceae; |
| 59 | k_Bacteria; | p_Firmicutes; | c_Bacilli; | o_Bacillales; | f_Paenibacillaceae; |
| 60 | k_Bacteria; | p_Proteobacteria; | c_Betaproteobacteria; | o_Burkholderiales; | f_Oxalobacteraceae; |
| 61 | k_Bacteria; | p_Firmicutes; | c_Bacilli; | o_Bacillales; | f_Paenibacillaceae; |
| 62 | k_Bacteria; | p_Proteobacteria; | c_Betaproteobacteria; | o_Neisseriales; | f_Neisseriaceae; |
| 63 | k_Bacteria; | p_Proteobacteria; | c_Betaproteobacteria; | o_Burkholderiales; | f_Oxalobacteraceae; |
| 64 | k_Bacteria; | p_Firmicutes; | c_Bacilli; | o_Bacillales; | f_Paenibacillaceae; |
| 65 | k_Bacteria; | p_Proteobacteria; | c_Betaproteobacteria; | o_Neisseriales; | f_Neisseriaceae; |
| 66 | k_Bacteria; | p_Firmicutes; | c_Bacilli; | o_Bacillales; | f_Paenibacillaceae; |
| 67 | k_Bacteria; | p_Proteobacteria; | c_Gammaproteobacteria; | o_Pseudomonadales; | f_Pseudomonadaceae; |
| 68 | k_Bacteria; | p_Proteobacteria; | c_Gammaproteobacteria; | o_Pseudomonadales; | f_Pseudomonadaceae; |
| 69 | k_Bacteria; | p_Proteobacteria; | c_Gammaproteobacteria; | o_Pseudomonadales; | f_Pseudomonadaceae; |
| 70 | k_Bacteria; | p_Proteobacteria; | c_Betaproteobacteria; | o_Neisseriales; | f_Neisseriaceae; |
| 71 | k_Bacteria; | p_Proteobacteria; | c_Gammaproteobacteria; | o_Pseudomonadales; | f_Pseudomonadaceae; |
| 72 | k_Bacteria; | p_Firmicutes; | c_Bacilli; | o_Bacillales; | f_Paenibacillaceae; |
| 73 | k_Bacteria; | p_Proteobacteria; | c_Betaproteobacteria; | o_Neisseriales; | f_Neisseriaceae |
| 74 | k_Bacteria; | p_Proteobacteria; | c_Betaproteobacteria; | o_Burkholderiales; | f_Oxalobacteraceae; |
| 75 | k_Bacteria; | p_Proteobacteria; | c_Alphaproteobacteria; | o_Sphingomonadales; | f_Sphingomonadaceae; |
| 76 | k_Bacteria; | p_Proteobacteria; | c_Betaproteobacteria; | o_Burkholderiales; | f_Comamonadaceae; |
| 77 | k_Bacteria; | p_Proteobacteria; | c_Betaproteobacteria; | o_Burkholderiales; | f_Oxalobacteraceae; |
| 78 | k_Bacteria; | p_Proteobacteria; | c_Gammaproteobacteria; | o_Aeromonadales; | f_Aeromonadaceae; |
| 79 | k_Bacteria; | p_Bacteroidetes; | c_[Saprospirae]; | o_[Saprospirales]; | f_Chitinophagaceae; |
| 80 | k_Bacteria; | p_Proteobacteria; | c_Gammaproteobacteria; | o_Xanthomonadales; | f_Sinobacteraceae; |
| 81 | k_Bacteria; | p_Firmicutes; | c_Bacilli; | o_Bacillales; | f_Paenibacillaceae; |
| 82 | k_Bacteria; | p_Firmicutes; | c_Bacilli; | o_Bacillales; | f_Paenibacillaceae; |
| 83 | k_Bacteria; | p_Proteobacteria; | c_Gammaproteobacteria; | o_Pseudomonadales; | f_Pseudomonadaceae; |
| 84 | k_Bacteria; | p_Proteobacteria; | c_Betaproteobacteria; | o_Neisseriales; | f_Neisseriaceae |
| 85 | k_Bacteria; | p_Proteobacteria; | c_Betaproteobacteria; | o_Burkholderiales; | f_Oxalobacteraceae |
| 86 | k_Bacteria; | p_Firmicutes; | c_Bacilli; | o_Bacillales; | f_Paenibacillaceae; |
| 87 | k_Bacteria; | p_Firmicutes; | c_Bacilli; | o_Bacillales; | f_Planococcaceae; |
| 88 | k_Bacteria; | p_Firmicutes; | c_Bacilli; | o_Bacillales; | f_Paenibacillaceae; |
| 89 | k_Bacteria; | p_Firmicutes; | c_Bacilli; | o_Bacillales; | f_Paenibacillaceae; |
| 90 | k_Bacteria; | p_Firmicutes; | c_Bacilli; | o_Bacillales; | f_Paenibacillaceae; |
| 91 | k_Bacteria; | p_Proteobacteria; | c_Betaproteobacteria | | |
| 92 | k_Bacteria; | p_Firmicutes; | c_Bacilli; | o_Bacillales; | f_Paenibacillaceae; |
| 93 | k_Bacteria; | p_Proteobacteria; | c_Gammaproteobacteria; | o_Aeromonadales; | f_Aeromonadaceae; |
| 94 | k_Bacteria; | p_Proteobacteria; | c_Gammaproteobacteria; | o_Legionellales; | f_; |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | |
|---|---|---|---|---|
| 95 | k_Bacteria; | p_Proteobacteria; | c_Betaproteobacteria; | o_Burkholderiales; | f_Oxalobacteraceae; |
| 96 | k_Bacteria; | p_Firmicutes; | c_Bacilli; | o_Bacillales; | f_Paenibacillaceae; |
| 97 | k_Bacteria; | p_Bacteroidetes; | c_[Saprospirae]; | o_[Saprospirales]; | f_Chitinophagaceae; |
| 98 | k_Bacteria; | p_Proteobacteria; | c_Betaproteobacteria; | o_Burkholderiales; | f_Comamonadaceae; |
| 99 | k_Bacteria; | p_Proteobacteria; | c_Betaproteobacteria; | o_Rhodocyclales; | f_Rhodocyclaceae; |
| 100 | k_Bacteria; | p_Proteobacteria; | c_Betaproteobacteria; | o_Burkholderiales; | f_Oxalobacteraceae; |
| 101 | k_Bacteria; | p_Firmicutes; | c_Bacilli; | o_Bacillales; | f_Bacillaceae; |
| 102 | k_Bacteria; | p_Firmicutes; | c_Bacilli; | o_Bacillales; | f_Paenibacillaceae; |
| 103 | k_Bacteria; | p_Proteobacteria; | c_Gammaproteobacteria; | o_Pseudomonadales; | f_Pseudomonadaceae; |
| 104 | k_Bacteria; | p_Firmicutes; | c_Bacilli; | o_Bacillales; | f_Paenibacillaceae; |
| 105 | k_Bacteria; | p_Firmicutes; | c_Bacilli; | o_Bacillales; | f_Paenibacillaceae; |
| 106 | k_Bacteria; | p_Firmicutes; | c_Clostridia; | o_Clostridiales; | f_Ruminococcaceae; |
| 107 | k_Bacteria; | p_Firmicutes; | c_Bacilli; | o_Bacillales; | f_Paenibacillaceae; |
| 108 | k_Bacteria; | p_Proteobacteria; | c_Betaproteobacteria; | o_Burkholderiales; | f_Oxalobacteraceae; |
| 109 | k_Bacteria; | p_Proteobacteria; | c_Gammaproteobacteria; | o_Xanthomonadales; | f_Sinobacteraceae; |
| 110 | k_Bacteria; | p_Firmicutes; | c_Bacilli; | o_Bacillales; | f_Bacillaceae; |
| 111 | k_Bacteria; | p_Planctomycetes; | c_Planctomycetia; | o_Gemmatales; | f_Gemmataceae; |
| 112 | k_Bacteria; | p_Firmicutes; | c_Bacilli; | o_Bacillales; | f_Paenibacillaceae; |
| 113 | k_Bacteria; | p_Proteobacteria; | c_Betaproteobacteria; | o_Rhodocyclales; | f_Rhodocyclaceae; |
| 114 | k_Bacteria; | p_Proteobacteria; | c_Betaproteobacteria; | o_Burkholderiales; | f_Oxalobacteraceae; |
| 115 | k_Bacteria; | p_Proteobacteria; | c_Gammaproteobacteria; | o_Pseudomonadales; | f_Pseudomonadaceae; |
| 116 | k_Bacteria; | p_Firmicutes; | c_Bacilli; | o_Bacillales; | f_Paenibacillaceae; |
| 117 | k_Bacteria; | p_Firmicutes; | c_Bacilli; | o_Bacillales; | f_Paenibacillaceae; |
| 118 | k_Bacteria; | p_Chlorobi; | c_OPB56; | o_; | f_; |
| 119 | k_Bacteria; | p_Proteobacteria; | c_Alphaproteobacteria; | o_Sphingomonadales; | f_Sphingomonadaceae; |
| 120 | k_Bacteria; | p_Proteobacteria; | c_Betaproteobacteria; | o_Neisseriales; | f_Neisseriaceae |
| 121 | k_Bacteria; | p_Proteobacteria; | c_Betaproteobacteria; | o_Burkholderiales; | f_Oxalobacteraceae; |
| 122 | k_Bacteria; | p_Proteobacteria; | c_Betaproteobacteria; | o_Burkholderiales; | f_Oxalobacteraceae; |
| 123 | k_Bacteria; | p_Proteobacteria; | c_Gammaproteobacteria; | o_Pseudomonadales; | f_Pseudomonadaceae; |
| 124 | k_Bacteria; | p_Firmicutes; | c_Bacilli; | o_Bacillales; | f_Bacillaceae; |
| 125 | k_Bacteria; | p_Proteobacteria; | c_Betaproteobacteria; | o_Burkholderiales; | f_Comamonadaceae; |
| 126 | k_Bacteria; | p_Proteobacteria; | c_Betaproteobacteria; | o_Burkholderiales; | f_Oxalobacteraceae; |
| 127 | k_Bacteria; | p_Proteobacteria; | c_Gammaproteobacteria; | o_Pseudomonadales; | f_Pseudomonadaceae; |
| 128 | k_Bacteria; | p_Proteobacteria; | c_Betaproteobacteria; | o_Burkholderiales; | f_Comamonadaceae; |
| 129 | k_Bacteria; | p_Firmicutes; | c_Clostridia; | o_Clostridiales; | f_Lachnospiraceae; |
| 130 | k_Bacteria; | p_Proteobacteria; | c_Betaproteobacteria; | o_Burkholderiales; | f_Oxalobacteraceae; |
| 131 | k_Bacteria; | p_Proteobacteria; | c_Betaproteobacteria; | o_Burkholderiales; | f_Oxalobacteraceae; |
| 132 | k_Bacteria; | p_Proteobacteria; | c_Betaproteobacteria; | o_Procabacteriales; | f_Procabacteriaceae |
| 133 | k_Bacteria; | p_Proteobacteria; | c_Gammaproteobacteria; | o_Pseudomonadales; | f_Pseudomonadaceae; |
| 134 | k_Bacteria; | p_Proteobacteria; | c_Betaproteobacteria; | o_Burkholderiales; | f_Oxalobacteraceae; |
| 135 | k_Bacteria; | p_Proteobacteria; | c_Betaproteobacteria; | o_Neisseriales; | f_Neisseriaceae; |
| 136 | k_Bacteria; | p_Firmicutes; | c_Bacilli; | o_Bacillales; | f_Paenibacillaceae; |
| 137 | k_Bacteria; | p_Proteobacteria; | c_Betaproteobacteria; | o_Rhodocyclales; | f_Rhodocyclaceae; |
| 138 | k_Bacteria; | p_Proteobacteria; | c_Gammaproteobacteria; | o_Pseudomonadales; | f_Pseudomonadaceae; |
| 139 | k_Bacteria; | p_Firmicutes; | c_Clostridia; | o_Clostridiales; | f_Clostridiaceae; |
| 140 | k_Bacteria; | p_Proteobacteria; | c_Betaproteobacteria; | o_Burkholderiales; | f_Comamonadaceae; |
| 141 | k_Bacteria; | p_Firmicutes; | c_Bacilli; | o_Bacillales; | f_Paenibacillaceae; |
| 142 | k_Bacteria; | p_Firmicutes; | c_Bacilli; | o_Bacillales; | f_Paenibacillaceae; |
| 143 | k_Bacteria; | p_Firmicutes; | c_Clostridia; | o_Clostridiales; | f_Veillonellaceae; |
| 144 | k_Bacteria; | p_Proteobacteria; | c_Gammaproteobacteria; | o_Pseudomonadales; | f_Moraxellaceae; |
| 145 | k_Bacteria; | p_Proteobacteria; | c_Betaproteobacteria; | o_Neisseriales; | f_Neisseriaceae; |
| 146 | k_Bacteria; | p_Proteobacteria; | c_Gammaproteobacteria; | o_Xanthomonadales; | f_Xanthomonadaceae; |
| 147 | k_Bacteria; | p_Proteobacteria; | c_Betaproteobacteria; | o_Burkholderiales; | f_Oxalobacteraceae; |
| 148 | k_Bacteria; | p_Firmicutes; | c_Bacilli; | o_Bacillales; | f_Paenibacillaceae; |
| 149 | k_Bacteria; | p_Actinobacteria; | c_Actinobacteria; | o_Actinomycetales; | f_Micrococcaceae; |
| 150 | k_Bacteria; | p_Proteobacteria; | c_Alphaproteobacteria; | o_Caulobacterales; | f_Caulobacteraceae; |
| 151 | k_Bacteria; | p_Proteobacteria; | c_Gammaproteobacteria; | o_Pseudomonadales; | f_Pseudomonadaceae; |
| 152 | k_Bacteria; | p_Proteobacteria; | c_Gammaproteobacteria; | o_Pseudomonadales; | f_Pseudomonadaceae; |
| 153 | k_Bacteria; | p_Firmicutes; | c_Bacilli; | o_Bacillales; | f_Paenibacillaceae; |
| 154 | k_Bacteria; | p_Proteobacteria; | c_Betaproteobacteria; | o_Burkholderiales; | f_Oxalobacteraceae; |
| 155 | k_Bacteria; | p_Proteobacteria; | c_Gammaproteobacteria; | o_Xanthomonadales; | f_Xanthomonadaceae; |
| 156 | k_Bacteria; | p_Firmicutes; | c_Bacilli; | o_Bacillales; | f_Planococcaceae; |
| 157 | k_Bacteria; | p_Proteobacteria; | c_Gammaproteobacteria; | o_Pseudomonadales; | f_Pseudomonadaceae; |
| 158 | k_Bacteria; | p_Firmicutes; | c_Clostridia; | o_Clostridiales; | f_Veillonellaceae; |
| 159 | k_Bacteria; | p_Proteobacteria; | c_Betaproteobacteria; | o_Burkholderiales; | f_Comamonadaceae; |
| 160 | k_Bacteria; | p_Proteobacteria; | c_Alphaproteobacteria; | o_Rhizobiales; | f_Bradyrhizobiaceae; |
| 161 | k_Bacteria; | p_Proteobacteria; | c_Gammaproteobacteria; | o_Pseudomonadales; | f_Pseudomonadaceae; |
| 162 | k_Bacteria; | p_Actinobacteria; | c_Actinobacteria; | o_Actinomycetales; | f_Streptomycetaceae; |
| 163 | k_Bacteria; | p_Firmicutes; | c_Bacilli; | o_Bacillales; | f_Bacillaceae; |
| 164 | k_Bacteria; | p_Proteobacteria; | c_Alphaproteobacteria; | o_Caulobacterales; | f_Caulobacteraceae; |
| 165 | k_Bacteria; | p_Firmicutes; | c_Clostridia; | o_Clostridiales; | f_Lachnospiraceae; |
| 166 | k_Bacteria; | p_Firmicutes; | c_Bacilli; | o_Bacillales; | f_Bacillaceae; |
| 167 | k_Bacteria; | p_Proteobacteria; | c_Betaproteobacteria; | o_Neisseriales; | f_Neisseriaceae; |
| 168 | k_Bacteria; | p_Proteobacteria; | c_Gammaproteobacteria; | o_Pseudomonadales; | f_Pseudomonadaceae; |
| 169 | k_Bacteria; | p_Proteobacteria; | c_Gammaproteobacteria; | o_Pseudomonadales; | f_Moraxellaceae; |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | |
|---|---|---|---|---|
| 170 | k_Bacteria; | p_Proteobacteria; | c_Betaproteobacteria; | o_Burkholderiales; | f_Oxalobacteraceae; |
| 171 | k_Bacteria; | p_Firmicutes; | c_Bacilli; | o_Bacillales; | f_Paenibacillaceae; |
| 172 | k_Bacteria; | p_Proteobacteria; | c_Gammaproteobacteria; | o_Enterobacteriales; | f_Enterobacteriaceae; |
| 173 | k_Bacteria; | p_Proteobacteria; | c_Gammaproteobacteria; | o_Enterobacteriales; | f_Enterobacteriaceae; |
| 174 | k_Bacteria; | p_Proteobacteria; | c_Betaproteobacteria; | o_Burkholderiales; | f_Oxalobacteraceae; |
| 175 | k_Bacteria; | p_Acidobacteria; | c_Holophagae; | o_Holophagales; | f_Holophagaceae; |
| 176 | k_Bacteria; | p_Proteobacteria; | c_Gammaproteobacteria; | o_Pseudomonadales; | f_Pseudomonadaceae; |
| 177 | k_Bacteria; | p_Proteobacteria; | c_Betaproteobacteria; | o_Burkholderiales; | f_Comamonadaceae; |
| 178 | k_Bacteria; | p_Proteobacteria; | c_Gammaproteobacteria; | o_Pseudomonadales; | f_Pseudomonadaceae; |
| 179 | k_Bacteria; | p_Proteobacteria; | c_Gammaproteobacteria; | o_Pseudomonadales; | f_Pseudomonadaceae; |
| 180 | k_Bacteria; | p_Firmicutes; | c_Bacilli; | o_Bacillales; | f_Bacillaceae; |
| 181 | k_Bacteria; | p_Proteobacteria; | c_Gammaproteobacteria; | o_Pseudomonadales; | f_Pseudomonadaceae; |
| 182 | k_Bacteria; | p_Firmicutes; | c_Bacilli; | o_Bacillales; | f_Paenibacillaceae; |
| 183 | k_Bacteria; | p_Proteobacteria; | c_Gammaproteobacteria; | o_Pseudomonadales; | f_Pseudomonadaceae; |
| 184 | k_Bacteria; | p_Proteobacteria; | c_Betaproteobacteria; | o_Rhodocyclales; | f_Rhodocyclaceae; |
| 185 | k_Bacteria; | p_Proteobacteria; | c_Gammaproteobacteria; | o_Pseudomonadales; | f_Pseudomonadaceae; |
| 186 | k_Bacteria; | p_Firmicutes; | c_Bacilli; | o_Bacillales; | f_Paenibacillaceae; |
| 187 | k_Bacteria; | p_Firmicutes; | c_Bacilli; | o_Bacillales; | f_Paenibacillaceae; |
| 188 | k_Bacteria; | p_Firmicutes; | c_Bacilli; | o_Bacillales; | f_Bacillaceae; |
| 189 | k_Bacteria; | p_Proteobacteria; | c_Betaproteobacteria; | o_Rhodocyclales; | f_Rhodocyclaceae; |
| 190 | k_Bacteria; | p_Proteobacteria; | c_Gammaproteobacteria; | o_Pseudomonadales; | f_Pseudomonadaceae; |
| 191 | k_Bacteria; | p_Proteobacteria; | c_Gammaproteobacteria; | o_Pseudomonadales; | f_Pseudomonadaceae; |
| 192 | k_Bacteria; | p_Proteobacteria; | c_Gammaproteobacteria; | o_Pseudomonadales; | f_Pseudomonadaceae; |
| 193 | k_Bacteria; | p_Firmicutes; | c_Bacilli; | o_Bacillales; | f_Paenibacillaceae; |
| 194 | k_Bacteria; | p_Proteobacteria; | c_Betaproteobacteria; | o_Burkholderiales; | f_Oxalobacteraceae; |
| 195 | k_Bacteria; | p_Proteobacteria; | c_Gammaproteobacteria; | o_Pseudomonadales; | f_Pseudomonadaceae; |
| 196 | k_Bacteria; | p_Proteobacteria; | c_Alphaproteobacteria; | o_Sphingomonadales; | f_Sphingomonadaceae; |
| 197 | k_Bacteria; | p_Firmicutes; | c_Bacilli; | o_Bacillales; | f_Paenibacillaceae; |
| 198 | k_Bacteria; | p_Proteobacteria; | c_Gammaproteobacteria; | o_Pseudomonadales; | f_Pseudomonadaceae; |
| 199 | k_Bacteria; | p_Firmicutes; | c_Bacilli; | o_Bacillales; | f_Bacillaceae; |
| 200 | k_Bacteria; | p_Chlorobi; | c_OPB56; | o_; | f_; |
| 201 | k_Bacteria; | p_Proteobacteria; | c_Gammaproteobacteria; | o_Pseudomonadales; | f_Pseudomonadaceae; |
| 202 | k_Bacteria; | p_Proteobacteria; | c_Gammaproteobacteria; | o_Pseudomonadales; | f_Pseudomonadaceae; |
| 203 | k_Bacteria; | p_Proteobacteria; | c_Betaproteobacteria; | o_Burkholderiales; | f_Oxalobacteraceae; |
| 204 | k_Bacteria; | p_Proteobacteria; | c_Gammaproteobacteria; | o_Pseudomonadales; | f_Pseudomonadaceae; |
| 205 | k_Bacteria; | p_Proteobacteria; | c_Betaproteobacteria; | o_Burkholderiales; | f_Oxalobacteraceae; |
| 206 | k_Bacteria; | p_Firmicutes; | c_Bacilli; | o_Bacillales; | f_Bacillaceae; |
| 207 | k_Bacteria; | p_Proteobacteria; | c_Alphaproteobacteria; | o_Rhodospirillales; | f_Rhodospirillaceae; |
| 208 | k_Bacteria; | p_Proteobacteria; | c_Gammaproteobacteria; | o_Enterobacteriales; | f_Enterobacteriaceae; |
| 209 | k_Bacteria; | p_Proteobacteria; | c_Betaproteobacteria; | o_Burkholderiales; | f_Oxalobacteraceae; |
| 210 | k_Bacteria; | p_Proteobacteria; | c_Gammaproteobacteria; | o_Pseudomonadales; | f_Pseudomonadaceae; |
| 211 | k_Bacteria; | p_Firmicutes; | c_Bacilli; | o_Bacillales; | f_Paenibacillaceae; |
| 212 | k_Bacteria; | p_Proteobacteria; | c_Gammaproteobacteria; | o_Pseudomonadales; | f_Pseudomonadaceae; |
| 213 | k_Bacteria; | p_Proteobacteria; | c_Gammaproteobacteria; | o_Pseudomonadales; | f_Pseudomonadaceae; |
| 214 | k_Bacteria; | p_Proteobacteria; | c_Gammaproteobacteria; | o_Pseudomonadales; | f_Pseudomonadaceae; |
| 215 | k_Bacteria; | p_Proteobacteria; | c_Gammaproteobacteria; | o_Pseudomonadales; | f_Pseudomonadaceae; |
| 216 | k_Bacteria; | p_Bacteroidetes; | c_[Saprospirae]; | o_[Saprospirales]; | f_Chitinophagaceae; |
| 217 | k_Bacteria; | p_Proteobacteria; | c_Gammaproteobacteria; | o_Pseudomonadales; | f_Pseudomonadaceae; |
| 218 | k_Bacteria; | p_Firmicutes; | c_Bacilli; | o_Bacillales; | f_Bacillaceae; |
| 219 | k_Bacteria; | p_Proteobacteria; | c_Gammaproteobacteria; | o_Pseudomonadales; | f_Pseudomonadaceae; |
| 220 | k_Bacteria; | p_Proteobacteria; | c_Gammaproteobacteria; | o_Aeromonadales; | f_Aeromonadaceae; |
| 221 | k_Bacteria; | p_Proteobacteria; | c_Gammaproteobacteria; | o_Pseudomonadales; | f_Pseudomonadaceae; |
| 222 | k_Bacteria; | p_Proteobacteria; | c_Gammaproteobacteria; | o_Pseudomonadales; | f_Pseudomonadaceae; |
| 223 | k_Bacteria; | p_Bacteroidetes; | c_[Saprospirae]; | o_[Saprospirales]; | f_Chitinophagaceae; |
| 224 | k_Bacteria; | p_Proteobacteria; | c_Gammaproteobacteria; | o_Pseudomonadales; | f_Pseudomonadaceae; |
| 225 | k_Bacteria; | p_Proteobacteria; | c_Betaproteobacteria; | o_Burkholderiales; | f_Oxalobacteraceae; |
| 226 | k_Bacteria; | p_Firmicutes; | c_Bacilli; | o_Bacillales; | f_Bacillaceae; |
| 227 | k_Bacteria; | p_Proteobacteria; | c_Alphaproteobacteria; | o_Caulobacterales; | f_Caulobacteraceae; |
| 228 | k_Bacteria; | p_Proteobacteria; | c_Gammaproteobacteria; | o_Pseudomonadales; | f_Pseudomonadaceae; |
| 229 | k_Bacteria; | p_Firmicutes; | c_Bacilli; | o_Bacillales; | f_Planococcaceae; |
| 230 | k_Bacteria; | p_Proteobacteria; | c_Gammaproteobacteria; | o_Pseudomonadales; | f_Pseudomonadaceae; |
| 231 | k_Bacteria; | p_Proteobacteria; | c_Betaproteobacteria; | o_Burkholderiales; | f_Oxalobacteraceae; |
| 232 | k_Bacteria; | p_Proteobacteria; | c_Betaproteobacteria; | o_Burkholderiales; | f_Comamonadaceae; |
| 233 | k_Bacteria; | p_Proteobacteria; | c_Betaproteobacteria; | o_Burkholderiales; | f_Oxalobacteraceae |
| 234 | k_Bacteria; | p_Proteobacteria; | c_Gammaproteobacteria; | o_Xanthomonadales; | f_Xanthomonadaceae |
| 235 | k_Bacteria; | p_Firmicutes; | c_Bacilli; | o_Bacillales; | f_Planococcaceae; |
| 236 | k_Bacteria; | p_Proteobacteria; | c_Betaproteobacteria; | o_Burkholderiales; | f_Comamonadaceae; |
| 237 | k_Bacteria; | p_Firmicutes; | c_Bacilli; | o_Bacillales; | f_Planococcaceae; |
| 238 | k_Bacteria; | p_Proteobacteria; | c_Gammaproteobacteria; | o_Pseudomonadales; | f_Pseudomonadaceae; |
| 239 | k_Bacteria; | p_Proteobacteria; | c_Gammaproteobacteria; | o_Pseudomonadales; | f_Pseudomonadaceae; |
| 240 | k_Bacteria; | p_Proteobacteria; | c_Alphaproteobacteria; | o_Rhodospirillales; | f_Rhodospirillaceae; |
| 241 | k_Bacteria; | p_Proteobacteria; | c_Deltaproteobacteria; | o_Syntrophobacterales; | f_Syntrophobacteraceae; |
| 242 | k_Bacteria; | p_Proteobacteria; | c_Gammaproteobacteria; | o_Pseudomonadales; | f_Pseudomonadaceae; |
| 243 | k_Bacteria; | p_Proteobacteria; | c_Betaproteobacteria; | o_Burkholderiales; | f_Oxalobacteraceae; |
| 244 | k_Bacteria; | p_Proteobacteria; | c_Alphaproteobacteria; | o_Rhodospirillales; | f_Rhodospirillaceae; |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | |
|---|---|---|---|---|---|
| 245 | k_Bacteria; | p_Firmicutes; | c_Bacilli; | o_Bacillales; | f_Bacillaceae; |
| 246 | k_Bacteria; | p_Proteobacteria; | c_Gammaproteobacteria; | o_Enterobacteriales; | f_Enterobacteriaceae; |
| 247 | k_Bacteria; | p_Firmicutes; | c_Bacilli; | o_Bacillales; | f_Bacillaceae; |
| 248 | k_Bacteria; | p_Proteobacteria; | c_Gammaproteobacteria; | o_Pseudomonadales; | f_Pseudomonadaceae; |
| 249 | k_Bacteria; | p_Firmicutes; | c_Bacilli; | o_Bacillales; | f_Bacillaceae; |
| 250 | k_Bacteria; | p_Firmicutes; | c_Bacilli; | o_Bacillales; | f_Bacillaceae; |
| 251 | k_Bacteria; | p_Proteobacteria; | c_Gammaproteobacteria; | o_Pseudomonadales; | f_Pseudomonadaceae; |
| 252 | k_Bacteria; | p_Proteobacteria; | c_Gammaproteobacteria; | o_Enterobacteriales; | f_Enterobacteriaceae; |
| 253 | k_Bacteria; | p_Proteobacteria; | c_Betaproteobacteria; | o_Burkholderiales; | f_Comamonadaceae; |
| 254 | k_Bacteria; | p_Proteobacteria; | c_Gammaproteobacteria; | o_Pseudomonadales; | f_Pseudomonadaceae; |
| 255 | k_Bacteria; | p_Proteobacteria; | c_Gammaproteobacteria; | o_Pseudomonadales; | f_Pseudomonadaceae; |
| 256 | k_Bacteria; | p_Firmicutes; | c_Bacilli; | o_Bacillales; | f_Paenibacillaceae; |
| 257 | k_Bacteria; | p_Firmicutes; | c_Bacilli; | o_Bacillales; | f_Bacillaceae; |
| 258 | k_Bacteria; | p_Proteobacteria; | c_Betaproteobacteria; | o_Neisseriales; | f_Neisseriaceae |
| 259 | k_Bacteria; | p_Proteobacteria; | c_Gammaproteobacteria; | o_Pseudomonadales; | f_Pseudomonadaceae; |
| 260 | k_Bacteria; | p_Firmicutes; | c_Bacilli; | o_Bacillales; | f_Paenibacillaceae; |
| 261 | k_Bacteria; | p_Proteobacteria; | c_Gammaproteobacteria; | o_Pseudomonadales; | f_Pseudomonadaceae; |
| 262 | k_Bacteria; | p_Firmicutes; | c_Bacilli; | o_Bacillales; | f_Paenibacillaceae; |
| 263 | k_Bacteria; | p_Proteobacteria; | c_Gammaproteobacteria; | o_Enterobacteriales; | f_Enterobacteriaceae; |
| 264 | k_Bacteria; | p_Firmicutes; | c_Bacilli; | o_Bacillales; | f_Bacillaceae; |
| 265 | k_Bacteria; | p_Proteobacteria; | c_Gammaproteobacteria; | o_Pseudomonadales; | f_Pseudomonadaceae; |
| 266 | k_Bacteria; | p_Firmicutes; | c_Bacilli; | o_Bacillales; | f_Paenibacillaceae; |
| 267 | k_Bacteria; | p_Proteobacteria; | c_Betaproteobacteria; | o_Procabacteriales; | f_Procabacteriaceae; |
| 268 | k_Bacteria; | p_Bacteroidetes; | c_Cytophagia; | o_Cytophagales; | f_Cytophagaceae; |
| 269 | k_Bacteria; | p_Proteobacteria; | c_Gammaproteobacteria; | o_Pseudomonadales; | f_Pseudomonadaceae; |
| 270 | k_Bacteria; | p_Proteobacteria; | c_Gammaproteobacteria; | o_Pseudomonadales; | f_Pseudomonadaceae; |
| 271 | k_Bacteria; | p_Proteobacteria; | c_Gammaproteobacteria; | o_Pseudomonadales; | f_Pseudomonadaceae; |
| 272 | k_Bacteria; | p_Proteobacteria; | c_Gammaproteobacteria; | o_Enterobacteriales; | f_Enterobacteriaceae; |
| 273 | k_Bacteria; | p_Proteobacteria; | c_Betaproteobacteria; | o_Burkholderiales; | f_Oxalobacteraceae; |
| 274 | k_Bacteria; | p_Firmicutes; | c_Bacilli; | o_Bacillales; | f_Bacillaceae; |
| 275 | k_Bacteria; | p_Proteobacteria; | c_Betaproteobacteria; | o_Rhodocyclales; | f_Rhodocyclaceae; |
| 276 | k_Bacteria; | p_Proteobacteria; | c_Betaproteobacteria; | o_Neisseriales; | f_Neisseriaceae |
| 277 | k_Bacteria; | p_Proteobacteria; | c_Betaproteobacteria; | o_Burkholderiales; | f_Oxalobacteraceae; |
| 278 | k_Bacteria; | p_Verrucomicrobia; | c_Opitutae; | o_Opitutales; | f_Opitutaceae; |
| 279 | k_Bacteria; | p_Proteobacteria; | c_Betaproteobacteria; | o_Burkholderiales; | f_Oxalobacteraceae; |
| 280 | k_Bacteria; | p_Firmicutes; | c_Clostridia; | o_Clostridiales; | f_Lachnospiraceae; |
| 281 | k_Bacteria; | p_Proteobacteria; | c_Gammaproteobacteria; | o_Pseudomonadales; | f_Pseudomonadaceae; |
| 282 | k_Bacteria; | p_Proteobacteria; | c_Gammaproteobacteria; | o_Pseudomonadales; | f_Pseudomonadaceae; |
| 283 | k_Bacteria; | p_Proteobacteria; | c_Gammaproteobacteria; | o_Pseudomonadales; | f_Pseudomonadaceae; |
| 284 | k_Bacteria; | p_Proteobacteria; | c_Gammaproteobacteria; | o_Pseudomonadales; | f_Pseudomonadaceae; |
| 285 | k_Bacteria; | p_Firmicutes; | c_Bacilli; | o_Bacillales; | f_Bacillaceae; |
| 286 | k_Bacteria; | p_Proteobacteria; | c_Alphaproteobacteria; | o_Rhizobiales; | f_Hyphomicrobiaceae; |
| 287 | k_Bacteria; | p_Proteobacteria; | c_Betaproteobacteria; | o_Burkholderiales; | f_Oxalobacteraceae; |
| 288 | k_Bacteria; | p_Firmicutes; | c_Clostridia; | o_Clostridiales; | f_Veillonellaceae; |
| 289 | k_Bacteria; | p_Proteobacteria; | c_Gammaproteobacteria; | o_Enterobacteriales; | f_Enterobacteriaceae |
| 290 | k_Bacteria; | p_Proteobacteria; | c_Gammaproteobacteria; | o_Pseudomonadales; | f_Moraxellaceae; |
| 291 | k_Bacteria; | p_Proteobacteria; | c_Betaproteobacteria; | o_Burkholderiales; | f_Oxalobacteraceae |
| 292 | k_Bacteria; | p_Proteobacteria; | c_Betaproteobacteria; | o_Burkholderiales; | f_Oxalobacteraceae; |
| 293 | k_Bacteria; | p_Proteobacteria; | c_Gammaproteobacteria; | o_Enterobacteriales; | f_Enterobacteriaceae; |
| 294 | k_Bacteria; | p_Proteobacteria; | c_Gammaproteobacteria; | o_Pseudomonadales; | f_Pseudomonadaceae; |
| 295 | k_Bacteria; | p_Proteobacteria; | c_Gammaproteobacteria; | o_Pseudomonadales; | f_Pseudomonadaceae; |
| 296 | k_Bacteria; | p_Proteobacteria; | c_Gammaproteobacteria; | o_Pseudomonadales; | f_Pseudomonadaceae; |
| 297 | k_Bacteria; | p_Proteobacteria; | c_Gammaproteobacteria; | o_Xanthomonadales; | f_Xanthomonadaceae; |
| 298 | k_Bacteria; | p_Firmicutes; | c_Bacilli; | o_Bacillales; | f_Bacillaceae; |
| 299 | k_Bacteria; | p_Proteobacteria; | c_Gammaproteobacteria; | o_Aeromonadales; | f_Aeromonadaceae; |
| 300 | k_Bacteria; | p_Proteobacteria; | c_Gammaproteobacteria; | o_Pseudomonadales; | f_Pseudomonadaceae; |
| 301 | k_Bacteria; | p_Firmicutes; | c_Bacilli; | o_Bacillales; | f_Bacillaceae; |
| 302 | k_Bacteria; | p_Firmicutes; | c_Bacilli; | o_Bacillales; | f_Bacillaceae; |
| 303 | k_Bacteria; | p_Firmicutes; | c_Bacilli; | o_Bacillales; | f_Paenibacillaceae; |
| 304 | k_Bacteria; | p_Firmicutes; | c_Bacilli; | o_Bacillales; | f_Bacillaceae; |
| 305 | k_Bacteria; | p_Proteobacteria; | c_Gammaproteobacteria; | o_Pseudomonadales; | f_Pseudomonadaceae; |
| 306 | k_Bacteria; | p_Proteobacteria; | c_Betaproteobacteria; | o_Burkholderiales; | f_Oxalobacteraceae |
| 307 | k_Bacteria; | p_Proteobacteria; | c_Gammaproteobacteria; | o_Pseudomonadales; | f_Pseudomonadaceae; |
| 308 | k_Bacteria; | p_Proteobacteria; | c_Betaproteobacteria; | o_Burkholderiales; | f_Oxalobacteraceae; |
| 309 | k_Bacteria; | p_Proteobacteria; | c_Gammaproteobacteria; | o_Enterobacteriales; | f_Enterobacteriaceae; |
| 310 | k_Bacteria; | p_Firmicutes; | c_Bacilli; | o_Bacillales; | f_Bacillaceae; |
| 311 | k_Bacteria; | p_Proteobacteria; | c_Gammaproteobacteria; | o_Enterobacteriales; | f_Enterobacteriaceae; |
| 312 | k_Bacteria; | p_Proteobacteria; | c_Gammaproteobacteria; | o_Pseudomonadales; | f_Moraxellaceae; |
| 313 | k_Bacteria; | p_Bacteroidetes; | c_Flavobacteriia; | o_Flavobacteriales; | f_[Weeksellaceae]; |
| 314 | k_Bacteria; | p_Firmicutes; | c_Bacilli; | o_Bacillales; | f_Bacillaceae; |
| 315 | k_Bacteria; | p_Proteobacteria; | c_Betaproteobacteria; | o_Neisseriales; | f_Neisseriaceae; |
| 316 | k_Bacteria; | p_Bacteroidetes; | c_Bacteroidia; | o_Bacteroidales; | f_Porphyromonadaceae; |
| 317 | k_Bacteria; | p_Firmicutes; | c_Bacilli; | o_Bacillales; | f_Bacillaceae; |
| 318 | k_Bacteria; | p_Proteobacteria; | c_Betaproteobacteria; | o_Burkholderiales; | f_Comamonadaceae; |
| 319 | k_Bacteria; | p_Proteobacteria; | c_Betaproteobacteria; | o_Burkholderiales; | f_Comamonadaceae; |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | |
|---|---|---|---|---|
| 320 | k_Bacteria; | p_Proteobacteria; | c_Betaproteobacteria; | o_Burkholderiales; | f_Oxalobacteraceae; |
| 321 | k_Bacteria; | p_Proteobacteria; | c_Betaproteobacteria; | o_Burkholderiales; | f_Comamonadaceae; |
| 322 | k_Bacteria; | p_Proteobacteria; | c_Alphaproteobacteria; | o_Sphingomonadales; | f_Sphingomonadaceae; |
| 323 | k_Bacteria; | p_Proteobacteria; | c_Gammaproteobacteria; | o_Enterobacteriales; | f_Enterobacteriaceae; |
| 324 | k_Bacteria; | p_Proteobacteria; | c_Betaproteobacteria; | o_Burkholderiales; | f_Oxalobacteraceae; |
| 325 | k_Bacteria; | p_Bacteroidetes; | c_[Saprospirae]; | o_[Saprospirales]; | f_Chitinophagaceae; |
| 326 | k_Bacteria; | p_Proteobacteria; | c_Betaproteobacteria; | o_Burkholderiales; | f_Comamonadaceae; |
| 327 | k_Bacteria; | p_Proteobacteria; | c_Betaproteobacteria; | o_; | f_; |
| 328 | k_Bacteria; | p_Proteobacteria; | c_Betaproteobacteria; | o_Burkholderiales; | f_Oxalobacteraceae; |
| 329 | k_Bacteria; | p_Proteobacteria; | c_Betaproteobacteria; | o_Burkholderiales; | f_Comamonadaceae; |
| 330 | k_Bacteria; | p_Proteobacteria; | c_Betaproteobacteria; | o_Burkholderiales; | f_Oxalobacteraceae; |
| 331 | k_Bacteria; | p_Firmicutes; | c_Bacilli; | o_Bacillales; | f_Bacillaceae; |
| 332 | k_Bacteria; | p_Proteobacteria; | c_Alphaproteobacteria; | o_Rhodospirillales; | f_Rhodospirillaceae; |
| 333 | k_Bacteria; | p_Proteobacteria; | c_Alphaproteobacteria; | o_Rhodobacterales; | f_Hyphomonadaceae; |
| 334 | k_Bacteria; | p_Proteobacteria; | c_Betaproteobacteria; | o_Burkholderiales; | f_Comamonadaceae; |
| 335 | k_Bacteria; | p_Proteobacteria; | c_Gammaproteobacteria; | o_Pseudomonadales; | f_Pseudomonadaceae; |
| 336 | k_Bacteria; | p_Proteobacteria; | c_Alphaproteobacteria; | o_Sphingomonadales; | f_Sphingomonadaceae; |
| 337 | k_Bacteria; | p_Proteobacteria; | c_Betaproteobacteria; | o_Neisseriales; | f_Neisseriaceae; |
| 338 | k_Bacteria; | p_Proteobacteria; | c_Gammaproteobacteria; | o_Pseudomonadales; | f_Pseudomonadaceae; |
| 339 | k_Bacteria; | p_Firmicutes; | c_Bacilli; | o_Bacillales; | f_Bacillaceae; |
| 340 | k_Bacteria; | p_Firmicutes; | c_Bacilli; | o_Bacillales; | f_Paenibacillaceae; |
| 341 | k_Bacteria; | p_Proteobacteria; | c_Alphaproteobacteria; | o_Sphingomonadales; | f_Sphingomonadaceae; |
| 342 | k_Bacteria; | p_Firmicutes; | c_Bacilli; | o_Bacillales; | f_Bacillaceae; |
| 343 | k_Bacteria; | p_Firmicutes; | c_Bacilli; | o_Bacillales; | f_Bacillaceae; |
| 344 | k_Bacteria; | p_Proteobacteria; | c_Gammaproteobacteria; | o_Enterobacteriales; | f_Enterobacteriaceae; |
| 345 | k_Bacteria; | p_Proteobacteria; | c_Alphaproteobacteria; | o_Rhodospirillales; | f_Rhodospirillaceae; |
| 346 | k_Bacteria; | p_Actinobacteria; | c_Actinobacteria; | o_Actinomycetales; | f_Micrococcaceae; |
| 347 | k_Bacteria; | p_Proteobacteria; | c_Betaproteobacteria; | o_Burkholderiales; | f_Comamonadaceae; |
| 348 | k_Bacteria; | p_Proteobacteria; | c_Gammaproteobacteria; | o_Pseudomonadales; | f_Pseudomonadaceae; |
| 349 | k_Bacteria; | p_Firmicutes; | c_Clostridia; | o_Clostridiales; | f_Clostridiaceae; |
| 350 | k_Bacteria; | p_Firmicutes; | c_Bacilli; | o_Bacillales; | f_Bacillaceae; |
| 351 | k_Bacteria; | p_Proteobacteria; | c_Gammaproteobacteria; | o_Pseudomonadales; | f_Pseudomonadaceae; |
| 352 | k_Bacteria; | p_Proteobacteria; | c_Alphaproteobacteria; | o_Rhodospirillales; | f_Rhodospirillaceae; |
| 353 | k_Bacteria; | p_Proteobacteria; | c_Gammaproteobacteria; | o_Aeromonadales; | f_Aeromonadaceae; |
| 354 | k_Bacteria; | p_Proteobacteria; | c_Gammaproteobacteria; | o_Pseudomonadales; | f_Pseudomonadaceae; |
| 355 | k_Bacteria; | p_Proteobacteria; | c_Gammaproteobacteria; | o_Aeromonadales; | f_Aeromonadaceae; |
| 356 | k_Bacteria; | p_Proteobacteria; | c_Gammaproteobacteria; | o_Pseudomonadales; | f_Pseudomonadaceae; |
| 357 | k_Bacteria; | p_Firmicutes; | c_Bacilli; | o_Bacillales; | f_Planococcaceae; |
| 358 | k_Bacteria; | p_Firmicutes; | c_Bacilli; | o_Bacillales; | f_Bacillaceae; |
| 359 | k_Bacteria; | p_Bacteroidetes; | c_Flavobacteriia; | o_Flavobacteriales; | f_[Weeksellaceae]; |
| 360 | k_Bacteria; | p_Actinobacteria; | c_Actinobacteria; | o_Actinomycetales; | f_Micrococcaceae; |
| 361 | k_Bacteria; | p_Firmicutes; | c_Bacilli; | o_Bacillales; | f_Bacillaceae; |
| 362 | k_Bacteria; | p_Proteobacteria; | c_Gammaproteobacteria; | o_Pseudomonadales; | f_Pseudomonadaceae; |
| 363 | k_Bacteria; | p_Proteobacteria; | c_Gammaproteobacteria; | o_Enterobacteriales; | f_Enterobacteriaceae; |
| 364 | k_Bacteria; | p_Proteobacteria; | c_Alphaproteobacteria; | o_Sphingomonadales; | f_Sphingomonadaceae; |
| 365 | k_Bacteria; | p_Proteobacteria; | c_Gammaproteobacteria; | o_Enterobacteriales; | f_Enterobacteriaceae; |
| 366 | k_Bacteria; | p_Proteobacteria; | c_Gammaproteobacteria; | o_Pseudomonadales; | f_Pseudomonadaceae; |
| 367 | k_Bacteria; | p_Proteobacteria; | c_Gammaproteobacteria; | o_Enterobacteriales; | f_Enterobacteriaceae; |
| 368 | k_Bacteria; | p_WPS-2; | c_; | o_; | f_; |
| 369 | k_Bacteria; | p_Proteobacteria; | c_Gammaproteobacteria; | o_Pseudomonadales; | f_Pseudomonadaceae; |
| 370 | k_Bacteria; | p_Firmicutes; | c_Bacilli; | o_Bacillales; | f_Bacillaceae; |
| 371 | k_Bacteria; | p_Firmicutes; | c_Bacilli; | o_Bacillales; | f_Bacillaceae; |
| 372 | k_Bacteria; | p_Proteobacteria; | c_Gammaproteobacteria; | o_Xanthomonadales; | f_Xanthomonadaceae; |
| 373 | k_Bacteria; | p_Firmicutes; | c_Bacilli; | o_Bacillales; | f_Bacillaceae; |
| 374 | k_Bacteria; | p_Proteobacteria; | c_Gammaproteobacteria; | o_Pseudomonadales; | f_Pseudomonadaceae; |
| 375 | k_Bacteria; | p_Proteobacteria; | c_Gammaproteobacteria; | o_Pseudomonadales; | f_Pseudomonadaceae; |
| 376 | k_Bacteria; | p_Proteobacteria; | c_Gammaproteobacteria; | o_Enterobacteriales; | f_Enterobacteriaceae; |
| 377 | k_Bacteria; | p_Proteobacteria; | c_Gammaproteobacteria; | o_Pseudomonadales; | f_Pseudomonadaceae; |
| 378 | k_Bacteria; | p_Proteobacteria; | c_Betaproteobacteria; | o_Burkholderiales; | f_Oxalobacteraceae; |
| 379 | k_Bacteria; | p_Proteobacteria; | c_Betaproteobacteria; | o_Burkholderiales; | f_Oxalobacteraceae; |
| 380 | k_Bacteria; | p_Proteobacteria; | c_Betaproteobacteria; | o_Burkholderiales; | f_Oxalobacteraceae; |
| 381 | k_Bacteria; | p_Actinobacteria; | c_Actinobacteria; | o_Actinomycetales; | f_Micrococcaceae; |
| 382 | k_Bacteria; | p_Proteobacteria; | c_Alphaproteobacteria; | o_Rhizobiales; | f_Bradyrhizobiaceae; |
| 383 | k_Bacteria; | p_Firmicutes; | c_Clostridia; | o_Clostridiales; | f_Ruminococcaceae; |
| 384 | k_Bacteria; | p_Proteobacteria; | c_Gammaproteobacteria; | o_Aeromonadales; | f_Aeromonadaceae; |
| 385 | k_Bacteria; | p_Proteobacteria; | c_Gammaproteobacteria; | o_Pseudomonadales; | f_Pseudomonadaceae; |
| 386 | k_Bacteria; | p_Proteobacteria; | c_Gammaproteobacteria; | o_Aeromonadales; | f_Aeromonadaceae; |
| 387 | k_Bacteria; | p_Proteobacteria; | c_Gammaproteobacteria; | o_Pseudomonadales; | f_Pseudomonadaceae; |
| 388 | k_Bacteria; | p_Proteobacteria; | c_Gammaproteobacteria; | o_Aeromonadales; | f_Aeromonadaceae; |
| 389 | k_Bacteria; | p_Proteobacteria; | c_Gammaproteobacteria; | o_Aeromonadales; | f_Aeromonadaceae; |
| 390 | k_Bacteria; | p_Proteobacteria; | c_Gammaproteobacteria; | o_Aeromonadales; | f_Aeromonadaceae; |
| 391 | k_Bacteria; | p_Proteobacteria; | c_Gammaproteobacteria; | o_Pseudomonadales; | f_Moraxellaceae; |
| 392 | k_Bacteria; | p_Firmicutes; | c_Bacilli; | o_Bacillales; | f_Paenibacillaceae; |
| 393 | k_Bacteria; | p_Proteobacteria; | c_Alphaproteobacteria; | o_Caulobacterales; | f_Caulobacteraceae; |
| 394 | k_Bacteria; | p_Proteobacteria; | c_Gammaproteobacteria; | o_Pseudomonadales; | f_Pseudomonadaceae; |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| 395 | k_Bacteria; | p_Proteobacteria; | c_Gammaproteobacteria; | o_Enterobacteriales; | f_Enterobacteriaceae; |
| 396 | k_Bacteria; | p_Proteobacteria; | c_Gammaproteobacteria; | o_Pseudomonadales; | f_Pseudomonadaceae; |
| 397 | k_Bacteria; | p_Proteobacteria; | c_Gammaproteobacteria; | o_Xanthomonadales; | f_Xanthomonadaceae; |
| 398 | k_Bacteria; | p_Firmicutes; | c_Clostridia; | o_Clostridiales; | f_Lachnospiraceae; |
| 399 | k_Bacteria; | p_Proteobacteria; | c_Gammaproteobacteria; | o_Enterobacteriales; | f_Enterobacteriaceae; |

| | Column Number | | | | |
| --- | --- | --- | --- | --- | --- |
| Row Number | 6 genus | 7 species | 8 OTU | 9 anaerobic MPN | 10 anaerobic MPN upper bound (95% confidence) |
| 1 | | | New.CleanUp.ReferenceOTU1006 | 0.096 | 0.685 |
| 2 | | | New.CleanUp.ReferenceOTU1022 | 0.096 | 0.685 |
| 3 | g_Pseudomonas; | s_ | New.CleanUp.ReferenceOTU1029 | NA | NA |
| 4 | | | New.CleanUp.ReferenceOTU1031 | 0.292 | 0.906 |
| 5 | g_Cupriavidus; | s_ | New.CleanUp.ReferenceOTU1035 | NA | NA |
| 6 | | | New.CleanUp.ReferenceOTU104 | 0.096 | 0.685 |
| 7 | g_Paenibacillus; | s_ | New.CleanUp.ReferenceOTU1042 | 0.291 | 0.904 |
| 8 | g_Paenibacillus; | s_ | New.CleanUp.ReferenceOTU1063 | 0.096 | 0.685 |
| 9 | g_Paenibacillus; | s_ | New.CleanUp.ReferenceOTU1073 | 0.096 | 0.685 |
| 10 | g_Paenibacillus; | s_ | New.CleanUp.ReferenceOTU1079 | 0.291 | 0.904 |
| 11 | g_; | s_ | New.CleanUp.ReferenceOTU1098 | 0.096 | 0.685 |
| 12 | g_Paenibacillus; | s_ | New.CleanUp.ReferenceOTU1126 | 0.096 | 0.685 |
| 13 | g_Pseudomonas; | s_ | New.CleanUp.ReferenceOTU1167 | NA | NA |
| 14 | g_; | s_ | New.CleanUp.ReferenceOTU120 | NA | NA |
| 15 | g_Pseudomonas; | s_ | New.CleanUp.ReferenceOTU1211 | NA | NA |
| 16 | | | New.CleanUp.ReferenceOTU1224 | 0.096 | 0.685 |
| 17 | g_Paenibacillus; | s_ | New.CleanUp.ReferenceOTU1225 | 0.096 | 0.685 |
| 18 | g_Pseudomonas; | s_ | New.CleanUp.ReferenceOTU1230 | 0.096 | 0.685 |
| 19 | | | New.CleanUp.ReferenceOTU1246 | 0.492 | 1.181 |
| 20 | g_; | s_ | New.CleanUp.ReferenceOTU1281 | 0.096 | 0.685 |
| 21 | g_Candidatus | Xiphinematobacter; | New.CleanUp.ReferenceOTU1284 | 0.096 | 0.685 |
| 22 | g_; | s_ | New.CleanUp.ReferenceOTU1297 | 0.096 | 0.685 |
| 23 | g_Janthinobacterium | | New.CleanUp.ReferenceOTU1327 | 0.096 | 0.685 |
| 24 | g_; | s_ | New.CleanUp.ReferenceOTU1342 | NA | NA |
| 25 | g_Paenibacillus; | s_ | New.CleanUp.ReferenceOTU1352 | 0.887 | 1.713 |
| 26 | g_Paenibacillus; | s_ | New.CleanUp.ReferenceOTU1358 | 0.488 | 1.175 |
| 27 | g_Paenibacillus; | s_ | New.CleanUp.ReferenceOTU1366 | 0.693 | 1.454 |
| 28 | g_; | s_ | New.CleanUp.ReferenceOTU1370 | 0.096 | 0.685 |
| 29 | g_; | s_ | New.CleanUp.ReferenceOTU139 | 0.194 | 0.775 |
| 30 | | | New.CleanUp.ReferenceOTU1396 | 0.096 | 0.685 |
| 31 | g_Paenibacillus; | s_ | New.CleanUp.ReferenceOTU1399 | 0.390 | 1.040 |
| 32 | g_Pseudomonas | | New.CleanUp.ReferenceOTU1404 | NA | NA |
| 33 | g_Paenibacillus; | s_ | New.CleanUp.ReferenceOTU1407 | 0.292 | 0.906 |
| 34 | g_Paenibacillus; | s_ | New.CleanUp.ReferenceOTU1429 | 0.096 | 0.685 |
| 35 | g_; | s_ | New.CleanUp.ReferenceOTU1448 | 0.096 | 0.685 |
| 36 | g_Paenibacillus; | s_ | New.CleanUp.ReferenceOTU1454 | 2.373 | 3.599 |
| 37 | g_Coprococcus; | s_ | New.CleanUp.ReferenceOTU1462 | 0.096 | 0.685 |
| 38 | g_Paenibacillus; | s_ | New.CleanUp.ReferenceOTU1479 | 0.096 | 0.685 |
| 39 | g_; | s_ | New.CleanUp.ReferenceOTU1500 | 0.096 | 0.685 |
| 40 | g_Paenibacillus; | s_ | New.CleanUp.ReferenceOTU1505 | 0.896 | 1.724 |
| 41 | g_Paenibacillus; | s_ | New.CleanUp.ReferenceOTU1514 | 0.096 | 0.685 |
| 42 | g_Pseudomonas; | s_veronii | New.CleanUp.ReferenceOTU1516 | 0.096 | 0.685 |
| 43 | g_; | s_ | New.CleanUp.ReferenceOTU163 | 0.096 | 0.685 |
| 44 | g_Janthinobacterium; | s_ | New.CleanUp.ReferenceOTU165 | 0.096 | 0.685 |
| 45 | g_Pseudomonas; | s_ | New.CleanUp.ReferenceOTU172 | NA | NA |
| 46 | g_Bacillus; | s_cereus | New.CleanUp.ReferenceOTU188 | 0.194 | 0.775 |
| 47 | g_Paenibacillus; | s_ | New.CleanUp.ReferenceOTU192 | 0.096 | 0.685 |
| 48 | g_Pseudomonas; | s_ | New.CleanUp.ReferenceOTU2 | 0.292 | 0.906 |
| 49 | g_; | s_ | New.CleanUp.ReferenceOTU248 | 0.096 | 0.685 |
| 50 | g_Paenibacillus; | s_ | New.CleanUp.ReferenceOTU250 | 0.194 | 0.775 |
| 51 | g_Paenibacillus; | s_ | New.CleanUp.ReferenceOTU26 | 0.194 | 0.775 |
| 52 | g_Pseudomonas; | s_ | New.CleanUp.ReferenceOTU275 | NA | NA |
| 53 | g_Pseudomonas; | s_ | New.CleanUp.ReferenceOTU309 | NA | NA |
| 54 | g_Paenibacillus; | s_ | New.CleanUp.ReferenceOTU312 | 0.292 | 0.906 |
| 55 | g_Flavobacterium; | s_columnare | New.CleanUp.ReferenceOTU337 | NA | NA |
| 56 | g_Janthinobacterium; | s_lividum | New.CleanUp.ReferenceOTU340 | 1.540 | 2.558 |
| 57 | g_Paenibacillus; | s_ | New.CleanUp.ReferenceOTU364 | 0.193 | 0.774 |
| 58 | g_; | s_ | New.CleanUp.ReferenceOTU380 | 0.194 | 0.775 |
| 59 | g_Paenibacillus; | s_ | New.CleanUp.ReferenceOTU382 | 0.696 | 1.458 |
| 60 | g_Cupriavidus; | s_ | New.CleanUp.ReferenceOTU393 | NA | NA |
| 61 | g_Paenibacillus; | s_ | New.CleanUp.ReferenceOTU406 | 0.096 | 0.685 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | |
|---|---|---|---|---|---|
| 62 | g_; | s_ | New.CleanUp.ReferenceOTU410 | 0.096 | 0.685 |
| 63 | g_Janthinobacterium; | s_ | New.CleanUp.ReferenceOTU420 | NA | NA |
| 64 | g_Paenibacillus; | s_ | New.CleanUp.ReferenceOTU427 | 0.096 | 0.685 |
| 65 | g_Chromobacterium; | s_ | New.CleanUp.ReferenceOTU430 | NA | NA |
| 66 | g_Paenibacillus; | s_ | New.CleanUp.ReferenceOTU443 | 0.096 | 0.685 |
| 67 | g_Pseudomonas; | s_ | New.CleanUp.ReferenceOTU459 | NA | NA |
| 68 | g_Pseudomonas | | New.CleanUp.ReferenceOTU464 | 0.096 | 0.685 |
| 69 | g_Pseudomonas; | s_ | New.CleanUp.ReferenceOTU5 | 0.096 | 0.685 |
| 70 | g_Chromobacterium; | s_ | New.CleanUp.ReferenceOTU500 | 0.194 | 0.775 |
| 71 | g_Pseudomonas; | s_ | New.CleanUp.ReferenceOTU504 | 0.096 | 0.685 |
| 72 | g_Paenibacillus; | s_ | New.CleanUp.ReferenceOTU524 | 0.193 | 0.774 |
| 73 | | | New.CleanUp.ReferenceOTU545 | 0.096 | 0.685 |
| 74 | g_; | s_ | New.CleanUp.ReferenceOTU558 | NA | NA |
| 75 | g_Sphingobium; | s_xenophagum | New.CleanUp.ReferenceOTU560 | 0.096 | 0.685 |
| 76 | g_; | s_ | New.CleanUp.ReferenceOTU587 | 0.096 | 0.685 |
| 77 | g_; | s_ | New.CleanUp.ReferenceOTU592 | NA | NA |
| 78 | g_; | s_ | New.CleanUp.ReferenceOTU593 | 0.096 | 0.685 |
| 79 | g_Sediminibacterium; | s_ | New.CleanUp.ReferenceOTU596 | 0.096 | 0.685 |
| 80 | g_; | s_ | New.CleanUp.ReferenceOTU61 | 0.096 | 0.685 |
| 81 | g_Paenibacillus; | s_ | New.CleanUp.ReferenceOTU616 | 0.096 | 0.685 |
| 82 | g_Paenibacillus; | s_ | New.CleanUp.ReferenceOTU617 | 2.014 | 3.154 |
| 83 | g_Pseudomonas; | s_ | New.CleanUp.ReferenceOTU63 | NA | NA |
| 84 | | | New.CleanUp.ReferenceOTU630 | 0.096 | 0.685 |
| 85 | | | New.CleanUp.ReferenceOTU634 | 0.290 | 0.902 |
| 86 | g_Paenibacillus; | s_ | New.CleanUp.ReferenceOTU635 | 0.096 | 0.685 |
| 87 | g_; | s_ | New.CleanUp.ReferenceOTU646 | NA | NA |
| 88 | g_Paenibacillus; | s_ | New.CleanUp.ReferenceOTU655 | 1.308 | 2.261 |
| 89 | g_Paenibacillus; | s_ | New.CleanUp.ReferenceOTU671 | 0.096 | 0.685 |
| 90 | g_Paenibacillus; | s_ | New.CleanUp.ReferenceOTU681 | 0.096 | 0.685 |
| 91 | | | New.CleanUp.ReferenceOTU693 | 0.096 | 0.685 |
| 92 | g_Paenibacillus; | s_ | New.CleanUp.ReferenceOTU697 | NA | NA |
| 93 | g_; | s_ | New.CleanUp.ReferenceOTU702 | 0.192 | 0.773 |
| 94 | g_; | s_ | New.CleanUp.ReferenceOTU707 | 0.096 | 0.685 |
| 95 | g_Janthinobacterium; | s_lividum | New.CleanUp.ReferenceOTU730 | NA | NA |
| 96 | g_Paenibacillus; | s_ | New.CleanUp.ReferenceOTU735 | 0.392 | 1.043 |
| 97 | g_Sediminibacterium; | s_ | New.CleanUp.ReferenceOTU74 | 0.096 | 0.685 |
| 98 | g_; | s_ | New.CleanUp.ReferenceOTU75 | 0.096 | 0.685 |
| 99 | g_Dechloromonas; | s_ | New.CleanUp.ReferenceOTU752 | 0.392 | 1.043 |
| 100 | g_Janthinobacterium; | s_lividum | New.CleanUp.ReferenceOTU766 | 1.782 | 2.863 |
| 101 | g_Bacillus; | s_cereus | New.CleanUp.ReferenceOTU77 | 0.096 | 0.685 |
| 102 | g_Paenibacillus; | s_ | New.CleanUp.ReferenceOTU772 | 0.096 | 0.685 |
| 103 | g_Pseudomonas; | s_ | New.CleanUp.ReferenceOTU784 | NA | NA |
| 104 | g_Paenibacillus; | s_ | New.CleanUp.ReferenceOTU797 | 0.096 | 0.685 |
| 105 | g_Paenibacillus; | s_ | New.CleanUp.ReferenceOTU839 | 0.194 | 0.775 |
| 106 | g_; | s_ | New.CleanUp.ReferenceOTU844 | 0.904 | 1.735 |
| 107 | g_Paenibacillus; | s_ | New.CleanUp.ReferenceOTU849 | 0.194 | 0.775 |
| 108 | g_; | s_ | New.CleanUp.ReferenceOTU864 | NA | NA |
| 109 | g_; | s_ | New.CleanUp.ReferenceOTU910 | 0.096 | 0.685 |
| 110 | g_Bacillus; | s_cereus | New.CleanUp.ReferenceOTU911 | 0.194 | 0.775 |
| 111 | g_; | s_ | New.CleanUp.ReferenceOTU914 | 0.096 | 0.685 |
| 112 | g_Paenibacillus; | s_ | New.CleanUp.ReferenceOTU938 | 0.292 | 0.906 |
| 113 | g_Azoarcus; | s_ | New.CleanUp.ReferenceOTU939 | 0.593 | 1.320 |
| 114 | g_; | s_ | New.CleanUp.ReferenceOTU953 | 0.292 | 0.906 |
| 115 | g_Pseudomonas | | New.CleanUp.ReferenceOTU954 | NA | NA |
| 116 | g_Paenibacillus; | s_ | New.CleanUp.ReferenceOTU960 | 0.096 | 0.685 |
| 117 | g_Paenibacillus; | s_ | New.CleanUp.ReferenceOTU969 | 0.096 | 0.685 |
| 118 | g_; | s_ | New.CleanUp.ReferenceOTU973 | 0.096 | 0.685 |
| 119 | g_Sphingomonas; | s_wittichii | New.CleanUp.ReferenceOTU981 | 0.096 | 0.685 |
| 120 | | | New.ReferenceOTU0 | 3.495 | 4.972 |
| 121 | g_Cupriavidus; | s_ | New.ReferenceOTU1 | 0.096 | 0.685 |
| 122 | g_; | s_ | New.ReferenceOTU10 | NA | NA |
| 123 | g_Pseudomonas; | | New.ReferenceOTU11 | 0.193 | 0.774 |
| 124 | g_Bacillus | | New.ReferenceOTU12 | 1.423 | 2.409 |
| 125 | g_; | s_ | New.ReferenceOTU13 | NA | NA |
| 126 | g_; | s_ | New.ReferenceOTU14 | 0.996 | 1.856 |
| 127 | g_Pseudomonas; | s_ | New.ReferenceOTU16 | 0.096 | 0.685 |
| 128 | g_Hydrogenophaga; | s_ | New.ReferenceOTU18 | 0.096 | 0.685 |
| 129 | g_Coprococcus; | s_ | New.ReferenceOTU19 | 0.392 | 1.043 |
| 130 | g_; | s_ | New.ReferenceOTU20 | 2.514 | 3.774 |
| 131 | g_; | s_ | New.ReferenceOTU21 | 0.590 | 1.316 |
| 132 | | | New.ReferenceOTU22 | 11.495 | 14.563 |
| 133 | g_Pseudomonas; | s_ | New.ReferenceOTU24 | NA | NA |
| 134 | g_; | s_ | New.ReferenceOTU25 | NA | NA |
| 135 | g_Chromobacterium; | s_ | New.ReferenceOTU26 | 2.469 | 3.718 |
| 136 | g_Paenibacillus; | s_ | New.ReferenceOTU28 | 1.423 | 2.408 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | |
|---|---|---|---|---|---|
| 137 | g_Azospira; | s_ | New.ReferenceOTU29 | 0.194 | 0.775 |
| 138 | g_Pseudomonas; | s_ | New.ReferenceOTU30 | 842.021 | 1200.875 |
| 139 | g_; | s_ | New.ReferenceOTU32 | 0.096 | 0.685 |
| 140 | g_Curvibacter; | s_ | New.ReferenceOTU33 | 0.682 | 1.440 |
| 141 | g_Paenibacillus; | s_ | New.ReferenceOTU35 | 10.267 | 13.087 |
| 142 | g_Paenibacillus; | s_ | New.ReferenceOTU37 | 9.789 | 12.515 |
| 143 | g_Pelosinus; | s_ | New.ReferenceOTU38 | 0.292 | 0.906 |
| 144 | g_Alkanindiges; | s_ | New.ReferenceOTU4 | NA | NA |
| 145 | g_Chromobacterium; | s_ | New.ReferenceOTU6 | 0.693 | 1.454 |
| 146 | g_Rhodanobacter; | s_ | New.ReferenceOTU7 | 1.081 | 1.967 |
| 147 | g_Janthinobacterium; | s_lividum | New.ReferenceOTU9 | 31.494 | 39.863 |
| 148 | g_Paenibacillus; | s_ | X1001564 | 22.280 | 27.871 |
| 149 | g_Arthrobacter | | X1002005 | NA | NA |
| 150 | g_Phenylobacterium; | s_ | X1009440 | 0.096 | 0.685 |
| 151 | g_Pseudomonas; | s_ | X106711 | NA | NA |
| 152 | g_Pseudomonas; | s_ | X106985 | 31.013 | 39.224 |
| 153 | g_Brevibacillus | | X1071927 | NA | NA |
| 154 | g_; | s_ | X1074016 | NA | NA |
| 155 | g_; | s_ | X1083508 | NA | NA |
| 156 | g_; | s_ | X1084045 | NA | NA |
| 157 | g_Pseudomonas; | s_ | X108909 | 0.192 | 0.773 |
| 158 | g_Pelosinus; | s_ | X1100798 | 0.392 | 1.043 |
| 159 | g_; | s_ | X110220 | NA | NA |
| 160 | g_; | s_ | X1105814 | 0.193 | 0.774 |
| 161 | g_Pseudomonas; | s_ | X1105944 | 2.363 | 3.586 |
| 162 | g_Streptomyces | | X1106130 | NA | NA |
| 163 | g_; | s_ | X1108282 | 0.096 | 0.685 |
| 164 | g_Mycoplana; | s_ | X1108959 | 0.096 | 0.685 |
| 165 | g_; | s_ | X1110135 | 0.096 | 0.685 |
| 166 | g_; | s_ | X1112200 | 0.096 | 0.685 |
| 167 | g_; | s_ | X1112438 | 0.904 | 1.735 |
| 168 | g_Pseudomonas; | s_ | X1112793 | 0.096 | 0.685 |
| 169 | g_Alkanindiges; | s_ | X1116669 | 0.291 | 0.904 |
| 170 | g_; | s_ | X1126662 | 0.492 | 1.181 |
| 171 | g_Paenibacillus; | s_ | X1141746 | 0.593 | 1.320 |
| 172 | g_; | s_ | X121180 | 0.096 | 0.685 |
| 173 | g_; | s_ | X123510 | 0.096 | 0.685 |
| 174 | g_; | s_ | X126195 | 0.193 | 0.774 |
| 175 | g_; | s_ | X133176 | NA | NA |
| 176 | g_Pseudomonas; | s_ | X133533 | 0.096 | 0.685 |
| 177 | g_; | s_ | X136395 | 0.096 | 0.685 |
| 178 | g_Pseudomonas; | s_ | X138840 | NA | NA |
| 179 | g_Pseudomonas; | s_ | X138914 | 0.096 | 0.685 |
| 180 | g_; | s_ | X139137 | 0.690 | 1.450 |
| 181 | g_; | s_ | X140880 | NA | NA |
| 182 | g_Paenibacillus; | s_ | X141688 | 12.615 | 15.914 |
| 183 | g_Pseudomonas; | s_ | X142419 | NA | NA |
| 184 | g_Dechloromonas; | s_ | X142606 | 0.194 | 0.775 |
| 185 | g_Pseudomonas | | X143131 | 49.580 | 64.466 |
| 186 | g_Paenibacillus; | s_ | X143178 | 0.487 | 1.175 |
| 187 | g_Paenibacillus; | s_ | X144713 | 1.423 | 2.408 |
| 188 | g_; | s_ | X14962 | 0.690 | 1.450 |
| 189 | g_Dechloromonas; | s_ | X153255 | 1.444 | 2.435 |
| 190 | g_Pseudomonas | | X155962 | NA | NA |
| 191 | g_Pseudomonas; | s_ | X156652 | NA | NA |
| 192 | g_Pseudomonas; | s_ | X161169 | NA | NA |
| 193 | g_Paenibacillus; | s_ | X163836 | 0.096 | 0.685 |
| 194 | g_Janthinobacterium; | s_lividum | X166064 | 5.100 | 6.907 |
| 195 | g_Pseudomonas; | s_ | X170405 | 4.453 | 6.129 |
| 196 | g_Sphingomonas; | s_ | X17329 | 0.096 | 0.685 |
| 197 | g_Paenibacillus; | s_ | X179040 | 0.392 | 1.043 |
| 198 | g_Pseudomonas; | s_ | X187390 | NA | NA |
| 199 | g_Bacillus; | s_cereus | X1891556 | 0.096 | 0.685 |
| 200 | g_; | s_ | X1930655 | 0.193 | 0.774 |
| 201 | g_Pseudomonas; | s_ | X202466 | 0.192 | 0.773 |
| 202 | g_Pseudomonas; | s_ | X2061792 | NA | NA |
| 203 | g_Janthinobacterium; | s_lividum | X208929 | 18.020 | 22.528 |
| 204 | g_Pseudomonas; | s_ | X217410 | 0.291 | 0.904 |
| 205 | g_; | s_ | X217506 | NA | NA |
| 206 | g_Bacillus; | s_cereus | X218254 | 1.101 | 1.993 |
| 207 | g_; | s_ | X227453 | 0.096 | 0.685 |
| 208 | g_; | s_ | X228556 | 0.096 | 0.685 |
| 209 | g_Janthinobacterium; | s_ | X2353709 | 1.106 | 2.000 |
| 210 | g_Pseudomonas | | X237173 | 0.192 | 0.773 |
| 211 | g_Brevibacillus; | s_ | X242098 | NA | NA |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | |
|---|---|---|---|---|---|
| 212 | g_Pseudomonas | | X246575 | NA | NA |
| 213 | g_Pseudomonas; | s_ | X2468881 | 0.194 | 0.775 |
| 214 | g_Pseudomonas; | s_ | X2534143 | 0.192 | 0.773 |
| 215 | g_Pseudomonas; | s_ | X256834 | 0.192 | 0.773 |
| 216 | g_; | s_ | X257647 | 0.096 | 0.685 |
| 217 | g_Pseudomonas; | s_veronii | X2589305 | 0.386 | 1.035 |
| 218 | g_; | s_ | X260900 | 0.096 | 0.685 |
| 219 | g_Pseudomonas; | s_ | X268162 | NA | NA |
| 220 | g_; | s_ | X2686724 | NA | NA |
| 221 | g_Pseudomonas | | X274827 | NA | NA |
| 222 | g_Pseudomonas | | X277094 | 6.529 | 8.616 |
| 223 | g_Sediminibacterium; | s_ | X2792167 | 0.192 | 0.773 |
| 224 | g_Pseudomonas; | s_ | X280459 | 0.194 | 0.775 |
| 225 | g_Janthinobacterium; | s_lividum | X284177 | 7.197 | 9.414 |
| 226 | g_Bacillus | | X2874742 | 0.292 | 0.906 |
| 227 | g_; | s_ | X288283 | 0.096 | 0.685 |
| 228 | g_Pseudomonas; | s_fragi | X295031 | 4.259 | 5.895 |
| 229 | g_; | s_ | X296964 | NA | NA |
| 230 | g_Pseudomonas; | s_ | X311522 | 2.857 | 4.195 |
| 231 | g_Janthinobacterium; | s_lividum | X317157 | 0.194 | 0.775 |
| 232 | g_; | s_ | X317487 | NA | NA |
| 233 | | | X3242243 | 0.193 | 0.774 |
| 234 | | | X328917 | NA | NA |
| 235 | g_Lysinibacillus; | s_boronitolerans | X332556 | NA | NA |
| 236 | g_; | s_ | X33410 | NA | NA |
| 237 | g_Lysinibacillus | | X334666 | NA | NA |
| 238 | g_Pseudomonas; | s_ | X338140 | 0.483 | 1.169 |
| 239 | g_Pseudomonas; | s_ | X338200 | NA | NA |
| 240 | g_; | s_ | X3412843 | 0.192 | 0.773 |
| 241 | g_; | s_ | X346925 | 0.096 | 0.685 |
| 242 | g_Pseudomonas; | s_ | X350105 | NA | NA |
| 243 | g_Janthinobacterium; | s_lividum | X353532 | 34.866 | 44.387 |
| 244 | g_; | s_ | X357011 | 0.096 | 0.685 |
| 245 | g_Bacillus; | s_ | X357169 | NA | NA |
| 246 | g_Serratia; | s_ | X3714917 | NA | NA |
| 247 | g_Bacillus | | X3780125 | 0.194 | 0.775 |
| 248 | g_; | s_ | X388763 | NA | NA |
| 249 | g_Bacillus; | s_cereus | X392994 | 0.492 | 1.181 |
| 250 | g_; | s_ | X398350 | 0.390 | 1.040 |
| 251 | g_Pseudomonas; | s_ | X398604 | 1.470 | 2.468 |
| 252 | g_; | s_ | X410307 | 0.096 | 0.685 |
| 253 | g_; | s_ | X412392 | 0.490 | 1.178 |
| 254 | g_Pseudomonas; | s_ | X4128270 | 0.096 | 0.685 |
| 255 | g_Pseudomonas; | s_ | X4253984 | 10.039 | 12.814 |
| 256 | g_Paenibacillus; | s_ | X425938 | 14.994 | 18.805 |
| 257 | g_Bacillus | | X427239 | 0.392 | 1.043 |
| 258 | | | X4288321 | 5.162 | 6.980 |
| 259 | g_Pseudomonas; | s_ | X4309216 | NA | NA |
| 260 | g_Paenibacillus; | s_ | X4314582 | 0.096 | 0.685 |
| 261 | g_Pseudomonas; | s_ | X4316720 | NA | NA |
| 262 | g_Paenibacillus; | s_ | X4321227 | 1.643 | 2.688 |
| 263 | g_; | s_ | X4333020 | 0.096 | 0.685 |
| 264 | g_Bacillus | | X4333556 | 0.996 | 1.856 |
| 265 | g_Pseudomonas; | s_ | X4353093 | NA | NA |
| 266 | g_Paenibacillus; | s_ | X4355275 | 0.096 | 0.685 |
| 267 | | | X4361424 | 1.384 | 2.358 |
| 268 | g_Emticicia; | s_ | X4362005 | NA | NA |
| 269 | g_Pseudomonas; | s_ | X4364813 | NA | NA |
| 270 | g_Pseudomonas; | s_ | X4365172 | NA | NA |
| 271 | g_; | s_ | X4371191 | NA | NA |
| 272 | g_; | s_ | X4376234 | 0.096 | 0.685 |
| 273 | g_Janthinobacterium; | s_lividum | X4382894 | 0.194 | 0.775 |
| 274 | g_Bacillus; | s_cereus | X4385067 | 0.896 | 1.724 |
| 275 | g_Zoogloea; | s_ | X4402114 | NA | NA |
| 276 | | | X4405546 | 0.194 | 0.775 |
| 277 | g_Janthinobacterium; | s_ | X4412134 | NA | NA |
| 278 | g_; | s_ | X4414809 | 0.096 | 0.685 |
| 279 | g_Janthinobacterium; | s_lividum | X4418009 | NA | NA |
| 280 | g_; | s_ | X4420272 | 0.096 | 0.685 |
| 281 | g_Pseudomonas; | s_ | X4422388 | NA | NA |
| 282 | g_Pseudomonas; | s_ | X4435982 | 3.434 | 4.898 |
| 283 | g_Pseudomonas; | s_ | X4455861 | 0.096 | 0.685 |
| 284 | g_Pseudomonas; | s_ | X4456889 | NA | NA |
| 285 | g_Bacillus | | X4463224 | 0.194 | 0.775 |
| 286 | g_Pedomicrobium; | s_ | X4614 | 0.096 | 0.685 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | |
|---|---|---|---|---|---|
| 287 | g_Janthinobacterium; | s_lividum | X509212 | 1.713 | 2.776 |
| 288 | g_Pelosinus; | s_ | X514095 | 0.392 | 1.043 |
| 289 | | | X527323 | NA | NA |
| 290 | g_Acinetobacter; | s_ | X532569 | 0.194 | 0.775 |
| 291 | | | X534714 | 3.226 | 4.645 |
| 292 | g_Janthinobacterium; | s_lividum | X539915 | 0.292 | 0.906 |
| 293 | g_; | s_ | X541119 | 0.096 | 0.685 |
| 294 | g_Pseudomonas; | s_ | X541223 | NA | NA |
| 295 | g_Pseudomonas; | s_ | X541859 | 11.448 | 14.507 |
| 296 | g_Pseudomonas; | s_ | X544313 | NA | NA |
| 297 | g_; | s_ | X544847 | NA | NA |
| 298 | g_Bacillus; | s_ | X544851 | 0.096 | 0.685 |
| 299 | g_; | s_ | X546546 | 0.290 | 0.902 |
| 300 | g_Pseudomonas; | s_ | X549293 | NA | NA |
| 301 | g_; | s_ | X551871 | 0.696 | 1.458 |
| 302 | g_Bacillus; | s_flexus | X552143 | NA | NA |
| 303 | g_Paenibacillus; | s_ | X553697 | 3.237 | 4.659 |
| 304 | g_; | s_ | X554916 | 0.690 | 1.450 |
| 305 | g_Pseudomonas; | s_ | X557974 | 5.653 | 7.569 |
| 306 | | | X558014 | NA | NA |
| 307 | g_Pseudomonas; | s_ | X560886 | 12.489 | 15.762 |
| 308 | g_; | s_ | X561647 | 0.292 | 0.906 |
| 309 | g_Serratia; | s_ | X564290 | NA | NA |
| 310 | g_; | s_ | X572117 | 0.392 | 1.043 |
| 311 | g_; | s_ | X572750 | 0.096 | 0.685 |
| 312 | g_Acinetobacter; | s_ | X573124 | 0.096 | 0.685 |
| 313 | g_Chryseobacterium; | s_ | X573326 | NA | NA |
| 314 | g_Bacillus | | X573338 | 0.194 | 0.775 |
| 315 | g_; | s_ | X574480 | 0.193 | 0.774 |
| 316 | g_Paludibacter; | s_ | X575486 | 0.096 | 0.685 |
| 317 | g_Bacillus; | s_ | X576724 | NA | NA |
| 318 | g_; | s_ | X576785 | NA | NA |
| 319 | g_; | s_ | X576928 | 0.490 | 1.178 |
| 320 | g_Cupriavidus; | s_ | X580571 | 0.780 | 1.571 |
| 321 | g_; | s_ | X580578 | NA | NA |
| 322 | g_Sphingomonas; | s_yabuuchiae | X580992 | NA | NA |
| 323 | g_; | s_ | X581021 | 0.096 | 0.685 |
| 324 | g_Janthinobacterium; | s_ | X582997 | 0.096 | 0.685 |
| 325 | g_Sedminibacterium; | s_ | X58374 | 0.096 | 0.685 |
| 326 | g_; | s_ | X584177 | 0.096 | 0.685 |
| 327 | g_; | s_ | X588520 | 0.096 | 0.685 |
| 328 | g_Janthinobacterium; | s_ | X589123 | 0.096 | 0.685 |
| 329 | g_; | s_ | X589483 | NA | NA |
| 330 | g_; | s_ | X590601 | 0.096 | 0.685 |
| 331 | g_Bacillus; | s_cereus | X591907 | 1.207 | 2.131 |
| 332 | g_Phaeospirillum; | s_fulvum | X593171 | 0.096 | 0.685 |
| 333 | g_Oceanicaulis; | s_ | X593605 | NA | NA |
| 334 | g_Curvibacter; | s_ | X610486 | 20.842 | 26.054 |
| 335 | g_Pseudomonas; | s_ | X633252 | 1.621 | 2.660 |
| 336 | g_Novosphingobium; | s_ | X635323 | 0.096 | 0.685 |
| 337 | g_Chromobacterium; | s_ | X6374 | 2.122 | 3.288 |
| 338 | g_Pseudomonas; | s_ | X646549 | 10.037 | 12.811 |
| 339 | g_Bacillus; | s_flexus | X656443 | NA | NA |
| 340 | g_Paenibacillus; | s_chondroitinus | X662808 | NA | NA |
| 341 | g_Sphingopyxis; | s_alaskensis | X674655 | 0.096 | 0.685 |
| 342 | g_Bacillus; | s_flexus | X680608 | NA | NA |
| 343 | g_Bacillus; | s_cereus | X697578 | 2.080 | 3.235 |
| 344 | g_; | s_ | X702443 | 0.096 | 0.685 |
| 345 | g_; | s_ | X709657 | 0.096 | 0.685 |
| 346 | g_; | s_ | X712797 | NA | NA |
| 347 | g_; | s_ | X720353 | 1.111 | 2.006 |
| 348 | g_Pseudomonas; | s_ | X728119 | 0.288 | 0.900 |
| 349 | g_Clostridium; | s_ | X741139 | 0.096 | 0.685 |
| 350 | g_Bacillus; | s_cereus | X746246 | 1.207 | 2.131 |
| 351 | g_Pseudomonas; | s_veronii | X751973 | 1.068 | 1.951 |
| 352 | g_Azospirillum; | s_ | X753767 | 0.193 | 0.774 |
| 353 | g_; | s_ | X756819 | 0.096 | 0.685 |
| 354 | g_Pseudomonas; | s_ | X764682 | 0.488 | 1.175 |
| 355 | g_; | s_ | X778059 | 0.192 | 0.773 |
| 356 | g_Pseudomonas; | s_ | X780555 | 5.707 | 7.633 |
| 357 | g_Lysinibacillus; | s_boronitolerans | X801579 | NA | NA |
| 358 | g_Bacillus | | X805055 | 1.533 | 2.548 |
| 359 | g_Chryseobacterium; | s_ | X810955 | NA | NA |
| 360 | g_; | s_ | X812902 | 0.593 | 1.320 |
| 361 | g_Bacillus | | X812929 | 0.194 | 0.775 |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | |
|---|---|---|---|---|---|
| 362 | g_Pseudomonas; | s_ | X813216 | 0.096 | 0.685 |
| 363 | g_; | s_ | X813217 | 0.096 | 0.685 |
| 364 | g_Novosphingobium; | s_ | X813418 | 0.096 | 0.685 |
| 365 | g_; | s_ | X813457 | 0.096 | 0.685 |
| 366 | g_Pseudomonas; | s_ | X813617 | 0.487 | 1.175 |
| 367 | g_; | s_ | X814442 | 0.096 | 0.685 |
| 368 | g_; | s_ | X814489 | 0.096 | 0.685 |
| 369 | g_Pseudomonas; | s_veronii | X816090 | 0.096 | 0.685 |
| 370 | g_; | s_ | X816219 | 0.792 | 1.587 |
| 371 | g_Bacillus; | s_cereus | X816470 | 1.207 | 2.131 |
| 372 | g_Rhodanobacter; | s_ | X816868 | 1.180 | 2.096 |
| 373 | g_Bacillus; | s_cereus | X817115 | 0.591 | 1.316 |
| 374 | g_Pseudomonas; | s_ | X817734 | 0.096 | 0.685 |
| 375 | g_Pseudomonas; | s_ | X818602 | 0.096 | 0.685 |
| 376 | g_; | s_ | X821080 | 0.096 | 0.685 |
| 377 | g_; | s_ | X821562 | NA | NA |
| 378 | g_; | s_ | X821579 | 0.193 | 0.774 |
| 379 | g_Janthinobacterium; | s_lividum | X822337 | 19.124 | 23.901 |
| 380 | g_; | s_ | X822419 | 8.493 | 10.963 |
| 381 | g_; | s_ | X824723 | NA | NA |
| 382 | g_; | s_ | X826270 | 0.096 | 0.685 |
| 383 | g_; | s_ | X826749 | 0.392 | 1.043 |
| 384 | g_; | s_ | X827943 | 0.096 | 0.685 |
| 385 | g_Pseudomonas; | s_ | X829851 | 0.488 | 1.175 |
| 386 | g_; | s_ | X832784 | 0.192 | 0.773 |
| 387 | g_Pseudomonas; | s_ | X833174 | 4.072 | 5.670 |
| 388 | g_; | s_ | X835586 | 0.096 | 0.685 |
| 389 | g_; | s_ | X837068 | 0.192 | 0.773 |
| 390 | g_; | s_ | X839235 | 0.288 | 0.900 |
| 391 | g_Alkanindiges; | s_ | X84033 | NA | NA |
| 392 | g_Paenibacillus; | s_ | X846283 | 19.513 | 24.386 |
| 393 | g_Caulobacter | | X866365 | 0.096 | 0.685 |
| 394 | g_Pseudomonas; | s_viridiflava | X91834 | 0.096 | 0.685 |
| 395 | g_; | s_ | X922761 | 0.096 | 0.685 |
| 396 | g_; | s_ | X961783 | 1.202 | 2.124 |
| 397 | g_; | s_ | X967275 | NA | NA |
| 398 | g_Coprococcus; | s_ | X976470 | 0.292 | 0.906 |
| 399 | g_; | s_ | X9846 | 0.096 | 0.685 |

| | Column Number | | | | | | | |
|---|---|---|---|---|---|---|---|---|
| Row Number | 11 anaerobic MPN lower bound (95% confidence) | 12 anaerobic MPN rarity | 13 anaerobic rarity category | 14 $NO_3\text{-}10^{-1}$ number of communities | 15 $NO_3\text{-}10^{-2}$ number of communities | 16 $NO_3\text{-}10^{-3}$ number of communities | 17 $NO_3\text{-}10^{-4}$ number of communities | 18 $NO_3\text{-}10^{-5}$ number of communities |
| 1 | 0.013 | 0.092 | 1 | 0 | 1 | 0 | 0 | 0 |
| 2 | 0.014 | 0.911 | 1 | 1 | 0 | 0 | 0 | 0 |
| 3 | NA | NA | 0 | 0 | 0 | 0 | 0 | 0 |
| 4 | 0.094 | 0.910 | 1 | 3 | 0 | 0 | 0 | 0 |
| 5 | NA | NA | 0 | 0 | 0 | 0 | 0 | 0 |
| 6 | 0.014 | 0.911 | 1 | 1 | 0 | 0 | 0 | 0 |
| 7 | 0.094 | 0.280 | 1 | 2 | 1 | 0 | 0 | 0 |
| 8 | 0.014 | 0.911 | 1 | 1 | 0 | 0 | 0 | 0 |
| 9 | 0.014 | 0.911 | 1 | 1 | 0 | 0 | 0 | 0 |
| 10 | 0.094 | 0.280 | 1 | 2 | 1 | 0 | 0 | 0 |
| 11 | 0.013 | 0.005 | 3 | 0 | 0 | 1 | 0 | 0 |
| 12 | 0.014 | 0.911 | 1 | 1 | 0 | 0 | 0 | 0 |
| 13 | NA | NA | 0 | 0 | 0 | 0 | 0 | 0 |
| 14 | NA | NA | 0 | 0 | 0 | 0 | 0 | 0 |
| 15 | NA | NA | 0 | 0 | 0 | 0 | 0 | 0 |
| 16 | 0.014 | 0.911 | 1 | 1 | 0 | 0 | 0 | 0 |
| 17 | 0.014 | 0.911 | 1 | 1 | 0 | 0 | 0 | 0 |
| 18 | 0.013 | 0.092 | 1 | 0 | 1 | 0 | 0 | 0 |
| 19 | 0.205 | 0.908 | 1 | 5 | 0 | 0 | 0 | 0 |
| 20 | 0.013 | 0.092 | 1 | 0 | 1 | 0 | 0 | 0 |
| 21 | 0.013 | 0.005 | 3 | 0 | 0 | 1 | 0 | 0 |
| 22 | 0.014 | 0.911 | 1 | 1 | 0 | 0 | 0 | 0 |
| 23 | 0.014 | 0.911 | 1 | 1 | 0 | 0 | 0 | 0 |
| 24 | NA | NA | 0 | 0 | 0 | 0 | 0 | 0 |
| 25 | 0.459 | 0.003 | 3 | 5 | 3 | 1 | 0 | 0 |
| 26 | 0.202 | 0.096 | 1 | 3 | 2 | 0 | 0 | 0 |
| 27 | 0.330 | 0.667 | 1 | 6 | 1 | 0 | 0 | 0 |
| 28 | 0.013 | 0.092 | 1 | 0 | 1 | 0 | 0 | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 29 | 0.049 | 0.911 | 1 | 2 | 0 | 0 | 0 | 0 |
| 30 | 0.014 | 0.911 | 1 | 1 | 0 | 0 | 0 | 0 |
| 31 | 0.146 | 0.375 | 1 | 3 | 1 | 0 | 0 | 0 |
| 32 | NA | NA | 0 | 0 | 0 | 0 | 0 | 0 |
| 33 | 0.094 | 0.910 | 1 | 3 | 0 | 0 | 0 | 0 |
| 34 | 0.014 | 0.911 | 1 | 1 | 0 | 0 | 0 | 0 |
| 35 | 0.013 | 0.005 | 3 | 0 | 0 | 1 | 0 | 0 |
| 36 | 1.565 | 0.319 | 1 | 22 | 0 | 0 | 0 | 0 |
| 37 | 0.014 | 0.911 | 1 | 1 | 0 | 0 | 0 | 0 |
| 38 | 0.014 | 0.911 | 1 | 1 | 0 | 0 | 0 | 0 |
| 39 | 0.013 | 0.005 | 3 | 0 | 0 | 1 | 0 | 0 |
| 40 | 0.465 | 0.362 | 1 | 7 | 2 | 0 | 0 | 0 |
| 41 | 0.013 | 0.005 | 3 | 0 | 0 | 1 | 0 | 0 |
| 42 | 0.014 | 0.911 | 1 | 1 | 0 | 0 | 0 | 0 |
| 43 | 0.014 | 0.911 | 1 | 1 | 0 | 0 | 0 | 0 |
| 44 | 0.014 | 0.911 | 1 | 1 | 0 | 0 | 0 | 0 |
| 45 | NA | NA | 0 | 0 | 0 | 0 | 0 | 0 |
| 46 | 0.049 | 0.911 | 1 | 2 | 0 | 0 | 0 | 0 |
| 47 | 0.014 | 0.911 | 1 | 1 | 0 | 0 | 0 | 0 |
| 48 | 0.094 | 0.910 | 1 | 3 | 0 | 0 | 0 | 0 |
| 49 | 0.014 | 0.911 | 1 | 1 | 0 | 0 | 0 | 0 |
| 50 | 0.049 | 0.911 | 1 | 2 | 0 | 0 | 0 | 0 |
| 51 | 0.049 | 0.911 | 1 | 2 | 0 | 0 | 0 | 0 |
| 52 | NA | NA | 0 | 0 | 0 | 0 | 0 | 0 |
| 53 | NA | NA | 0 | 0 | 0 | 0 | 0 | 0 |
| 54 | 0.094 | 0.910 | 1 | 3 | 0 | 0 | 0 | 0 |
| 55 | NA | NA | 0 | 0 | 0 | 0 | 0 | 0 |
| 56 | 0.928 | 0.737 | 1 | 13 | 2 | 0 | 0 | 0 |
| 57 | 0.048 | 0.186 | 1 | 1 | 1 | 0 | 0 | 0 |
| 58 | 0.049 | 0.911 | 1 | 2 | 0 | 0 | 0 | 0 |
| 59 | 0.332 | 0.906 | 1 | 7 | 0 | 0 | 0 | 0 |
| 60 | NA | NA | 0 | 0 | 0 | 0 | 0 | 0 |
| 61 | 0.014 | 0.911 | 1 | 1 | 0 | 0 | 0 | 0 |
| 62 | 0.014 | 0.911 | 1 | 1 | 0 | 0 | 0 | 0 |
| 63 | NA | NA | 0 | 0 | 0 | 0 | 0 | 0 |
| 64 | 0.014 | 0.911 | 1 | 1 | 0 | 0 | 0 | 0 |
| 65 | NA | NA | 0 | 0 | 0 | 0 | 0 | 0 |
| 66 | 0.014 | 0.911 | 1 | 1 | 0 | 0 | 0 | 0 |
| 67 | NA | NA | 0 | 0 | 0 | 0 | 0 | 0 |
| 68 | 0.014 | 0.911 | 1 | 1 | 0 | 0 | 0 | 0 |
| 69 | 0.014 | 0.911 | 1 | 1 | 0 | 0 | 0 | 0 |
| 70 | 0.049 | 0.911 | 1 | 2 | 0 | 0 | 0 | 0 |
| 71 | 0.013 | 0.092 | 1 | 0 | 1 | 0 | 0 | 0 |
| 72 | 0.048 | 0.010 | 2 | 1 | 0 | 1 | 0 | 0 |
| 73 | 0.014 | 0.911 | 1 | 1 | 0 | 0 | 0 | 0 |
| 74 | NA | NA | 0 | 0 | 0 | 0 | 0 | 0 |
| 75 | 0.013 | 0.005 | 3 | 0 | 0 | 1 | 0 | 0 |
| 76 | 0.013 | 0.005 | 3 | 0 | 0 | 1 | 0 | 0 |
| 77 | NA | NA | 0 | 0 | 0 | 0 | 0 | 0 |
| 78 | 0.013 | 0.092 | 1 | 0 | 1 | 0 | 0 | 0 |
| 79 | 0.013 | 0.005 | 3 | 0 | 0 | 1 | 0 | 0 |
| 80 | 0.013 | 0.005 | 3 | 0 | 0 | 1 | 0 | 0 |
| 81 | 0.014 | 0.911 | 1 | 1 | 0 | 0 | 0 | 0 |
| 82 | 1.287 | 0.436 | 1 | 19 | 0 | 0 | 0 | 0 |
| 83 | NA | NA | 0 | 0 | 0 | 0 | 0 | 0 |
| 84 | 0.014 | 0.911 | 1 | 1 | 0 | 0 | 0 | 0 |
| 85 | 0.093 | 0.003 | 3 | 1 | 1 | 1 | 0 | 0 |
| 86 | 0.013 | 0.092 | 1 | 0 | 1 | 0 | 0 | 0 |
| 87 | NA | NA | 0 | 0 | 0 | 0 | 0 | 0 |
| 88 | 0.757 | 0.014 | 2 | 9 | 3 | 1 | 0 | 0 |
| 89 | 0.013 | 0.092 | 1 | 0 | 1 | 0 | 0 | 0 |
| 90 | 0.013 | 0.005 | 3 | 0 | 0 | 1 | 0 | 0 |
| 91 | 0.014 | 0.911 | 1 | 1 | 0 | 0 | 0 | 0 |
| 92 | NA | NA | 0 | 0 | 0 | 0 | 0 | 0 |
| 93 | 0.048 | 0.009 | 3 | 0 | 2 | 0 | 0 | 0 |
| 94 | 0.013 | 0.005 | 3 | 0 | 0 | 1 | 0 | 0 |
| 95 | NA | NA | 0 | 0 | 0 | 0 | 0 | 0 |
| 96 | 0.147 | 0.909 | 1 | 4 | 0 | 0 | 0 | 0 |
| 97 | 0.013 | 0.005 | 3 | 0 | 0 | 1 | 0 | 0 |
| 98 | 0.014 | 0.911 | 1 | 1 | 0 | 0 | 0 | 0 |
| 99 | 0.147 | 0.909 | 1 | 4 | 0 | 0 | 0 | 0 |
| 100 | 1.109 | 0.499 | 1 | 17 | 0 | 0 | 0 | 0 |
| 101 | 0.014 | 0.911 | 1 | 1 | 0 | 0 | 0 | 0 |
| 102 | 0.014 | 0.911 | 1 | 1 | 0 | 0 | 0 | 0 |
| 103 | NA | NA | 0 | 0 | 0 | 0 | 0 | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 104 | 0.014 | 0.911 | 1 | 1 | 0 | 0 | 0 | 0 |
| 105 | 0.049 | 0.911 | 1 | 2 | 0 | 0 | 0 | 0 |
| 106 | 0.471 | 0.904 | 1 | 9 | 0 | 0 | 0 | 0 |
| 107 | 0.049 | 0.911 | 1 | 2 | 0 | 0 | 0 | 0 |
| 108 | NA | NA | 0 | 0 | 0 | 0 | 0 | 0 |
| 109 | 0.013 | 0.005 | 3 | 0 | 0 | 1 | 0 | 0 |
| 110 | 0.049 | 0.911 | 1 | 2 | 0 | 0 | 0 | 0 |
| 111 | 0.013 | 0.005 | 3 | 0 | 0 | 1 | 0 | 0 |
| 112 | 0.094 | 0.910 | 1 | 3 | 0 | 0 | 0 | 0 |
| 113 | 0.267 | 0.907 | 1 | 6 | 0 | 0 | 0 | 0 |
| 114 | 0.094 | 0.910 | 1 | 3 | 0 | 0 | 0 | 0 |
| 115 | NA | NA | 0 | 0 | 0 | 0 | 0 | 0 |
| 116 | 0.014 | 0.911 | 1 | 1 | 0 | 0 | 0 | 0 |
| 117 | 0.014 | 0.911 | 1 | 1 | 0 | 0 | 0 | 0 |
| 118 | 0.013 | 0.005 | 3 | 0 | 0 | 1 | 0 | 0 |
| 119 | 0.013 | 0.005 | 3 | 0 | 0 | 1 | 0 | 0 |
| 120 | 2.457 | 0.854 | 1 | 29 | 2 | 0 | 0 | 0 |
| 121 | 0.013 | 0.092 | 1 | 0 | 1 | 0 | 0 | 0 |
| 122 | NA | NA | 0 | 0 | 0 | 0 | 0 | 0 |
| 123 | 0.048 | 0.186 | 1 | 1 | 1 | 0 | 0 | 0 |
| 124 | 0.841 | 0.289 | 1 | 11 | 3 | 0 | 0 | 0 |
| 125 | NA | NA | 0 | 0 | 0 | 0 | 0 | 0 |
| 126 | 0.534 | 0.126 | 1 | 7 | 3 | 0 | 0 | 0 |
| 127 | 0.014 | 0.911 | 1 | 1 | 0 | 0 | 0 | 0 |
| 128 | 0.013 | 0.005 | 3 | 0 | 0 | 1 | 0 | 0 |
| 129 | 0.147 | 0.909 | 1 | 4 | 0 | 0 | 0 | 0 |
| 130 | 1.675 | 0.002 | 3 | 16 | 7 | 1 | 0 | 0 |
| 131 | 0.265 | 0.032 | 2 | 5 | 0 | 1 | 0 | 0 |
| 132 | 9.073 | 0.491 | 1 | 63 | 12 | 1 | 0 | 0 |
| 133 | NA | NA | 0 | 0 | 0 | 0 | 0 | 0 |
| 134 | NA | NA | 0 | 0 | 0 | 0 | 0 | 0 |
| 135 | 1.640 | 0.111 | 1 | 21 | 1 | 1 | 0 | 0 |
| 136 | 0.841 | 0.049 | 2 | 11 | 2 | 1 | 0 | 0 |
| 137 | 0.049 | 0.911 | 1 | 2 | 0 | 0 | 0 | 0 |
| 138 | 590.403 | 0.000 | 3 | 94 | 94 | 42 | 0 | 0 |
| 139 | 0.014 | 0.911 | 1 | 1 | 0 | 0 | 0 | 0 |
| 140 | 0.323 | 0.000 | 3 | 3 | 0 | 4 | 0 | 0 |
| 141 | 8.054 | 0.116 | 1 | 57 | 14 | 1 | 0 | 0 |
| 142 | 7.657 | 0.082 | 1 | 55 | 14 | 1 | 0 | 0 |
| 143 | 0.094 | 0.910 | 1 | 3 | 0 | 0 | 0 | 0 |
| 144 | NA | NA | 0 | 0 | 0 | 0 | 0 | 0 |
| 145 | 0.330 | 0.667 | 1 | 6 | 1 | 0 | 0 | 0 |
| 146 | 0.594 | 0.000 | 3 | 4 | 7 | 0 | 0 | 0 |
| 147 | 24.881 | 0.103 | 1 | 91 | 21 | 4 | 0 | 0 |
| 148 | 17.811 | 0.000 | 3 | 79 | 23 | 9 | 0 | 0 |
| 149 | NA | NA | 0 | 0 | 0 | 0 | 0 | 0 |
| 150 | 0.013 | 0.005 | 3 | 0 | 0 | 1 | 0 | 0 |
| 151 | NA | NA | 0 | 0 | 0 | 0 | 0 | 0 |
| 152 | 24.521 | 0.000 | 3 | 79 | 51 | 7 | 0 | 0 |
| 153 | NA | NA | 0 | 0 | 0 | 0 | 0 | 0 |
| 154 | NA | NA | 0 | 0 | 0 | 0 | 0 | 0 |
| 155 | NA | NA | 0 | 0 | 0 | 0 | 0 | 0 |
| 156 | NA | NA | 0 | 0 | 0 | 0 | 0 | 0 |
| 157 | 0.048 | 0.009 | 3 | 0 | 2 | 0 | 0 | 0 |
| 158 | 0.147 | 0.909 | 1 | 4 | 0 | 0 | 0 | 0 |
| 159 | NA | NA | 0 | 0 | 0 | 0 | 0 | 0 |
| 160 | 0.048 | 0.010 | 2 | 1 | 0 | 1 | 0 | 0 |
| 161 | 1.556 | 0.000 | 3 | 12 | 11 | 0 | 0 | 0 |
| 162 | NA | NA | 0 | 0 | 0 | 0 | 0 | 0 |
| 163 | 0.014 | 0.911 | 1 | 1 | 0 | 0 | 0 | 0 |
| 164 | 0.013 | 0.005 | 3 | 0 | 0 | 1 | 0 | 0 |
| 165 | 0.014 | 0.911 | 1 | 1 | 0 | 0 | 0 | 0 |
| 166 | 0.014 | 0.911 | 1 | 1 | 0 | 0 | 0 | 0 |
| 167 | 0.471 | 0.904 | 1 | 9 | 0 | 0 | 0 | 0 |
| 168 | 0.013 | 0.092 | 1 | 0 | 1 | 0 | 0 | 0 |
| 169 | 0.094 | 0.016 | 2 | 2 | 0 | 1 | 0 | 0 |
| 170 | 0.205 | 0.908 | 1 | 5 | 0 | 0 | 0 | 0 |
| 171 | 0.267 | 0.907 | 1 | 6 | 0 | 0 | 0 | 0 |
| 172 | 0.014 | 0.911 | 1 | 1 | 0 | 0 | 0 | 0 |
| 173 | 0.014 | 0.911 | 1 | 1 | 0 | 0 | 0 | 0 |
| 174 | 0.048 | 0.186 | 1 | 1 | 1 | 0 | 0 | 0 |
| 175 | NA | NA | NA | 0 | 0 | 0 | 0 | 1 |
| 176 | 0.014 | 0.911 | 1 | 1 | 0 | 0 | 0 | 0 |
| 177 | 0.014 | 0.911 | 1 | 1 | 0 | 0 | 0 | 0 |
| 178 | NA | NA | 0 | 0 | 0 | 0 | 0 | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 179 | 0.014 | 0.911 | 1 | 1 | 0 | 0 | 0 | 0 |
| 180 | 0.328 | 0.206 | 1 | 5 | 2 | 0 | 0 | 0 |
| 181 | NA | NA | 0 | 0 | 0 | 0 | 0 | 0 |
| 182 | 9.999 | 0.281 | 1 | 65 | 15 | 1 | 0 | 0 |
| 183 | NA | NA | 0 | 0 | 0 | 0 | 0 | 0 |
| 184 | 0.049 | 0.911 | 1 | 2 | 0 | 0 | 0 | 0 |
| 185 | 38.132 | 0.000 | 3 | 76 | 78 | 37 | 0 | 0 |
| 186 | 0.202 | 0.011 | 2 | 3 | 1 | 1 | 0 | 0 |
| 187 | 0.841 | 0.049 | 2 | 11 | 2 | 1 | 0 | 0 |
| 188 | 0.328 | 0.206 | 1 | 5 | 2 | 0 | 0 | 0 |
| 189 | 0.856 | 0.631 | 1 | 14 | 0 | 0 | 0 | 0 |
| 190 | NA | NA | 0 | 0 | 0 | 0 | 0 | 0 |
| 191 | NA | NA | 0 | 0 | 0 | 0 | 0 | 0 |
| 192 | NA | NA | 0 | 0 | 0 | 0 | 0 | 0 |
| 193 | 0.013 | 0.092 | 1 | 0 | 1 | 0 | 0 | 0 |
| 194 | 3.767 | 0.437 | 1 | 40 | 2 | 0 | 0 | 0 |
| 195 | 3.236 | 0.056 | 1 | 30 | 9 | 0 | 0 | 0 |
| 196 | 0.013 | 0.005 | 3 | 0 | 0 | 1 | 0 | 0 |
| 197 | 0.147 | 0.909 | 1 | 4 | 0 | 0 | 0 | 0 |
| 198 | NA | NA | 0 | 0 | 0 | 0 | 0 | 0 |
| 199 | 0.014 | 0.911 | 1 | 1 | 0 | 0 | 0 | 0 |
| 200 | 0.048 | 0.010 | 2 | 1 | 0 | 1 | 0 | 0 |
| 201 | 0.048 | 0.009 | 3 | 0 | 2 | 0 | 0 | 0 |
| 202 | NA | NA | 0 | 0 | 0 | 0 | 0 | 0 |
| 203 | 14.414 | 0.021 | 2 | 81 | 9 | 3 | 0 | 0 |
| 204 | 0.094 | 0.280 | 1 | 2 | 1 | 0 | 0 | 0 |
| 205 | NA | NA | 0 | 0 | 0 | 0 | 0 | 0 |
| 206 | 0.608 | 0.164 | 1 | 8 | 3 | 0 | 0 | 0 |
| 207 | 0.013 | 0.005 | 3 | 0 | 0 | 1 | 0 | 0 |
| 208 | 0.014 | 0.911 | 1 | 1 | 0 | 0 | 0 | 0 |
| 209 | 0.612 | 0.528 | 1 | 9 | 2 | 0 | 0 | 0 |
| 210 | 0.048 | 0.009 | 3 | 0 | 2 | 0 | 0 | 0 |
| 211 | NA | NA | 0 | 0 | 0 | 0 | 0 | 0 |
| 212 | NA | NA | 0 | 0 | 0 | 0 | 0 | 0 |
| 213 | 0.049 | 0.911 | 1 | 2 | 0 | 0 | 0 | 0 |
| 214 | 0.048 | 0.001 | 3 | 0 | 1 | 1 | 0 | 0 |
| 215 | 0.048 | 0.009 | 3 | 0 | 2 | 0 | 0 | 0 |
| 216 | 0.013 | 0.005 | 3 | 0 | 0 | 1 | 0 | 0 |
| 217 | 0.144 | 0.001 | 3 | 1 | 2 | 1 | 0 | 0 |
| 218 | 0.014 | 0.911 | 1 | 1 | 0 | 0 | 0 | 0 |
| 219 | NA | NA | 0 | 0 | 0 | 0 | 0 | 0 |
| 220 | NA | NA | 0 | 0 | 0 | 0 | 0 | 0 |
| 221 | NA | NA | 0 | 0 | 0 | 0 | 0 | 0 |
| 222 | 4.947 | 0.000 | 3 | 34 | 21 | 0 | 0 | 0 |
| 223 | 0.048 | 0.000 | 3 | 0 | 0 | 2 | 0 | 0 |
| 224 | 0.049 | 0.911 | 1 | 2 | 0 | 0 | 0 | 0 |
| 225 | 5.502 | 0.989 | 1 | 49 | 6 | 0 | 0 | 0 |
| 226 | 0.094 | 0.910 | 1 | 3 | 0 | 0 | 0 | 0 |
| 227 | 0.013 | 0.005 | 3 | 0 | 0 | 1 | 0 | 0 |
| 228 | 3.077 | 0.001 | 3 | 27 | 9 | 2 | 0 | 0 |
| 229 | NA | NA | 0 | 0 | 0 | 0 | 0 | 0 |
| 230 | 1.946 | 0.658 | 1 | 25 | 1 | 0 | 0 | 0 |
| 231 | 0.049 | 0.911 | 1 | 2 | 0 | 0 | 0 | 0 |
| 232 | NA | NA | 0 | 0 | 0 | 0 | 0 | 0 |
| 233 | 0.048 | 0.186 | 1 | 1 | 1 | 0 | 0 | 0 |
| 234 | NA | NA | 0 | 0 | 0 | 0 | 0 | 0 |
| 235 | NA | NA | 0 | 0 | 0 | 0 | 0 | 0 |
| 236 | NA | NA | 0 | 0 | 0 | 0 | 0 | 0 |
| 237 | NA | NA | 0 | 0 | 0 | 0 | 0 | 0 |
| 238 | 0.200 | 0.000 | 3 | 1 | 4 | 0 | 0 | 0 |
| 239 | NA | NA | 0 | 0 | 0 | 0 | 0 | 0 |
| 240 | 0.048 | 0.000 | 3 | 0 | 0 | 2 | 0 | 0 |
| 241 | 0.013 | 0.005 | 3 | 0 | 0 | 1 | 0 | 0 |
| 242 | NA | NA | 0 | 0 | 0 | 0 | 0 | 0 |
| 243 | 27.387 | 0.025 | 2 | 89 | 32 | 5 | 0 | 0 |
| 244 | 0.013 | 0.005 | 3 | 0 | 0 | 1 | 0 | 0 |
| 245 | NA | NA | 0 | 0 | 0 | 0 | 0 | 0 |
| 246 | NA | NA | 0 | 0 | 0 | 0 | 0 | 0 |
| 247 | 0.049 | 0.911 | 1 | 2 | 0 | 0 | 0 | 0 |
| 248 | NA | NA | 0 | 0 | 0 | 0 | 0 | 0 |
| 249 | 0.205 | 0.908 | 1 | 5 | 0 | 0 | 0 | 0 |
| 250 | 0.146 | 0.375 | 1 | 3 | 1 | 0 | 0 | 0 |
| 251 | 0.875 | 0.000 | 3 | 3 | 11 | 1 | 0 | 0 |
| 252 | 0.014 | 0.911 | 1 | 1 | 0 | 0 | 0 | 0 |
| 253 | 0.204 | 0.471 | 1 | 4 | 1 | 0 | 0 | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 254 | 0.014 | 0.911 | 1 | 1 | 0 | 0 | 0 | 0 |
| 255 | 7.865 | 0.538 | 1 | 62 | 6 | 0 | 0 | 0 |
| 256 | 11.955 | 0.660 | 1 | 72 | 15 | 1 | 0 | 0 |
| 257 | 0.147 | 0.909 | 1 | 4 | 0 | 0 | 0 | 0 |
| 258 | 3.817 | 0.279 | 1 | 38 | 4 | 1 | 0 | 0 |
| 259 | NA | NA | 0 | 0 | 0 | 0 | 0 | 0 |
| 260 | 0.013 | 0.092 | 1 | 0 | 1 | 0 | 0 | 0 |
| 261 | NA | NA | 0 | 0 | 0 | 0 | 0 | 0 |
| 262 | 1.005 | 0.068 | 1 | 13 | 2 | 1 | 0 | 0 |
| 263 | 0.014 | 0.911 | 1 | 1 | 0 | 0 | 0 | 0 |
| 264 | 0.534 | 0.126 | 1 | 7 | 3 | 0 | 0 | 0 |
| 265 | NA | NA | 0 | 0 | 0 | 0 | 0 | 0 |
| 266 | 0.014 | 0.911 | 1 | 1 | 0 | 0 | 0 | 0 |
| 267 | 0.812 | 0.000 | 3 | 5 | 8 | 1 | 0 | 0 |
| 268 | NA | NA | 0 | 0 | 0 | 0 | 0 | 0 |
| 269 | NA | NA | 0 | 0 | 0 | 0 | 0 | 0 |
| 270 | NA | NA | 0 | 0 | 0 | 0 | 0 | 0 |
| 271 | NA | NA | 0 | 0 | 0 | 0 | 0 | 0 |
| 272 | 0.014 | 0.911 | 1 | 1 | 0 | 0 | 0 | 0 |
| 273 | 0.049 | 0.911 | 1 | 2 | 0 | 0 | 0 | 0 |
| 274 | 0.465 | 0.362 | 1 | 7 | 2 | 0 | 0 | 0 |
| 275 | NA | NA | 0 | 0 | 0 | 0 | 0 | 0 |
| 276 | 0.049 | 0.911 | 1 | 2 | 0 | 0 | 0 | 0 |
| 277 | NA | NA | 0 | 0 | 0 | 0 | 0 | 0 |
| 278 | 0.013 | 0.005 | 3 | 0 | 0 | 1 | 0 | 0 |
| 279 | NA | NA | 0 | 0 | 0 | 0 | 0 | 0 |
| 280 | 0.014 | 0.911 | 1 | 1 | 0 | 0 | 0 | 0 |
| 281 | NA | NA | 0 | 0 | 0 | 0 | 0 | 0 |
| 282 | 2.408 | 0.000 | 3 | 8 | 17 | 9 | 0 | 0 |
| 283 | 0.014 | 0.911 | 1 | 1 | 0 | 0 | 0 | 0 |
| 284 | NA | NA | 0 | 0 | 0 | 0 | 0 | 0 |
| 285 | 0.049 | 0.911 | 1 | 2 | 0 | 0 | 0 | 0 |
| 286 | 0.013 | 0.005 | 3 | 0 | 0 | 1 | 0 | 0 |
| 287 | 1.057 | 0.000 | 3 | 9 | 5 | 3 | 0 | 0 |
| 288 | 0.147 | 0.909 | 1 | 4 | 0 | 0 | 0 | 0 |
| 289 | NA | NA | 0 | 0 | 0 | 0 | 0 | 0 |
| 290 | 0.049 | 0.911 | 1 | 2 | 0 | 0 | 0 | 0 |
| 291 | 2.241 | 0.000 | 3 | 14 | 13 | 4 | 0 | 0 |
| 292 | 0.094 | 0.910 | 1 | 3 | 0 | 0 | 0 | 0 |
| 293 | 0.014 | 0.911 | 1 | 1 | 0 | 0 | 0 | 0 |
| 294 | NA | NA | 0 | 0 | 0 | 0 | 0 | 0 |
| 295 | 9.034 | 0.000 | 3 | 49 | 33 | 2 | 0 | 0 |
| 296 | NA | NA | 0 | 0 | 0 | 0 | 0 | 0 |
| 297 | NA | NA | 0 | 0 | 0 | 0 | 0 | 0 |
| 298 | 0.014 | 0.911 | 1 | 1 | 0 | 0 | 0 | 0 |
| 299 | 0.093 | 0.028 | 2 | 1 | 2 | 0 | 0 | 0 |
| 300 | NA | NA | 0 | 0 | 0 | 0 | 0 | 0 |
| 301 | 0.332 | 0.906 | 1 | 7 | 0 | 0 | 0 | 0 |
| 302 | NA | NA | 0 | 0 | 0 | 0 | 0 | 0 |
| 303 | 2.250 | 0.003 | 3 | 21 | 8 | 1 | 0 | 0 |
| 304 | 0.328 | 0.206 | 1 | 5 | 2 | 0 | 0 | 0 |
| 305 | 4.222 | 0.000 | 3 | 17 | 20 | 16 | 0 | 0 |
| 306 | NA | NA | 0 | 0 | 0 | 0 | 0 | 0 |
| 307 | 9.895 | 0.000 | 3 | 58 | 23 | 4 | 0 | 0 |
| 308 | 0.094 | 0.910 | 1 | 3 | 0 | 0 | 0 | 0 |
| 309 | NA | NA | 0 | 0 | 0 | 0 | 0 | 0 |
| 310 | 0.147 | 0.909 | 1 | 4 | 0 | 0 | 0 | 0 |
| 311 | 0.014 | 0.911 | 1 | 1 | 0 | 0 | 0 | 0 |
| 312 | 0.014 | 0.911 | 1 | 1 | 0 | 0 | 0 | 0 |
| 313 | NA | NA | 0 | 0 | 0 | 0 | 0 | 0 |
| 314 | 0.049 | 0.911 | 1 | 2 | 0 | 0 | 0 | 0 |
| 315 | 0.048 | 0.186 | 1 | 1 | 1 | 0 | 0 | 0 |
| 316 | 0.014 | 0.911 | 1 | 1 | 0 | 0 | 0 | 0 |
| 317 | NA | NA | 0 | 0 | 0 | 0 | 0 | 0 |
| 318 | NA | NA | 0 | 0 | 0 | 0 | 0 | 0 |
| 319 | 0.204 | 0.471 | 1 | 4 | 1 | 0 | 0 | 0 |
| 320 | 0.388 | 0.000 | 3 | 3 | 2 | 3 | 0 | 0 |
| 321 | NA | NA | 0 | 0 | 0 | 0 | 0 | 0 |
| 322 | NA | NA | 0 | 0 | 0 | 0 | 0 | 0 |
| 323 | 0.014 | 0.911 | 1 | 1 | 0 | 0 | 0 | 0 |
| 324 | 0.014 | 0.911 | 1 | 1 | 0 | 0 | 0 | 0 |
| 325 | 0.013 | 0.005 | 3 | 0 | 0 | 1 | 0 | 0 |
| 326 | 0.013 | 0.092 | 1 | 0 | 1 | 0 | 0 | 0 |
| 327 | 0.013 | 0.005 | 3 | 0 | 0 | 1 | 0 | 0 |
| 328 | 0.014 | 0.911 | 1 | 1 | 0 | 0 | 0 | 0 |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | | | | |
|---|---|---|---|---|---|---|---|---|
| 329 | NA | NA | 0 | 0 | 0 | 0 | 0 | 0 |
| 330 | 0.014 | 0.911 | 1 | 1 | 0 | 0 | 0 | 0 |
| 331 | 0.684 | 0.201 | 1 | 9 | 3 | 0 | 0 | 0 |
| 332 | 0.013 | 0.005 | 3 | 0 | 0 | 1 | 0 | 0 |
| 333 | NA | NA | 0 | 0 | 0 | 0 | 0 | 0 |
| 334 | 16.673 | 0.000 | 3 | 61 | 53 | 13 | 0 | 0 |
| 335 | 0.988 | 0.006 | 3 | 10 | 6 | 0 | 0 | 0 |
| 336 | 0.013 | 0.005 | 3 | 0 | 0 | 1 | 0 | 0 |
| 337 | 1.369 | 0.928 | 1 | 19 | 1 | 0 | 0 | 0 |
| 338 | 7.863 | 1.000 | 0 | 60 | 9 | 0 | 0 | 0 |
| 339 | NA | NA | 0 | 0 | 0 | 0 | 0 | 0 |
| 340 | NA | NA | 0 | 0 | 0 | 0 | 0 | 0 |
| 341 | 0.013 | 0.005 | 3 | 0 | 0 | 1 | 0 | 0 |
| 342 | NA | NA | 0 | 0 | 0 | 0 | 0 | 0 |
| 343 | 1.337 | 0.030 | 2 | 15 | 4 | 1 | 0 | 0 |
| 344 | 0.014 | 0.911 | 1 | 1 | 0 | 0 | 0 | 0 |
| 345 | 0.013 | 0.005 | 3 | 0 | 0 | 1 | 0 | 0 |
| 346 | NA | NA | 0 | 0 | 0 | 0 | 0 | 0 |
| 347 | 0.615 | 0.056 | 1 | 10 | 0 | 1 | 0 | 0 |
| 348 | 0.092 | 0.001 | 3 | 0 | 3 | 0 | 0 | 0 |
| 349 | 0.014 | 0.911 | 1 | 1 | 0 | 0 | 0 | 0 |
| 350 | 0.684 | 0.201 | 1 | 9 | 3 | 0 | 0 | 0 |
| 351 | 0.585 | 0.000 | 3 | 2 | 2 | 7 | 0 | 0 |
| 352 | 0.048 | 0.010 | 2 | 1 | 0 | 1 | 0 | 0 |
| 353 | 0.013 | 0.092 | 1 | 0 | 1 | 0 | 0 | 0 |
| 354 | 0.202 | 0.096 | 1 | 3 | 2 | 0 | 0 | 0 |
| 355 | 0.048 | 0.009 | 3 | 0 | 2 | 0 | 0 | 0 |
| 356 | 4.267 | 0.000 | 3 | 32 | 15 | 2 | 0 | 0 |
| 357 | NA | NA | 0 | 0 | 0 | 0 | 0 | 0 |
| 358 | 0.922 | 0.340 | 1 | 12 | 3 | 0 | 0 | 0 |
| 359 | NA | NA | 0 | 0 | 0 | 0 | 0 | 0 |
| 360 | 0.267 | 0.907 | 1 | 6 | 0 | 0 | 0 | 0 |
| 361 | 0.049 | 0.911 | 1 | 2 | 0 | 0 | 0 | 0 |
| 362 | 0.013 | 0.092 | 1 | 0 | 1 | 0 | 0 | 0 |
| 363 | 0.014 | 0.911 | 1 | 1 | 0 | 0 | 0 | 0 |
| 364 | 0.013 | 0.005 | 3 | 0 | 0 | 1 | 0 | 0 |
| 365 | 0.014 | 0.911 | 1 | 1 | 0 | 0 | 0 | 0 |
| 366 | 0.202 | 0.011 | 2 | 3 | 1 | 1 | 0 | 0 |
| 367 | 0.014 | 0.911 | 1 | 1 | 0 | 0 | 0 | 0 |
| 368 | 0.013 | 0.005 | 3 | 0 | 0 | 1 | 0 | 0 |
| 369 | 0.013 | 0.092 | 1 | 0 | 1 | 0 | 0 | 0 |
| 370 | 0.395 | 0.278 | 1 | 6 | 2 | 0 | 0 | 0 |
| 371 | 0.684 | 0.201 | 1 | 9 | 3 | 0 | 0 | 0 |
| 372 | 0.664 | 0.000 | 3 | 4 | 8 | 0 | 0 | 0 |
| 373 | 0.265 | 0.569 | 1 | 5 | 1 | 0 | 0 | 0 |
| 374 | 0.013 | 0.092 | 1 | 0 | 1 | 0 | 0 | 0 |
| 375 | 0.014 | 0.911 | 1 | 1 | 0 | 0 | 0 | 0 |
| 376 | 0.014 | 0.911 | 1 | 1 | 0 | 0 | 0 | 0 |
| 377 | NA | NA | 0 | 0 | 0 | 0 | 0 | 0 |
| 378 | 0.048 | 0.186 | 1 | 1 | 1 | 0 | 0 | 0 |
| 379 | 15.302 | 0.014 | 2 | 83 | 9 | 3 | 0 | 0 |
| 380 | 6.579 | 0.461 | 1 | 54 | 7 | 1 | 0 | 0 |
| 381 | NA | NA | 0 | 0 | 0 | 0 | 0 | 0 |
| 382 | 0.013 | 0.005 | 3 | 0 | 0 | 1 | 0 | 0 |
| 383 | 0.147 | 0.909 | 1 | 4 | 0 | 0 | 0 | 0 |
| 384 | 0.013 | 0.092 | 1 | 0 | 1 | 0 | 0 | 0 |
| 385 | 0.202 | 0.096 | 1 | 3 | 2 | 0 | 0 | 0 |
| 386 | 0.048 | 0.009 | 3 | 0 | 2 | 0 | 0 | 0 |
| 387 | 2.925 | 0.000 | 3 | 9 | 21 | 10 | 0 | 0 |
| 388 | 0.013 | 0.092 | 1 | 0 | 1 | 0 | 0 | 0 |
| 389 | 0.048 | 0.009 | 3 | 0 | 2 | 0 | 0 | 0 |
| 390 | 0.092 | 0.001 | 3 | 0 | 3 | 0 | 0 | 0 |
| 391 | NA | NA | 0 | 0 | 0 | 0 | 0 | 0 |
| 392 | 15.614 | 0.001 | 3 | 77 | 20 | 6 | 0 | 0 |
| 393 | 0.013 | 0.005 | 3 | 0 | 0 | 1 | 0 | 0 |
| 394 | 0.014 | 0.911 | 1 | 1 | 0 | 0 | 0 | 0 |
| 395 | 0.014 | 0.911 | 1 | 1 | 0 | 0 | 0 | 0 |
| 396 | 0.680 | 0.046 | 2 | 8 | 4 | 0 | 0 | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| 397 | NA | NA | 0 | 0 | 0 | 0 | 0 | 0 |
| 398 | 0.094 | 0.910 | 1 | 3 | 0 | 0 | 0 | 0 |
| 399 | 0.014 | 0.911 | 1 | 1 | 0 | 0 | 0 | 0 |

Column Number

| Row Number | 19 percent of anaerobic cultivable community | 20 average percent abundance when present in $NO_3\text{-}10^{-1}$ | 21 competitive ability in $NO_3\text{-}10^{-1}$ | 22 aerobic MPN | 23 aerobic MPN upper bound (95% confidence) | 24 aerobic MPN lower bound (95% confidence) | 25 aerobic MPN rarity | 26 aerobic rarity category |
|---|---|---|---|---|---|---|---|---|
| 1 | 0.007 | NA | NA | NA | NA | NA | NA | 0 |
| 2 | 0.007 | 0.548 | average | NA | NA | NA | NA | 0 |
| 3 | NA | NA | NA | 0.094 | 0.670 | 0.013 | 0.090 | 1 |
| 4 | 0.021 | 0.034 | weak | NA | NA | NA | NA | 0 |
| 5 | NA | NA | NA | 0.094 | 0.670 | 0.013 | 0.000 | 3 |
| 6 | 0.007 | 0.129 | weak | NA | NA | NA | NA | 0 |
| 7 | 0.021 | 0.011 | weak | NA | NA | NA | NA | 0 |
| 8 | 0.007 | 0.007 | weak | NA | NA | NA | NA | 0 |
| 9 | 0.007 | 0.007 | weak | NA | NA | NA | NA | 0 |
| 10 | 0.021 | 0.017 | weak | NA | NA | NA | NA | 0 |
| 11 | 0.007 | NA | NA | NA | NA | NA | NA | 0 |
| 12 | 0.007 | 0.016 | weak | NA | NA | NA | NA | 0 |
| 13 | NA | NA | NA | 0.094 | 0.670 | 0.013 | 0.911 | 1 |
| 14 | NA | NA | NA | 0.094 | 0.670 | 0.013 | 0.911 | 1 |
| 15 | NA | NA | NA | 0.094 | 0.670 | 0.013 | 0.911 | 1 |
| 16 | 0.007 | 0.014 | weak | NA | NA | NA | NA | 0 |
| 17 | 0.007 | 0.007 | weak | NA | NA | NA | NA | 0 |
| 18 | 0.007 | NA | NA | NA | NA | NA | NA | 0 |
| 19 | 0.036 | 0.020 | weak | 0.383 | 1.020 | 0.144 | 0.908 | 1 |
| 20 | 0.007 | NA | NA | NA | NA | NA | NA | 0 |
| 21 | 0.007 | NA | NA | NA | NA | NA | NA | 0 |
| 22 | 0.007 | 0.131 | weak | NA | NA | NA | NA | 0 |
| 23 | 0.007 | 0.007 | weak | NA | NA | NA | NA | 0 |
| 24 | NA | NA | NA | 0.190 | 0.758 | 0.047 | 0.910 | 1 |
| 25 | 0.065 | 0.013 | weak | NA | NA | NA | NA | 0 |
| 26 | 0.036 | 0.012 | weak | NA | NA | NA | NA | 0 |
| 27 | 0.051 | 0.013 | weak | NA | NA | NA | NA | 0 |
| 28 | 0.007 | NA | NA | NA | NA | NA | NA | 0 |
| 29 | 0.014 | 1.625 | average | NA | NA | NA | NA | 0 |
| 30 | 0.007 | 0.067 | weak | NA | NA | NA | NA | 0 |
| 31 | 0.029 | 0.012 | weak | NA | NA | NA | NA | 0 |
| 32 | NA | NA | NA | 0.094 | 0.670 | 0.013 | 0.911 | 1 |
| 33 | 0.021 | 0.011 | weak | NA | NA | NA | NA | 0 |
| 34 | 0.007 | 0.007 | weak | NA | NA | NA | NA | 0 |
| 35 | 0.007 | NA | NA | NA | NA | NA | NA | 0 |
| 36 | 0.174 | 0.022 | weak | 0.094 | 0.670 | 0.013 | 0.090 | 1 |
| 37 | 0.007 | 0.014 | weak | NA | NA | NA | NA | 0 |
| 38 | 0.007 | 0.009 | weak | NA | NA | NA | NA | 0 |
| 39 | 0.007 | NA | NA | NA | NA | NA | NA | 0 |
| 40 | 0.066 | 0.013 | weak | NA | NA | NA | NA | 0 |
| 41 | 0.007 | NA | NA | NA | NA | NA | NA | 0 |
| 42 | 0.007 | 0.016 | weak | 0.094 | 0.670 | 0.013 | 0.090 | 1 |
| 43 | 0.007 | 0.046 | weak | NA | NA | NA | NA | 0 |
| 44 | 0.007 | 0.007 | weak | NA | NA | NA | NA | 0 |
| 45 | NA | NA | NA | 0.094 | 0.670 | 0.013 | 0.090 | 1 |
| 46 | 0.014 | 0.012 | weak | NA | NA | NA | NA | 0 |
| 47 | 0.007 | 0.007 | weak | NA | NA | NA | NA | 0 |
| 48 | 0.021 | 0.105 | weak | 0.475 | 1.147 | 0.197 | 0.009 | 3 |
| 49 | 0.007 | 0.179 | weak | NA | NA | NA | NA | 0 |
| 50 | 0.014 | 0.007 | weak | NA | NA | NA | NA | 0 |
| 51 | 0.014 | 0.006 | weak | NA | NA | NA | NA | 0 |
| 52 | NA | NA | NA | 0.094 | 0.670 | 0.013 | 0.090 | 1 |
| 53 | NA | NA | NA | 0.094 | 0.670 | 0.013 | 0.090 | 1 |
| 54 | 0.021 | 0.008 | weak | 0.094 | 0.670 | 0.013 | 0.090 | 1 |
| 55 | NA | NA | NA | 0.190 | 0.758 | 0.047 | 0.910 | 1 |
| 56 | 0.113 | 0.034 | weak | NA | NA | NA | NA | 0 |
| 57 | 0.014 | 0.006 | weak | NA | NA | NA | NA | 0 |
| 58 | 0.014 | 0.092 | weak | 0.094 | 0.670 | 0.013 | 0.911 | 1 |
| 59 | 0.051 | 0.022 | weak | NA | NA | NA | NA | 0 |
| 60 | NA | NA | NA | 0.094 | 0.670 | 0.013 | 0.000 | 3 |
| 61 | 0.007 | 0.007 | weak | NA | NA | NA | NA | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 62 | 0.007 | 0.009 | weak | NA | NA | NA | NA | 0 |
| 63 | NA | NA | NA | 0.094 | 0.670 | 0.013 | 0.911 | 1 |
| 64 | 0.007 | 0.007 | weak | NA | NA | NA | NA | 0 |
| 65 | NA | NA | NA | 0.094 | 0.670 | 0.013 | 0.911 | 1 |
| 66 | 0.007 | 0.007 | weak | NA | NA | NA | NA | 0 |
| 67 | NA | NA | NA | 0.094 | 0.670 | 0.013 | 0.090 | 1 |
| 68 | 0.007 | 0.007 | weak | NA | NA | NA | NA | 0 |
| 69 | 0.007 | 0.054 | weak | 0.475 | 1.147 | 0.197 | 0.009 | 3 |
| 70 | 0.014 | 0.073 | weak | NA | NA | NA | NA | 0 |
| 71 | 0.007 | NA | NA | NA | NA | NA | NA | 0 |
| 72 | 0.014 | 0.007 | weak | NA | NA | NA | NA | 0 |
| 73 | 0.007 | 0.007 | weak | NA | NA | NA | NA | 0 |
| 74 | NA | NA | NA | 0.383 | 1.020 | 0.144 | 0.908 | 1 |
| 75 | 0.007 | NA | NA | NA | NA | NA | NA | 0 |
| 76 | 0.007 | NA | NA | NA | NA | NA | NA | 0 |
| 77 | NA | NA | NA | 0.094 | 0.670 | 0.013 | 0.911 | 1 |
| 78 | 0.007 | NA | NA | 0.094 | 0.670 | 0.013 | 0.911 | 1 |
| 79 | 0.007 | NA | NA | NA | NA | NA | NA | 0 |
| 80 | 0.007 | NA | NA | NA | NA | NA | NA | 0 |
| 81 | 0.007 | 0.031 | weak | NA | NA | NA | NA | 0 |
| 82 | 0.148 | 0.025 | weak | 0.094 | 0.670 | 0.013 | 0.090 | 1 |
| 83 | NA | NA | NA | 0.190 | 0.758 | 0.047 | 0.910 | 1 |
| 84 | 0.007 | 0.017 | weak | NA | NA | NA | NA | 0 |
| 85 | 0.021 | 0.007 | weak | 1.363 | 2.318 | 0.802 | 0.000 | 3 |
| 86 | 0.007 | NA | NA | NA | NA | NA | NA | 0 |
| 87 | NA | NA | NA | 0.094 | 0.670 | 0.013 | 0.911 | 1 |
| 88 | 0.096 | 0.019 | weak | NA | NA | NA | NA | 0 |
| 89 | 0.007 | NA | NA | NA | NA | NA | NA | 0 |
| 90 | 0.007 | NA | NA | NA | NA | NA | NA | 0 |
| 91 | 0.007 | 0.096 | weak | NA | NA | NA | NA | 0 |
| 92 | NA | NA | NA | 0.286 | 0.886 | 0.092 | 0.909 | 1 |
| 93 | 0.014 | NA | NA | NA | NA | NA | NA | 0 |
| 94 | 0.007 | NA | NA | NA | NA | NA | NA | 0 |
| 95 | NA | NA | NA | 0.190 | 0.758 | 0.047 | 0.910 | 1 |
| 96 | 0.029 | 0.009 | weak | NA | NA | NA | NA | 0 |
| 97 | 0.007 | NA | NA | NA | NA | NA | NA | 0 |
| 98 | 0.007 | 0.043 | weak | NA | NA | NA | NA | 0 |
| 99 | 0.029 | 0.114 | weak | NA | NA | NA | NA | 0 |
| 100 | 0.131 | 0.026 | weak | NA | NA | NA | NA | 0 |
| 101 | 0.007 | 0.018 | weak | NA | NA | NA | NA | 0 |
| 102 | 0.007 | 0.010 | weak | NA | NA | NA | NA | 0 |
| 103 | NA | NA | NA | 0.094 | 0.670 | 0.013 | 0.090 | 1 |
| 104 | 0.007 | 0.006 | weak | NA | NA | NA | NA | 0 |
| 105 | 0.014 | 0.011 | weak | NA | NA | NA | NA | 0 |
| 106 | 0.066 | 0.159 | weak | NA | NA | NA | NA | 0 |
| 107 | 0.014 | 0.007 | weak | NA | NA | NA | NA | 0 |
| 108 | NA | NA | NA | 0.286 | 0.886 | 0.092 | 0.909 | 1 |
| 109 | 0.007 | NA | NA | NA | NA | NA | NA | 0 |
| 110 | 0.014 | 0.014 | weak | NA | NA | NA | NA | 0 |
| 111 | 0.007 | NA | NA | NA | NA | NA | NA | 0 |
| 112 | 0.021 | 0.010 | weak | NA | NA | NA | NA | 0 |
| 113 | 0.043 | 0.169 | weak | NA | NA | NA | NA | 0 |
| 114 | 0.021 | 0.016 | weak | NA | NA | NA | NA | 0 |
| 115 | NA | NA | NA | 0.094 | 0.670 | 0.013 | 0.090 | 1 |
| 116 | 0.007 | 0.019 | weak | NA | NA | NA | NA | 0 |
| 117 | 0.007 | 0.007 | weak | NA | NA | NA | NA | 0 |
| 118 | 0.007 | NA | NA | NA | NA | NA | NA | 0 |
| 119 | 0.007 | NA | NA | NA | NA | NA | NA | 0 |
| 120 | 0.256 | 1.782 | average | 2.282 | 3.471 | 1.501 | 0.723 | 1 |
| 121 | 0.007 | NA | NA | 0.855 | 1.658 | 0.440 | 0.000 | 3 |
| 122 | NA | NA | NA | 0.094 | 0.670 | 0.013 | 0.000 | 3 |
| 123 | 0.014 | 0.006 | weak | 39.545 | 50.578 | 30.919 | 0.000 | 3 |
| 124 | 0.104 | 0.533 | average | 0.094 | 0.670 | 0.013 | 0.911 | 1 |
| 125 | NA | NA | NA | 0.282 | 0.881 | 0.090 | 0.000 | 3 |
| 126 | 0.073 | 0.039 | weak | 2.927 | 4.262 | 2.010 | 0.199 | 1 |
| 127 | 0.007 | 0.051 | weak | 4.109 | 5.694 | 2.965 | 0.000 | 3 |
| 128 | 0.007 | NA | NA | NA | NA | NA | NA | 0 |
| 129 | 0.029 | 0.610 | average | NA | NA | NA | NA | 0 |
| 130 | 0.184 | 0.033 | weak | 0.381 | 1.018 | 0.143 | 0.030 | 2 |
| 131 | 0.043 | 0.032 | weak | 1.629 | 2.656 | 1.000 | 0.550 | 1 |
| 132 | 0.842 | 1.124 | average | 5.998 | 7.957 | 4.521 | 0.011 | 2 |
| 133 | NA | NA | NA | 1.371 | 2.328 | 0.807 | 0.000 | 3 |
| 134 | NA | NA | NA | 0.190 | 0.758 | 0.047 | 0.910 | 1 |
| 135 | 0.181 | 32.010 | strong | 2.773 | 4.074 | 1.887 | 0.972 | 1 |
| 136 | 0.104 | 0.041 | weak | NA | NA | NA | NA | 0 |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | | | | |
|---|---|---|---|---|---|---|---|---|
| 137 | 0.014 | 6.143 | strong | 0.189 | 0.757 | 0.047 | 0.015 | 2 |
| 138 | 61.705 | 9.448 | weak | 2596.266 | 3445.401 | 1956.405 | 0.000 | 3 |
| 139 | 0.007 | 33.268 | strong | NA | NA | NA | NA | 0 |
| 140 | 0.050 | 0.018 | weak | 5.979 | 7.935 | 4.506 | 0.000 | 3 |
| 141 | 0.752 | 0.137 | weak | 1.076 | 1.948 | 0.594 | 0.039 | 2 |
| 142 | 0.717 | 0.064 | weak | 0.378 | 1.013 | 0.141 | 0.001 | 3 |
| 143 | 0.021 | 0.096 | weak | NA | NA | NA | NA | 0 |
| 144 | NA | NA | NA | 1.254 | 2.178 | 0.722 | 0.000 | 3 |
| 145 | 0.051 | 1.162 | average | NA | NA | NA | NA | 0 |
| 146 | 0.079 | 2.973 | average | NA | NA | NA | NA | 0 |
| 147 | 2.308 | 1.403 | average | 2.071 | 3.209 | 1.336 | 0.077 | 1 |
| 148 | 1.633 | 32.099 | strong | 14.982 | 18.743 | 11.975 | 0.374 | 1 |
| 149 | NA | NA | NA | 0.094 | 0.670 | 0.013 | 0.090 | 1 |
| 150 | 0.007 | NA | NA | NA | NA | NA | NA | 0 |
| 151 | NA | NA | NA | 0.477 | 1.150 | 0.198 | 0.092 | 1 |
| 152 | 2.273 | 0.375 | average | 135.165 | 170.413 | 107.208 | 0.002 | 3 |
| 153 | NA | NA | NA | 0.094 | 0.670 | 0.013 | 0.090 | 1 |
| 154 | NA | NA | NA | 0.094 | 0.670 | 0.013 | 0.911 | 1 |
| 155 | NA | NA | NA | 0.094 | 0.670 | 0.013 | 0.911 | 1 |
| 156 | NA | NA | NA | 0.190 | 0.758 | 0.047 | 0.910 | 1 |
| 157 | 0.014 | NA | NA | 0.377 | 1.011 | 0.140 | 0.000 | 3 |
| 158 | 0.029 | 0.202 | weak | NA | NA | NA | NA | 0 |
| 159 | NA | NA | NA | 0.190 | 0.758 | 0.047 | 0.910 | 1 |
| 160 | 0.014 | 0.017 | weak | NA | NA | NA | NA | 0 |
| 161 | 0.173 | 0.033 | weak | 58.244 | 75.780 | 44.765 | 0.000 | 3 |
| 162 | NA | NA | NA | 0.094 | 0.670 | 0.013 | 0.090 | 1 |
| 163 | 0.007 | 0.006 | weak | NA | NA | NA | NA | 0 |
| 164 | 0.007 | NA | NA | NA | NA | NA | NA | 0 |
| 165 | 0.007 | 0.043 | weak | NA | NA | NA | NA | 0 |
| 166 | 0.007 | 0.006 | weak | NA | NA | NA | NA | 0 |
| 167 | 0.066 | 0.022 | weak | 0.094 | 0.670 | 0.013 | 0.911 | 1 |
| 168 | 0.007 | NA | NA | NA | NA | NA | NA | 0 |
| 169 | 0.021 | 0.030 | weak | 19.212 | 23.950 | 15.411 | 0.000 | 3 |
| 170 | 0.036 | 0.018 | weak | NA | NA | NA | NA | 0 |
| 171 | 0.043 | 0.011 | weak | NA | NA | NA | NA | 0 |
| 172 | 0.007 | 0.009 | weak | NA | NA | NA | NA | 0 |
| 173 | 0.007 | 0.170 | weak | NA | NA | NA | NA | 0 |
| 174 | 0.014 | 0.016 | weak | NA | NA | NA | NA | 0 |
| 175 | NA | NA | NA | NA | NA | NA | NA | NA |
| 176 | 0.007 | 0.009 | weak | NA | NA | NA | NA | 0 |
| 177 | 0.007 | 0.010 | weak | NA | NA | NA | NA | 0 |
| 178 | NA | NA | NA | 1.365 | 2.321 | 0.803 | 0.000 | 3 |
| 179 | 0.007 | 0.006 | weak | 0.956 | 1.791 | 0.510 | 0.000 | 3 |
| 180 | 0.051 | 0.020 | weak | NA | NA | NA | NA | 0 |
| 181 | NA | NA | NA | 0.189 | 0.757 | 0.047 | 0.182 | 1 |
| 182 | 0.924 | 0.355 | average | 1.484 | 2.472 | 0.891 | 0.009 | 3 |
| 183 | NA | NA | NA | 0.094 | 0.670 | 0.013 | 0.007 | 3 |
| 184 | 0.014 | 0.071 | weak | NA | NA | NA | NA | 0 |
| 185 | 3.633 | 0.154 | weak | 36.383 | 46.294 | 28.593 | 0.000 | 3 |
| 186 | 0.036 | 0.015 | weak | NA | NA | NA | NA | 0 |
| 187 | 0.104 | 0.021 | weak | 0.189 | 0.757 | 0.047 | 0.015 | 2 |
| 188 | 0.051 | 0.061 | weak | NA | NA | NA | NA | 0 |
| 189 | 0.106 | 2.967 | average | 0.380 | 1.016 | 0.142 | 0.054 | 1 |
| 190 | NA | NA | NA | 1.692 | 2.734 | 1.046 | 0.004 | 3 |
| 191 | NA | NA | NA | 1.684 | 2.726 | 1.041 | 0.001 | 3 |
| 192 | NA | NA | NA | 4.154 | 5.749 | 3.002 | 0.003 | 3 |
| 193 | 0.007 | NA | NA | NA | NA | NA | NA | 0 |
| 194 | 0.374 | 0.072 | weak | 0.094 | 0.670 | 0.013 | 0.911 | 1 |
| 195 | 0.326 | 0.049 | weak | 28.186 | 35.393 | 22.446 | 0.000 | 3 |
| 196 | 0.007 | NA | NA | NA | NA | NA | NA | 0 |
| 197 | 0.029 | 0.023 | weak | NA | NA | NA | NA | 0 |
| 198 | NA | NA | NA | 0.188 | 0.756 | 0.047 | 0.009 | 3 |
| 199 | 0.007 | 0.011 | weak | NA | NA | NA | NA | 0 |
| 200 | 0.014 | 0.009 | weak | NA | NA | NA | NA | 0 |
| 201 | 0.014 | NA | NA | 0.479 | 1.152 | 0.199 | 0.461 | 1 |
| 202 | NA | NA | NA | 0.094 | 0.670 | 0.013 | 0.090 | 1 |
| 203 | 1.321 | 0.288 | weak | 0.383 | 1.020 | 0.144 | 0.908 | 1 |
| 204 | 0.021 | 0.013 | weak | 0.094 | 0.670 | 0.013 | 0.911 | 1 |
| 205 | NA | NA | NA | 0.094 | 0.670 | 0.013 | 0.911 | 1 |
| 206 | 0.081 | 0.072 | weak | NA | NA | NA | NA | 0 |
| 207 | 0.007 | NA | NA | NA | NA | NA | NA | 0 |
| 208 | 0.007 | 0.076 | weak | NA | NA | NA | NA | 0 |
| 209 | 0.081 | 0.033 | weak | 8.820 | 11.323 | 6.870 | 0.006 | 3 |
| 210 | 0.014 | NA | NA | 0.094 | 0.670 | 0.013 | 0.090 | 1 |
| 211 | NA | NA | NA | 0.094 | 0.670 | 0.013 | 0.090 | 1 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 212 | NA | NA | NA | 0.094 | 0.670 | 0.013 | 0.911 | 1 |
| 213 | 0.014 | 0.026 | weak | 0.094 | 0.670 | 0.013 | 0.090 | 1 |
| 214 | 0.014 | NA | NA | 0.380 | 1.016 | 0.142 | 0.054 | 1 |
| 215 | 0.014 | NA | NA | 1.837 | 2.918 | 1.157 | 0.000 | 3 |
| 216 | 0.007 | NA | NA | NA | NA | NA | NA | 0 |
| 217 | 0.028 | 0.018 | weak | 0.188 | 0.756 | 0.047 | 0.009 | 3 |
| 218 | 0.007 | 0.011 | weak | NA | NA | NA | NA | 0 |
| 219 | NA | NA | NA | 0.094 | 0.670 | 0.013 | 0.090 | 1 |
| 220 | NA | NA | NA | 0.094 | 0.670 | 0.013 | 0.911 | 1 |
| 221 | NA | NA | NA | 1.062 | 1.930 | 0.584 | 0.000 | 3 |
| 222 | 0.478 | 0.084 | weak | 26.407 | 33.080 | 21.080 | 0.011 | 2 |
| 223 | 0.014 | NA | NA | NA | NA | NA | NA | 0 |
| 224 | 0.014 | 0.073 | weak | NA | NA | NA | NA | 0 |
| 225 | 0.527 | 0.132 | weak | NA | NA | NA | NA | 0 |
| 226 | 0.021 | 0.020 | weak | NA | NA | NA | NA | 0 |
| 227 | 0.007 | NA | NA | 3.038 | 4.397 | 2.098 | 0.609 | 1 |
| 228 | 0.312 | 0.067 | weak | 25.582 | 32.015 | 20.441 | 0.000 | 3 |
| 229 | NA | NA | NA | 0.094 | 0.670 | 0.013 | 0.911 | 1 |
| 230 | 0.209 | 0.061 | weak | 2.293 | 3.485 | 1.509 | 0.992 | 1 |
| 231 | 0.014 | 0.015 | weak | NA | NA | NA | NA | 0 |
| 232 | NA | NA | NA | 0.572 | 1.279 | 0.256 | 0.000 | 3 |
| 233 | 0.014 | 0.007 | weak | 0.383 | 1.020 | 0.144 | 0.908 | 1 |
| 234 | NA | NA | NA | 0.094 | 0.670 | 0.013 | 0.911 | 1 |
| 235 | NA | NA | NA | 0.094 | 0.670 | 0.013 | 0.911 | 1 |
| 236 | NA | NA | NA | 0.094 | 0.670 | 0.013 | 0.911 | 1 |
| 237 | NA | NA | NA | 0.094 | 0.670 | 0.013 | 0.911 | 1 |
| 238 | 0.035 | 0.007 | weak | 3.810 | 5.333 | 2.721 | 0.000 | 3 |
| 239 | NA | NA | NA | 0.285 | 0.884 | 0.092 | 0.001 | 3 |
| 240 | 0.014 | NA | NA | NA | NA | NA | NA | 0 |
| 241 | 0.007 | NA | NA | NA | NA | NA | NA | 0 |
| 242 | NA | NA | NA | 0.771 | 1.546 | 0.384 | 0.000 | 3 |
| 243 | 2.555 | 0.886 | average | 18.429 | 22.977 | 14.781 | 0.000 | 3 |
| 244 | 0.007 | NA | NA | NA | NA | NA | NA | 0 |
| 245 | NA | NA | NA | 0.094 | 0.670 | 0.013 | 0.911 | 1 |
| 246 | NA | NA | NA | 0.094 | 0.670 | 0.013 | 0.911 | 1 |
| 247 | 0.014 | 0.012 | weak | NA | NA | NA | NA | 0 |
| 248 | NA | NA | NA | 0.094 | 0.670 | 0.013 | 0.090 | 1 |
| 249 | 0.036 | 0.016 | weak | NA | NA | NA | NA | 0 |
| 250 | 0.029 | 0.015 | weak | NA | NA | NA | NA | 0 |
| 251 | 0.108 | 0.039 | weak | 23.969 | 29.946 | 19.185 | 0.000 | 3 |
| 252 | 0.007 | 0.028 | weak | NA | NA | NA | NA | 0 |
| 253 | 0.036 | 0.008 | weak | 0.383 | 1.020 | 0.144 | 0.908 | 1 |
| 254 | 0.007 | 0.042 | weak | NA | NA | NA | NA | 0 |
| 255 | 0.736 | 0.248 | weak | 12.525 | 15.765 | 9.951 | 0.299 | 1 |
| 256 | 1.099 | 1.283 | average | 4.786 | 6.508 | 3.520 | 0.042 | 2 |
| 257 | 0.029 | 0.017 | weak | NA | NA | NA | NA | 0 |
| 258 | 0.378 | 40.399 | strong | 3.006 | 4.359 | 2.073 | 0.956 | 1 |
| 259 | NA | NA | NA | 0.094 | 0.670 | 0.013 | 0.911 | 1 |
| 260 | 0.007 | NA | NA | NA | NA | NA | NA | 0 |
| 261 | NA | NA | NA | 0.094 | 0.670 | 0.013 | 0.911 | 1 |
| 262 | 0.120 | 0.018 | weak | 0.094 | 0.670 | 0.013 | 0.911 | 1 |
| 263 | 0.007 | 0.019 | weak | NA | NA | NA | NA | 0 |
| 264 | 0.073 | 0.028 | weak | NA | NA | NA | NA | 0 |
| 265 | NA | NA | NA | 0.189 | 0.757 | 0.047 | 0.182 | 1 |
| 266 | 0.007 | 0.107 | weak | NA | NA | NA | NA | 0 |
| 267 | 0.101 | 0.115 | weak | 0.094 | 0.670 | 0.013 | 0.911 | 1 |
| 268 | NA | NA | NA | 0.094 | 0.670 | 0.013 | 0.911 | 1 |
| 269 | NA | NA | NA | 2.340 | 3.542 | 1.545 | 0.001 | 3 |
| 270 | NA | NA | NA | 0.094 | 0.670 | 0.013 | 0.911 | 1 |
| 271 | NA | NA | NA | 5.850 | 7.780 | 4.399 | 0.000 | 3 |
| 272 | 0.007 | 0.047 | weak | NA | NA | NA | NA | 0 |
| 273 | 0.014 | 0.008 | weak | NA | NA | NA | NA | 0 |
| 274 | 0.066 | 0.050 | weak | NA | NA | NA | NA | 0 |
| 275 | NA | NA | NA | 0.094 | 0.670 | 0.013 | 0.911 | 1 |
| 276 | 0.014 | 8.868 | strong | NA | NA | NA | NA | 0 |
| 277 | NA | NA | NA | 0.094 | 0.670 | 0.013 | 0.911 | 1 |
| 278 | 0.007 | NA | NA | NA | NA | NA | NA | 0 |
| 279 | NA | NA | NA | 0.094 | 0.670 | 0.013 | 0.911 | 1 |
| 280 | 0.007 | 0.043 | weak | NA | NA | NA | NA | 0 |
| 281 | NA | NA | NA | 0.378 | 1.013 | 0.141 | 0.004 | 3 |
| 282 | 0.252 | 0.014 | weak | 3.700 | 5.201 | 2.633 | 0.000 | 3 |
| 283 | 0.007 | 0.051 | weak | NA | NA | NA | NA | 0 |
| 284 | NA | NA | NA | 0.286 | 0.886 | 0.092 | 0.909 | 1 |
| 285 | 0.014 | 0.009 | weak | NA | NA | NA | NA | 0 |
| 286 | 0.007 | NA | NA | NA | NA | NA | NA | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 287 | 0.126 | 0.013 | weak | 21.563 | 26.893 | 17.289 | 0.000 | 3 |
| 288 | 0.029 | 0.617 | average | NA | NA | NA | NA | 0 |
| 289 | NA | NA | NA | 0.094 | 0.670 | 0.013 | 0.911 | 1 |
| 290 | 0.014 | 0.115 | weak | NA | NA | NA | NA | 0 |
| 291 | 0.236 | 0.040 | weak | 22.899 | 28.584 | 18.345 | 0.000 | 3 |
| 292 | 0.021 | 0.009 | weak | NA | NA | NA | NA | 0 |
| 293 | 0.007 | 0.028 | weak | NA | NA | NA | NA | 0 |
| 294 | NA | NA | NA | 0.383 | 1.020 | 0.144 | 0.908 | 1 |
| 295 | 0.839 | 0.384 | average | 16.722 | 20.872 | 13.398 | 0.000 | 3 |
| 296 | NA | NA | NA | 0.094 | 0.670 | 0.013 | 0.090 | 1 |
| 297 | NA | NA | NA | 0.094 | 0.670 | 0.013 | 0.911 | 1 |
| 298 | 0.007 | 0.024 | weak | NA | NA | NA | NA | 0 |
| 299 | 0.021 | 5.293 | strong | 0.094 | 0.670 | 0.013 | 0.911 | 1 |
| 300 | NA | NA | NA | 0.286 | 0.886 | 0.092 | 0.909 | 1 |
| 301 | 0.051 | 0.018 | weak | NA | NA | NA | NA | 0 |
| 302 | NA | NA | NA | 0.094 | 0.670 | 0.013 | 0.911 | 1 |
| 303 | 0.237 | 0.024 | weak | 0.094 | 0.670 | 0.013 | 0.007 | 3 |
| 304 | 0.051 | 0.034 | weak | NA | NA | NA | NA | 0 |
| 305 | 0.414 | 0.018 | weak | 6.937 | 9.077 | 5.302 | 0.000 | 3 |
| 306 | NA | NA | NA | 0.094 | 0.670 | 0.013 | 0.090 | 1 |
| 307 | 0.915 | 0.101 | weak | 100.281 | 128.092 | 78.508 | 0.000 | 3 |
| 308 | 0.021 | 0.010 | weak | 1.629 | 2.656 | 1.000 | 0.550 | 1 |
| 309 | NA | NA | NA | 0.094 | 0.670 | 0.013 | 0.911 | 1 |
| 310 | 0.029 | 0.018 | weak | NA | NA | NA | NA | 0 |
| 311 | 0.007 | 0.009 | weak | NA | NA | NA | NA | 0 |
| 312 | 0.007 | 0.010 | weak | NA | NA | NA | NA | 0 |
| 313 | NA | NA | NA | 0.189 | 0.757 | 0.047 | 0.182 | 1 |
| 314 | 0.014 | 0.017 | weak | NA | NA | NA | NA | 0 |
| 315 | 0.014 | 0.321 | weak | 0.190 | 0.758 | 0.047 | 0.910 | 1 |
| 316 | 0.007 | 0.064 | weak | NA | NA | NA | NA | 0 |
| 317 | NA | NA | NA | 0.094 | 0.670 | 0.013 | 0.911 | 1 |
| 318 | NA | NA | NA | 0.286 | 0.886 | 0.092 | 0.909 | 1 |
| 319 | 0.036 | 0.037 | weak | NA | NA | NA | NA | 0 |
| 320 | 0.057 | 0.115 | weak | 3.224 | 4.625 | 2.248 | 0.005 | 3 |
| 321 | NA | NA | NA | 0.286 | 0.886 | 0.092 | 0.909 | 1 |
| 322 | NA | NA | NA | 0.094 | 0.670 | 0.013 | 0.090 | 1 |
| 323 | 0.007 | 33.207 | strong | NA | NA | NA | NA | 0 |
| 324 | 0.007 | 0.009 | weak | NA | NA | NA | NA | 0 |
| 325 | 0.007 | NA | NA | NA | NA | NA | NA | 0 |
| 326 | 0.007 | NA | NA | NA | NA | NA | NA | 0 |
| 327 | 0.007 | NA | NA | NA | NA | NA | NA | 0 |
| 328 | 0.007 | 0.007 | weak | NA | NA | NA | NA | 0 |
| 329 | NA | NA | NA | 1.168 | 2.068 | 0.660 | 0.000 | 3 |
| 330 | 0.007 | 0.009 | weak | 0.188 | 0.756 | 0.047 | 0.001 | 3 |
| 331 | 0.088 | 0.098 | weak | NA | NA | NA | NA | 0 |
| 332 | 0.007 | NA | NA | NA | NA | NA | NA | 0 |
| 333 | NA | NA | NA | 0.094 | 0.670 | 0.013 | 0.911 | 1 |
| 334 | 1.527 | 0.066 | weak | 83.284 | 107.416 | 64.573 | 0.000 | 3 |
| 335 | 0.119 | 0.072 | weak | 4.775 | 6.494 | 3.511 | 0.000 | 3 |
| 336 | 0.007 | NA | NA | NA | NA | NA | NA | 0 |
| 337 | 0.155 | 8.048 | strong | 2.897 | 4.225 | 1.986 | 0.968 | 1 |
| 338 | 0.736 | 0.967 | average | 24.252 | 30.308 | 19.406 | 0.000 | 3 |
| 339 | NA | NA | NA | 0.094 | 0.670 | 0.013 | 0.911 | 1 |
| 340 | NA | NA | NA | 0.094 | 0.670 | 0.013 | 0.090 | 1 |
| 341 | 0.007 | NA | NA | NA | NA | NA | NA | 0 |
| 342 | NA | NA | NA | 0.094 | 0.670 | 0.013 | 0.911 | 1 |
| 343 | 0.152 | 55.360 | strong | 0.481 | 1.155 | 0.200 | 0.907 | 1 |
| 344 | 0.007 | 0.019 | weak | NA | NA | NA | NA | 0 |
| 345 | 0.007 | NA | NA | NA | NA | NA | NA | 0 |
| 346 | NA | NA | NA | 0.094 | 0.670 | 0.013 | 0.007 | 3 |
| 347 | 0.081 | 0.020 | weak | 13.443 | 16.874 | 10.709 | 0.250 | 1 |
| 348 | 0.021 | NA | NA | 0.960 | 1.797 | 0.513 | 0.000 | 3 |
| 349 | 0.007 | 3.389 | strong | NA | NA | NA | NA | 0 |
| 350 | 0.088 | 0.122 | weak | NA | NA | NA | NA | 0 |
| 351 | 0.078 | 0.011 | weak | 0.565 | 1.270 | 0.252 | 0.000 | 3 |
| 352 | 0.014 | 0.006 | weak | NA | NA | NA | NA | 0 |
| 353 | 0.007 | NA | NA | NA | NA | NA | NA | 0 |
| 354 | 0.036 | 0.041 | weak | 5.029 | 6.799 | 3.720 | 0.046 | 2 |
| 355 | 0.014 | NA | NA | 0.094 | 0.670 | 0.013 | 0.911 | 1 |
| 356 | 0.418 | 0.686 | average | 13.402 | 16.825 | 10.676 | 0.000 | 3 |
| 357 | NA | NA | NA | 0.477 | 1.150 | 0.198 | 0.092 | 1 |
| 358 | 0.112 | 3.081 | average | 0.286 | 0.886 | 0.092 | 0.909 | 1 |
| 359 | NA | NA | NA | 0.189 | 0.757 | 0.047 | 0.182 | 1 |
| 360 | 0.043 | 0.013 | weak | 1.135 | 2.024 | 0.636 | 0.000 | 3 |
| 361 | 0.014 | 0.012 | weak | NA | NA | NA | NA | 0 |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 362 | 0.007 | NA | NA | 0.094 | 0.670 | 0.013 | 0.911 | 1 |
| 363 | 0.007 | 0.085 | weak | NA | NA | NA | NA | 0 |
| 364 | 0.007 | NA | NA | NA | NA | NA | NA | 0 |
| 365 | 0.007 | 0.019 | weak | NA | NA | NA | NA | 0 |
| 366 | 0.036 | 0.061 | weak | 2.172 | 3.334 | 1.415 | 0.000 | 3 |
| 367 | 0.007 | 0.019 | weak | NA | NA | NA | NA | 0 |
| 368 | 0.007 | NA | NA | NA | NA | NA | NA | 0 |
| 369 | 0.007 | NA | NA | 0.094 | 0.670 | 0.013 | 0.090 | 1 |
| 370 | 0.058 | 0.092 | weak | NA | NA | NA | NA | 0 |
| 371 | 0.088 | 0.145 | weak | NA | NA | NA | NA | 0 |
| 372 | 0.086 | 3.565 | average | NA | NA | NA | NA | 0 |
| 373 | 0.043 | 0.022 | weak | NA | NA | NA | NA | 0 |
| 374 | 0.007 | NA | NA | 1.175 | 2.076 | 0.665 | 0.043 | 2 |
| 375 | 0.007 | 0.054 | weak | 1.057 | 1.924 | 0.581 | 0.000 | 3 |
| 376 | 0.007 | 0.019 | weak | NA | NA | NA | NA | 0 |
| 377 | NA | NA | NA | 0.285 | 0.884 | 0.092 | 0.274 | 1 |
| 378 | 0.014 | 0.016 | weak | 1.190 | 2.096 | 0.676 | 0.002 | 3 |
| 379 | 1.401 | 0.387 | average | 0.884 | 1.697 | 0.460 | 0.903 | 1 |
| 380 | 0.622 | 0.210 | weak | 0.383 | 1.020 | 0.144 | 0.908 | 1 |
| 381 | NA | NA | NA | 2.216 | 3.389 | 1.449 | 0.000 | 3 |
| 382 | 0.007 | NA | NA | NA | NA | NA | NA | 0 |
| 383 | 0.029 | 0.091 | weak | NA | NA | NA | NA | 0 |
| 384 | 0.007 | NA | NA | NA | NA | NA | NA | 0 |
| 385 | 0.036 | 0.045 | weak | 7.828 | 10.139 | 6.043 | 0.906 | 1 |
| 386 | 0.014 | NA | NA | NA | NA | NA | NA | 0 |
| 387 | 0.298 | 0.021 | weak | 6.369 | 8.400 | 4.829 | 0.000 | 3 |
| 388 | 0.007 | NA | NA | NA | NA | NA | NA | 0 |
| 389 | 0.014 | NA | NA | 0.190 | 0.758 | 0.047 | 0.910 | 1 |
| 390 | 0.021 | NA | NA | 0.094 | 0.670 | 0.013 | 0.911 | 1 |
| 391 | NA | NA | NA | 0.094 | 0.670 | 0.013 | 0.007 | 3 |
| 392 | 1.430 | 22.870 | strong | 15.373 | 19.220 | 12.296 | 0.349 | 1 |
| 393 | 0.007 | NA | NA | 0.094 | 0.670 | 0.013 | 0.911 | 1 |
| 394 | 0.007 | 0.016 | weak | 1.555 | 2.562 | 0.943 | 0.000 | 3 |
| 395 | 0.007 | 62.167 | strong | NA | NA | NA | NA | 0 |
| 396 | 0.088 | 0.018 | weak | 98.821 | 126.324 | 77.306 | 0.000 | 3 |
| 397 | NA | NA | NA | 0.094 | 0.670 | 0.013 | 0.911 | 1 |
| 398 | 0.021 | 0.182 | weak | NA | NA | NA | NA | 0 |
| 399 | 0.007 | 0.019 | weak | NA | NA | NA | NA | 0 |

| | Column Number | | | | | | | |
|---|---|---|---|---|---|---|---|---|
| Row Number | 27 $O_2$-$10^{-1}$ number of communities | 28 $O_2$-$10^{-2}$ number of communities | 29 $O_2$-$10^{-3}$ number of communities | 30 $O_2$-$10^{-4}$ number of communities | 31 $O_2$-$10^{-5}$ number of communities | 32 percent of anaerobic cultivable community | 33 average abundance when present in $O_2$-$10^{-1}$ | 34 competitive ability in $O_2$-$10^{-1}$ |
| 1 | 0 | 0 | 0 | 0 | 0 | NA | NA | NA |
| 2 | 0 | 0 | 0 | 0 | 0 | NA | NA | NA |
| 3 | 0 | 1 | 0 | 0 | 0 | 0.003 | NA | NA |
| 4 | 0 | 0 | 0 | 0 | 0 | NA | NA | NA |
| 5 | 0 | 0 | 0 | 1 | 0 | 0.003 | NA | NA |
| 6 | 0 | 0 | 0 | 0 | 0 | NA | NA | NA |
| 7 | 0 | 0 | 0 | 0 | 0 | NA | NA | NA |
| 8 | 0 | 0 | 0 | 0 | 0 | NA | NA | NA |
| 9 | 0 | 0 | 0 | 0 | 0 | NA | NA | NA |
| 10 | 0 | 0 | 0 | 0 | 0 | NA | NA | NA |
| 11 | 0 | 0 | 0 | 0 | 0 | NA | NA | NA |
| 12 | 0 | 0 | 0 | 0 | 0 | NA | NA | NA |
| 13 | 1 | 0 | 0 | 0 | 0 | 0.003 | 0.027 | weak |
| 14 | 1 | 0 | 0 | 0 | 0 | 0.003 | 0.027 | weak |
| 15 | 1 | 0 | 0 | 0 | 0 | 0.003 | 0.017 | weak |
| 16 | 0 | 0 | 0 | 0 | 0 | NA | NA | NA |
| 17 | 0 | 0 | 0 | 0 | 0 | NA | NA | NA |
| 18 | 0 | 0 | 0 | 0 | 0 | NA | NA | NA |
| 19 | 4 | 0 | 0 | 0 | 0 | 0.011 | 0.053 | weak |
| 20 | 0 | 0 | 0 | 0 | 0 | NA | NA | NA |
| 21 | 0 | 0 | 0 | 0 | 0 | NA | NA | NA |
| 22 | 0 | 0 | 0 | 0 | 0 | NA | NA | NA |
| 23 | 0 | 0 | 0 | 0 | 0 | NA | NA | NA |
| 24 | 2 | 0 | 0 | 0 | 0 | 0.005 | 0.016 | weak |
| 25 | 0 | 0 | 0 | 0 | 0 | NA | NA | NA |
| 26 | 0 | 0 | 0 | 0 | 0 | NA | NA | NA |
| 27 | 0 | 0 | 0 | 0 | 0 | NA | NA | NA |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 28  | 0 | 0 | 0 | 0 | 0 | NA    | NA    | NA   |
| 29  | 0 | 0 | 0 | 0 | 0 | NA    | NA    | NA   |
| 30  | 0 | 0 | 0 | 0 | 0 | NA    | NA    | NA   |
| 31  | 0 | 0 | 0 | 0 | 0 | NA    | NA    | NA   |
| 32  | 1 | 0 | 0 | 0 | 0 | 0.003 | 0.013 | weak |
| 33  | 0 | 0 | 0 | 0 | 0 | NA    | NA    | NA   |
| 34  | 0 | 0 | 0 | 0 | 0 | NA    | NA    | NA   |
| 35  | 0 | 0 | 0 | 0 | 0 | NA    | NA    | NA   |
| 36  | 0 | 1 | 0 | 0 | 0 | 0.003 | NA    | NA   |
| 37  | 0 | 0 | 0 | 0 | 0 | NA    | NA    | NA   |
| 38  | 0 | 0 | 0 | 0 | 0 | NA    | NA    | NA   |
| 39  | 0 | 0 | 0 | 0 | 0 | NA    | NA    | NA   |
| 40  | 0 | 0 | 0 | 0 | 0 | NA    | NA    | NA   |
| 41  | 0 | 0 | 0 | 0 | 0 | NA    | NA    | NA   |
| 42  | 0 | 1 | 0 | 0 | 0 | 0.003 | NA    | NA   |
| 43  | 0 | 0 | 0 | 0 | 0 | NA    | NA    | NA   |
| 44  | 0 | 0 | 0 | 0 | 0 | NA    | NA    | NA   |
| 45  | 0 | 1 | 0 | 0 | 0 | 0.003 | NA    | NA   |
| 46  | 0 | 0 | 0 | 0 | 0 | NA    | NA    | NA   |
| 47  | 0 | 0 | 0 | 0 | 0 | NA    | NA    | NA   |
| 48  | 2 | 3 | 0 | 0 | 0 | 0.013 | 0.016 | weak |
| 49  | 0 | 0 | 0 | 0 | 0 | NA    | NA    | NA   |
| 50  | 0 | 0 | 0 | 0 | 0 | NA    | NA    | NA   |
| 51  | 0 | 0 | 0 | 0 | 0 | NA    | NA    | NA   |
| 52  | 0 | 1 | 0 | 0 | 0 | 0.003 | NA    | NA   |
| 53  | 0 | 1 | 0 | 0 | 0 | 0.003 | NA    | NA   |
| 54  | 0 | 1 | 0 | 0 | 0 | 0.003 | NA    | NA   |
| 55  | 2 | 0 | 0 | 0 | 0 | 0.005 | 0.049 | weak |
| 56  | 0 | 0 | 0 | 0 | 0 | NA    | NA    | NA   |
| 57  | 0 | 0 | 0 | 0 | 0 | NA    | NA    | NA   |
| 58  | 1 | 0 | 0 | 0 | 0 | 0.003 | 0.025 | weak |
| 59  | 0 | 0 | 0 | 0 | 0 | NA    | NA    | NA   |
| 60  | 0 | 0 | 0 | 1 | 0 | 0.003 | NA    | NA   |
| 61  | 0 | 0 | 0 | 0 | 0 | NA    | NA    | NA   |
| 62  | 0 | 0 | 0 | 0 | 0 | NA    | NA    | NA   |
| 63  | 1 | 0 | 0 | 0 | 0 | 0.003 | 0.012 | weak |
| 64  | 0 | 0 | 0 | 0 | 0 | NA    | NA    | NA   |
| 65  | 1 | 0 | 0 | 0 | 0 | 0.003 | 0.025 | weak |
| 66  | 0 | 0 | 0 | 0 | 0 | NA    | NA    | NA   |
| 67  | 0 | 1 | 0 | 0 | 0 | 0.003 | NA    | NA   |
| 68  | 0 | 0 | 0 | 0 | 0 | NA    | NA    | NA   |
| 69  | 2 | 3 | 0 | 0 | 0 | 0.013 | 0.017 | weak |
| 70  | 0 | 0 | 0 | 0 | 0 | NA    | NA    | NA   |
| 71  | 0 | 0 | 0 | 0 | 0 | NA    | NA    | NA   |
| 72  | 0 | 0 | 0 | 0 | 0 | NA    | NA    | NA   |
| 73  | 0 | 0 | 0 | 0 | 0 | NA    | NA    | NA   |
| 74  | 4 | 0 | 0 | 0 | 0 | 0.011 | 0.086 | weak |
| 75  | 0 | 0 | 0 | 0 | 0 | NA    | NA    | NA   |
| 76  | 0 | 0 | 0 | 0 | 0 | NA    | NA    | NA   |
| 77  | 1 | 0 | 0 | 0 | 0 | 0.003 | 0.020 | weak |
| 78  | 1 | 0 | 0 | 0 | 0 | 0.003 | 0.070 | weak |
| 79  | 0 | 0 | 0 | 0 | 0 | NA    | NA    | NA   |
| 80  | 0 | 0 | 0 | 0 | 0 | NA    | NA    | NA   |
| 81  | 0 | 0 | 0 | 0 | 0 | NA    | NA    | NA   |
| 82  | 0 | 1 | 0 | 0 | 0 | 0.003 | NA    | NA   |
| 83  | 2 | 0 | 0 | 0 | 0 | 0.005 | 0.049 | weak |
| 84  | 0 | 0 | 0 | 0 | 0 | NA    | NA    | NA   |
| 85  | 7 | 2 | 5 | 0 | 0 | 0.038 | 0.047 | weak |
| 86  | 0 | 0 | 0 | 0 | 0 | NA    | NA    | NA   |
| 87  | 1 | 0 | 0 | 0 | 0 | 0.003 | 0.043 | weak |
| 88  | 0 | 0 | 0 | 0 | 0 | NA    | NA    | NA   |
| 89  | 0 | 0 | 0 | 0 | 0 | NA    | NA    | NA   |
| 90  | 0 | 0 | 0 | 0 | 0 | NA    | NA    | NA   |
| 91  | 0 | 0 | 0 | 0 | 0 | NA    | NA    | NA   |
| 92  | 3 | 0 | 0 | 0 | 0 | 0.008 | 0.052 | weak |
| 93  | 0 | 0 | 0 | 0 | 0 | NA    | NA    | NA   |
| 94  | 0 | 0 | 0 | 0 | 0 | NA    | NA    | NA   |
| 95  | 2 | 0 | 0 | 0 | 0 | 0.005 | 0.022 | weak |
| 96  | 0 | 0 | 0 | 0 | 0 | NA    | NA    | NA   |
| 97  | 0 | 0 | 0 | 0 | 0 | NA    | NA    | NA   |
| 98  | 0 | 0 | 0 | 0 | 0 | NA    | NA    | NA   |
| 99  | 0 | 0 | 0 | 0 | 0 | NA    | NA    | NA   |
| 100 | 0 | 0 | 0 | 0 | 0 | NA    | NA    | NA   |
| 101 | 0 | 0 | 0 | 0 | 0 | NA    | NA    | NA   |
| 102 | 0 | 0 | 0 | 0 | 0 | NA    | NA    | NA   |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | | | | | |
|---|---|---|---|---|---|---|---|---|---|
| 103 | 0 | 1 | 0 | 0 | 0 | 0.003 | NA | NA |
| 104 | 0 | 0 | 0 | 0 | 0 | NA | NA | NA |
| 105 | 0 | 0 | 0 | 0 | 0 | NA | NA | NA |
| 106 | 0 | 0 | 0 | 0 | 0 | NA | NA | NA |
| 107 | 0 | 0 | 0 | 0 | 0 | NA | NA | NA |
| 108 | 3 | 0 | 0 | 0 | 0 | 0.008 | 0.302 | average |
| 109 | 0 | 0 | 0 | 0 | 0 | NA | NA | NA |
| 110 | 0 | 0 | 0 | 0 | 0 | NA | NA | NA |
| 111 | 0 | 0 | 0 | 0 | 0 | NA | NA | NA |
| 112 | 0 | 0 | 0 | 0 | 0 | NA | NA | NA |
| 113 | 0 | 0 | 0 | 0 | 0 | NA | NA | NA |
| 114 | 0 | 0 | 0 | 0 | 0 | NA | NA | NA |
| 115 | 0 | 1 | 0 | 0 | 0 | 0.003 | NA | NA |
| 116 | 0 | 0 | 0 | 0 | 0 | NA | NA | NA |
| 117 | 0 | 0 | 0 | 0 | 0 | NA | NA | NA |
| 118 | 0 | 0 | 0 | 0 | 0 | NA | NA | NA |
| 119 | 0 | 0 | 0 | 0 | 0 | NA | NA | NA |
| 120 | 19 | 3 | 0 | 0 | 0 | 0.063 | 0.195 | average |
| 121 | 2 | 1 | 5 | 1 | 0 | 0.024 | 0.014 | weak |
| 122 | 0 | 0 | 0 | 0 | 1 | 0.003 | NA | NA |
| 123 | 85 | 62 | 2 | 1 | 0 | 1.097 | 0.266 | average |
| 124 | 1 | 0 | 0 | 0 | 0 | 0.003 | 0.435 | average |
| 125 | 0 | 0 | 1 | 2 | 0 | 0.008 | NA | NA |
| 126 | 27 | 0 | 0 | 0 | 0 | 0.081 | 0.131 | average |
| 127 | 20 | 16 | 1 | 2 | 0 | 0.114 | 0.052 | weak |
| 128 | 0 | 0 | 0 | 0 | 0 | NA | NA | NA |
| 129 | 0 | 0 | 0 | 0 | 0 | NA | NA | NA |
| 130 | 3 | 0 | 1 | 0 | 0 | 0.011 | 0.042 | weak |
| 131 | 16 | 0 | 0 | 0 | 0 | 0.045 | 0.090 | weak |
| 132 | 48 | 0 | 0 | 0 | 0 | 0.166 | 0.235 | average |
| 133 | 8 | 4 | 1 | 1 | 0 | 0.038 | 0.038 | weak |
| 134 | 2 | 0 | 0 | 0 | 0 | 0.005 | 8.626 | strong |
| 135 | 24 | 2 | 0 | 0 | 0 | 0.077 | 21.852 | strong |
| 136 | 0 | 0 | 0 | 0 | 0 | NA | NA | NA |
| 137 | 1 | 0 | 1 | 0 | 0 | 0.005 | 0.012 | weak |
| 138 | 96 | 96 | 70 | 11 | 2 | 71.992 | 12.161 | weak |
| 139 | 0 | 0 | 0 | 0 | 0 | NA | NA | NA |
| 140 | 21 | 23 | 11 | 1 | 0 | 0.166 | 0.101 | weak |
| 141 | 8 | 2 | 1 | 0 | 0 | 0.030 | 0.037 | weak |
| 142 | 1 | 2 | 1 | 0 | 0 | 0.010 | 0.012 | weak |
| 143 | 0 | 0 | 0 | 0 | 0 | NA | NA | NA |
| 144 | 5 | 3 | 5 | 0 | 0 | 0.035 | 0.045 | weak |
| 145 | 0 | 0 | 0 | 0 | 0 | NA | NA | NA |
| 146 | 0 | 0 | 0 | 0 | 0 | NA | NA | NA |
| 147 | 19 | 0 | 1 | 0 | 0 | 0.057 | 0.071 | weak |
| 148 | 76 | 10 | 2 | 0 | 0 | 0.415 | 2.369 | average |
| 149 | 0 | 1 | 0 | 0 | 0 | 0.003 | NA | NA |
| 150 | 0 | 0 | 0 | 0 | 0 | NA | NA | NA |
| 151 | 3 | 2 | 0 | 0 | 0 | 0.013 | 0.019 | weak |
| 152 | 96 | 72 | 6 | 3 | 0 | 3.748 | 11.616 | average |
| 153 | 0 | 1 | 0 | 0 | 0 | 0.003 | NA | NA |
| 154 | 1 | 0 | 0 | 0 | 0 | 0.003 | 0.500 | average |
| 155 | 1 | 0 | 0 | 0 | 0 | 0.003 | 0.045 | weak |
| 156 | 2 | 0 | 0 | 0 | 0 | 0.005 | 13.553 | strong |
| 157 | 0 | 4 | 0 | 0 | 0 | 0.010 | NA | NA |
| 158 | 0 | 0 | 0 | 0 | 0 | NA | NA | NA |
| 159 | 2 | 0 | 0 | 0 | 0 | 0.005 | 0.057 | weak |
| 160 | 0 | 0 | 0 | 0 | 0 | NA | NA | NA |
| 161 | 92 | 57 | 5 | 2 | 0 | 1.615 | 0.285 | average |
| 162 | 0 | 1 | 0 | 0 | 0 | 0.003 | NA | NA |
| 163 | 0 | 0 | 0 | 0 | 0 | NA | NA | NA |
| 164 | 0 | 0 | 0 | 0 | 0 | NA | NA | NA |
| 165 | 0 | 0 | 0 | 0 | 0 | NA | NA | NA |
| 166 | 0 | 0 | 0 | 0 | 0 | NA | NA | NA |
| 167 | 1 | 0 | 0 | 0 | 0 | 0.003 | 0.416 | average |
| 168 | 0 | 0 | 0 | 0 | 0 | NA | NA | NA |
| 169 | 73 | 31 | 6 | 0 | 0 | 0.533 | 0.195 | average |
| 170 | 0 | 0 | 0 | 0 | 0 | NA | NA | NA |
| 171 | 0 | 0 | 0 | 0 | 0 | NA | NA | NA |
| 172 | 0 | 0 | 0 | 0 | 0 | NA | NA | NA |
| 173 | 0 | 0 | 0 | 0 | 0 | NA | NA | NA |
| 174 | 0 | 0 | 0 | 0 | 0 | NA | NA | NA |
| 175 | 0 | 0 | 0 | 0 | 0 | NA | NA | NA |
| 176 | 0 | 0 | 0 | 0 | 0 | NA | NA | NA |
| 177 | 0 | 0 | 0 | 0 | 0 | NA | NA | NA |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | |
|---|---|---|---|---|---|---|---|---|
| 178 | 7 | 6 | 1 | 0 | 0 | 0.038 | 0.034 | weak |
| 179 | 3 | 5 | 2 | 0 | 0 | 0.027 | 0.037 | weak |
| 180 | 0 | 0 | 0 | 0 | 0 | NA | NA | NA |
| 181 | 1 | 1 | 0 | 0 | 0 | 0.005 | 0.015 | weak |
| 182 | 10 | 4 | 1 | 0 | 0 | 0.041 | 0.058 | weak |
| 183 | 0 | 0 | 1 | 0 | 0 | 0.003 | NA | NA |
| 184 | 0 | 0 | 0 | 0 | 0 | NA | NA | NA |
| 185 | 64 | 67 | 59 | 7 | 1 | 1.009 | 0.274 | average |
| 186 | 0 | 0 | 0 | 0 | 0 | NA | NA | NA |
| 187 | 1 | 0 | 1 | 0 | 0 | 0.005 | 0.017 | weak |
| 188 | 0 | 0 | 0 | 0 | 0 | NA | NA | NA |
| 189 | 2 | 2 | 0 | 0 | 0 | 0.011 | 0.070 | weak |
| 190 | 11 | 5 | 1 | 0 | 0 | 0.047 | 0.064 | weak |
| 191 | 10 | 7 | 0 | 0 | 0 | 0.047 | 0.038 | weak |
| 192 | 27 | 10 | 1 | 0 | 0 | 0.115 | 0.093 | weak |
| 193 | 0 | 0 | 0 | 0 | 0 | NA | NA | NA |
| 194 | 1 | 0 | 0 | 0 | 0 | 0.003 | 0.015 | weak |
| 195 | 82 | 41 | 6 | 1 | 0 | 0.782 | 8.270 | strong |
| 196 | 0 | 0 | 0 | 0 | 0 | NA | NA | NA |
| 197 | 0 | 0 | 0 | 0 | 0 | NA | NA | NA |
| 198 | 0 | 2 | 0 | 0 | 0 | 0.005 | NA | NA |
| 199 | 0 | 0 | 0 | 0 | 0 | NA | NA | NA |
| 200 | 0 | 0 | 0 | 0 | 0 | NA | NA | NA |
| 201 | 4 | 1 | 0 | 0 | 0 | 0.013 | 0.294 | average |
| 202 | 0 | 1 | 0 | 0 | 0 | 0.003 | NA | NA |
| 203 | 4 | 0 | 0 | 0 | 0 | 0.011 | 0.020 | weak |
| 204 | 1 | 0 | 0 | 0 | 0 | 0.003 | 0.020 | weak |
| 205 | 1 | 0 | 0 | 0 | 0 | 0.003 | 0.686 | average |
| 206 | 0 | 0 | 0 | 0 | 0 | NA | NA | NA |
| 207 | 0 | 0 | 0 | 0 | 0 | NA | NA | NA |
| 208 | 0 | 0 | 0 | 0 | 0 | NA | NA | NA |
| 209 | 61 | 1 | 1 | 0 | 0 | 0.245 | 0.174 | average |
| 210 | 0 | 1 | 0 | 0 | 0 | 0.003 | NA | NA |
| 211 | 0 | 1 | 0 | 0 | 0 | 0.003 | NA | NA |
| 212 | 1 | 0 | 0 | 0 | 0 | 0.003 | 0.015 | weak |
| 213 | 0 | 1 | 0 | 0 | 0 | 0.003 | NA | NA |
| 214 | 2 | 2 | 0 | 0 | 0 | 0.011 | 0.019 | weak |
| 215 | 5 | 8 | 5 | 1 | 0 | 0.051 | 0.054 | weak |
| 216 | 0 | 0 | 0 | 0 | 0 | NA | NA | NA |
| 217 | 0 | 2 | 0 | 0 | 0 | 0.005 | NA | NA |
| 218 | 0 | 0 | 0 | 0 | 0 | NA | NA | NA |
| 219 | 0 | 1 | 0 | 0 | 0 | 0.003 | NA | NA |
| 220 | 1 | 0 | 0 | 0 | 0 | 0.003 | 0.044 | weak |
| 221 | 5 | 5 | 1 | 0 | 0 | 0.029 | 0.037 | weak |
| 222 | 91 | 16 | 3 | 1 | 0 | 0.732 | 9.152 | strong |
| 223 | 0 | 0 | 0 | 0 | 0 | NA | NA | NA |
| 224 | 0 | 0 | 0 | 0 | 0 | NA | NA | NA |
| 225 | 0 | 0 | 0 | 0 | 0 | NA | NA | NA |
| 226 | 0 | 0 | 0 | 0 | 0 | NA | NA | NA |
| 227 | 27 | 1 | 0 | 0 | 0 | 0.084 | 0.080 | weak |
| 228 | 87 | 22 | 3 | 3 | 0 | 0.709 | 0.649 | average |
| 229 | 1 | 0 | 0 | 0 | 0 | 0.003 | 0.032 | weak |
| 230 | 20 | 2 | 0 | 0 | 0 | 0.064 | 0.144 | average |
| 231 | 0 | 0 | 0 | 0 | 0 | NA | NA | NA |
| 232 | 3 | 0 | 1 | 2 | 0 | 0.016 | 0.024 | weak |
| 233 | 4 | 0 | 0 | 0 | 0 | 0.011 | 0.052 | weak |
| 234 | 1 | 0 | 0 | 0 | 0 | 0.003 | 0.056 | weak |
| 235 | 1 | 0 | 0 | 0 | 0 | 0.003 | 0.088 | weak |
| 236 | 1 | 0 | 0 | 0 | 0 | 0.003 | 0.032 | weak |
| 237 | 1 | 0 | 0 | 0 | 0 | 0.003 | 0.043 | weak |
| 238 | 16 | 15 | 5 | 1 | 0 | 0.106 | 0.062 | weak |
| 239 | 2 | 0 | 0 | 1 | 0 | 0.008 | 0.018 | weak |
| 240 | 0 | 0 | 0 | 0 | 0 | NA | NA | NA |
| 241 | 0 | 0 | 0 | 0 | 0 | NA | NA | NA |
| 242 | 5 | 1 | 1 | 1 | 0 | 0.021 | 0.037 | weak |
| 243 | 71 | 27 | 8 | 3 | 0 | 0.511 | 0.198 | average |
| 244 | 0 | 0 | 0 | 0 | 0 | NA | NA | NA |
| 245 | 1 | 0 | 0 | 0 | 0 | 0.003 | 0.075 | weak |
| 246 | 1 | 0 | 0 | 0 | 0 | 0.003 | 1.649 | strong |
| 247 | 0 | 0 | 0 | 0 | 0 | NA | NA | NA |
| 248 | 0 | 1 | 0 | 0 | 0 | 0.003 | NA | NA |
| 249 | 0 | 0 | 0 | 0 | 0 | NA | NA | NA |
| 250 | 0 | 0 | 0 | 0 | 0 | NA | NA | NA |
| 251 | 74 | 47 | 6 | 1 | 0 | 0.665 | 0.142 | average |
| 252 | 0 | 0 | 0 | 0 | 0 | NA | NA | NA |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | | | | | | | | | |
|---|---|---|---|---|---|---|---|---|---|
| 253 | 4 | 0 | 0 | 0 | 0 | 0.011 | 0.032 | weak |
| 254 | 0 | 0 | 0 | 0 | 0 | NA | NA | NA |
| 255 | 70 | 8 | 2 | 0 | 0 | 0.347 | 10.175 | strong |
| 256 | 34 | 6 | 2 | 0 | 0 | 0.133 | 0.122 | weak |
| 257 | 0 | 0 | 0 | 0 | 0 | NA | NA | NA |
| 258 | 25 | 3 | 0 | 0 | 0 | 0.083 | 5.524 | strong |
| 259 | 1 | 0 | 0 | 0 | 0 | 0.003 | 0.013 | weak |
| 260 | 0 | 0 | 0 | 0 | 0 | NA | NA | NA |
| 261 | 1 | 0 | 0 | 0 | 0 | 0.003 | 0.032 | weak |
| 262 | 1 | 0 | 0 | 0 | 0 | 0.003 | 0.032 | weak |
| 263 | 0 | 0 | 0 | 0 | 0 | NA | NA | NA |
| 264 | 0 | 0 | 0 | 0 | 0 | NA | NA | NA |
| 265 | 1 | 1 | 0 | 0 | 0 | 0.005 | 0.013 | weak |
| 266 | 0 | 0 | 0 | 0 | 0 | NA | NA | NA |
| 267 | 1 | 0 | 0 | 0 | 0 | 0.003 | 0.015 | weak |
| 268 | 1 | 0 | 0 | 0 | 0 | 0.003 | 0.020 | weak |
| 269 | 15 | 6 | 2 | 0 | 0 | 0.065 | 0.087 | weak |
| 270 | 1 | 0 | 0 | 0 | 0 | 0.003 | 0.022 | weak |
| 271 | 30 | 21 | 1 | 0 | 0 | 0.162 | 0.068 | weak |
| 272 | 0 | 0 | 0 | 0 | 0 | NA | NA | NA |
| 273 | 0 | 0 | 0 | 0 | 0 | NA | NA | NA |
| 274 | 0 | 0 | 0 | 0 | 0 | NA | NA | NA |
| 275 | 1 | 0 | 0 | 0 | 0 | 0.003 | 0.020 | weak |
| 276 | 0 | 0 | 0 | 0 | 0 | NA | NA | NA |
| 277 | 1 | 0 | 0 | 0 | 0 | 0.003 | 0.062 | weak |
| 278 | 0 | 0 | 0 | 0 | 0 | NA | NA | NA |
| 279 | 1 | 0 | 0 | 0 | 0 | 0.003 | 0.012 | weak |
| 280 | 0 | 0 | 0 | 0 | 0 | NA | NA | NA |
| 281 | 1 | 3 | 0 | 0 | 0 | 0.010 | 0.032 | weak |
| 282 | 1 | 7 | 26 | 4 | 1 | 0.103 | 0.032 | weak |
| 283 | 0 | 0 | 0 | 0 | 0 | NA | NA | NA |
| 284 | 3 | 0 | 0 | 0 | 0 | 0.008 | 0.016 | weak |
| 285 | 0 | 0 | 0 | 0 | 0 | NA | NA | NA |
| 286 | 0 | 0 | 0 | 0 | 0 | NA | NA | NA |
| 287 | 75 | 31 | 9 | 3 | 0 | 0.598 | 0.238 | average |
| 288 | 0 | 0 | 0 | 0 | 0 | NA | NA | NA |
| 289 | 1 | 0 | 0 | 0 | 0 | 0.003 | 0.095 | weak |
| 290 | 0 | 0 | 0 | 0 | 0 | NA | NA | NA |
| 291 | 81 | 27 | 7 | 0 | 0 | 0.635 | 0.563 | average |
| 292 | 0 | 0 | 0 | 0 | 0 | NA | NA | NA |
| 293 | 0 | 0 | 0 | 0 | 0 | NA | NA | NA |
| 294 | 4 | 0 | 0 | 0 | 0 | 0.011 | 0.024 | weak |
| 295 | 65 | 36 | 2 | 3 | 0 | 0.464 | 0.243 | average |
| 296 | 0 | 1 | 0 | 0 | 0 | 0.003 | NA | NA |
| 297 | 1 | 0 | 0 | 0 | 0 | 0.003 | 0.173 | average |
| 298 | 0 | 0 | 0 | 0 | 0 | NA | NA | NA |
| 299 | 1 | 0 | 0 | 0 | 0 | 0.003 | 1.521 | strong |
| 300 | 3 | 0 | 0 | 0 | 0 | 0.008 | 0.031 | weak |
| 301 | 0 | 0 | 0 | 0 | 0 | NA | NA | NA |
| 302 | 1 | 0 | 0 | 0 | 0 | 0.003 | 0.102 | weak |
| 303 | 0 | 0 | 1 | 0 | 0 | 0.003 | NA | NA |
| 304 | 0 | 0 | 0 | 0 | 0 | NA | NA | NA |
| 305 | 3 | 14 | 48 | 6 | 1 | 0.192 | 0.036 | weak |
| 306 | 0 | 1 | 0 | 0 | 0 | 0.003 | NA | NA |
| 307 | 95 | 69 | 2 | 3 | 0 | 2.781 | 30.647 | strong |
| 308 | 16 | 0 | 0 | 0 | 0 | 0.045 | 0.078 | weak |
| 309 | 1 | 0 | 0 | 0 | 0 | 0.003 | 2.142 | strong |
| 310 | 0 | 0 | 0 | 0 | 0 | NA | NA | NA |
| 311 | 0 | 0 | 0 | 0 | 0 | NA | NA | NA |
| 312 | 0 | 0 | 0 | 0 | 0 | NA | NA | NA |
| 313 | 1 | 1 | 0 | 0 | 0 | 0.005 | 0.103 | weak |
| 314 | 0 | 0 | 0 | 0 | 0 | NA | NA | NA |
| 315 | 2 | 0 | 0 | 0 | 0 | 0.005 | 0.426 | average |
| 316 | 0 | 0 | 0 | 0 | 0 | NA | NA | NA |
| 317 | 1 | 0 | 0 | 0 | 0 | 0.003 | 0.052 | weak |
| 318 | 3 | 0 | 0 | 0 | 0 | 0.008 | 0.067 | weak |
| 319 | 0 | 0 | 0 | 0 | 0 | NA | NA | NA |
| 320 | 25 | 4 | 0 | 1 | 0 | 0.089 | 0.206 | average |
| 321 | 3 | 0 | 0 | 0 | 0 | 0.008 | 0.031 | weak |
| 322 | 0 | 1 | 0 | 0 | 0 | 0.003 | NA | NA |
| 323 | 0 | 0 | 0 | 0 | 0 | NA | NA | NA |
| 324 | 0 | 0 | 0 | 0 | 0 | NA | NA | NA |
| 325 | 0 | 0 | 0 | 0 | 0 | NA | NA | NA |
| 326 | 0 | 0 | 0 | 0 | 0 | NA | NA | NA |
| 327 | 0 | 0 | 0 | 0 | 0 | NA | NA | NA |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | | | | | | | | |
|---|---|---|---|---|---|---|---|---|
| 328 | 0 | 0 | 0 | 0 | 0 | NA | NA | NA |
| 329 | 7 | 2 | 1 | 2 | 0 | 0.032 | 0.091 | weak |
| 330 | 0 | 1 | 1 | 0 | 0 | 0.005 | NA | NA |
| 331 | 0 | 0 | 0 | 0 | 0 | NA | NA | NA |
| 332 | 0 | 0 | 0 | 0 | 0 | NA | NA | NA |
| 333 | 1 | 0 | 0 | 0 | 0 | 0.003 | 0.013 | weak |
| 334 | 89 | 87 | 15 | 1 | 0 | 2.309 | 0.933 | average |
| 335 | 25 | 15 | 3 | 1 | 0 | 0.132 | 0.584 | average |
| 336 | 0 | 0 | 0 | 0 | 0 | NA | NA | NA |
| 337 | 25 | 2 | 0 | 0 | 0 | 0.080 | 6.625 | strong |
| 338 | 81 | 36 | 2 | 0 | 0 | 0.672 | 0.719 | average |
| 339 | 1 | 0 | 0 | 0 | 0 | 0.003 | 1.892 | strong |
| 340 | 0 | 1 | 0 | 0 | 0 | 0.003 | NA | NA |
| 341 | 0 | 0 | 0 | 0 | 0 | NA | NA | NA |
| 342 | 1 | 0 | 0 | 0 | 0 | 0.003 | 3.390 | strong |
| 343 | 5 | 0 | 0 | 0 | 0 | 0.013 | 7.324 | strong |
| 344 | 0 | 0 | 0 | 0 | 0 | NA | NA | NA |
| 345 | 0 | 0 | 0 | 0 | 0 | NA | NA | NA |
| 346 | 0 | 0 | 1 | 0 | 0 | 0.003 | NA | NA |
| 347 | 74 | 7 | 1 | 0 | 0 | 0.373 | 0.185 | average |
| 348 | 4 | 5 | 0 | 1 | 0 | 0.027 | 0.073 | weak |
| 349 | 0 | 0 | 0 | 0 | 0 | NA | NA | NA |
| 350 | 0 | 0 | 0 | 0 | 0 | NA | NA | NA |
| 351 | 0 | 5 | 1 | 0 | 0 | 0.016 | NA | NA |
| 352 | 0 | 0 | 0 | 0 | 0 | NA | NA | NA |
| 353 | 0 | 0 | 0 | 0 | 0 | NA | NA | NA |
| 354 | 34 | 10 | 0 | 0 | 0 | 0.139 | 0.205 | average |
| 355 | 1 | 0 | 0 | 0 | 0 | 0.003 | 66.012 | strong |
| 356 | 60 | 24 | 6 | 2 | 0 | 0.372 | 0.364 | average |
| 357 | 3 | 2 | 0 | 0 | 0 | 0.013 | 6.680 | strong |
| 358 | 3 | 0 | 0 | 0 | 0 | 0.008 | 0.436 | average |
| 359 | 1 | 1 | 0 | 0 | 0 | 0.005 | 0.111 | weak |
| 360 | 1 | 2 | 9 | 0 | 0 | 0.031 | 0.022 | weak |
| 361 | 0 | 0 | 0 | 0 | 0 | NA | NA | NA |
| 362 | 1 | 0 | 0 | 0 | 0 | 0.003 | 0.017 | weak |
| 363 | 0 | 0 | 0 | 0 | 0 | NA | NA | NA |
| 364 | 0 | 0 | 0 | 0 | 0 | NA | NA | NA |
| 365 | 0 | 0 | 0 | 0 | 0 | NA | NA | NA |
| 366 | 9 | 9 | 1 | 3 | 0 | 0.060 | 0.047 | weak |
| 367 | 0 | 0 | 0 | 0 | 0 | NA | NA | NA |
| 368 | 0 | 0 | 0 | 0 | 0 | NA | NA | NA |
| 369 | 0 | 1 | 0 | 0 | 0 | 0.003 | NA | NA |
| 370 | 0 | 0 | 0 | 0 | 0 | NA | NA | NA |
| 371 | 0 | 0 | 0 | 0 | 0 | NA | NA | NA |
| 372 | 0 | 0 | 0 | 0 | 0 | NA | NA | NA |
| 373 | 0 | 0 | 0 | 0 | 0 | NA | NA | NA |
| 374 | 8 | 4 | 0 | 0 | 0 | 0.033 | 0.092 | weak |
| 375 | 4 | 7 | 0 | 0 | 0 | 0.029 | 0.023 | weak |
| 376 | 0 | 0 | 0 | 0 | 0 | NA | NA | NA |
| 377 | 2 | 1 | 0 | 0 | 0 | 0.008 | 0.023 | weak |
| 378 | 11 | 0 | 0 | 1 | 0 | 0.033 | 0.051 | weak |
| 379 | 9 | 0 | 0 | 0 | 0 | 0.025 | 0.038 | weak |
| 380 | 4 | 0 | 0 | 0 | 0 | 0.011 | 0.518 | average |
| 381 | 13 | 8 | 1 | 0 | 0 | 0.061 | 0.145 | average |
| 382 | 0 | 0 | 0 | 0 | 0 | NA | NA | NA |
| 383 | 0 | 0 | 0 | 0 | 0 | NA | NA | NA |
| 384 | 0 | 0 | 0 | 0 | 0 | NA | NA | NA |
| 385 | 52 | 8 | 0 | 0 | 0 | 0.217 | 1.153 | average |
| 386 | 0 | 0 | 0 | 0 | 0 | NA | NA | NA |
| 387 | 6 | 17 | 36 | 5 | 1 | 0.177 | 0.038 | weak |
| 388 | 0 | 0 | 0 | 0 | 0 | NA | NA | NA |
| 389 | 2 | 0 | 0 | 0 | 0 | 0.005 | 0.120 | weak |
| 390 | 1 | 0 | 0 | 0 | 0 | 0.003 | 6.305 | strong |
| 391 | 0 | 0 | 1 | 0 | 0 | 0.003 | NA | NA |
| 392 | 77 | 10 | 2 | 0 | 0 | 0.426 | 1.488 | average |
| 393 | 1 | 0 | 0 | 0 | 0 | 0.003 | 0.015 | weak |
| 394 | 6 | 8 | 2 | 0 | 0 | 0.043 | 2.922 | strong |
| 395 | 0 | 0 | 0 | 0 | 0 | NA | NA | NA |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| 396 | 95 | 69 | 2 | 2 | 0 | 2.740 | 2.873 | average |
| 397 | 1 | 0 | 0 | 0 | 0 | 0.003 | 6.672 | strong |
| 398 | 0 | 0 | 0 | 0 | 0 | NA | NA | NA |
| 399 | 0 | 0 | 0 | 0 | 0 | NA | NA | NA |

| Row Number | Column Number 35 complete taxonomy |
|---|---|
| 1 | k_Bacteria; p_Proteobacteria; c_Betaproteobacteria |
| 2 | k_Bacteria; p_Proteobacteria; c_Betaproteobacteria; o_Neisseriales; f_Neisseriaceae |
| 3 | k_Bacteria; p_Proteobacteria; c_Gammaproteobacteria; o_Pseudomonadales; f_Pseudomonadaceae; g_Pseudomonas; s_ |
| 4 | k_Bacteria; p_Proteobacteria; c_Betaproteobacteria; o_Burkholderiales; f_Oxalobacteraceae |
| 5 | k_Bacteria; p_Proteobacteria; c_Betaproteobacteria; o_Burkholderiales; f_Oxalobacteraceae; g_Cupriavidus; s_ |
| 6 | k_Bacteria; p_Proteobacteria; c_Betaproteobacteria; o_Neisseriales; f_Neisseriaceae |
| 7 | k_Bacteria; p_Firmicutes; c_Bacilli; o_Bacillales; f_Paenibacillaceae; g_Paenibacillus; s_ |
| 8 | k_Bacteria; p_Firmicutes; c_Bacilli; o_Bacillales; f_Paenibacillaceae; g_Paenibacillus; s_ |
| 9 | k_Bacteria; p_Firmicutes; c_Bacilli; o_Bacillales; f_Paenibacillaceae; g_Paenibacillus; s_ |
| 10 | k_Bacteria; p_Firmicutes; c_Bacilli; o_Bacillales; f_Paenibacillaceae; g_Paenibacillus; s_ |
| 11 | k_Bacteria; p_Proteobacteria; c_Betaproteobacteria; o_Burkholderiales; f_Comamonadaceae; g_; s_ |
| 12 | k_Bacteria; p_Firmicutes; c_Bacilli; o_Bacillales; f_Paenibacillaceae; g_Paenibacillus; s_ |
| 13 | k_Bacteria; p_Proteobacteria; c_Gammaproteobacteria; o_Pseudomonadales; f_Pseudomonadaceae; g_Pseudomonas; s_ |
| 14 | k_Bacteria; p_Proteobacteria; c_Gammaproteobacteria; o_Pseudomonadales; f_Pseudomonadaceae; g_; s_ |
| 15 | k_Bacteria; p_Proteobacteria; c_Gammaproteobacteria; o_Pseudomonadales; f_Pseudomonadaceae; g_Pseudomonas; s_ |
| 16 | k_Bacteria; p_Proteobacteria; c_Betaproteobacteria; o_Neisseriales; f_Neisseriaceae |
| 17 | k_Bacteria; p_Firmicutes; c_Bacilli; o_Bacillales; f_Paenibacillaceae; g_Paenibacillus; s_ |
| 18 | k_Bacteria; p_Proteobacteria; c_Gammaproteobacteria; o_Pseudomonadales; f_Pseudomonadaceae; g_Pseudomonas; s_ |
| 19 | k_Bacteria; p_Proteobacteria; c_Betaproteobacteria |
| 20 | k_Bacteria; p_Proteobacteria; c_Betaproteobacteria; o_Neisseriales; f_Neisseriaceae; g_; s_ |
| 21 | k_Bacteria; p_Verrucomicrobia; c_[Spartobacteria]; o_[Chthoniobacterales]; f_[Chthoniobacteraceae]; g_Candidatus Xiphinematobacter; s_ |
| 22 | k_Bacteria; p_Proteobacteria; c_Betaproteobacteria; o_Neisseriales; f_Neisseriaceae; g_; s_ |
| 23 | k_Bacteria; p_Proteobacteria; c_Betaproteobacteria; o_Burkholderiales; f_Oxalobacteraceae; g_Janthinobacterium |
| 24 | k_Bacteria; p_Proteobacteria; c_Alphaproteobacteria; o_Caulobacterales; f_Caulobacteraceae; g_; s_ |
| 25 | k_Bacteria; p_Firmicutes; c_Bacilli; o_Bacillales; f_Paenibacillaceae; g_Paenibacillus; s_ |
| 26 | k_Bacteria; p_Firmicutes; c_Bacilli; o_Bacillales; f_Paenibacillaceae; g_Paenibacillus; s_ |
| 27 | k_Bacteria; p_Firmicutes; c_Bacilli; o_Bacillales; f_Paenibacillaceae; g_Paenibacillus; s_ |
| 28 | k_Bacteria; p_Proteobacteria; c_Gammaproteobacteria; o_Aeromonadales; f_Aeromonadaceae; g_; s_ |
| 29 | k_Bacteria; p_Firmicutes; c_Clostridia; o_Clostridiales; f_Lachnospiraceae; g_; s_ |
| 30 | k_Bacteria; p_Proteobacteria; c_Betaproteobacteria; o_Neisseriales; f_Neisseriaceae |
| 31 | k_Bacteria; p_Firmicutes; c_Bacilli; o_Bacillales; f_Paenibacillaceae; g_Paenibacillus; s_ |
| 32 | k_Bacteria; p_Proteobacteria; c_Gammaproteobacteria; o_Pseudomonadales; f_Pseudomonadaceae; g_Pseudomonas |
| 33 | k_Bacteria; p_Firmicutes; c_Bacilli; o_Bacillales; f_Paenibacillaceae; g_Paenibacillus; s_ |
| 34 | k_Bacteria; p_Firmicutes; c_Bacilli; o_Bacillales; f_Paenibacillaceae; g_Paenibacillus; s_ |
| 35 | k_Bacteria; p_Bacteroidetes; c_[Saprospirae]; o_[Saprospirales]; f_Chitinophagaceae; g_; s_ |
| 36 | k_Bacteria; p_Firmicutes; c_Bacilli; o_Bacillales; f_Paenibacillaceae; g_Paenibacillus; s_ |
| 37 | k_Bacteria; p_Firmicutes; c_Clostridia; o_Clostridiales; f_Lachnospiraceae; g_Coprococcus; s_ |
| 38 | k_Bacteria; p_Firmicutes; c_Bacilli; o_Bacillales; f_Paenibacillaceae; g_Paenibacillus; s_ |
| 39 | k_Bacteria; p_Cyanobacteria; c_4C0d-2; o_MLE1-12; f_; g_; s_ |
| 40 | k_Bacteria; p_Firmicutes; c_Bacilli; o_Bacillales; f_Paenibacillaceae; g_Paenibacillus; s_ |
| 41 | k_Bacteria; p_Firmicutes; c_Bacilli; o_Bacillales; f_Paenibacillaceae; g_Paenibacillus; s_ |
| 42 | k_Bacteria; p_Proteobacteria; c_Gammaproteobacteria; o_Pseudomonadales; f_Pseudomonadaceae; g_Pseudomonas; s_veronii |
| 43 | k_Bacteria; p_Proteobacteria; c_Betaproteobacteria; o_Neisseriales; f_Neisseriaceae; g_; s_ |
| 44 | k_Bacteria; p_Proteobacteria; c_Betaproteobacteria; o_Burkholderiales; f_Oxalobacteraceae; g_Janthinobacterium; s_ |
| 45 | k_Bacteria; p_Proteobacteria; c_Gammaproteobacteria; o_Pseudomonadales; f_Pseudomonadaceae; g_Pseudomonas; s_ |
| 46 | k_Bacteria; p_Firmicutes; c_Bacilli; o_Bacillales; f_Bacillaceae; g_Bacillus; s_cereus |
| 47 | k_Bacteria; p_Firmicutes; c_Bacilli; o_Bacillales; f_Paenibacillaceae; g_Paenibacillus; s_ |
| 48 | k_Bacteria; p_Proteobacteria; c_Gammaproteobacteria; o_Pseudomonadales; f_Pseudomonadaceae; g_Pseudomonas; s_ |
| 49 | k_Bacteria; p_Proteobacteria; c_Gammaproteobacteria; o_Enterobacteriales; f_Enterobacteriaceae; g_; s_ |
| 50 | k_Bacteria; p_Firmicutes; c_Bacilli; o_Bacillales; f_Paenibacillaceae; g_Paenibacillus; s_ |
| 51 | k_Bacteria; p_Firmicutes; c_Bacilli; o_Bacillales; f_Paenibacillaceae; g_Paenibacillus; s_ |
| 52 | k_Bacteria; p_Proteobacteria; c_Gammaproteobacteria; o_Pseudomonadales; f_Pseudomonadaceae; g_Pseudomonas; s_ |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | |
|---|---|
| 53 | k_Bacteria; p_Proteobacteria; c_Gammaproteobacteria; o_Pseudomonadales; f_Pseudomonadaceae; g_Pseudomonas; s_ |
| 54 | k_Bacteria; p_Firmicutes; c_Bacilli; o_Bacillales; f_Paenibacillaceae; g_Paenibacillus; s_ |
| 55 | k_Bacteria; p_Bacteroidetes; c_Flavobacteriia; o_Flavobacteriales; f_Flavobacteriaceae; g_Flavobacterium; s_columnare |
| 56 | k_Bacteria; p_Proteobacteria; c_Betaproteobacteria; o_Burkholderiales; f_Oxalobacteraceae; g_Janthinobacterium; s_lividum |
| 57 | k_Bacteria; p_Firmicutes; c_Bacilli; o_Bacillales; f_Paenibacillaceae; g_Paenibacillus; s_ |
| 58 | k_Bacteria; p_Proteobacteria; c_Betaproteobacteria; o_Burkholderiales; f_Oxalobacteraceae; g_; s_ |
| 59 | k_Bacteria; p_Firmicutes; c_Bacilli; o_Bacillales; f_Paenibacillaceae; g_Paenibacillus; s_ |
| 60 | k_Bacteria; p_Proteobacteria; c_Betaproteobacteria; o_Burkholderiales; f_Oxalobacteraceae; g_Cupriavidus; s_ |
| 61 | k_Bacteria; p_Firmicutes; c_Bacilli; o_Bacillales; f_Paenibacillaceae; g_Paenibacillus; s_ |
| 62 | k_Bacteria; p_Proteobacteria; c_Betaproteobacteria; o_Neisseriales; f_Neisseriaceae; g_; s_ |
| 63 | k_Bacteria; p_Proteobacteria; c_Betaproteobacteria; o_Burkholderiales; f_Oxalobacteraceae; g_Janthinobacterium; s_ |
| 64 | k_Bacteria; p_Firmicutes; c_Bacilli; o_Bacillales; f_Paenibacillaceae; g_Paenibacillus; s_ |
| 65 | k_Bacteria; p_Proteobacteria; c_Betaproteobacteria; o_Neisseriales; f_Neisseriaceae; g_Chromobacterium; s_ |
| 66 | k_Bacteria; p_Firmicutes; c_Bacilli; o_Bacillales; f_Paenibacillaceae; g_Paenibacillus; s_ |
| 67 | k_Bacteria; p_Proteobacteria; c_Gammaproteobacteria; o_Pseudomonadales; f_Pseudomonadaceae; g_Pseudomonas; s_ |
| 68 | k_Bacteria; p_Proteobacteria; c_Gammaproteobacteria; o_Pseudomonadales; f_Pseudomonadaceae; g_Pseudomonas |
| 69 | k_Bacteria; p_Proteobacteria; c_Gammaproteobacteria; o_Pseudomonadales; f_Pseudomonadaceae; g_Pseudomonas; s_ |
| 70 | k_Bacteria; p_Proteobacteria; c_Betaproteobacteria; o_Neisseriales; f_Neisseriaceae; g_Chromobacterium; s_ |
| 71 | k_Bacteria; p_Proteobacteria; c_Gammaproteobacteria; o_Pseudomonadales; f_Pseudomonadaceae; g_Pseudomonas; s_ |
| 72 | k_Bacteria; p_Firmicutes; c_Bacilli; o_Bacillales; f_Paenibacillaceae; g_Paenibacillus; s_ |
| 73 | k_Bacteria; p_Proteobacteria; c_Betaproteobacteria; o_Neisseriales; f_Neisseriaceae |
| 74 | k_Bacteria; p_Proteobacteria; c_Betaproteobacteria; o_Burkholderiales; f_Oxalobacteraceae; g_; s_ |
| 75 | k_Bacteria; p_Proteobacteria; c_Alphaproteobacteria; o_Sphingomonadales; f_Sphingomonadaceae; g_Sphingobium; s_xenophagum |
| 76 | k_Bacteria; p_Proteobacteria; c_Betaproteobacteria; o_Burkholderiales; f_Comamonadaceae; g_; s_ |
| 77 | k_Bacteria; p_Proteobacteria; c_Betaproteobacteria; o_Burkholderiales; f_Oxalobacteraceae; g_; s_ |
| 78 | k_Bacteria; p_Proteobacteria; c_Gammaproteobacteria; o_Aeromonadales; f_Aeromonadaceae; g_; s_ |
| 79 | k_Bacteria; p_Bacteroidetes; c_[Saprospirae]; o_[Saprospirales]; f_Chitinophagaceae; g_Sediminibacterium; s_ |
| 80 | k_Bacteria; p_Proteobacteria; c_Gammaproteobacteria; o_Xanthomonadales; f_Sinobacteraceae; g_; s_ |
| 81 | k_Bacteria; p_Firmicutes; c_Bacilli; o_Bacillales; f_Paenibacillaceae; g_Paenibacillus; s_ |
| 82 | k_Bacteria; p_Firmicutes; c_Bacilli; o_Bacillales; f_Paenibacillaceae; g_Paenibacillus; s_ |
| 83 | k_Bacteria; p_Proteobacteria; c_Gammaproteobacteria; o_Pseudomonadales; f_Pseudomonadaceae; g_Pseudomonas; s_ |
| 84 | k_Bacteria; p_Proteobacteria; c_Betaproteobacteria; o_Neisseriales; f_Neisseriaceae |
| 85 | k_Bacteria; p_Proteobacteria; c_Betaproteobacteria; o_Burkholderiales; f_Oxalobacteraceae |
| 86 | k_Bacteria; p_Firmicutes; c_Bacilli; o_Bacillales; f_Paenibacillaceae; g_Paenibacillus; s_ |
| 87 | k_Bacteria; p_Firmicutes; c_Bacilli; o_Bacillales; f_Planococcaceae; g_; s_ |
| 88 | k_Bacteria; p_Firmicutes; c_Bacilli; o_Bacillales; f_Paenibacillaceae; g_Paenibacillus; s_ |
| 89 | k_Bacteria; p_Firmicutes; c_Bacilli; o_Bacillales; f_Paenibacillaceae; g_Paenibacillus; s_ |
| 90 | k_Bacteria; p_Firmicutes; c_Bacilli; o_Bacillales; f_Paenibacillaceae; g_Paenibacillus; s_ |
| 91 | k_Bacteria; p_Proteobacteria; c_Betaproteobacteria |
| 92 | k_Bacteria; p_Firmicutes; c_Bacilli; o_Bacillales; f_Paenibacillaceae; g_Paenibacillus; s_ |
| 93 | k_Bacteria; p_Proteobacteria; c_Gammaproteobacteria; o_Aeromonadales; f_Aeromonadaceae; g_; s_ |
| 94 | k_Bacteria; p_Proteobacteria; c_Gammaproteobacteria; o_Legionellales; f_; g_; s_ |
| 95 | k_Bacteria; p_Proteobacteria; c_Betaproteobacteria; o_Burkholderiales; f_Oxalobacteraceae; g_Janthinobacterium; s_lividum |
| 96 | k_Bacteria; p_Firmicutes; c_Bacilli; o_Bacillales; f_Paenibacillaceae; g_Paenibacillus; s_ |
| 97 | k_Bacteria; p_Bacteroidetes; c_[Saprospirae]; o_[Saprospirales]; f_Chitinophagaceae; g_Sediminibacterium; s_ |
| 98 | k_Bacteria; p_Proteobacteria; c_Betaproteobacteria; o_Burkholderiales; f_Comamonadaceae; g_; s_ |
| 99 | k_Bacteria; p_Proteobacteria; c_Betaproteobacteria; o_Rhodocyclales; f_Rhodocyclaceae; g_Dechloromonas; s_ |
| 100 | k_Bacteria; p_Proteobacteria; c_Betaproteobacteria; o_Burkholderiales; f_Oxalobacteraceae; g_Janthinobacterium; s_lividum |
| 101 | k_Bacteria; p_Firmicutes; c_Bacilli; o_Bacillales; f_Bacillaceae; g_Bacillus; s_cereus |
| 102 | k_Bacteria; p_Firmicutes; c_Bacilli; o_Bacillales; f_Paenibacillaceae; g_Paenibacillus; s_ |
| 103 | k_Bacteria; p_Proteobacteria; c_Gammaproteobacteria; o_Pseudomonadales; f_Pseudomonadaceae; g_Pseudomonas; s_ |
| 104 | k_Bacteria; p_Firmicutes; c_Bacilli; o_Bacillales; f_Paenibacillaceae; g_Paenibacillus; s_ |
| 105 | k_Bacteria; p_Firmicutes; c_Bacilli; o_Bacillales; f_Paenibacillaceae; g_Paenibacillus; s_ |
| 106 | k_Bacteria; p_Firmicutes; c_Clostridia; o_Clostridiales; f_Ruminococcaceae; g_; s_ |
| 107 | k_Bacteria; p_Firmicutes; c_Bacilli; o_Bacillales; f_Paenibacillaceae; g_Paenibacillus; s_ |
| 108 | k_Bacteria; p_Proteobacteria; c_Betaproteobacteria; o_Burkholderiales; f_Oxalobacteraceae; g_; s_ |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | |
|---|---|
| 109 | k_Bacteria; p_Proteobacteria; c_Gammaproteobacteria; o_Xanthomonadales; f_Sinobacteraceae; g_; s_ |
| 110 | k_Bacteria; p_Firmicutes; c_Bacilli; o_Bacillales; f_Bacillaceae; g_Bacillus; s_cereus |
| 111 | k_Bacteria; p_Planctomycetes; c_Planctomycetia; o_Gemmatales; f_Gemmataceae; g_; s_ |
| 112 | k_Bacteria; p_Firmicutes; c_Bacilli; o_Bacillales; f_Paenibacillaceae; g_Paenibacillus; s_ |
| 113 | k_Bacteria; p_Proteobacteria; c_Betaproteobacteria; o_Rhodocyclales; f_Rhodocyclaceae; g_Azoarcus; s_ |
| 114 | k_Bacteria; p_Proteobacteria; c_Betaproteobacteria; o_Burkholderiales; f_Oxalobacteraceae; g_; s_ |
| 115 | k_Bacteria; p_Proteobacteria; c_Gammaproteobacteria; o_Pseudomonadales; f_Pseudomonadaceae; g_Pseudomonas |
| 116 | k_Bacteria; p_Firmicutes; c_Bacilli; o_Bacillales; f_Paenibacillaceae; g_Paenibacillus; s_ |
| 117 | k_Bacteria; p_Firmicutes; c_Bacilli; o_Bacillales; f_Paenibacillaceae; g_Paenibacillus; s_ |
| 118 | k_Bacteria; p_Chlorobi; c_OPB56; o_; f_; g_; s_ |
| 119 | k_Bacteria; p_Proteobacteria; c_Alphaproteobacteria; o_Sphingomonadales; f_Sphingomonadaceae; g_Sphingomonas; s_wittichii |
| 120 | k_Bacteria; p_Proteobacteria; c_Betaproteobacteria; o_Neisseriales; f_Neisseriaceae |
| 121 | k_Bacteria; p_Proteobacteria; c_Betaproteobacteria; o_Burkholderiales; f_Oxalobacteraceae; g_Cupriavidus; s_ |
| 122 | k_Bacteria; p_Proteobacteria; c_Betaproteobacteria; o_Burkholderiales; f_Oxalobacteraceae; g_; s_ |
| 123 | k_Bacteria; p_Proteobacteria; c_Gammaproteobacteria; o_Pseudomonadales; f_Pseudomonadaceae; g_Pseudomonas; s_ |
| 124 | k_Bacteria; p_Firmicutes; c_Bacilli; o_Bacillales; f_Bacillaceae; g_Bacillus |
| 125 | k_Bacteria; p_Proteobacteria; c_Betaproteobacteria; o_Burkholderiales; f_Comamonadaceae; g_; s_ |
| 126 | k_Bacteria; p_Proteobacteria; c_Betaproteobacteria; o_Burkholderiales; f_Oxalobacteraceae; g_; s_ |
| 127 | k_Bacteria; p_Proteobacteria; c_Gammaproteobacteria; o_Pseudomonadales; f_Pseudomonadaceae; g_Pseudomonas; s_ |
| 128 | k_Bacteria; p_Proteobacteria; c_Betaproteobacteria; o_Burkholderiales; f_Comamonadaceae; g_Hydrogenophaga; s_ |
| 129 | k_Bacteria; p_Firmicutes; c_Clostridia; o_Clostridiales; f_Lachnospiraceae; g_Coprococcus; s_ |
| 130 | k_Bacteria; p_Proteobacteria; c_Betaproteobacteria; o_Burkholderiales; f_Oxalobacteraceae; g_; s_ |
| 131 | k_Bacteria; p_Proteobacteria; c_Betaproteobacteria; o_Burkholderiales; f_Oxalobacteraceae; g_; s_ |
| 132 | k_Bacteria; p_Proteobacteria; c_Betaproteobacteria; o_Procabacteriales; f_Procabacteriaceae |
| 133 | k_Bacteria; p_Proteobacteria; c_Gammaproteobacteria; o_Pseudomonadales; f_Pseudomonadaceae; g_Pseudomonas; s_ |
| 134 | k_Bacteria; p_Proteobacteria; c_Betaproteobacteria; o_Burkholderiales; f_Oxalobacteraceae; g_; s_ |
| 135 | k_Bacteria; p_Proteobacteria; c_Betaproteobacteria; o_Neisseriales; f_Neisseriaceae; g_Chromobacterium; s_ |
| 136 | k_Bacteria; p_Firmicutes; c_Bacilli; o_Bacillales; f_Paenibacillaceae; g_Paenibacillus; s_ |
| 137 | k_Bacteria; p_Proteobacteria; c_Betaproteobacteria; o_Rhodocyclales; f_Rhodocyclaceae; g_Azospira; s_ |
| 138 | k_Bacteria; p_Proteobacteria; c_Gammaproteobacteria; o_Pseudomonadales; f_Pseudomonadaceae; g_Pseudomonas; s_ |
| 139 | k_Bacteria; p_Firmicutes; c_Clostridia; o_Clostridiales; f_Clostridiaceae; g_; s_ |
| 140 | k_Bacteria; p_Proteobacteria; c_Betaproteobacteria; o_Burkholderiales; f_Comamonadaceae; g_Curvibacter; s_ |
| 141 | k_Bacteria; p_Firmicutes; c_Bacilli; o_Bacillales; f_Paenibacillaceae; g_Paenibacillus; s_ |
| 142 | k_Bacteria; p_Firmicutes; c_Bacilli; o_Bacillales; f_Paenibacillaceae; g_Paenibacillus; s_ |
| 143 | k_Bacteria; p_Firmicutes; c_Clostridia; o_Clostridiales; f_Veillonellaceae; g_Pelosinus; s_ |
| 144 | k_Bacteria; p_Proteobacteria; c_Gammaproteobacteria; o_Pseudomonadales; f_Moraxellaceae; g_Alkanindiges; s_ |
| 145 | k_Bacteria; p_Proteobacteria; c_Betaproteobacteria; o_Neisseriales; f_Neisseriaceae; g_Chromobacterium; s_ |
| 146 | k_Bacteria; p_Proteobacteria; c_Gammaproteobacteria; o_Xanthomonadales; f_Xanthomonadaceae; g_Rhodanobacter; s_ |
| 147 | k_Bacteria; p_Proteobacteria; c_Betaproteobacteria; o_Burkholderiales; f_Oxalobacteraceae; g_Janthinobacterium; s_lividum |
| 148 | k_Bacteria; p_Firmicutes; c_Bacilli; o_Bacillales; f_Paenibacillaceae; g_Paenibacillus; s_ |
| 149 | k_Bacteria; p_Actinobacteria; c_Actinobacteria; o_Actinomycetales; f_Micrococcaceae; g_Arthrobacter |
| 150 | k_Bacteria; p_Proteobacteria; c_Alphaproteobacteria; o_Caulobacterales; f_Caulobacteraceae; g_Phenylobacterium; s_ |
| 151 | k_Bacteria; p_Proteobacteria; c_Gammaproteobacteria; o_Pseudomonadales; f_Pseudomonadaceae; g_Pseudomonas; s_ |
| 152 | k_Bacteria; p_Proteobacteria; c_Gammaproteobacteria; o_Pseudomonadales; f_Pseudomonadaceae; g_Pseudomonas; s_ |
| 153 | k_Bacteria; p_Firmicutes; c_Bacilli; o_Bacillales; f_Paenibacillaceae; g_Brevibacillus |
| 154 | k_Bacteria; p_Proteobacteria; c_Betaproteobacteria; o_Burkholderiales; f_Oxalobacteraceae; g_; s_ |
| 155 | k_Bacteria; p_Proteobacteria; c_Gammaproteobacteria; o_Xanthomonadales; f_Xanthomonadaceae; g_; s_ |
| 156 | k_Bacteria; p_Firmicutes; c_Bacilli; o_Bacillales; f_Planococcaceae; g_; s_ |
| 157 | k_Bacteria; p_Proteobacteria; c_Gammaproteobacteria; o_Pseudomonadales; f_Pseudomonadaceae; g_Pseudomonas; s_ |
| 158 | k_Bacteria; p_Firmicutes; c_Clostridia; o_Clostridiales; f_Veillonellaceae; g_Pelosinus; s_ |
| 159 | k_Bacteria; p_Proteobacteria; c_Betaproteobacteria; o_Burkholderiales; f_Comamonadaceae; g_; s_ |
| 160 | k_Bacteria; p_Proteobacteria; c_Alphaproteobacteria; o_Rhizobiales; f_Bradyrhizobiaceae; g_; s_ |
| 161 | k_Bacteria; p_Proteobacteria; c_Gammaproteobacteria; o_Pseudomonadales; f_Pseudomonadaceae; g_Pseudomonas; s_ |
| 162 | k_Bacteria; p_Actinobacteria; c_Actinobacteria; o_Actinomycetales; f_Streptomycetaceae; g_Streptomyces |
| 163 | k_Bacteria; p_Firmicutes; c_Bacilli; o_Bacillales; f_Bacillaceae; g_; s_ |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | |
|---|---|
| 164 | k_Bacteria; p_Proteobacteria; c_Alphaproteobacteria; o_Caulobacterales; f_Caulobacteraceae; g_Mycoplana; s_ |
| 165 | k_Bacteria; p_Firmicutes; c_Clostridia; o_Clostridiales; f_Lachnospiraceae; g_; s_ |
| 166 | k_Bacteria; p_Firmicutes; c_Bacilli; o_Bacillales; f_Bacillaceae; g_; s_ |
| 167 | k_Bacteria; p_Proteobacteria; c_Betaproteobacteria; o_Neisseriales; f_Neisseriaceae; g_; s_ |
| 168 | k_Bacteria; p_Proteobacteria; c_Gammaproteobacteria; o_Pseudomonadales; f_Pseudomonadaceae; g_Pseudomonas; s_ |
| 169 | k_Bacteria; p_Proteobacteria; c_Gammaproteobacteria; o_Pseudomonadales; f_Moraxellaceae; g_Alkanindiges; s_ |
| 170 | k_Bacteria; p_Proteobacteria; c_Betaproteobacteria; o_Burkholderiales; f_Oxalobacteraceae; g_; s_ |
| 171 | k_Bacteria; p_Firmicutes; c_Bacilli; o_Bacillales; f_Paenibacillaceae; g_Paenibacillus; s_ |
| 172 | k_Bacteria; p_Proteobacteria; c_Gammaproteobacteria; o_Enterobacteriales; f_Enterobacteriaceae; g_; s_ |
| 173 | k_Bacteria; p_Proteobacteria; c_Gammaproteobacteria; o_Enterobacteriales; f_Enterobacteriaceae; g_; s_ |
| 174 | k_Bacteria; p_Proteobacteria; c_Betaproteobacteria; o_Burkholderiales; f_Oxalobacteraceae; g_; s_ |
| 175 | k_Bacteria; p_Acidobacteria; c_Holophagae; o_Holophagales; f_Holophagaceae; g_; s_ |
| 176 | k_Bacteria; p_Proteobacteria; c_Gammaproteobacteria; o_Pseudomonadales; f_Pseudomonadaceae; g_Pseudomonas; s_ |
| 177 | k_Bacteria; p_Proteobacteria; c_Betaproteobacteria; o_Burkholderiales; f_Comamonadaceae; g_; s_ |
| 178 | k_Bacteria; p_Proteobacteria; c_Gammaproteobacteria; o_Pseudomonadales; f_Pseudomonadaceae; g_Pseudomonas; s_ |
| 179 | k_Bacteria; p_Proteobacteria; c_Gammaproteobacteria; o_Pseudomonadales; f_Pseudomonadaceae; g_Pseudomonas; s_ |
| 180 | k_Bacteria; p_Firmicutes; c_Bacilli; o_Bacillales; f_Bacillaceae; g_; s_ |
| 181 | k_Bacteria; p_Proteobacteria; c_Gammaproteobacteria; o_Pseudomonadales; f_Pseudomonadaceae; g_; s_ |
| 182 | k_Bacteria; p_Firmicutes; c_Bacilli; o_Bacillales; f_Paenibacillaceae; g_Paenibacillus; s_ |
| 183 | k_Bacteria; p_Proteobacteria; c_Gammaproteobacteria; o_Pseudomonadales; f_Pseudomonadaceae; g_Pseudomonas; s_ |
| 184 | k_Bacteria; p_Proteobacteria; c_Betaproteobacteria; o_Rhodocyclales; f_Rhodocyclaceae; g_Dechloromonas; s_ |
| 185 | k_Bacteria; p_Proteobacteria; c_Gammaproteobacteria; o_Pseudomonadales; f_Pseudomonadaceae; g_Pseudomonas |
| 186 | k_Bacteria; p_Firmicutes; c_Bacilli; o_Bacillales; f_Paenibacillaceae; g_Paenibacillus; s_ |
| 187 | k_Bacteria; p_Firmicutes; c_Bacilli; o_Bacillales; f_Paenibacillaceae; g_Paenibacillus; s_ |
| 188 | k_Bacteria; p_Firmicutes; c_Bacilli; o_Bacillales; f_Bacillaceae; g_; s_ |
| 189 | k_Bacteria; p_Proteobacteria; c_Betaproteobacteria; o_Rhodocyclales; f_Rhodocyclaceae; g_Dechloromonas; s_ |
| 190 | k_Bacteria; p_Proteobacteria; c_Gammaproteobacteria; o_Pseudomonadales; f_Pseudomonadaceae; g_Pseudomonas |
| 191 | k_Bacteria; p_Proteobacteria; c_Gammaproteobacteria; o_Pseudomonadales; f_Pseudomonadaceae; g_Pseudomonas; s_ |
| 192 | k_Bacteria; p_Proteobacteria; c_Gammaproteobacteria; o_Pseudomonadales; f_Pseudomonadaceae; g_Pseudomonas; s_ |
| 193 | k_Bacteria; p_Firmicutes; c_Bacilli; o_Bacillales; f_Paenibacillaceae; g_Paenibacillus; s_ |
| 194 | k_Bacteria; p_Proteobacteria; c_Betaproteobacteria; o_Burkholderiales; f_Oxalobacteraceae; g_Janthinobacterium; s_lividum |
| 195 | k_Bacteria; p_Proteobacteria; c_Gammaproteobacteria; o_Pseudomonadales; f_Pseudomonadaceae; g_Pseudomonas; s_ |
| 196 | k_Bacteria; p_Proteobacteria; c_Alphaproteobacteria; o_Sphingomonadales; f_Sphingomonadaceae; g_Sphingomonas; s_ |
| 197 | k_Bacteria; p_Firmicutes; c_Bacilli; o_Bacillales; f_Paenibacillaceae; g_Paenibacillus; s_ |
| 198 | k_Bacteria; p_Proteobacteria; c_Gammaproteobacteria; o_Pseudomonadales; f_Pseudomonadaceae; g_Pseudomonas; s_ |
| 199 | k_Bacteria; p_Firmicutes; c_Bacilli; o_Bacillales; f_Bacillaceae; g_Bacillus; s_cereus |
| 200 | k_Bacteria; p_Chlorobi; c_OPB56; o_; f_; g_; s_ |
| 201 | k_Bacteria; p_Proteobacteria; c_Gammaproteobacteria; o_Pseudomonadales; f_Pseudomonadaceae; g_Pseudomonas; s_ |
| 202 | k_Bacteria; p_Proteobacteria; c_Gammaproteobacteria; o_Pseudomonadales; f_Pseudomonadaceae; g_Pseudomonas; s_ |
| 203 | k_Bacteria; p_Proteobacteria; c_Betaproteobacteria; o_Burkholderiales; f_Oxalobacteraceae; g_Janthinobacterium; s_lividum |
| 204 | k_Bacteria; p_Proteobacteria; c_Gammaproteobacteria; o_Pseudomonadales; f_Pseudomonadaceae; g_Pseudomonas; s_ |
| 205 | k_Bacteria; p_Proteobacteria; c_Betaproteobacteria; o_Burkholderiales; f_Oxalobacteraceae; g_; s_ |
| 206 | k_Bacteria; p_Firmicutes; c_Bacilli; o_Bacillales; f_Bacillaceae; g_Bacillus; s_cereus |
| 207 | k_Bacteria; p_Proteobacteria; c_Alphaproteobacteria; o_Rhodospirillales; f_Rhodospirillaceae; g_; s_ |
| 208 | k_Bacteria; p_Proteobacteria; c_Gammaproteobacteria; o_Enterobacteriales; f_Enterobacteriaceae; g_; s_ |
| 209 | k_Bacteria; p_Proteobacteria; c_Betaproteobacteria; o_Burkholderiales; f_Oxalobacteraceae; g_Janthinobacterium; s_ |
| 210 | k_Bacteria; p_Proteobacteria; c_Gammaproteobacteria; o_Pseudomonadales; f_Pseudomonadaceae; g_Pseudomonas |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | |
|---|---|
| 211 | k_Bacteria; p_Firmicutes; c_Bacilli; o_Bacillales; f_Paenibacillaceae; g_Brevibacillus; s_ |
| 212 | k_Bacteria; p_Proteobacteria; c_Gammaproteobacteria; o_Pseudomonadales; f_Pseudomonadaceae; g_Pseudomonas |
| 213 | k_Bacteria; p_Proteobacteria; c_Gammaproteobacteria; o_Pseudomonadales; f_Pseudomonadaceae; g_Pseudomonas; s_ |
| 214 | k_Bacteria; p_Proteobacteria; c_Gammaproteobacteria; o_Pseudomonadales; f_Pseudomonadaceae; g_Pseudomonas; s_ |
| 215 | k_Bacteria; p_Proteobacteria; c_Gammaproteobacteria; o_Pseudomonadales; f_Pseudomonadaceae; g_Pseudomonas; s_ |
| 216 | k_Bacteria; p_Bacteroidetes; c_[Saprospirae]; o_[Saprospirales]; f_Chitinophagaceae; g_; s_ |
| 217 | k_Bacteria; p_Proteobacteria; c_Gammaproteobacteria; o_Pseudomonadales; f_Pseudomonadaceae; g_Pseudomonas; s_veronii |
| 218 | k_Bacteria; p_Firmicutes; c_Bacilli; o_Bacillales; f_Bacillaceae; g_; s_ |
| 219 | k_Bacteria; p_Proteobacteria; c_Gammaproteobacteria; o_Pseudomonadales; f_Pseudomonadaceae; g_Pseudomonas; s_ |
| 220 | k_Bacteria; p_Proteobacteria; c_Gammaproteobacteria; o_Aeromonadales; f_Aeromonadaceae; g_; s_ |
| 221 | k_Bacteria; p_Proteobacteria; c_Gammaproteobacteria; o_Pseudomonadales; f_Pseudomonadaceae; g_Pseudomonas |
| 222 | k_Bacteria; p_Proteobacteria; c_Gammaproteobacteria; o_Pseudomonadales; f_Pseudomonadaceae; g_Pseudomonas |
| 223 | k_Bacteria; p_Bacteroidetes; c_[Saprospirae]; o_[Saprospirales]; f_Chitinophagaceae; g_Sediminibacterium; s_ |
| 224 | k_Bacteria; p_Proteobacteria; c_Gammaproteobacteria; o_Pseudomonadales; f_Pseudomonadaceae; g_Pseudomonas; s_ |
| 225 | k_Bacteria; p_Proteobacteria; c_Betaproteobacteria; o_Burkholderiales; f_Oxalobacteraceae; g_Janthinobacterium; s_lividum |
| 226 | k_Bacteria; p_Firmicutes; c_Bacilli; o_Bacillales; f_Bacillaceae; g_Bacillus |
| 227 | k_Bacteria; p_Proteobacteria; c_Alphaproteobacteria; o_Caulobacterales; f_Caulobacteraceae; g_; s_ |
| 228 | k_Bacteria; p_Proteobacteria; c_Gammaproteobacteria; o_Pseudomonadales; f_Pseudomonadaceae; g_Pseudomonas; s_fragi |
| 229 | k_Bacteria; p_Firmicutes; c_Bacilli; o_Bacillales; f_Planococcaceae; g_; s_ |
| 230 | k_Bacteria; p_Proteobacteria; c_Gammaproteobacteria; o_Pseudomonadales; f_Pseudomonadaceae; g_Pseudomonas; s_ |
| 231 | k_Bacteria; p_Proteobacteria; c_Betaproteobacteria; o_Burkholderiales; f_Oxalobacteraceae; g_Janthinobacterium; s_lividum |
| 232 | k_Bacteria; p_Proteobacteria; c_Betaproteobacteria; o_Burkholderiales; f_Comamonadaceae; g_; s_ |
| 233 | k_Bacteria; p_Proteobacteria; c_Betaproteobacteria; o_Burkholderiales; f_Oxalobacteraceae |
| 234 | k_Bacteria; p_Proteobacteria; c_Gammaproteobacteria; o_Xanthomonadales; f_Xanthomonadaceae |
| 235 | k_Bacteria; p_Firmicutes; c_Bacilli; o_Bacillales; f_Planococcaceae; g_Lysinibacillus; s_boronitolerans |
| 236 | k_Bacteria; p_Proteobacteria; c_Betaproteobacteria; o_Burkholderiales; f_Comamonadaceae; g_; s_ |
| 237 | k_Bacteria; p_Firmicutes; c_Bacilli; o_Bacillales; f_Planococcaceae; g_Lysinibacillus |
| 238 | k_Bacteria; p_Proteobacteria; c_Gammaproteobacteria; o_Pseudomonadales; f_Pseudomonadaceae; g_Pseudomonas; s_ |
| 239 | k_Bacteria; p_Proteobacteria; c_Gammaproteobacteria; o_Pseudomonadales; f_Pseudomonadaceae; g_Pseudomonas; s_ |
| 240 | k_Bacteria; p_Proteobacteria; c_Alphaproteobacteria; o_Rhodospirillales; f_Rhodospirillaceae; g_; s_ |
| 241 | k_Bacteria; p_Proteobacteria; c_Deltaproteobacteria; o_Syntrophobacterales; f_Syntrophobacteraceae; g_; s_ |
| 242 | k_Bacteria; p_Proteobacteria; c_Gammaproteobacteria; o_Pseudomonadales; f_Pseudomonadaceae; g_Pseudomonas; s_ |
| 243 | k_Bacteria; p_Proteobacteria; c_Betaproteobacteria; o_Burkholderiales; f_Oxalobacteraceae; g_Janthinobacterium; s_lividum |
| 244 | k_Bacteria; p_Proteobacteria; c_Alphaproteobacteria; o_Rhodospirillales; f_Rhodospirillaceae; g_; s_ |
| 245 | k_Bacteria; p_Firmicutes; c_Bacilli; o_Bacillales; f_Bacillaceae; g_Bacillus; s_ |
| 246 | k_Bacteria; p_Proteobacteria; c_Gammaproteobacteria; o_Enterobacteriales; f_Enterobacteriaceae; g_Serratia; s_ |
| 247 | k_Bacteria; p_Firmicutes; c_Bacilli; o_Bacillales; f_Bacillaceae; g_Bacillus |
| 248 | k_Bacteria; p_Proteobacteria; c_Gammaproteobacteria; o_Pseudomonadales; f_Pseudomonadaceae; g_; s_ |
| 249 | k_Bacteria; p_Firmicutes; c_Bacilli; o_Bacillales; f_Bacillaceae; g_Bacillus; s_cereus |
| 250 | k_Bacteria; p_Firmicutes; c_Bacilli; o_Bacillales; f_Bacillaceae; g_; s_ |
| 251 | k_Bacteria; p_Proteobacteria; c_Gammaproteobacteria; o_Pseudomonadales; f_Pseudomonadaceae; g_Pseudomonas; s_ |
| 252 | k_Bacteria; p_Proteobacteria; c_Gammaproteobacteria; o_Enterobacteriales; f_Enterobacteriaceae; g_; s_ |
| 253 | k_Bacteria; p_Proteobacteria; c_Betaproteobacteria; o_Burkholderiales; f_Comamonadaceae; g_; s_ |
| 254 | k_Bacteria; p_Proteobacteria; c_Gammaproteobacteria; o_Pseudomonadales; f_Pseudomonadaceae; g_Pseudomonas; s_ |
| 255 | k_Bacteria; p_Proteobacteria; c_Gammaproteobacteria; o_Pseudomonadales; f_Pseudomonadaceae; g_Pseudomonas; s_ |
| 256 | k_Bacteria; p_Firmicutes; c_Bacilli; o_Bacillales; f_Paenibacillaceae; g_Paenibacillus; s_ |
| 257 | k_Bacteria; p_Firmicutes; c_Bacilli; o_Bacillales; f_Bacillaceae; g_Bacillus |
| 258 | k_Bacteria; p_Proteobacteria; c_Betaproteobacteria; o_Neisseriales; f_Neisseriaceae |
| 259 | k_Bacteria; p_Proteobacteria; c_Gammaproteobacteria; o_Pseudomonadales; f_Pseudomonadaceae; g_Pseudomonas; s_ |
| 260 | k_Bacteria; p_Firmicutes; c_Bacilli; o_Bacillales; f_Paenibacillaceae; g_Paenibacillus; s_ |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | |
|---|---|
| 261 | k_Bacteria; p_Proteobacteria; c_Gammaproteobacteria; o_Pseudomonadales; f_Pseudomonadaceae; g_Pseudomonas; s_ |
| 262 | k_Bacteria; p_Firmicutes; c_Bacilli; o_Bacillales; f_Paenibacillaceae; g_Paenibacillus; s_ |
| 263 | k_Bacteria; p_Proteobacteria; c_Gammaproteobacteria; o_Enterobacteriales; f_Enterobacteriaceae; g_; s_ |
| 264 | k_Bacteria; p_Firmicutes; c_Bacilli; o_Bacillales; f_Bacillaceae; g_Bacillus |
| 265 | k_Bacteria; p_Proteobacteria; c_Gammaproteobacteria; o_Pseudomonadales; f_Pseudomonadaceae; g_Pseudomonas; s_ |
| 266 | k_Bacteria; p_Firmicutes; c_Bacilli; o_Bacillales; f_Paenibacillaceae; g_Paenibacillus; s_ |
| 267 | k_Bacteria; p_Proteobacteria; c_Betaproteobacteria; o_Procabacteriales; f_Procabacteriaceae |
| 268 | k_Bacteria; p_Bacteroidetes; c_Cytophagia; o_Cytophagales; f_Cytophagaceae; g_Emticicia; s_ |
| 269 | k_Bacteria; p_Proteobacteria; c_Gammaproteobacteria; o_Pseudomonadales; f_Pseudomonadaceae; g_Pseudomonas; s_ |
| 270 | k_Bacteria; p_Proteobacteria; c_Gammaproteobacteria; o_Pseudomonadales; f_Pseudomonadaceae; g_Pseudomonas; s_ |
| 271 | k_Bacteria; p_Proteobacteria; c_Gammaproteobacteria; o_Pseudomonadales; f_Pseudomonadaceae; g_; s_ |
| 272 | k_Bacteria; p_Proteobacteria; c_Gammaproteobacteria; o_Enterobacteriales; f_Enterobacteriaceae; g_; s_ |
| 273 | k_Bacteria; p_Proteobacteria; c_Betaproteobacteria; o_Burkholderiales; f_Oxalobacteraceae; g_Janthinobacterium; s_lividum |
| 274 | k_Bacteria; p_Firmicutes; c_Bacilli; o_Bacillales; f_Bacillaceae; g_Bacillus; s_cereus |
| 275 | k_Bacteria; p_Proteobacteria; c_Betaproteobacteria; o_Rhodocyclales; f_Rhodocyclaceae; g_Zoogloea; s_ |
| 276 | k_Bacteria; p_Proteobacteria; c_Betaproteobacteria; o_Neisseriales; f_Neisseriaceae |
| 277 | k_Bacteria; p_Proteobacteria; c_Betaproteobacteria; o_Burkholderiales; f_Oxalobacteraceae; g_Janthinobacterium; s_ |
| 278 | k_Bacteria; p_Verrucomicrobia; c_Opitutae; o_Opitutales; f_Opitutaceae; g_; s_ |
| 279 | k_Bacteria; p_Proteobacteria; c_Betaproteobacteria; o_Burkholderiales; f_Oxalobacteraceae; g_Janthinobacterium; s_lividum |
| 280 | k_Bacteria; p_Firmicutes; c_Clostridia; o_Clostridiales; f_Lachnospiraceae; g_; s_ |
| 281 | k_Bacteria; p_Proteobacteria; c_Gammaproteobacteria; o_Pseudomonadales; f_Pseudomonadaceae; g_Pseudomonas; s_ |
| 282 | k_Bacteria; p_Proteobacteria; c_Gammaproteobacteria; o_Pseudomonadales; f_Pseudomonadaceae; g_Pseudomonas; s_ |
| 283 | k_Bacteria; p_Proteobacteria; c_Gammaproteobacteria; o_Pseudomonadales; f_Pseudomonadaceae; g_Pseudomonas; s_ |
| 284 | k_Bacteria; p_Proteobacteria; c_Gammaproteobacteria; o_Pseudomonadales; f_Pseudomonadaceae; g_Pseudomonas; s_ |
| 285 | k_Bacteria; p_Firmicutes; c_Bacilli; o_Bacillales; f_Bacillaceae; g_Bacillus |
| 286 | k_Bacteria; p_Proteobacteria; c_Alphaproteobacteria; o_Rhizobiales; f_Hyphomicrobiaceae; g_Pedomicrobium; s_ |
| 287 | k_Bacteria; p_Proteobacteria; c_Betaproteobacteria; o_Burkholderiales; f_Oxalobacteraceae; g_Janthinobacterium; s_lividum |
| 288 | k_Bacteria; p_Firmicutes; c_Clostridia; o_Clostridiales; f_Veillonellaceae; g_Pelosinus; s_ |
| 289 | k_Bacteria; p_Proteobacteria; c_Gammaproteobacteria; o_Enterobacteriales; f_Enterobacteriaceae |
| 290 | k_Bacteria; p_Proteobacteria; c_Gammaproteobacteria; o_Pseudomonadales; f_Moraxellaceae; g_Acinetobacter; s_ |
| 291 | k_Bacteria; p_Proteobacteria; c_Betaproteobacteria; o_Burkholderiales; f_Oxalobacteraceae |
| 292 | k_Bacteria; p_Proteobacteria; c_Betaproteobacteria; o_Burkholderiales; f_Oxalobacteraceae; g_Janthinobacterium; s_lividum |
| 293 | k_Bacteria; p_Proteobacteria; c_Gammaproteobacteria; o_Enterobacteriales; f_Enterobacteriaceae; g_; s_ |
| 294 | k_Bacteria; p_Proteobacteria; c_Gammaproteobacteria; o_Pseudomonadales; f_Pseudomonadaceae; g_Pseudomonas; s_ |
| 295 | k_Bacteria; p_Proteobacteria; c_Gammaproteobacteria; o_Pseudomonadales; f_Pseudomonadaceae; g_Pseudomonas; s_ |
| 296 | k_Bacteria; p_Proteobacteria; c_Gammaproteobacteria; o_Pseudomonadales; f_Pseudomonadaceae; g_Pseudomonas; s_ |
| 297 | k_Bacteria; p_Proteobacteria; c_Gammaproteobacteria; o_Xanthomonadales; f_Xanthomonadaceae; g_; s_ |
| 298 | k_Bacteria; p_Firmicutes; c_Bacilli; o_Bacillales; f_Bacillaceae; g_Bacillus; s_ |
| 299 | k_Bacteria; p_Proteobacteria; c_Gammaproteobacteria; o_Aeromonadales; f_Aeromonadaceae; g_; s_ |
| 300 | k_Bacteria; p_Proteobacteria; c_Gammaproteobacteria; o_Pseudomonadales; f_Pseudomonadaceae; g_Pseudomonas; s_ |
| 301 | k_Bacteria; p_Firmicutes; c_Bacilli; o_Bacillales; f_Bacillaceae; g_; s_ |
| 302 | k_Bacteria; p_Firmicutes; c_Bacilli; o_Bacillales; f_Bacillaceae; g_Bacillus; s_flexus |
| 303 | k_Bacteria; p_Firmicutes; c_Bacilli; o_Bacillales; f_Paenibacillaceae; g_Paenibacillus; s_ |
| 304 | k_Bacteria; p_Firmicutes; c_Bacilli; o_Bacillales; f_Bacillaceae; g_; s_ |
| 305 | k_Bacteria; p_Proteobacteria; c_Gammaproteobacteria; o_Pseudomonadales; f_Pseudomonadaceae; g_Pseudomonas; s_ |
| 306 | k_Bacteria; p_Proteobacteria; c_Betaproteobacteria; o_Burkholderiales; f_Oxalobacteraceae |
| 307 | k_Bacteria; p_Proteobacteria; c_Gammaproteobacteria; o_Pseudomonadales; f_Pseudomonadaceae; g_Pseudomonas; s_ |
| 308 | k_Bacteria; p_Proteobacteria; c_Betaproteobacteria; o_Burkholderiales; f_Oxalobacteraceae; g_; s_ |
| 309 | k_Bacteria; p_Proteobacteria; c_Gammaproteobacteria; o_Enterobacteriales; f_Enterobacteriaceae; g_Serratia; s_ |
| 310 | k_Bacteria; p_Firmicutes; c_Bacilli; o_Bacillales; f_Bacillaceae; g_; s_ |
| 311 | k_Bacteria; p_Proteobacteria; c_Gammaproteobacteria; o_Enterobacteriales; f_Enterobacteriaceae; g_; s_ |

TABLE 2-continued

Growth of OTUs under different environmental conditions. Table 2 shows each OTU identified in this example, including the taxonomic identification, frequency of identification in each community, estimated MPN, rarity category, and percent of cultivable community in inoculum.

| | |
|---|---|
| 312 | k_Bacteria; p_Proteobacteria; c_Gammaproteobacteria; o_Pseudomonadales; f_Moraxellaceae; g_Acinetobacter; s_ |
| 313 | k_Bacteria; p_Bacteroidetes; c_Flavobacteriia; o_Flavobacteriales; f_[Weeksellaceae]; g_Chryseobacterium; s_ |
| 314 | k_Bacteria; p_Firmicutes; c_Bacilli; o_Bacillales; f_Bacillaceae; g_Bacillus |
| 315 | k_Bacteria; p_Proteobacteria; c_Betaproteobacteria; o_Neisseriales; f_Neisseriaceae; g_; s_ |
| 316 | k_Bacteria; p_Bacteroidetes; c_Bacteroidia; o_Bacteroidales; f_Porphyromonadaceae; g_Paludibacter; s_ |
| 317 | k_Bacteria; p_Firmicutes; c_Bacilli; o_Bacillales; f_Bacillaceae; g_Bacillus; s_ |
| 318 | k_Bacteria; p_Proteobacteria; c_Betaproteobacteria; o_Burkholderiales; f_Comamonadaceae; g_; s_ |
| 319 | k_Bacteria; p_Proteobacteria; c_Betaproteobacteria; o_Burkholderiales; f_Comamonadaceae; g_; s_ |
| 320 | k_Bacteria; p_Proteobacteria; c_Betaproteobacteria; o_Burkholderiales; f_Oxalobacteraceae; g_Cupriavidus; s_ |
| 321 | k_Bacteria; p_Proteobacteria; c_Betaproteobacteria; o_Burkholderiales; f_Comamonadaceae; g_; s_ |
| 322 | k_Bacteria; p_Proteobacteria; c_Alphaproteobacteria; o_Sphingomonadales; f_Sphingomonadaceae; g_Sphingomonas; s_yabuuchiae |
| 323 | k_Bacteria; p_Proteobacteria; c_Gammaproteobacteria; o_Enterobacteriales; f_Enterobacteriaceae; g_; s_ |
| 324 | k_Bacteria; p_Proteobacteria; c_Betaproteobacteria; o_Burkholderiales; f_Oxalobacteraceae; g_Janthinobacterium; s_ |
| 325 | k_Bacteria; p_Bacteroidetes; c_[Saprospirae]; o_[Saprospirales]; f_Chitinophagaceae; g_Sediminibacterium; s_ |
| 326 | k_Bacteria; p_Proteobacteria; c_Betaproteobacteria; o_Burkholderiales; f_Comamonadaceae; g_; s_ |
| 327 | k_Bacteria; p_Proteobacteria; c_Betaproteobacteria; o_; f_; g_; s_ |
| 328 | k_Bacteria; p_Proteobacteria; c_Betaproteobacteria; o_Burkholderiales; f_Oxalobacteraceae; g_Janthinobacterium; s_ |
| 329 | k_Bacteria; p_Proteobacteria; c_Betaproteobacteria; o_Burkholderiales; f_Comamonadaceae; g_; s_ |
| 330 | k_Bacteria; p_Proteobacteria; c_Betaproteobacteria; o_Burkholderiales; f_Oxalobacteraceae; g_; s_ |
| 331 | k_Bacteria; p_Firmicutes; c_Bacilli; o_Bacillales; f_Bacillaceae; g_Bacillus; s_cereus |
| 332 | k_Bacteria; p_Proteobacteria; c_Alphaproteobacteria; o_Rhodospirillales; f_Rhodospirillaceae; g_Phaeospirillum; s_fulvum |
| 333 | k_Bacteria; p_Proteobacteria; c_Alphaproteobacteria; o_Rhodobacterales; f_Hyphomonadaceae; g_Oceanicaulis; s_ |
| 334 | k_Bacteria; p_Proteobacteria; c_Betaproteobacteria; o_Burkholderiales; f_Comamonadaceae; g_Curvibacter; s_ |
| 335 | k_Bacteria; p_Proteobacteria; c_Gammaproteobacteria; o_Pseudomonadales; f_Pseudomonadaceae; g_Pseudomonas; s_ |
| 336 | k_Bacteria; p_Proteobacteria; c_Alphaproteobacteria; o_Sphingomonadales; f_Sphingomonadaceae; g_Novosphingobium; s_ |
| 337 | k_Bacteria; p_Proteobacteria; c_Betaproteobacteria; o_Neisseriales; f_Neisseriaceae; g_Chromobacterium; s_ |
| 338 | k_Bacteria; p_Proteobacteria; c_Gammaproteobacteria; o_Pseudomonadales; f_Pseudomonadaceae; g_Pseudomonas; s_ |
| 339 | k_Bacteria; p_Firmicutes; c_Bacilli; o_Bacillales; f_Bacillaceae; g_Bacillus; s_flexus |
| 340 | k_Bacteria; p_Firmicutes; c_Bacilli; o_Bacillales; f_Paenibacillaceae; g_Paenibacillus; s_chondroitinus |
| 341 | k_Bacteria; p_Proteobacteria; c_Alphaproteobacteria; o_Sphingomonadales; f_Sphingomonadaceae; g_Sphingopyxis; s_alaskensis |
| 342 | k_Bacteria; p_Firmicutes; c_Bacilli; o_Bacillales; f_Bacillaceae; g_Bacillus; s_flexus |
| 343 | k_Bacteria; p_Firmicutes; c_Bacilli; o_Bacillales; f_Bacillaceae; g_Bacillus; s_cereus |
| 344 | k_Bacteria; p_Proteobacteria; c_Gammaproteobacteria; o_Enterobacteriales; f_Enterobacteriaceae; g_; s_ |
| 345 | k_Bacteria; p_Proteobacteria; c_Alphaproteobacteria; o_Rhodospirillales; f_Rhodospirillaceae; g_; s_ |
| 346 | k_Bacteria; p_Actinobacteria; c_Actinobacteria; o_Actinomycetales; f_Micrococcaceae; g_; s_ |
| 347 | k_Bacteria; p_Proteobacteria; c_Betaproteobacteria; o_Burkholderiales; f_Comamonadaceae; g_; s_ |
| 348 | k_Bacteria; p_Proteobacteria; c_Gammaproteobacteria; o_Pseudomonadales; f_Pseudomonadaceae; g_Pseudomonas; s_ |
| 349 | k_Bacteria; p_Firmicutes; c_Clostridia; o_Clostridiales; f_Clostridiaceae; g_Clostridium; s_ |
| 350 | k_Bacteria; p_Firmicutes; c_Bacilli; o_Bacillales; f_Bacillaceae; g_Bacillus; s_cereus |
| 351 | k_Bacteria; p_Proteobacteria; c_Gammaproteobacteria; o_Pseudomonadales; f_Pseudomonadaceae; g_Pseudomonas; s_veronii |
| 352 | k_Bacteria; p_Proteobacteria; c_Alphaproteobacteria; o_Rhodospirillales; f_Rhodospirillaceae; g_Azospirillum; s_ |
| 353 | k_Bacteria; p_Proteobacteria; c_Gammaproteobacteria; o_Aeromonadales; f_Aeromonadaceae; g_; s_ |
| 354 | k_Bacteria; p_Proteobacteria; c_Gammaproteobacteria; o_Pseudomonadales; f_Pseudomonadaceae; g_Pseudomonas; s_ |
| 355 | k_Bacteria; p_Proteobacteria; c_Gammaproteobacteria; o_Aeromonadales; f_Aeromonadaceae; g_; s_ |
| 356 | k_Bacteria; p_Proteobacteria; c_Gammaproteobacteria; o_Pseudomonadales; f_Pseudomonadaceae; g_Pseudomonas; s_ |
| 357 | k_Bacteria; p_Firmicutes; c_Bacilli; o_Bacillales; f_Planococcaceae; g_Lysinibacillus; s_boronitolerans |
| 358 | k_Bacteria; p_Firmicutes; c_Bacilli; o_Bacillales; f_Bacillaceae; g_Bacillus |
| 359 | k_Bacteria; p_Bacteroidetes; c_Flavobacteriia; o_Flavobacteriales; f_[Weeksellaceae]; g_Chryseobacterium; s_ |
| 360 | k_Bacteria; p_Actinobacteria; c_Actinobacteria; o_Actinomycetales; f_Micrococcaceae; g_; s_ |
| 361 | k_Bacteria; p_Firmicutes; c_Bacilli; o_Bacillales; f_Bacillaceae; g_Bacillus |
| 362 | k_Bacteria; p_Proteobacteria; c_Gammaproteobacteria; o_Pseudomonadales; f_Pseudomonadaceae; g_Pseudomonas; s_ |

TABLE 2-continued

Growth of OTUs under different environmental conditions. Table 2 shows each
OTU identified in this example, including the taxonomic identification, frequency of
identification in each community, estimated MPN, rarity category, and percent of cultivable
community in inoculum.

| | |
|---|---|
| 363 | k_Bacteria; p_Proteobacteria; c_Gammaproteobacteria; o_Enterobacteriales; f_Enterobacteriaceae; g_; s_ |
| 364 | k_Bacteria; p_Proteobacteria; c_Alphaproteobacteria; o_Sphingomonadales; f_Sphingomonadaceae; g_Novosphingobium; s_ |
| 365 | k_Bacteria; p_Proteobacteria; c_Gammaproteobacteria; o_Enterobacteriales; f_Enterobacteriaceae; g_; s_ |
| 366 | k_Bacteria; p_Proteobacteria; c_Gammaproteobacteria; o_Pseudomonadales; f_Pseudomonadaceae; g_Pseudomonas; s_ |
| 367 | k_Bacteria; p_Proteobacteria; c_Gammaproteobacteria; o_Enterobacteriales; f_Enterobacteriaceae; g_; s_ |
| 368 | k_Bacteria; p_WPS-2; c_; o_; f_; g_; s_ |
| 369 | k_Bacteria; p_Proteobacteria; c_Gammaproteobacteria; o_Pseudomonadales; f_Pseudomonadaceae; g_Pseudomonas; s_veronii |
| 370 | k_Bacteria; p_Firmicutes; c_Bacilli; o_Bacillales; f_Bacillaceae; g_; s_ |
| 371 | k_Bacteria; p_Firmicutes; c_Bacilli; o_Bacillales; f_Bacillaceae; g_Bacillus; s_cereus |
| 372 | k_Bacteria; p_Proteobacteria; c_Gammaproteobacteria; o_Xanthomonadales; f_Xanthomonadaceae; g_Rhodanobacter; s_ |
| 373 | k_Bacteria; p_Firmicutes; c_Bacilli; o_Bacillales; f_Bacillaceae; g_Bacillus; s_cereus |
| 374 | k_Bacteria; p_Proteobacteria; c_Gammaproteobacteria; o_Pseudomonadales; f_Pseudomonadaceae; g_Pseudomonas; s_ |
| 375 | k_Bacteria; p_Proteobacteria; c_Gammaproteobacteria; o_Pseudomonadales; f_Pseudomonadaceae; g_Pseudomonas; s_ |
| 376 | k_Bacteria; p_Proteobacteria; c_Gammaproteobacteria; o_Enterobacteriales; f_Enterobacteriaceae; g_; s_ |
| 377 | k_Bacteria; p_Proteobacteria; c_Gammaproteobacteria; o_Pseudomonadales; f_Pseudomonadaceae; g_; s_ |
| 378 | k_Bacteria; p_Proteobacteria; c_Betaproteobacteria; o_Burkholderiales; f_Oxalobacteraceae; g_; s_ |
| 379 | k_Bacteria; p_Proteobacteria; c_Betaproteobacteria; o_Burkholderiales; f_Oxalobacteraceae; g_Janthinobacterium; s_lividum |
| 380 | k_Bacteria; p_Proteobacteria; c_Betaproteobacteria; o_Burkholderiales; f_Oxalobacteraceae; g_; s_ |
| 381 | k_Bacteria; p_Actinobacteria; c_Actinobacteria; o_Actinomycetales; f_Micrococcaceae; g_; s_ |
| 382 | k_Bacteria; p_Proteobacteria; c_Alphaproteobacteria; o_Rhizobiales; f_Bradyrhizobiaceae; g_; s_ |
| 383 | k_Bacteria; p_Firmicutes; c_Clostridia; o_Clostridiales; f_Ruminococcaceae; g_; s_ |
| 384 | k_Bacteria; p_Proteobacteria; c_Gammaproteobacteria; o_Aeromonadales; f_Aeromonadaceae; g_; s_ |
| 385 | k_Bacteria; p_Proteobacteria; c_Gammaproteobacteria; o_Pseudomonadales; f_Pseudomonadaceae; g_Pseudomonas; s_ |
| 386 | k_Bacteria; p_Proteobacteria; c_Gammaproteobacteria; o_Aeromonadales; f_Aeromonadaceae; g_; s_ |
| 387 | k_Bacteria; p_Proteobacteria; c_Gammaproteobacteria; o_Pseudomonadales; f_Pseudomonadaceae; g_Pseudomonas; s_ |
| 388 | k_Bacteria; p_Proteobacteria; c_Gammaproteobacteria; o_Aeromonadales; f_Aeromonadaceae; g_; s_ |
| 389 | k_Bacteria; p_Proteobacteria; c_Gammaproteobacteria; o_Aeromonadales; f_Aeromonadaceae; g_; s_ |
| 390 | k_Bacteria; p_Proteobacteria; c_Gammaproteobacteria; o_Aeromonadales; f_Aeromonadaceae; g_; s_ |
| 391 | k_Bacteria; p_Proteobacteria; c_Gammaproteobacteria; o_Pseudomonadales; f_Moraxellaceae; g_Alkanindiges; s_ |
| 392 | k_Bacteria; p_Firmicutes; c_Bacilli; o_Bacillales; f_Paenibacillaceae; g_Paenibacillus; s_ |
| 393 | k_Bacteria; p_Proteobacteria; c_Alphaproteobacteria; o_Caulobacterales; f_Caulobacteraceae; g_Caulobacter |
| 394 | k_Bacteria; p_Proteobacteria; c_Gammaproteobacteria; o_Pseudomonadales; f_Pseudomonadaceae; g_Pseudomonas; s_viridiflava |
| 395 | k_Bacteria; p_Proteobacteria; c_Gammaproteobacteria; o_Enterobacteriales; f_Enterobacteriaceae; g_; s_ |
| 396 | k_Bacteria; p_Proteobacteria; c_Gammaproteobacteria; o_Pseudomonadales; f_Pseudomonadaceae; g_; s_ |
| 397 | k_Bacteria; p_Proteobacteria; c_Gammaproteobacteria; o_Xanthomonadales; f_Xanthomonadaceae; g_; s_ |
| 398 | k_Bacteria; p_Firmicutes; c_Clostridia; o_Clostridiales; f_Lachnospiraceae; g_Coprococcus; s_ |
| 399 | k_Bacteria; p_Proteobacteria; c_Gammaproteobacteria; o_Enterobacteriales; f_Enterobacteriaceae; g_; s_ |

The effects of selection were apparent when comparing the communities formed between the two cultivation conditions. For example, cultivation conditions clearly structured the cultivability of different members of the inoculum both in terms of the number of times they were observed (FIG. 13) as well as their relative abundances (FIG. 9 and FIG. 11). The cultivation condition did not, however, have a noticeable effect on the average number of OTUs detected in each local community. The total number of unique OTUs across the nitrate-reducing communities, however, was higher than the number of unique OTUs across the aerobic communities, reflective of a greater number of low-abundance species cultivable under anaerobic nitrate-reducing conditions (FIG. 8). Overall, each community tended to be dominated by a few taxa—notably members of the Pseudomonadaceae, Bacillaceae, Paenibacillaceae, Comamonadaceae, and Neisseriaceae. Taxa of these families were commonly found in the ground waters of the Oak Ridge Field Site, and represented frequently identified heterotrophic members of bacterial soil and groundwater communities.

Often, members of the dominant families tended to prefer one of the two cultivation conditions. For example, members of the Paenibacillaceae tended to dominate in the low-dilution nitrate-reducing cultures (FIG. 9), and the majority of Paenibacillaceae OTUs were unique to anaerobic samples (FIG. 8). Despite the clear preference for anaerobic conditions, there were OTUs of the Paenibacillaceae unique to aerobic samples as well (FIG. 8). Likewise, although most Bacillaceae were identified only in nitrate-reducing anaerobic samples, some OTUs were also found uniquely in aerobic samples. On the other hand, most Pseudomonadaceae were found in either aerobic conditions or in both aerobic and nitrate-reducing conditions and yet 11% were unique to anaerobic samples. These results highlight that although relative distantly related taxa (i.e., same family) may be in general subject to similar selective pressures, considerable divergence in metabolic strategy may be common even amongst co-existing populations.

These data indicate that multiple dilutions in a highly replicated enrichment experiment can be used to understand how probabilistic recruitment and selection shape community assembly. This example shows that many distinct communities formed, influenced by the diversity and structure of the inoculum culture as well as the abiotic selective factors of the environment (aerobic or nitrate-reducing). These communities differ only in the specific and isolated parameters of cultivation conditions. Additionally, organism interactions were evidenced by significantly non-random OTU co-occurrences and these interactions may play important roles in structuring communities. Probabilistic subsampling can produce a range of community structure outcomes constrained by environmental selection.

Figure 7:
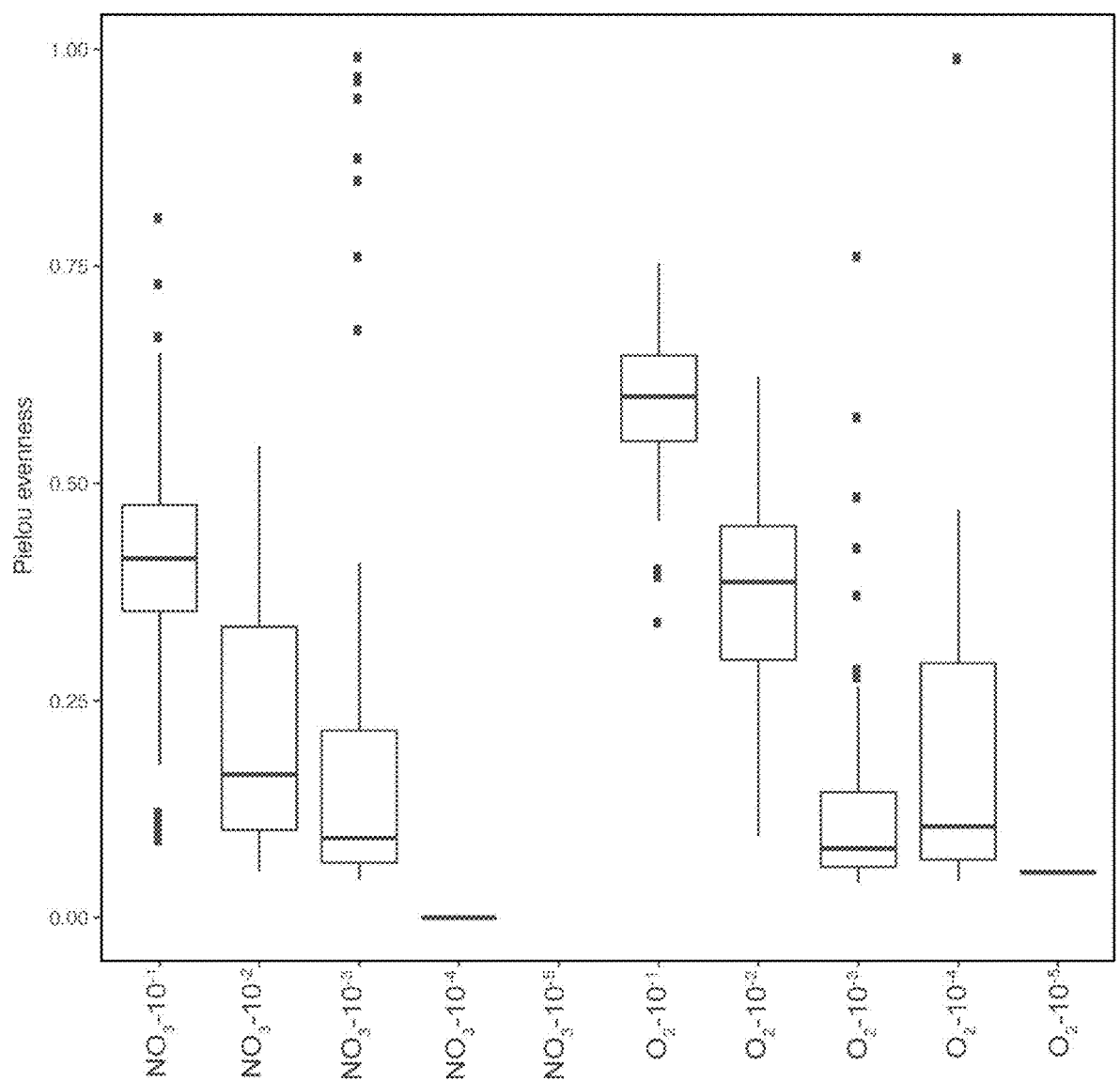
FIG. 7 is a plot showing an analysis of evenness of each community by Pielou's evenness metric (calculated as the Shannon index divided by the log of the total species in each community). Differences between the average evenness of communities at a given dilution were calculated as significant (p<0.05) by Tukey's Honest Significant Difference method.

Divergence among replicate communities formed from a single inoculum dilution and under a single selective pressure was rooted in varied recruitment. Together with this probabilistic process, selective forces acted by winnowing down the types and sizes of populations that will thrive. This effect, for example, was seen when comparing communities in the anaerobic versus aerobic enrichments of the first dilutions ($NO_3$-$10^{-1}$ and $O_2$-$10^{-1}$). The anaerobic cultivations, despite being seeded with the same numbers and populations of cells as the aerobic enrichments, favored the outgrowth and dominance of a smaller number of taxa, as indicated by Pielou's evenness index (FIG. 7). In other words, the $NO_3$-$10^{-1}$ communities were more varied because fewer organisms are fit and emerge as "winners," creating distinct sets of reproducible outcomes. The communities under the $O_2$-$10^{-1}$ condition were more cohesive because many organisms are fit.

As with strong selective pressures, dilution can create variance in community structures by bottlenecking the number of cultivable organisms. For example, the communities of the $O_2$-$10^{-1}$ enrichments tended to be more similar to each other than the communities of the $O_2$-$10^{-2}$ enrichments. Additionally, the $O_2$-$10^{-1}$ enrichments were more evenly structured than the communities of the $O_2$-$10^{-2}$ enrichments, which were often dominated by a single organism. These findings are consistent with stochastic recruitment creating fewer "winning" organisms and ultimately more divergent community structures in the $O_2$-$10^{-2}$ enrichments. Continuing to inoculate with more and more dilute inocula, however, ultimately reduced variance in community structure outcomes, because a single OTU came to dominate. Under aerobic conditions, this organism's relative cultivable abundance meant it dominated the $10^{-3}$ dilutions, while the overall reduced cultivability of other organisms in the stark selective pressures of the anaerobic environment led to this OTU's dominance in the $10^{-2}$ dilutions.

Strong selective pressures were also evident when examining how different phylogenetic groups were enriched under the different cultivation conditions. For example, the majority of Paenibacillaceae OTUs were unique to anaerobic samples (FIG. 8). Overall, the dominant detected families, including the Pseudomonadaceae, Bacillaceae, Paenibacillaceae, Comamonadaceae, and Neisseriaceae, are commonly found in the groundwaters of the Oak Ridge field site and represent frequently identified heterotrophic members of bacterial soil and groundwater communities.

Example 3

Rare Organisms can Dominate Cultures

This example demonstrates rare organisms can dominate cultures based on null model analysis.

Data Processing and Analysis

Figure 15:
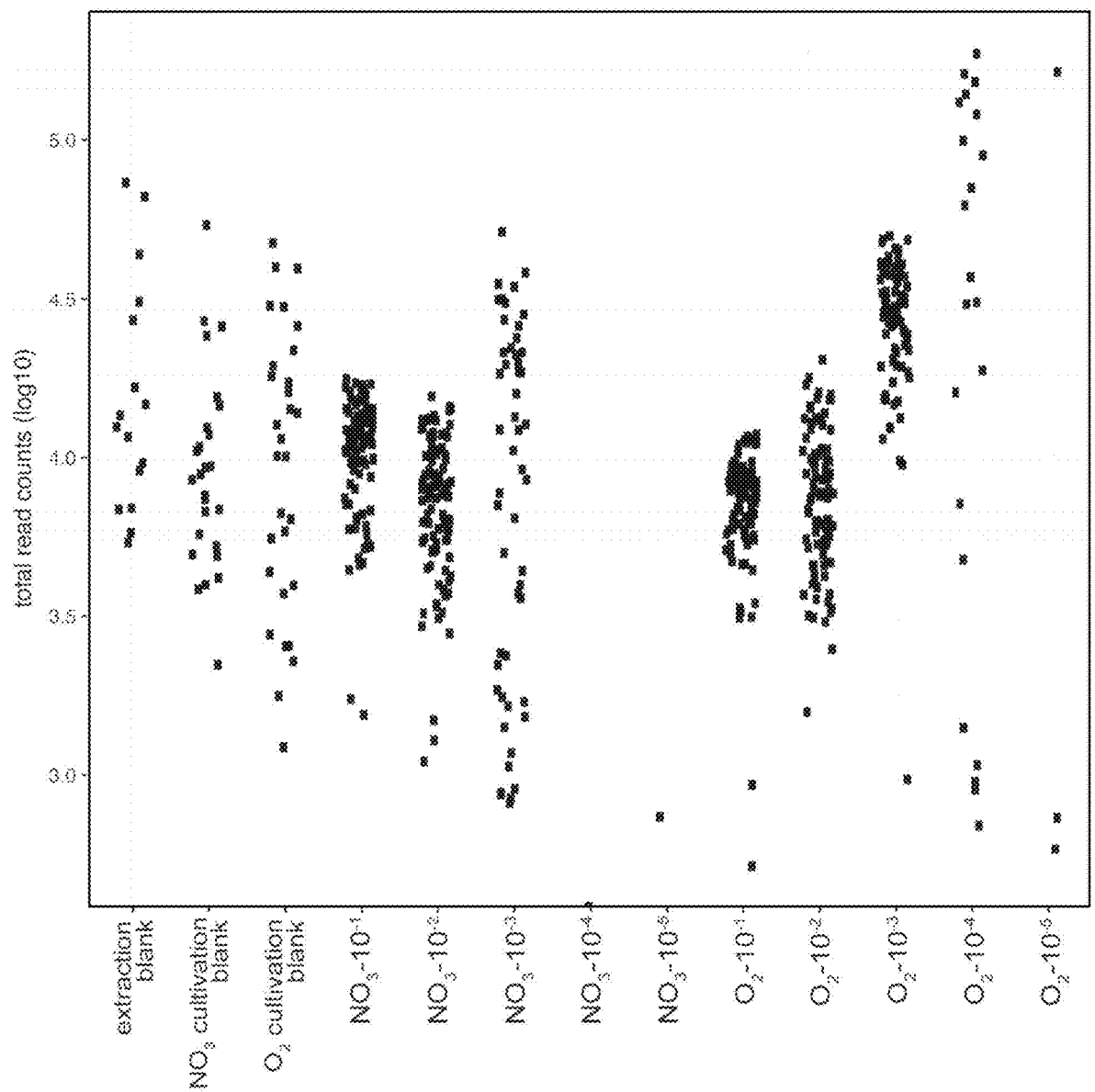
FIG. 15 is a plot showing the read depth of samples after following contaminate OTU filtering.

OTUs tables from QIIME were imported into R with custom Ruby scripts that assigned each well to the corresponding experiment (i.e., condition and dilution). As not all wells had positive growth but were extracted and sequenced anyway, it was useful to separate reads accumulated from either barcode sequencing errors or reagent contamination from true positive detected OTUs. These potential sources of error were controlled by sequencing and analyzing no-inoculum cultures and extraction-only blanks. First, R scripts were used to identify all OTUs that were found in the no-inoculum control samples and the extraction-blank samples. OTUs that represented more than 0.1% of summed reads in the no-inoculum control samples and the extraction-blank samples were called contaminants and excluded from the analysis. Next, in any given sample, any OTU with fewer reads than the summed read count of all contaminant OTUs in that sample was excluded from the analysis. Overall, contaminant reads were high (e.g., >0.5%) only in samples with few sequencing reads (<500) and with no detected growth by $OD_{600}$ (<0.055 absorbance). Finally, any sample with fewer than 500 total reads was excluded from the analysis. The median and mean read counts of samples kept in the analysis were 9,177 and 14,529, respectively. The read count data for each sample are depicted in FIG. 15.

The variance in community structures within samples and dilutions was calculated using the "betadispers" function in the R package vegan. The multivariate analyses of group dispersions were done by calculating each community's distance from a median point in multivariate space using Bray-Curtis dissimilarity.

The MPN technique was used to calculate the cultivable abundance of every taxon in the inoculum. This technique can provide the most probable number of cultivable units of an organism in an inoculum sample given a distribution of positive and negative outgrowths at several dilutions. The cultivable abundance was thus a function of both the number of cells of that organism in the inoculum as well as their ability to replicate under the prescribed cultivation condition. First, an overall estimated number of cultivable cells was calculated using $OD_{600}$ data. To obtain the OTU-specific cultivable units per ml, the same technique was coded into the statistical package R on the sequencing data of cultivations. Data from the last two anaerobic dilutions were excluded in the MPN calculations, given that there were no samples with detectable OTUs in the $NO_3$-$10^{-4}$ dilution and only a single sample with a single OTU in the $NO_3$-$10^{-5}$ dilution. Rarity values for each OTU's MPN-estimated cultivable abundance were calculated by dividing the likelihood of the observed outcome by the largest likelihood of any outcome at that same estimated inoculum concentration. All data, including raw reads, and processed and demultiplexed reads, as well as code for calculating most probable number and rarity values for each OTU were calculated in R with scripts available at http://genomicslbl.gov/supplemental/enrichments, content of which is incorporated herein in its entirety.

Null Model Analysis

In order to determine which OTUs were the strongest competitors and which were the weakest competitors, the average relative abundance of each OTU, across replicates, was compared with its average expected abundance. Expected abundances were derived by simulating the assembly of many communities using the cultivable units per ml for each OTU estimated from MPN analyses. The communities were assembled in a null model in which no organism interactions or fitness differences were allowed. As such, this model was not meant to accurately predict outcomes, only to serve as a metric against which to measure and compare the strength of nonrandom forces (e.g., relative fitness in light of environmental selection). For each dilution and experimental condition, 10,000 communities were simulated. In each simulation, the number of seeded cells for a given OTU was randomly sampled from a Poisson distribution with a mean value equal to the expected number of cells for that OTU under the condition/dilution. To account for potential error in the MPN-estimated cell abundances, both the mean number of cells for each OTU and the total number of cells (sum of all OTU's abundance) were allowed to vary twofold. A 99% confidence interval was calculated for the percent relative abundance of each OTU in all simulated communities for the condition/dilution.

Identifying Organism Relative Fitness

Figure 16:
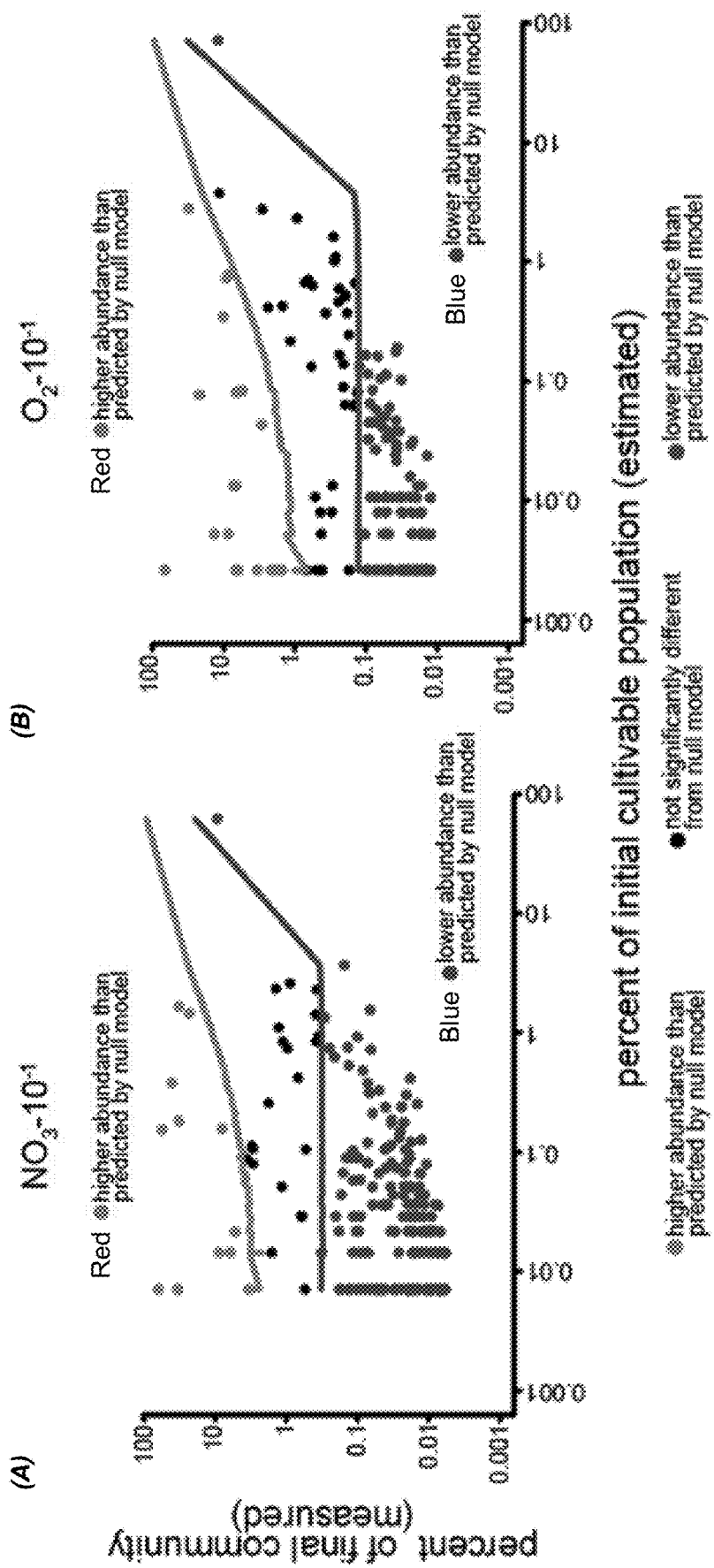
FIG. 16, panels (A)-(C) show each OTU's final average percent abundance plotted against initial estimated percent abundance for the nitrate-reducing (A and C) and aerobic (B) enrichments begun with the most concentrated inoculum. Red and blue lines indicate the upper and lower boundaries, respectively, of the 99% confidence interval of expected average abundance in 10,000 communities simulated in the null model of community assembly. Note the log scale. The right-most point in both graphs represents the *Pseudomonas* OTU New.ReferenceOTU30. Low abundance organisms that were disproportionally abundant in the final community structures under the anaerobic nitrate reducing communities of the lowest dilution are circled in FIG. 16, panel (C).
Figure 16:
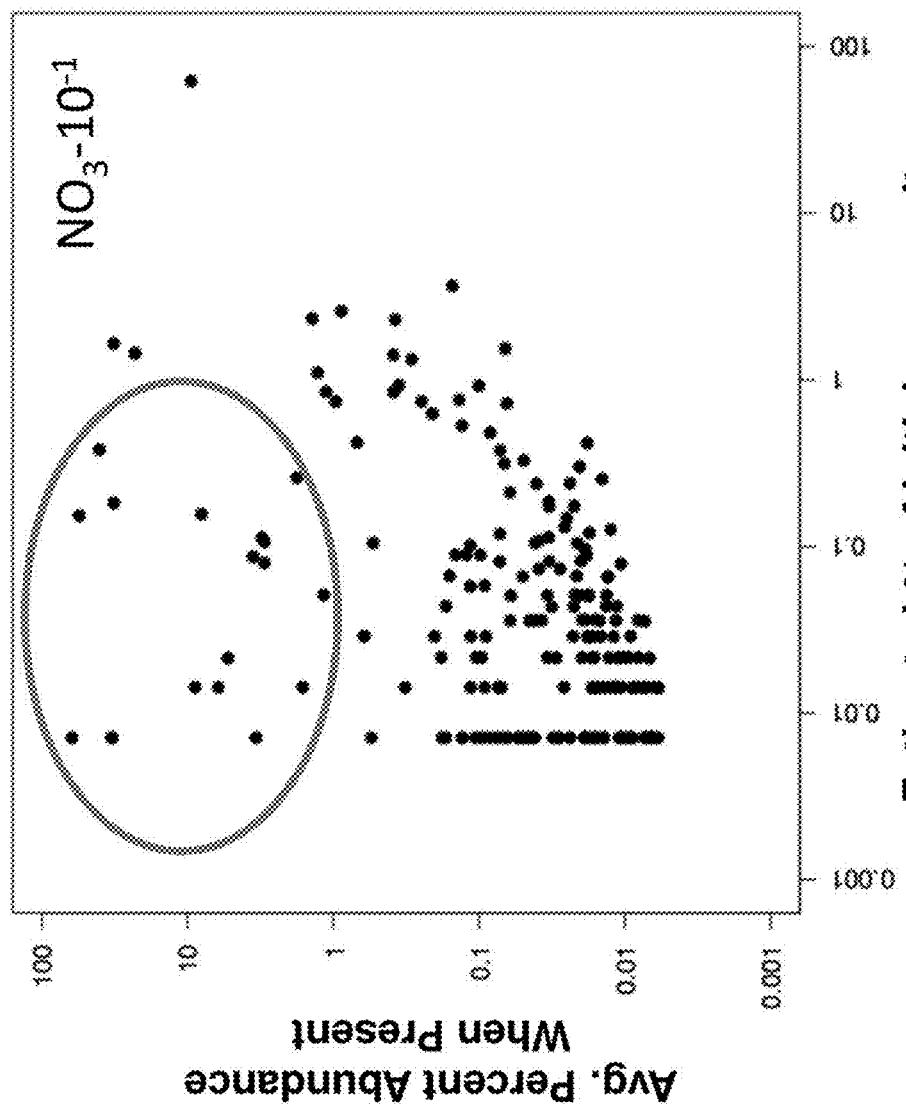

OTUs were classified as strong or weak competitors under each condition by comparing measured organism abundance with predicted organism abundance in a null model of community assembly in which all organisms have identical growth properties (no net positive or negative growth differences, and no interaction between OTUs). Using the estimated initial cultivable abundances of each OTU, the seeding and cultivation of 10,000 replicate communities from the lowest dilution inoculum into the aerobic and anaerobic environments were simulated. The lowest dilution cultures were the focus since these cultures represent the greatest inclusion of taxa and thus overall highest expected frequency of competition. These estimated average abundances were compared to the measured average abundance of each OTU and identified OTUs whose measured relative abundances were higher or lower than the predicted abundances at a 99% confidence level (FIG. 16). In essence, only the frequency at which each OTU was identified was used to create expectations of how abundant taxa were during inoculation. These expected values were compared to observed postcultivation average abundances. Most organisms tended to be poor competitors, including the most abundant OTU in our experiment, Pseudomonadaceae New.ReferenceOTU30. Using its estimated cultivable units per milliliter, the model predicts that this OTU should be an average of 19.5% of the $NO_3$-$10^{-1}$ communities and 32.4% of the $O_2$-$10^{-1}$ communities. The measured average relative abundances, however, were only 9.4% and 12.1%, respectively, reflecting the poor relative fitness of this taxon. Phrased different, this OTU was expected to be very abundant in the neutral model of cultivation because it was estimated to be very abundant in the inoculum (e.g., was found in many cultures). At the end of cultivation, however, its relative abundance was lower than that expectation.

Figure 17:
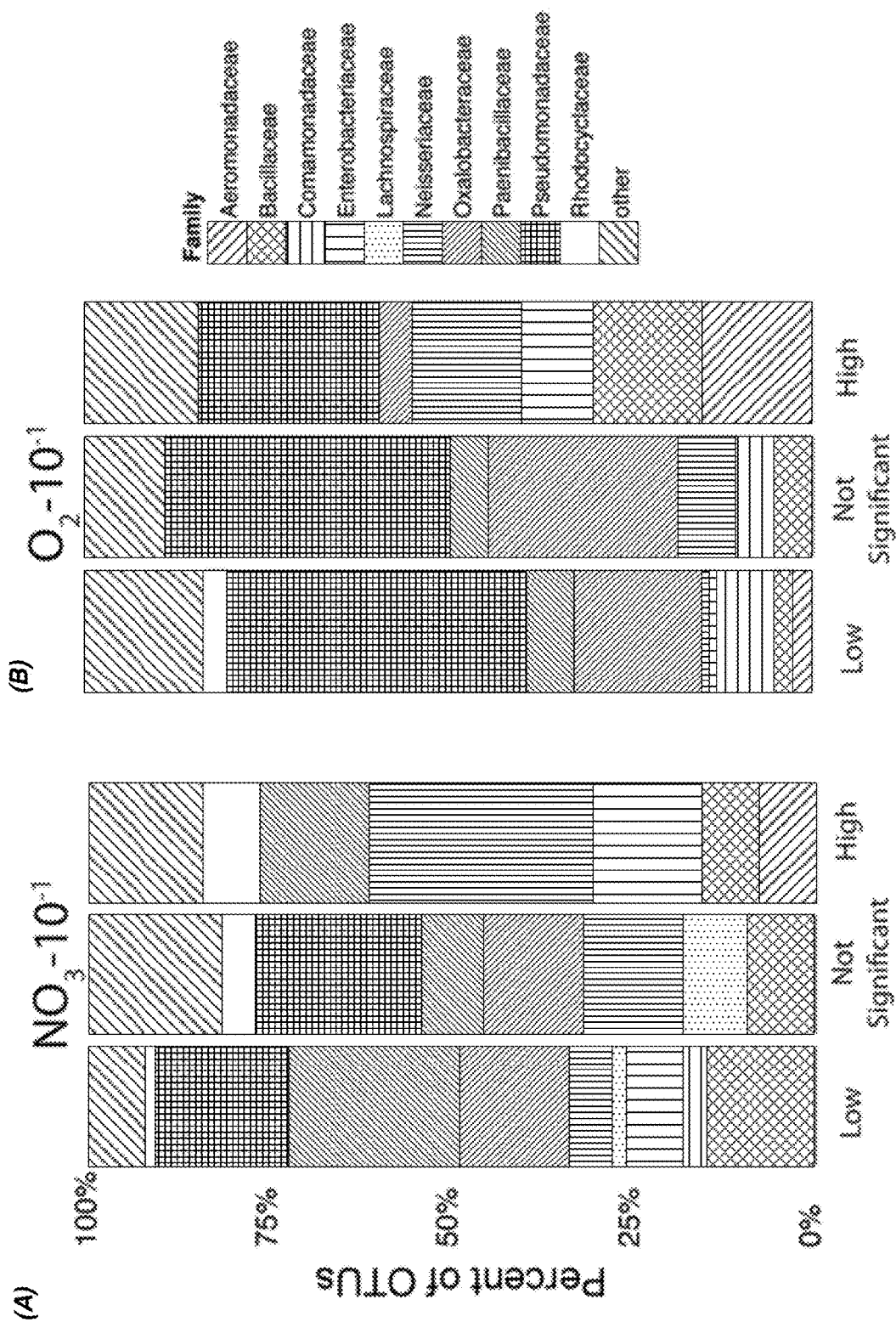
FIG. 17, panels (A)-(B) show OTUs binned as having high, low, or non-significant relative fitness advantages in the anaerobic nitrate reducing (A) and aerobic (B) communities of the lowest dilution.

Some OTUs, such as those belonging to the Neisseriaceae and Aeromonadaceae, tended to be strong competitors under both aerobic and nitrate-reducing conditions (FIG. 17). Others, like the Pseudomonadaceae and Paenibacillaceae, had strong competitors under only one condition (the Paenibacillaceae under anaerobic conditions and the Pseudomonadaceae under aerobic conditions). On the other hand, the Oxalobacteraceae had only a few, if any, strong competitors under either aerobic conditions or nitrate-reducing conditions. In some cases, rare taxa dominated cultures, including OTUs 581021 and 922761 (family Enterobacteriaceae), which were both predicted to be less than 0.008% of the cultivable inoculum and yet come to represent 33.2, and 62.1 percent of the anaerobic cultures in which they were found, respectively (Table 2). In the aerobic cultures a single taxon of Aeromonadaceae (778059), representing only 0.002% of the initial cultivable inoculum came to represent 66.0% of a single community.

As it may make the unrealistic assumption of no fitness difference between taxa, the null model simulation of community assembly did not predict true final organism abundances (FIG. 16). The true average abundances for the vast majority of taxa fell below the 99% confidence threshold of their expected abundances. Nearly all of these were predicted to be low-abundance taxa in the inoculum (e.g., <1%) that were driven to even lower relative abundances during cultivation. In addition to extraction and amplification biases, fitness differences and competition likely contribute to the lower than predicted abundances for many of these OTUs.

How the relative fitness of individual OTUs differed across environmental conditions were assessed by predicting the relative abundance of each OTU in a null-model of community assembly devoid of fitness differences, and compared this to actual measured relative abundance (FIG. 16). In this way, OTUs were identified as having either high, low, or no competitive fitness advantage in both the $NO_3$-$10^{-1}$ and $O_2$-$10^{-1}$ communities (FIG. 17). Again, some family-level differences in competitive abilities as a function of the enrichment conditions were observed. For example, some OTUs of Pseudomonadaceae were strong competitors in aerobic environments, yet none were identified as strongly competitive under nitrate-reducing conditions. This was somewhat surprising as members of the Pseudomonadaceae were frequent nitrate reducers and had many representatives capable of growth under anaerobic nitrate-reducing conditions (FIG. 8). The dominance of these Pseudomonadaceae in predominantly aerobic samples may be a reflection of an aerobic or facultatively aerobic ecological strategy in the natural environment of the Field Research Center (FRC) groundwater. On the other hand, representatives of the Paenibacillaceae were likely better adapted to conditions of low oxygen concentrations, as evidenced by their higher relative fitness in only anaerobic conditions (FIG. 17). Furthermore, despite their overall preference for anaerobic conditions (FIG. 8), some Bacillaceae were strong competitors even under aerobic environments (FIG. 17), reflecting the broad metabolic versatility of these organisms. In both aerobic and anaerobic environments, some of the most competitive taxa belonged to members of the Neisseriaceae, especially the genus Chromobacterium (Table 2).

These data indicate that family-level differences in competitive abilities as a function of the enrichment conditions can exist.

Example 4

Predicting Organism Interactions

This example demonstrates organism interaction determinations based on OTU co-occurrence patterns.

OTU co-occurrence patterns were examined for each dilution under each experimental condition using the R package 'cooccur'. Briefly, within all replicates of a condition and dilution, the number of times two taxa occur in the same cultivation well (e.g., replicate) and the number of times they occur apart were identified. The model provides the probability that occurrences would occur more or less often than the observed occurrences assuming random and independent distribution of OTUs. Only OTUs with a relative abundance greater than 0.1% were counted in order to focus on only the most abundant taxa as well as to reduce false positive associations from artifacts of OTU sequencing and clustering. Significant positive and negative associations ($\alpha=0.001$) were visualized as networks in Cytoscape by taking the union of all aerobic and nitrate-reducing experiments, respectively. Raw data can be downloaded from the Sequence Read Archive under project accession no. PRJNA387349, the content of which is incorporated by reference herein in its entirety.

Predicting Organism Interactions. Given the probabilistic nature of how each replicate was seeded, pairs of taxa were identified that may be interacting by observing if they were found more or less frequently together than one would expect by chance. For each condition and dilution, the total number of pairwise comparisons, the number of significant positive and negative associations, and the median strength of the associations for each condition and dilution are shown in Table 3.

In addition to revealing how abiotic factors and probabilistic immigration shape community assembly, the roles of organism interactions in structuring communities were identified. To that end, pairs of taxa were identified as potentially interacting if they were found more or less frequently together than expected by random chance. Given that every local community in a given condition was initially identical, co-occurrence patterns were not linked to initial abiotic conditions and 'habitat-filtering,' a common problem for studies done in situ.

Figure 18:
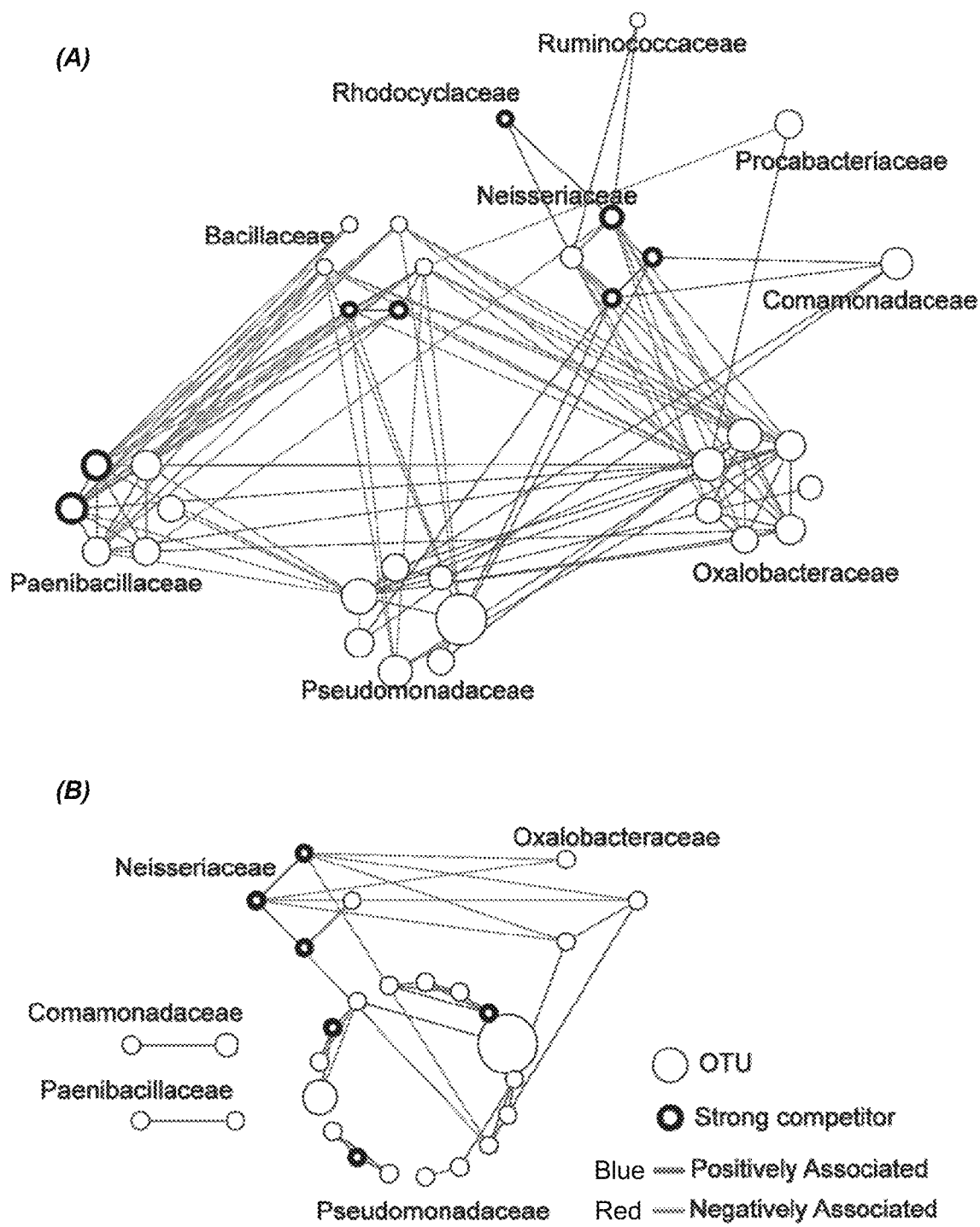
FIG. 18, panels (A) and (B) show networks depicting positive and negative associations between pairs of taxa in anaerobic nitrate-reducing communities (A) and aerobic communities (B). Graphs were made by the union of interaction graphs at each dilution for aerobic and anaerobic samples, respectively. Positive associations are shown in blue and negative associations in red. OTUs predicted to be strong competitors (FIG. 9 and FIG. 10) are indicated with a bold outline. The size of the node for each OTU scales with the estimated number of cultivable units of that OTU in the initial inoculum (FIG. 17). OTUs predicted to be strong competitors (FIG. 16 and FIG. 17) are indicated with a bold outline. The size of the node for each OTU scales with the estimated number of cultivable units of that OTU in the initial inoculum (FIG. 13).

Overall, a larger number of interactions in the anaerobic samples, compared to the aerobic samples, were observed (Table 1, FIG. 18). In general, negative interactions could be explained by antibiotic production or resource competition. Paenibacillaceae, Pseudomonadaceae, Bacillaceae, Neisseriaceae, and Oxalobacteraceae all harbor species capable of producing antibiotics. The higher number of negative interactions in the anaerobic samples may be linked to the regulation of antibiotic production by oxygen availability, as has been shown in species of *Pseudomonas*. Alternatively, anaerobic negative interactions might be linked to accumulations of by-products of fermentative metabolisms that

TABLE 3

Summary table of pairwise co-occurrences analyses for each environment and dilution including the number of samples, total species, total potential pairs of species, analyzed species combinations, and the number of significant positive and negative interactions at the $p < 0.001$ threshold. Analyzed combinations represent only those species pairs expected to have 1 or more co-occurrences. False discovery rates were calculated with alphas = 0.001.

|  | Samples | Species | Total species pair combinations | Analyzed combinations | Positive | Negative | Medium power (abs(obs-expected)) | FDR |
|---|---|---|---|---|---|---|---|---|
| $NO_3\text{-}10^{-1}$ | 94 | 230 | 26335 | 802 | 58 | 47 | 6.2 | 1.53% |
| $NO_3\text{-}10^{-2}$ | 96 | 124 | 7626 | 317 | 12 | 9 | 7.5 | 3.02% |
| $NO_3\text{-}10^{-3}$ | 54 | 91 | 4095 | 37 | 1 | 0 | 8.2 | 7.40% |
| $NO_3\text{-}10^{-4}$ | 0 | 0 | NA | NA | NA | NA | NA | NA |
| $NO_3\text{-}10^{-5}$ | 1 | 1 | NA | NA | NA | NA | NA | NA |
| $O_2\text{-}10^{-1}$ | 96 | 164 | 13366 | 1303 | 8 | 8 | 9.75 | 16.29% |
| $O_2\text{-}10^{-2}$ | 96 | 109 | 5886 | 564 | 15 | 3 | 9.85 | 6.27% |
| $O_2\text{-}10^{-3}$ | 79 | 65 | 2080 | 74 | 2 | 0 | 7.7 | 7.40% |
| $O_2\text{-}10^{-4}$ | 22 | 37 | 666 | 12 | 0 | 0 | NA | 0.00% |
| $O_2\text{-}10^{-5}$ | 3 | 6 | NA | NA | NA | NA | NA | 0.00% |

Overall, 115 putative interactions (56 negative and 59 positive) were identified amongst 34 OTUs in the nitrate-reducing samples, and 34 putative interactions (23 positive and 11 negative) amongst 15 OTUs in the aerobic samples (FIG. 18). There was very little overlap between interaction predictions across conditions, with only 14 OTUs and 5 predicted interactions shared in both aerobic and anaerobic communities. Of those five shared interactions, all were positive associations amongst pairs of closely related OTUs.

In the anaerobic samples, OTUs of the Pseudomonadaceae were positively associated with members of the Oxalobacteraceae, and negatively associated with members of the Bacillaceae and Paenibacillaceae. Oxalobacteraceae, on the other hand, were positively associated with the Paenibacillaceae, and negatively associated with members of the Neisseriaceae and Bacillaceae. The Bacillaceae had no positive connections to other families and were negatively associated with members of the Pseudomonadaceae, Oxalobacteraceae, and the Paenibacillaceae. In aerobic samples, some positive associations between the Pseudomonadaceae and Oxalobacteraceae were identified, and the Neisseriaceae share negative associations with members of both Oxalobacteraceae and Pseudomonadaceae families.

inhibit competing organisms. Further, negative interactions could be linked to the structured (e.g., unshaken) environment of the anaerobic cultures, with physical proximity possibly being an important factor. Members of the family Neisseriaceae and Oxalobacteraceae were unique in that they showed negative interaction patterns in both aerobic and anaerobic samples, even though no individual OTUs and interacting-pairs were preserved in both interaction networks.

Positive interactions can be more difficult to interpret as in some cases, co-occurring OTUs may be ultimately caused by sequence variation amongst copies of the 16S rRNA gene co-occurring within cells. For this reason, the focus was predominately on associations across broader phylogenetic distances. Intriguingly, members of the Oxalobacteraceae were positively associated with members of the Pseudomonadaceae and the Paenibacillaceae in anaerobic samples and with the Pseudomonadaceae alone in aerobic samples. Associations between Oxalobacteraceae and Pseudomonadaceae have been reported previously in human-associated samples. One possibility was that the Oxalobacteraceae were supported by $CO_2$ released from the oxidation of organic carbon in the media, as these organisms exhibited capnophilic physiologies.

Non-random positive co-occurrences might also be caused by colocalization on the same particle in the environment, and subsequent co-seeding in each enrichment community. These types of positive co-occurrences would be of particular interest since these organisms are more likely to be in close association in their natural environments. However, the poor overlap in positive co-occurrences between aerobic and anaerobic communities suggests that this may not be the case. Some positive interactions may also be a case of "the enemy-of-my-enemy-is-my-friend". In this case, negative interactions stemming from a broad-spectrum "killer", (e.g., members of the Bacillaceae), may eliminate multiple taxa from certain communities, leading to increased incidence of co-occurrence of those taxa in communities where the "killer" strain was not found.

Altogether, these data reveal how abiotic factors and probabilistic immigration shape community assembly.

As described herein, the combination of random dispersal with abiotic and biotic selections were shown to give rise to numerous and variegated communities. The taxonomic structure of the inoculum and physiological profile of its members. Although an organism's initial abundance in a local community is a function of its abundance in the inoculum, the final measured abundance is a product of the organism's relative fitness with respect to abiotic features of the cultivation condition as well as interactions with other species. How random variation in community outcome was strongly throttled by selective pressures and was examined to dissect how those selective pressures altered the structure of the cultivable inoculum and the competitive hierarchy of specific taxa. Ultimately, this approach offers a method to simultaneously explore the parameters of many coexisting populations (including "niche" parameters), identify organism interactions, and explore processes of community assembly for ecological or biotechnological applications.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for determining a microbial interaction, comprising:
   diluting a sample comprising a plurality of taxa of microorganisms to form a plurality of dilutions of the sample;
   cultivating a first subset of the plurality of dilutions of the sample in a first cultivation condition to generate a first plurality of cultivated dilutions, wherein the first subset of the plurality of dilutions comprises a first dilution and a second dilution with an identical inoculum density, wherein the first dilution comprises a first taxon and a second taxon, wherein the second dilution comprises the first taxon and not the second taxon, and wherein an abundance of the first taxon in a first cultivated dilution of the first plurality of cultivated dilutions cultivated from the first dilution is different from an abundance of the first taxon in a second cultivated dilution of the first plurality of cultivated dilutions cultivated from the second dilution;
   subjecting the first plurality of cultivated dilutions of the sample to sequencing to generate taxonomic information of taxa in the first plurality of cultivated dilutions, wherein the taxonomic information comprises abundances of at least one taxon of the taxa in the first plurality of cultivated dilutions; and
   processing the taxonomic information of the taxa in the first plurality of cultivated dilutions to identify a non-random occurrence of the first taxon in the presence or absence of the second taxon, thereby determining an interaction within the plurality of taxa of microorganisms in the sample in the first cultivation condition.

2. The method of claim 1, wherein diluting the sample to form plurality of dilutions of the sample comprises diluting the sample serially to form a plurality of serial dilutions of the sample.

3. The method of claim 2, wherein the plurality of serial dilutions of the sample comprises dilutions of the sample of about 1:10, 1:100, 1:1000, or 1:10000 dilution.

4. The method of claim 2, wherein the plurality of serial dilutions of the sample comprises dilutions of 1-9 orders of magnitude of the sample.

5. The method of claim 2, wherein the plurality of serial dilutions of the sample comprises about 2, 3, 4, 5, 6, 7, 8, 9, or 10 fold dilutions of the sample.

6. The method of claim 1, wherein the the first taxon corresponds to an operational taxonomic unit (OTU).

7. The method of claim 1, wherein the the first taxon corresponds to a species, a genus, or a family.

8. The method of claim 1, wherein subjecting the first plurality of cultivated dilutions of the sample to sequencing to generate taxonomic information of taxa in the first plurality of cultivated dilutions of the sample cultivated in the first cultivation condition comprises:
   determining the taxonomic information of the first subset of the plurality of cultivated dilutions of the sample based on sequencing of one or more genes selected form the group consisting of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof.

9. The method of claim 1, wherein subjecting the first plurality of cultivated dilutions of the sample to sequencing to generate taxonomic information of taxa in the first plurality of cultivated dilutions comprises:
   performing error correction to remove one or more errors in the taxonomic information of the taxa in the first plurality of cultivated dilutions.

10. The method of claim 9, wherein the one or more errors in the taxonomic information of the taxa in the first plurality of cultivated dilutions is a result of a barcode sequencing error or contamination of a reagent used in determining the taxonomic information of the taxa in the first plurality of cultivated dilutions.

11. The method of claim 10, comprising:
   cultivating a control sample in the first cultivation condition to generate a cultivated control sample;
   subjecting the cultivated control sample to sequencing to generate taxonomic information of one or more taxa in the cultivated control sample; and comparing the taxonomic information for the taxa in the first plurality of cultivated dilutions to the taxonomic information of the one or more taxa in the cultivated control sample.

12. The method of claim 11, wherein the control sample is cultivated in the absence of the sample or the plurality of dilutions of the sample cultivated in the first cultivation condition.

13. The method of claim 1, wherein the abundances of the taxa in the first plurality of cultivated dilutions are determined based on a threshold.

14. The method of claim 1, wherein the abundances of the taxa in the first plurality of cultivated dilutions comprise a relative abundance of the first taxon in the first cultivated dilution of the first plurality of cultivated dilutions.

15. The method of claim 1, wherein the interaction comprises the first taxon and the second taxon positively or negatively interact with each other.

16. The method of claim 15, wherein the first taxon and the second taxon negatively interact with each other if the first taxon inhibits growth or maintenance of the second taxon or the second taxon inhibits growth or maintenance of the first taxon.

17. The method of claim 1, wherein processing the taxonomic information comprises:
based on a null model of community assembly and the taxonomic information of the taxa in the first plurality of cultivated dilutions, using a computer processor to identify the non-random occurrence of the first taxon in the presence or absence of the second taxon.

18. The method of claim 17, wherein identifying the non-random occurrence of the first taxon in the presence or absence of the second taxon comprises:
determining a co-occurrence probability of the first taxon and the second taxon in the first cultivated dilution.

19. The method of claim 1, wherein the interaction comprises a biotic interaction.

20. The method of claim 1, wherein cultivating the first subset of the plurality of dilutions of the sample in the first cultivation condition comprises cultivating the first subset of the plurality of dilutions of the sample in the first cultivation condition, in parallel, for a plurality of time durations.

21. The method of claim 20, wherein the plurality of time durations comprises about 1 minute, 1 hour, 1 day, 1 week, 1 month, 1 year, or a combination thereof.

22. The method of claim 1, comprising:
cultivating a second subset of the plurality of dilutions of the sample in a second cultivation condition to generate a second plurality of cultivated dilutions;
subjecting the second plurality of cultivated dilutions of the sample to sequencing to generate taxonomic information of taxa in the second plurality of cultivated dilutions; and
processing the taxonomic information of the taxa in the second plurality of cultivated dilutions to identify a non-random occurrence of the first taxon in the presence or absence of the second taxon, thereby determining an interaction within the plurality of taxa of microorganisms in the sample in the second cultivation condition.

23. The method of claim 22, wherein the first subset and second subset are separately cultivated in the first cultivation condition and the second cultivation condition, respectively.

24. The method of claim 23, wherein the first cultivation condition comprises an aerobic cultivation condition, and wherein the second cultivation condition comprises an anaerobic cultivation condition.

25. The method of claim 24, wherein the anaerobic cultivation condition comprises a nitrate-reducing cultivation condition.

26. The method of claim 25, wherein the nitrate-reducing cultivation condition comprises presence of $NO_3$.

27. The method of claim 23, comprising:
determining one or more differences between the interaction within the plurality of taxa of microorganisms in the sample in the first cultivation condition and the interaction within the plurality of taxa of microorganisms in the sample in the second cultivation condition.

28. The method of claim 23, comprising:
determining, based on the interaction within the plurality of taxa of microorganisms in the sample in the first cultivation condition and the interactions of interaction within the plurality of taxa of microorganisms in the sample in the second cultivation condition, a preferred cultivation condition.

29. The method of claim 22, wherein the first subset and the second subset are different.

30. The method of claim 22, wherein the interactions are indicative of how at least the second cultivation condition alters one or more of cultivability, competitive fitness, or interspecific interactions of the plurality of taxa of microorganisms in at least the second cultivation condition.

31. The method of claim 22, wherein the interaction within the plurality of taxa of microorganisms in the sample in the first cultivation condition is different from the interaction within the plurality of taxa of microorganisms in the sample in the second cultivation condition, and the interactions are indicative of one or more condition-specific interactions.

32. The method of claim 1, wherein the first cultivation condition comprises the presence of a microorganism.

33. The method of claim 1, wherein the first cultivation condition is an environment of interest.

34. The method of claim 1, comprising:
determining, based on the interaction within the plurality of taxa of microorganisms in the sample in the first cultivation condition, the fitness of the first taxon in the first cultivation condition.

35. The method of claim 1, comprising:
determining, based on the interaction within the plurality of taxa of microorganisms in the sample in the first cultivation condition, that the first taxon and/or the second taxon contribute to a property of interest.

36. The method of claim 35, wherein the property of interest comprises performing a specific metabolic function.

37. The method of claim 35, wherein the property of interest comprises producing a molecule of interest.

38. The method of claim 35, wherein the property of interest comprises modifying a molecule of interest.

39. The method of claim 35, wherein the property of interest comprises stability in response to a perturbation.

40. The method of claim 35, further comprising designing a microbial community with the property of interest.

41. The method of claim 1, wherein the method is multiplexed.

42. The method of claim 1, wherein the first subset of the plurality of dilutions of the sample cultivated in the first cultivation condition comprises less than the plurality of dilutions of the sample.

43. The method of claim 1, wherein the interaction is indicative of how at least the first cultivation condition alters one or more of cultivability, competitive fitness, or interspecific interactions of the plurality of taxa of microorganisms in at least the first cultivation condition.

44. The method of claim 1, wherein the interaction is determined using (i) presence or absence data for the first taxon and the second taxon and (ii) the non-random occurrence of the first taxon in the presence or absence of the second taxon in the plurality of cultivated dilutions.

45. The method of claim 1, wherein the taxonomic information of taxa in the first plurality of cultivated dilutions comprises cultivable abundance information.

46. The method of claim 1, wherein the taxonomic information comprises sequences of 16S rRNA, 12S rRNA, 18S rRNA, 28S rRNA, 13S rRNA and 23S rRNA, internal transcribed spacer (ITS), ITS1, ITS2, cytochrome oxidase I (COI), cytochrome b, or any combination thereof.

47. The method of claim 1, wherein the plurality of taxa of microorganisms comprises isolates inoculated into the sample.

48. The method of claim 1, wherein the plurality of taxa of microorganisms comprise a consortium of mixed taxa, and wherein the sample comprises a sample of a natural environment and an isolate inoculated into the sample.

49. The method of claim 1, wherein the plurality of taxa of microorganisms comprises a natural consortia and isolates inoculated into the sample.

50. The method of claim 1, wherein the first cultivation condition comprises a selective factor.

51. The method of claim 50, wherein the selective factor comprises an abiotic condition, an aerobic condition, an anaerobic condition, a homogenizing environment, or a nitrate-reducing environment.

52. The method of claim 1, comprising subjecting the sample to one or more abiotic conditions, thereby selecting one of more taxa based on competitive fitness prior to cultivating the first subset the plurality of dilutions of the sample in the first cultivation condition.

53. The method of claim 52, comprising enriching the one or more selected taxa based on a phenotype that confers the competitive fitness.

54. A method for cultivating and sequencing a sample, comprising:
    diluting a sample comprising a plurality of taxa of microorganisms to form a plurality of dilutions of the sample;
    cultivating a first subset of the plurality of dilutions of the sample in a first cultivation condition to generate a first plurality of cultivated dilutions, wherein the first subset of the plurality of dilutions comprises a first dilution and a second dilution with an identical inoculum density, wherein the first dilution comprises a first taxon and a second taxon, wherein the second dilution comprises the first taxon and not the second taxon, and wherein an abundance of the first taxon in a first cultivated dilution of the first plurality of cultivated dilutions cultivated from the first dilution is different from an abundance of the first taxon in a second cultivated dilution of the first plurality of cultivated dilutions cultivated from the second dilution;
    subjecting the first plurality of cultivated dilutions of the sample to sequencing to generate taxonomic information of taxa in the first plurality of cultivated dilutions, wherein the taxonomic information comprises abundances of taxa in the first plurality of cultivated dilutions, and wherein a difference between the abundance of the first taxon in the first cultivated dilution in the taxonomic information and the abundance of the first taxon in the second cultivated dilution in the taxonomic information indicates the first taxon and the second taxon positively or negatively interact with each other.

55. The method of claim 54, wherein the abundance of the first taxon in the first cultivated dilution cultivated from the first dilution is higher than the abundance of the first taxon in the second cultivated dilution cultivated from the second dilution.

56. The method of claim 54, wherein the first subset of the plurality of dilutions comprises a third dilution with the identical inoculum density, wherein the third dilution comprises the second taxon and not the first taxon, and wherein an abundance of the second taxon in the first cultivated dilution of the first plurality of cultivated dilutions cultivated from the first dilution is higher than an abundance of the second taxon in a third cultivated dilution of the first plurality of cultivated dilutions cultivated from the third dilution.

57. A method for generating a microbial community, comprising:
    diluting a sample comprising a plurality of taxa of microorganisms to form a plurality of dilutions of the sample;
    cultivating a first subset of the plurality of dilutions of the sample in a first cultivation condition to generate a first plurality of cultivated dilutions, wherein the first subset of the plurality of dilutions comprises a first dilution with a higher first inoculum density and a second dilution with a lower second inoculum density, wherein the first dilution comprises a first taxon and a second taxon, wherein the second dilution comprises the first taxon and not the second taxon, and wherein an abundance of the first taxon in a first cultivated dilution of the first plurality of cultivated dilutions cultivated from the first dilution relative to the higher first inoculum density is lower than an abundance of the first taxon in a second cultivated dilution of the first plurality of cultivated dilutions cultivated from the second dilution relative to the lower second inoculum density;
    subjecting the first plurality of cultivated dilutions of the sample to sequencing to generate taxonomic information of taxa in the first plurality of cultivated dilutions, wherein the taxonomic information comprises abundances of taxa in the first plurality of cultivated dilutions;
    determining the first cultivated dilution comprises the first taxon and the second taxon, the second cultivated dilution comprises the first taxon and not the second taxon, and the abundance of the first taxon in the first cultivated dilution relative to the higher first inoculum density is lower than the abundance of the first taxon in the second cultivated dilution relative to the second lower inoculum density using the taxonomic information generated; and
    generating a microbial community comprising the first taxon and not the second taxon.

58. The method of claim 57, wherein the abundance of the first taxon in the first cultivated dilution cultivated from the first dilution is lower than the abundance of the first taxon in the second cultivated dilution cultivated from the second dilution.

59. The method of claim 57, wherein the first taxon in the microbial community contributes to a property of interest.

60. The method of claim 59, wherein the property of interest comprises performing a specific metabolic function, wherein the property of interest comprises producing a molecule of interest, wherein the property of interest comprises modifying a molecule of interest, and/or wherein the property of interest comprises stability in response to a perturbation.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 1
cctacgggag gcagcag                                                    17

<210> SEQ ID NO 2
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 2
ggactachvg ggtwtctaat                                                 20